United States Patent
Kajino et al.

(10) Patent No.: US 7,977,488 B2
(45) Date of Patent: Jul. 12, 2011

(54) 1-HETEROCYCLYLSULFONYL, 2-AMINOMETHYL, 5-(HETERO-) ARYL SUBSTITUTED 1-H-PYRROLE DERIVATIVES AS ACID SECRETION INHIBITORS

(75) Inventors: Masahiro Kajino, Osaka (JP); Atsushi Hasuoka, Osaka (JP); Haruyuki Nishida, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 713 days.

(21) Appl. No.: 11/991,307

(22) PCT Filed: Aug. 29, 2006

(86) PCT No.: PCT/JP2006/317408
§ 371 (c)(1),
(2), (4) Date: Feb. 27, 2008

(87) PCT Pub. No.: WO2007/026916
PCT Pub. Date: Mar. 8, 2007

(65) Prior Publication Data
US 2009/0275591 A1    Nov. 5, 2009

(30) Foreign Application Priority Data

Aug. 30, 2005 (JP) .................................. 2005-250356
Mar. 31, 2006 (JP) .................................. 2006-100626

(51) Int. Cl.
*C07D 401/02* (2006.01)
(52) U.S. Cl. .................................................. 546/276.4
(58) Field of Classification Search .................. None
See application file for complete search history.

(56) References Cited

U.S. PATENT DOCUMENTS

| | | | |
|---|---|---|---|
| 5,286,742 A | 2/1994 | Henegar et al. | |
| 5,480,902 A | 1/1996 | Addor et al. | |
| 6,365,620 B2 | 4/2002 | Eberle et al. | |
| 2002/0193410 A1 | 12/2002 | Burns et al. | |
| 2008/0139639 A1 | 6/2008 | Kajino et al. | |

FOREIGN PATENT DOCUMENTS

| | | |
|---|---|---|
| EP | 0 259 085 A1 | 8/1987 |
| EP | 0 464 845 A1 | 7/1991 |
| EP | 0464845 A1 | 1/1992 |
| EP | 0538231 A1 | 4/1993 |
| EP | 0597291 A1 | 5/1994 |
| EP | 0259085 A1 | 3/1998 |
| EP | 1061075 A2 | 12/2000 |
| EP | 1176139 A1 | 1/2002 |
| EP | 1 284 260 A1 | 2/2003 |
| EP | 1284260 A1 | 2/2003 |
| EP | 1432693 A2 | 6/2004 |
| EP | 1 466 902 A1 | 10/2004 |
| EP | 1466902 A1 | 10/2004 |
| EP | 1477489 A1 | 11/2004 |
| EP | 1655284 A1 | 5/2006 |
| JP | 9-30967 A | 1/1974 |
| JP | 63-63678 | 3/1988 |
| JP | 8-119936 A1 | 5/1996 |
| JP | 08119936 A1 | 5/1996 |
| JP | 11-209344 | 8/1999 |
| JP | 2004-315511 | 11/2004 |
| WO | 9204025 A1 | 3/1992 |
| WO | 9309100 A1 | 5/1993 |
| WO | WO-93/09100 | 5/1993 |
| WO | WO-98/08815 | 3/1998 |
| WO | 9828269 A1 | 7/1998 |
| WO | WO 98/28269 A1 | 7/1998 |
| WO | 00/58285 A1 | 10/2000 |
| WO | WO-00/58286 | 10/2000 |

(Continued)

OTHER PUBLICATIONS

Shum, P.W., "A convenient method for the synthesis of unsymmetrical 3, 4-disbustituted pyrroles," Tetrahedron Letters, vol. 31(47), pp. 6785-6788 (1990).

Okabe, K., et al., "The Second Generation Synthesis of a Tumor Promoter pendolmycin," Tetrahedron, vol. 47(36), pp. 7615-7624 (1991).

Banker, et al., "Modern Pharmaceutics, 3ed.," Marcel Dekker, New York, pp. 451 and 596, (1996).

Wolff, Manfred E., "Burger's Medicinal Chemistry, 5ed, Part I", John Wiley & Sons, pp. 975-977 (1995).

(Continued)

*Primary Examiner* — Zinna N Davis
(74) *Attorney, Agent, or Firm* — Edwards Angell Palmer & Dodge LLP; David G. Conlin, Esq.; Elbert Chiang

(57) ABSTRACT

The present invention provides a compound having a superior acid secretion inhibitory effect and showing an antiulcer activity and the like. The present invention provides a compound represented by the formula (I) wherein $R^1$ is a nitrogen-containing monocyclic heterocyclic group optionally condensed with a benzene ring or a heterocycle, the nitrogen-containing monocyclic heterocyclic group optionally condensed with a benzene ring or a heterocycle optionally has substituent(s), $R^2$ is an optionally substituted $C_{6-14}$ aryl group, an optionally substituted thienyl group or an optionally substituted pyridyl group, $R^3$ and $R^4$ are each a hydrogen atom, or one of $R^3$ and $R^4$ is a hydrogen atom and the other is an optionally substituted lower alkyl group, an acyl group, a halogen atom, a cyano group or a nitro group, and $R^5$ is an alkyl group or a salt thereof.

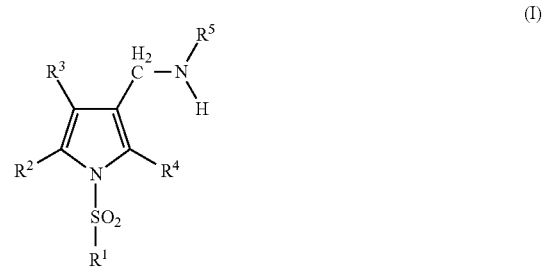

(I)

1 Claim, No Drawings

FOREIGN PATENT DOCUMENTS

| WO | 0202524 A1 | 1/2002 |
|---|---|---|
| WO | WO-02/02554 | 1/2002 |
| WO | 03028641 A2 | 4/2003 |
| WO | 03040147 A1 | 5/2003 |
| WO | 03044011 A1 | 5/2003 |
| WO | WO-03/044011 A1 | 5/2003 |
| WO | 03068738 A1 | 8/2003 |
| WO | 03068740 A1 | 8/2003 |
| WO | 03070729 A1 | 8/2003 |
| WO | 03106427 A2 | 12/2003 |
| WO | 2004014368 A1 | 2/2004 |
| WO | 2004103968 A1 | 12/2004 |
| WO | WO-2004/103968 A1 | 12/2004 |
| WO | 2006036024 A1 | 4/2006 |
| WO | WO-2006/036024 A1 | 4/2006 |

OTHER PUBLICATIONS

Trost, B., et al., "A[3+2] and [4+3] Cycloaddition Approach to N-Heterocycles via Pd-Catalyzed TMM Reactions with Imines", J. Am. Chemical Soc., vol. 115(15), pp. 6636-6645, XP 002141041, ISSN: 0002-7863 (1993).

Trost, B., et al., "A Selectivity Control Element for Palladium-Catalyzed Trimethylenemethane Cycloaddition", J. Am. Chemical Soc., vol. 113, pp. 9007-9009, XP 002513504, ISSN: 0002-7863 (1991).

Osipov, S., et al., "A radical pathway to alpha-aminoadipic acids," Tetrahedron Letters, vol. 41(30), pp. 5659-5662, XP 004209533, ISSN: 0040-4039 (2000).

Database Beilstein [online] Beilstein Institute for Organic Chemistry, Frankfurt-Main, DE; XP002544397, Mar. 2009, Database Accession No. 4558323 (BRN); Database Accession No. 4559246, 4574723, 4581745, 4584939, 4586270, 4588621, 4595969, 4595971, 4596723, 4600812, 4600844, 4604026 (BRNs). *abstract*—& Attanasi, Orazio; Santeusanio, Stefania: "Effect of Metal Ions in Organic Synthesis; XVIII. A Simple and High-Yield Direct Synthesis of 1-Arylamino-3-aminocarbonylpyrroles by the Copper(II) Chloride-Catalyzed Reaction of Arylazoalkenes with 3-Oxoalkanamides" Synthesis, vol. 1983, No. 9, 1983, pp. 742-744, XP002544392.

Database Beilstein, Beilstein Institute for Organic Chemistry, Frankfurt-Main, DE; XP002544398, Database Accession No. 4491404 (BRN); Database Accession Nos. 4511053, 4534506, 4549375, 4558933, 4573102, 4575926, 4577349, 4582906, 4592993, 4594785, 4600861, 4602984, 4605482, 4607805, 4612106, 4615190 (BRNs), *Abstract*.—& Attanasi, Orazio et al: "Effect of Metal Ions in Organic Synthesis; Part XXIII. Easy and High-Yield Direct Synthesis of 3-Aminocarbonylazoalkenes with 3-Oxoalkanamides" Synthesis, vol. 1984 (8), 1984, pp. 671-672, XP002544393.

Database Beilstein, Beilstein Institute for Organic Chemistry, Frankfurt-Main, DE; XP002544399; Database, Mar. 2009, Accession No. 4511416 (BRN); Database Accession Nos. 4517986, 4539949, 4553117, 4572075, 4574392, 4582793, 4586769, 4600919, 4606368, 4610346, 4612195 (BRNs), *Abstract*.—& Attanasi, Orazio et al: "Effect of Metal Ions in Organic Synthesis; part XXIV. Facile One-Flask Synthesis of 1-Alkoxycarbonylamino-3-aminocarbonylpyrro les by reaction of Alkoxycarbonylazoalkenes wtih 3-Oxoalkanamides under Copper (II) Chloride Catalysis" Synthesis, vol. 1984, No. 1984, pp. 873-874, XP002544394.

Database Beilstein, Beilstein Institute for Organic Chemistry, Frankfurt-Main, DE; Mar. 2009, XP002544400, Database Accession No. 4569762(BRN); Database Accession Nos. 4578166, 4593030, 4594930, 4595043, 4598160, 4602347, 4605011, 4609198, 4610824, 4612957, 4613094, 4613976, 4614957, 4615216, 4616410, 4618025, 4619789 (BRNs). *abstract*—& Attanasi, Orazio et al: "Effect of Metal Ions in organic Synthesis; part XXV. Simple Direct Synthesis of 1-Arylsulfonylamino-3-aminocarbonylpyrroles by Reaction of Arylsulfonylazoalkenes with 3-Oxoalkanamides under Copper(II) Chloride Catalysis" Synthesis, vol. 1984(10), 1984, pp. 874-876, XP002544395 *the whole document*.

Database Beilstein, Beilstein Institute for Organic Chemistry, Frankfurt-Main, DE; XP002544401; Database Accession No. 6443954 (BRN), Database Accession Nos. 6448183, 6448193, 6448674, 6449474, 6450364, 6453034, 6453229, 6453629, 6455895, 6457232 (BRNs). *Abstract* & Synthetic Communications, vol. 16, 1986, pp. 1411-1422.

Artico, et al., "Structure-Based Design, Synthesis, and Biological Evaluation of Novel Pyrrolyl Aryl Sulfones: HIV-1 Non-Nucleoside Reverse Transcriptase Inhibitors Active at Nanomolar Concentrations", J. Med. Chem., vol. 43, 2000, pp. 1886-1891, XP002544396, p. 1888, chart 2, compounds 26, 27; p. 1889, table 1, compounds 26, 27; experimental section.

Drug-Drug Interactions: An Important Negative Attribute in Drugs; Drugs of Today (2003), 39 (5); 301-338.

1-HETEROCYCLYLSULFONYL, 2-AMINOMETHYL, 5-(HETERO-) ARYL SUBSTITUTED 1-H-PYRROLE DERIVATIVES AS ACID SECRETION INHIBITORS

TECHNICAL FIELD

The present invention relates to pyrrole compounds having an acid secretion suppressive activity.

BACKGROUND ART

Proton pump inhibitors represented by omeprazole, which suppress secretion of gastric acid for the treatment of peptic ulcer, reflux esophagitis and the like, have been widely used in clinical situations. However, the existing proton pump inhibitors are associated with problems in terms of effect and side effects. To be specific, since the existing proton pump inhibitors are unstable under acidic conditions, they are often formulated as enteric preparations, in which case several hours are required before expression of the effect. In addition, since the existing proton pump inhibitors show inconsistent treatment effects due to metabolic enzyme polymorphism and drug interaction with pharmaceutical agents such as diazepam and the like, an improvement has been desired.

As pyrrole compounds having a proton pump inhibitory action, EP-A-0259085 describes a compound represented by the formula:

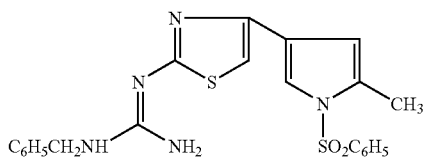

and the like.

As compounds having a thromboxane A2 (TXA2) antagonistic action and a TXA2 synthase inhibitory action, JP-A-8-119936 describes a compound represented by the formula:

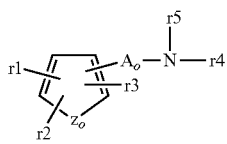

wherein r1 is carboxy, protected carboxy, carboxy(lower) alkyl, protected carboxy(lower)alkyl, carboxy(lower)alkenyl or protected carboxy(lower)alkenyl, r2 is hydrogen; lower alkyl; heterocyclic (lower)alkyl optionally having aminoimino or protected aminoimino; heterocyclic (lower)alkenyl; or heterocyclic carbonyl, r3 is hydrogen or lower alkyl, r4 is acyl, r5 is hydrogen, $A_0$ is lower alkylene, and $Z_0$ is S or NH, provided when r1 is carboxy or protected carboxy, then $Z_0$ is NH.

Moreover, as a therapeutic drug for neoplastic diseases or autoimmune diseases, WO2004/103968 describes a compound represented by the formula:

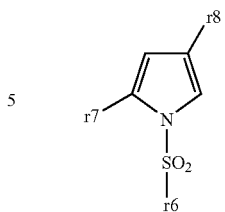

wherein r6 is aryl, aralkyl or heteroaryl, r7 is aryl or heteroaryl, and r8 is aryl, heteroaryl or optionally substituted aminomethyl.

DISCLOSURE OF THE INVENTION

Problems to be Solved by the Invention

A pharmaceutical agent that effectively suppresses gastric acid secretion as known proton pump inhibitors, which is improved in instability under acidic conditions, dispersion of effects due to metabolic enzyme polymorphism and drug interaction, which are problems of known proton pump inhibitors, is expected to show more superior treatment effect on peptic ulcer, reflux esophagitis and the like. As the situation stands, however, a proton pump inhibitor capable of sufficiently satisfying these requirements has not been found. It is therefore an object of the present invention to provide a compound having a superior acid secretion suppressive effect (particularly, proton pump inhibitory effect), which has been improved in these problems.

Means of Solving the Problems

The present inventors have conducted various studies and found that a compound represented by the formula (I):

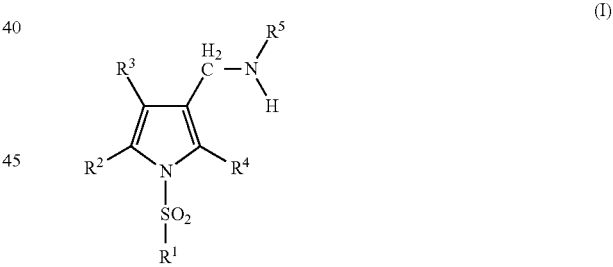

wherein $R^1$ is a monocyclic nitrogen-containing heterocyclic group optionally condensed with a benzene ring or a heterocycle, the monocyclic nitrogen-containing heterocyclic group optionally condensed with a benzene ring or a heterocycle optionally has substituent(s),
$R^2$ is an optionally substituted $C_{6-14}$ aryl group, an optionally substituted thienyl group or an optionally substituted pyridyl group,
$R^3$ and $R^4$ are each a hydrogen atom, or one of $R^3$ and $R^4$ is a hydrogen atom and the other is an optionally substituted lower alkyl group, an acyl group, a halogen atom, a cyano group or a nitro group, and
$R^5$ is an alkyl group, or a salt thereof [hereinafter to be abbreviated as compound (I)] unexpectedly has a very strong acid secretion suppressive effect (proton pump inhibitory effect), and is fully satisfactory as a pharmaceutical agent, which resulted in the completion of the present invention.

Accordingly, the present invention relates to the following.

[1] A compound represented by the formula (I):

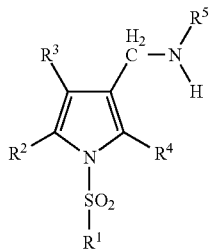

wherein R¹ is a monocyclic nitrogen-containing heterocyclic group optionally condensed with a benzene ring or a heterocycle, the monocyclic nitrogen-containing heterocyclic group optionally condensed with a benzene ring or a heterocycle optionally has substituent(s), R² is an optionally substituted $C_{6-14}$ aryl group, an optionally substituted thienyl group or an optionally substituted pyridyl group, R³ and R⁴ are each a hydrogen atom, or one of R³ and R⁴ is a hydrogen atom and the other is an optionally substituted lower alkyl group, an acyl group, a halogen atom, a cyano group or a nitro group, and R⁵ is an alkyl group, or a salt thereof.

[2] A compound represented by the formula (I):

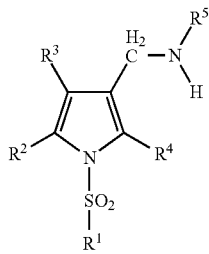

wherein R¹ is a monocyclic nitrogen-containing heterocyclic group optionally condensed with a benzene ring or a heterocycle, the monocyclic nitrogen-containing heterocyclic group optionally condensed with a benzene ring or a heterocycle optionally has substituent(s), R² is an optionally substituted $C_{6-14}$ aryl group or an optionally substituted thienyl group, R³ and R⁴ are each a hydrogen atom, or one of R³ and R⁴ is a hydrogen atom and the other is an optionally substituted lower alkyl group, an acyl group, a halogen atom, a cyano group or a nitro group, and R⁵ is an alkyl group, or a salt thereof.

[3] The compound of the above-mentioned [1] or [2], wherein R¹ is a monocyclic nitrogen-containing heterocyclic group.

[4] The compound of the above-mentioned [1] or [2], wherein the monocyclic nitrogen-containing heterocyclic group is a pyridyl group.

[5] The compound of the above-mentioned [1] or [2], wherein R² is a phenyl group optionally substituted by 1 to 5 substituents selected from (i) a halogen atom and (ii) a $C_{1-6}$ alkyl optionally substituted by 1 to 5 halogen atoms.

[6] The compound of the above-mentioned [1] or [2], wherein R² is a pyridyl group optionally substituted by 1 to 4 substituent(s) selected from $C_{1-6}$ alkyl, a halogen atom, alkoxy, cyano, acyl, nitro and amino.

[7] The compound of the above-mentioned [1] or [2], wherein R³ and R⁴ are each a hydrogen atom.

[8] The compound of the above-mentioned [1] or [2], wherein R⁵ is a methyl group.

[9] 1-{5-(2-Fluorophenyl)-1-[(6-methylpyridin-3-yl)sulfonyl]-1H-pyrrol-3-yl}-N-methylmethanamine or a salt thereof.

[10] 1-[4-Fluoro-5-phenyl-1-(pyridin-3-ylsulfonyl)-1H-pyrrol-3-yl]-N-methylmethanamine or a salt thereof.

[11] N-Methyl-1-[5-(4-methyl-3-thienyl)-1-(pyridin-3-ylsulfonyl)-1H-pyrrol-3-yl]methanamine or a salt thereof.

[12] 1-[5-(2-Fluoropyridin-3-yl)-1-(pyridin-3-ylsulfonyl)-1H-pyrrol-3-yl]-N-methylmethanamine or a salt thereof.

[13] 1-[5-(2-Fluorophenyl)-1-(pyridin-3-ylsulfonyl)-1H-pyrrol-3-yl]-N-methylmethanamine or a salt thereof.

[14] N-Methyl-1-[5-(2-methylphenyl)-1-(pyridin-3-ylsulfonyl)-1H-pyrrol-3-yl]methanamine or a salt thereof.

[15] A prodrug of the compound of the above-mentioned [1] or [2].

[16] A pharmaceutical composition comprising the compound of the above-mentioned [1] or [2] or a prodrug thereof.

[17] The pharmaceutical composition of the above-mentioned [16], which is an acid secretion inhibitor.

[18] The pharmaceutical composition of the above-mentioned [16], which is a potassium-competitive acid blocker.

[19] The pharmaceutical composition of the above-mentioned [16], which is an agent for the treatment or prophylaxis of peptic ulcer, Zollinger-Ellison syndrome, gastritis, erosive esophagitis, reflux esophagitis, symptomatic gastroesophageal reflux disease (symptomatic GERD), functional dyspepsia, gastric cancer, stomach MALT lymphoma, or gastric hyperacidity; or an inhibitor of upper gastrointestinal hemorrhage due to peptic ulcer, acute stress ulcer, hemorrhagic gastritis or invasive stress.

[20] A method of treating or preventing peptic ulcer, Zollinger-Ellison syndrome, gastritis, erosive esophagitis, reflux esophagitis, symptomatic gastroesophageal reflux disease (symptomatic GERD), functional dyspepsia, gastric cancer, stomach MALT lymphoma, or gastric hyperacidity; or a method of inhibiting upper gastrointestinal hemorrhage due to peptic ulcer, acute stress ulcer, hemorrhagic gastritis or invasive stress, which comprises administering an effective amount of the compound of the above-mentioned [1] or [2] or a prodrug thereof to a mammal.

[21] Use of the compound of the above-mentioned [1] or [2] or a prodrug thereof for the production of a pharmaceutical composition for the treatment or prophylaxis of peptic ulcer, Zollinger-Ellison syndrome, gastritis, erosive esophagitis, reflux esophagitis, symptomatic gastroesophageal reflux disease (symptomatic GERD), functional dyspepsia, gastric cancer, stomach MALT lymphoma, or gastric hyperacidity; or an inhibitor of upper gastrointestinal hemorrhage due to peptic ulcer, acute stress ulcer, hemorrhagic gastritis or invasive stress.

Effect of the Invention

Since compound (I) shows a superior proton pump inhibitory effect (while conventional proton pump inhibitors such as omeprazole, lansoprazole etc. form a covalent bond with a cysteine residue of H+/K+-ATPase and irreversibly inhibit the enzyme activity, since compound (I) inhibits the proton pump (H+/K+-ATPase) activity reversibly and in a K+ antagonist inhibitory manner to consequently suppress acid secretion, it is sometimes referred to as a potassium-competitive acid blocker: P-CAB or an acid pump antagonist (ACPA or APA)), it can provide a clinically useful pharmaceutical composition for the prophylaxis and/or treatment of peptic ulcer (e.g., gastric ulcer, gastric ulcer due to postoperative stress, duodenal ulcer, anastomotic ulcer, ulcer caused by non-steroidal anti-inflammatory agents, ulcer due to postoperative stress etc.); Zollinger-Ellison syndrome; gastritis; erosive esophagitis; reflux esophagitis such as erosive reflux esophagitis and the like; symptomatic gastroesophageal reflux disease (symptomatic GERD) such as non-erosive reflux disease or gastroesophageal reflux disease free of esophagitis and the like; functional dyspepsia; gastric cancer (including gastric cancer associated with promoted production of interleukin-1β due to gene polymorphism of interleukin-1); stomach MALT lymphoma; gastric hyperacidity; or an inhibitor of upper gastrointestinal hemorrhage due to peptic ulcer, acute stress ulcer, hemorrhagic gastritis or invasive stress (e.g. stress caused by major surgery requiring postoperative intensive management, and cerebrovascular disorder, head trauma, multiple organ failure and extensive burn, each requiring intensive treatment) and the like. Furthermore, compound (I) is used for the prophylaxis and/or treatment of airway disorders; asthma and the like, pre-anesthetic administration, eradication of *Helicobacter pylori* or eradication assistance and the like. Since compound (I) shows low toxicity and is superior in water-solubility, in vivo kinetics and efficacy expression, it is useful as a pharmaceutical composition. Moreover, since compound (I) is stable even under acidic conditions, which enables oral administration of the compound as a conventional tablet and the like without formulating an enteric-coated preparation. This has a consequence that the preparation of tablet and the like can be made smaller, which is advantageous in that it is easily swallowed by patients having difficulty in swallowing, particularly the elderly and children. In addition, since a sustained release effect afforded by enteric-coated preparations is absent, expression of a gastric acid secretion-suppressive action is rapid, and alleviation of symptoms such as pain and the like is rapid.

BEST MODE FOR EMBODYING THE INVENTION

In the formula (I), as the "nitrogen-containing monocyclic heterocyclic group optionally condensed with a benzene ring or a heterocycle" for $R^1$,
(1) a nitrogen-containing monocyclic heterocyclic group, and
(2) a fused ring group represented by the formula:

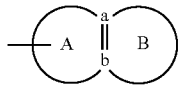

wherein ring A is a nitrogen-containing monocyclic heterocyclic group, ring B is a benzene ring or a heterocycle, a and b are each a bridgehead ring-constituting atom (e.g., a carbon atom, a nitrogen atom and the like), and = shows a single bond or a double bond, provided that a bond to an —SO$_2$— group in the formula (I) is present in a ring A-constituting atom (ring atom) other than the bridgehead ring-constituting atoms a and b, can be mentioned.

As used herein, ring A needs only to contain, as a ring A-constituting atom (ring atom), at least one (preferably 1 to 4, more preferably 1 or 2) nitrogen atom, and one or both of the bridgehead ring-constituting atoms a and b may be nitrogen atoms.

The "nitrogen-containing monocyclic heterocyclic group optionally condensed with a benzene ring or a heterocycle" optionally has substituent(s), and the substituent(s) may be present in any of ring A and ring B.

As the "nitrogen-containing monocyclic heterocyclic group" of the "nitrogen-containing monocyclic heterocyclic group optionally condensed with a benzene ring or a heterocycle" and the above-mentioned ring A, for example, an aromatic nitrogen-containing monocyclic heterocyclic group, a saturated or unsaturated non-aromatic nitrogen-containing monocyclic heterocyclic group (aliphatic nitrogen-containing monocyclic heterocyclic group) and the like containing, as a ring-constituting atom (ring atom), at least one (preferably 1 to 4, more preferably 1 or 2) nitrogen atom can be mentioned.

As the "aromatic nitrogen-containing monocyclic heterocyclic group", for example, aromatic nitrogen-containing monocyclic heterocyclic groups such as pyrrolyl, oxazolyl, isoxazolyl, thiazolyl, isothiazolyl, imidazolyl (1H-imidazol-1-yl, 1H-imidazol-4-yl etc.), pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl (1,2,4-triazol-1-yl, 1,2,4-triazol-4-yl etc.), tetrazolyl, pyridyl (2-, 3- or 4-pyridyl etc.), pyridazinyl, pyrimidinyl, pyrazinyl, triazinyl and the like, and N-oxide forms thereof and the like can be mentioned. Of these, a 5- or 6-membered aromatic nitrogen-containing monocyclic heterocyclic group is preferable, and thiazolyl, imidazolyl, pyrazolyl, pyridyl, pyrimidinyl and pyridazinyl are preferable, and pyridyl is particularly preferable.

As the "saturated or unsaturated non-aromatic nitrogen-containing monocyclic heterocyclic group", partially reduced forms (e.g., imidazolinyl, tetrahydropyrimidinyl and the like) of the above-mentioned "aromatic nitrogen-containing monocyclic heterocyclic group" and, for example, azetidinyl, pyrrolidinyl, piperidyl (2-, 3- or 4-piperidyl), morpholinyl, thiomorpholinyl, piperazinyl (1-piperazinyl etc.), homopiperazinyl and the like can be mentioned. Of these, a 5- or 6-membered non-aromatic nitrogen-containing monocyclic heterocyclic group is preferable.

As the "heterocycle" optionally condensed with a nitrogen-containing monocyclic heterocyclic group, for example, an aromatic heterocycle or non-aromatic heterocycle can be mentioned.

As the "aromatic heterocycle", for example, 5- or 6-membered aromatic heteromonocyclic rings such as a furan ring, a thiophene ring, a pyrrole ring, an oxazole ring, an isoxazole ring, a thiazole ring, an isothiazole ring, an imidazole ring, a pyrazole ring, a 1,2,3-oxadiazole ring, a 1,2,4-oxadiazole ring, a 1,3,4-oxadiazole ring, a furazan ring, a 1,2,3-thiadiazole ring, a 1,2,4-thiadiazole ring, a 1,3,4-thiadiazole ring, a 1,2,3-triazole ring, a 1,2,4-triazole ring, tetrazole ring, pyridine ring, pyridazine ring, pyrimidine ring, pyrazine ring, triazine ring and the like and, for example, 8- to 12-membered aromatic fused heterocycles such as a benzofuran ring, an isobenzofuran ring, a benzo[b]thiophene ring, an indole ring, an isoindole ring, a 1H-indazole ring, a benzindazole ring, a benzoxazole ring, a 1,2-benzoisoxazole ring, a benzothiazole ring, a benzopyran ring, a 1,2-benzoisothiazole ring, a 1H-benzotriazole ring, a quinoline ring, an isoquinoline ring, a cinnoline ring, a quinazoline ring, a quinoxaline ring, a phthalazine ring, a naphthyridine ring, a purine ring, a pteridine ring, a carbazole ring, an α-carboline ring, a β-carboline ring, a γ-carboline ring, an acridine ring, a phenoxazine ring, a phenothiazine ring, a phenazine ring, a phenoxathiine ring, a thianthrene ring, a phenanthridine ring, a phenanthrone ring, an indolizine ring, a pyrrolo[1,2-b]pyridazine ring, a pyrazolo[1,5-a]pyridine ring, an imidazo[1,2-a]pyridine ring, an imidazo[1,5-a]pyridine ring, an imidazo[1,2- b]pyridazine ring, an imidazo[1,2-a]pyrimidine ring, a 1,2,4-triazolo[4,3-a]pyridine ring, a 1,2,4-triazolo[4,3-b]pyridazine ring and the like (preferably, a heterocycle wherein the aforementioned 5- or 6-membered aromatic heteromonocyclic ring is condensed with a benzene ring or a heterocycle wherein the same or different two heterocycles of the aforementioned 5- or 6-membered aromatic heteromonocyclic ring are condensed, more preferably a heterocycle wherein the aforementioned 5- or 6-membered aromatic monocyclic heterocyclic group is condensed with a benzene ring, preferably imidazopyrimidinyl etc.) and the like can be mentioned.

As the "non-aromatic heterocycle", for example, 3- to 8-membered saturated or unsaturated non-aromatic heterocycles such as an oxirane ring, an azetidine ring, an oxetane ring, a thietane ring, a pyrrolidine ring, a tetrahydrofuran ring, a thioran ring, a piperidine ring, a tetrahydropyran ring, a morpholine ring, a thiomorpholine ring, a piperazine ring, a 3-hexahydrocyclopenta[c]pyrrole ring, a homopiperidine ring, a homopiperazine ring and the like, or non-aromatic heterocycles wherein the double bonds of the aforementioned aromatic heteromonocyclic ring or aromatic fused heterocycle are partly or entirely saturated such as a dihydropyridine ring, a dihydropyrimidine ring, a 1,2,3,4-tetrahydroquinoline ring, a 1,2,3,4-tetrahydroisoquinoline ring and the like, and the like can be mentioned.

As preferable nitrogen-containing monocyclic heterocyclic group condensed with a benzene ring or a heterocycle, for example, nitrogen-containing aromatic fused heterocyclic groups such as 8- to 16-membered (preferably 8- to 12-membered) nitrogen-containing aromatic bicyclic fused heterocyclic groups such as 2- or 3-indolyl, 1- or 3-isoindolyl, 1H-indazol-3-yl, 2-benzimidazolyl, 2-benzoxazolyl, 3-benzoisoxazolyl, 2-benzothiazolyl, 3-benzoisothiazolyl, 2-, 3- or 4-quinolyl, 1-, 3- or 4-isoquinolyl, 3- or 4-cinnolinyl, 2- or 4-quinazolinyl, 2- or 3-quinoxalinyl, 1- or 4-phthalazinyl, naphthyridinyl, purinyl, pteridinyl, 1,7-phenanthrolin-2-, 3- or 4-yl, 1-, 2- or 3-indolizinyl, pyrrolo[1,2-b]pyridazinyl, pyrazolo[1,5-a]pyridyl, imidazo[1,2-a]pyridyl, imidazo[1,2-b]pyrazolyl, imidazo[1,5-a]pyridyl, imidazo[4,5-c]pyridyl, pyrazolo[1,5-a]pyrimidinyl, pyrazolo[1,5-c]pyrimidinyl, pyrazolo[3,4-d]pyrimidinyl, imidazo[1,2-b]pyridazinyl, imidazo[1,5-b]pyridazinyl, pyrazolo[3,4-b]pyridyl, imidazo[1,2-a]pyrimidinyl, 1,2,4-triazolo[4,3-a]pyridyl, 1,2,4-triazolo[4,3-b]pyridazinyl, [1,2,4]triazolo[1,2-a]pyridazinyl, [1,2,3]triazolo[1,5-a]pyrimidinyl, [1,2,4]triazolo[1,5-c]pyrimidinyl, [1,2,4]triazolo[1,5-a]pyridyl, [1,2,4]triazolo[4,3-a]pyridyl, pyrazolo[5,1-b]thiazolyl, pyrrolo[2,1-f][1,2,4]triazinyl, pyrrolo[1,2-b]pyridazinyl, pyrrolo[2,3-d]pyrimidinyl, pyrrolo[2,3-b]pyridyl, thieno[3,2-b]pyrimidinyl, thieno[2,3-b]pyridyl, thieno[2,3-c]pyridyl, thieno[3,2-b]pyridyl, thieno[3,2-c]pyridyl, pyrido[2,3-b]pyrazyl, pyrido[3,4-b]pyrazyl, pyrido[2,3-d]pyrimidinyl, pyrido[3,2-d]pyrimidinyl, pyrido[4,3-d]pyrimidinyl and the like, and the like, and the like can be mentioned. As the nitrogen-containing aromatic fused heterocycle, fused pyridine wherein a pyridine ring is condensed with one or two (preferably one) of the aforementioned 5- or 6-membered nitrogen-containing aromatic monocyclic heterocycles or one or two (preferably one) benzene rings (when condensed with a benzene ring, the pyridine ring has a bond), fused pyrimidine wherein a pyrimidine ring is condensed with one or two (preferably one) of the aforementioned 5 or 6-membered nitrogen-containing aromatic monocyclic heterocycles, or one or two (preferably one) benzene rings (when condensed with a benzene ring, the pyrimidine ring has a bond) and the like are preferable.

As the "non-aromatic nitrogen-containing heterocycle", for example, 3- to 8-membered (preferably 5- or 6-membered) nitrogen-containing saturated or unsaturated (preferably saturated) non-aromatic heterocycle (aliphatic nitrogen-containing heterocycle) such as azetidine, pyrrolidine, imidazolidine, thiazolidine, oxazolidine, piperidine, morpholine, thiomorpholine, piperazine and the like, or nitrogen-containing non-aromatic heterocycle wherein the double bonds of the aforementioned nitrogen-containing aromatic monocyclic heterocycle or nitrogen-containing aromatic fused heterocycle are partly or entirely saturated, such as 1,2,3,4-tetrahydroquinoline, 1,2,3,4-tetrahydroisoquinoline and the like, and the like can be mentioned.

As the "nitrogen-containing monocyclic heterocyclic group optionally condensed with a benzene ring or a heterocycle", a 5- or 6-membered aromatic nitrogen-containing monocyclic heterocyclic group is preferable from among those mentioned above. Of them, a 6-membered aromatic nitrogen-containing heterocyclic group such as pyridyl (e.g., 2-, 3- or 4-pyridyl etc.), pyrimidinyl (e.g., 2-, 4- or 5-pyrimidinyl etc.), pyridazinyl (e.g., 3- or 4-pyridazinyl etc.) and the like is preferable, and pyridyl is particularly preferable.

As the substituent that the "nitrogen-containing monocyclic heterocyclic group optionally condensed with a benzene ring or a heterocycle" may have, (1) a halogen atom (e.g., fluorine atom, chlorine atom, bromine atom, iodine atom etc.), (2) nitro, (3) cyano, (4) hydroxy, (5) $C_{1-6}$ alkoxy (e.g., methoxy, ethoxy, propoxy, isopropoxy, butoxy, isobutoxy, sec-butoxy, pentyloxy, hexyloxy, fluoromethoxy etc.) optionally having 1 to 3 halogen atoms (e.g., fluorine, chlorine, bromine, iodine), (6) $C_{6-14}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio (e.g., methylthio, difluoromethylthio, trifluoromethylthio, ethylthio, propylthio, isopropylthio, butylthio, 4,4,4-trifluorobutylthio, pentylthio, hexylthio etc.) optionally having 1 to 3 halogen atoms (e.g., fluorine, chlorine, bromine, iodine), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.), (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ aryl-carbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkyl-carbamoyl (e.g., methylcarbamoyl, ethylcarbamoyl etc.), (28) di-$C_{1-6}$ alkyl-carbamoyl (e.g., dimethylcarbamoyl, diethylcarbamoyl, ethylmethylcarbamoyl etc.), (29) $C_{6-14}$ aryl-carbamoyl (e.g., phenylcarbamoyl, 1-naphthylcarbamoyl, 2-naphthylcarbamoyl etc.), (30) $C_{1-6}$ alkylsulfonyl (e.g., methylsulfonyl, ethylsulfonyl etc.), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ aryl-carbonylamino (e.g., benzoylamino, naphthoylamino etc.), (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.), (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxy-carbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) a 5- to 7-membered saturated cyclic amino (e.g., pyrrolidin-1-yl, piperidino, piperazin-1-yl, morpholino, thiomorpholino, hexahydroazepin-1-yl etc.) optionally containing, besides one nitrogen atom and carbon atom, 1 or 2 kinds of 1 to 4 hetero atoms selected from a nitrogen atom, a sulfur atom and an oxygen atom, (47) a 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.) containing, besides carbon atom, 1 or 2 kinds of 1 to 4 hetero atoms selected from a nitrogen atom, a sulfur atom and an oxygen atom, (48) $C_{1-3}$ alkylenedioxy (e.g., methylenedioxy, ethylenedioxy etc.), (49) $C_{3-7}$ cycloalkyl (e.g., cyclopropyl, cyclobutyl, cyclopentyl, cyclohexyl, cycloheptyl etc.), (50) $C_{1-6}$ alkyl group (e.g., methyl, ethyl, n-propyl, isopropyl, n-butyl, isobutyl, sec-butyl, tert-butyl, n-pentyl, sec-pentyl, isopentyl, neopentyl, n-hexyl, isohexyl etc.) optionally having 1 to 3 halogen atoms (e.g., fluorine, chlorine, bromine, iodine), (51) a $C_{2-6}$ alkenyl group (e.g., allyl, isopropenyl, isobutenyl, 1-methylallyl, 2-pentenyl, 2-hexenyl etc.) optionally having 1 to 3 halogen atoms (e.g., fluorine, chlorine, bromine, iodine), (52) a $C_{2-6}$ alkynyl group (e.g., propargyl, 2-butynyl, 3-butynyl, 3-pentynyl, 3-hexynyl etc.), (53) a $C_{1-6}$ alkyl group (e.g., hydroxymethyl, hydroxyethyl etc.) substituted by 1 to 3 hydroxy and the like can be mentioned.

The substituent may be present at a substitutable position, and the number of the substituents is 1 to 5, preferably 1 to 3.

As the "$C_{6-14}$ aryl group" of the "optionally substituted $C_{6-14}$ aryl group" for $R^2$, for example, phenyl, 1-naphthyl, 2-naphthyl, 2-biphenylyl, 3-biphenylyl, 4-biphenylyl, 2-anthryl and the like can be mentioned.

As the substituent that the "$C_{6-14}$ aryl group" optionally has, groups similar to the substituents that the "nitrogen-containing monocyclic heterocyclic group optionally condensed with a benzene ring or a heterocycle" for the aforementioned $R^1$ optionally has can be mentioned.

The number of the substituents is 1 to 5, preferably 1 to 3.

As the "thienyl group" of the "optionally substituted thienyl group" for $R^2$, 2- or 3-thienyl can be mentioned.

As the substituent that the "thienyl group" optionally has, groups similar to the substituents that the "nitrogen-containing monocyclic heterocyclic group optionally condensed with a benzene ring or a heterocycle" for the aforementioned $R^1$ optionally has can be mentioned.

The number of the substituents is 1 to 4, preferably 1 to 3.

As the "pyridyl group" of the "optionally substituted pyridyl group" for $R^2$, 2-, 3- or 4-pyridyl, or bipyridyl (e.g., 2,3'-bipyridin-5-yl) can be mentioned.

As the substituent that the "pyridyl group" optionally has, groups similar to the substituents that the "nitrogen-containing monocyclic heterocyclic group optionally condensed with a benzene ring or a heterocycle" for the aforementioned $R^1$ optionally has can be mentioned.

The number of the substituents is 1 to 4, preferably 1 to 3.

As the "lower alkyl group" of the "optionally substituted lower alkyl group" for $R^3$ or $R^4$, for example, $C_{1-4}$ alkyl groups such as methyl, ethyl, propyl, isopropyl, butyl, isobutyl, sec-butyl, tert-butyl and the like, and the like can be mentioned.

As the substituent that the "lower alkyl group" optionally has, (1) a halogen atom (e.g., fluorine atom, chlorine atom, bromine atom, iodine atom etc.), (2) nitro, (3) cyano, (4) hydroxy, (5) $C_{1-6}$ alkoxy (e.g., methoxy, ethoxy, propoxy, isopropoxy, butoxy, isobutoxy, sec-butoxy, pentyloxy, hexyloxy, fluoromethoxy etc.) optionally having 1 to 3 halogen atoms (e.g., fluorine, chlorine, bromine, iodine), (6) $C_{6-14}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio (e.g., methylthio, difluoromethylthio, trifluoromethylthio, ethylthio, propylthio, isopropylthio, butylthio, 4,4,4-trifluorobutylthio, pentylthio, hexylthio etc.) optionally having 1 to 3 halogen atoms (e.g., fluorine, chlorine, bromine, iodine), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.) (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ aryl-carbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkyl-carbamoyl (e.g., methylcarbamoyl, ethylcarbamoyl etc.), (28) di-$C_{1-6}$ alkyl-carbamoyl (e.g., dimethylcarbamoyl, diethylcarbamoyl, ethylmethylcarbamoyl etc.), (29) $C_{6-14}$ aryl-carbamoyl (e.g., phenylcarbamoyl, 1-naphthylcarbamoyl, 2-naphthylcarbamoyl etc.), (30) $C_{1-6}$ alkylsulfonyl (e.g., methylsulfonyl, ethylsulfonyl etc.), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ aryl-carbonylamino (e.g., benzoylamino, naphthoylamino etc.), (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.),

(40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxy-carbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) a 5- to 7-membered saturated cyclic amino optionally containing, besides one nitrogen atom and carbon atom, 1 or 2 kinds of 1 to 4 hetero atoms selected from a nitrogen atom, a sulfur atom and an oxygen atom (e.g., pyrrolidin-1-yl, piperidino, piperazin-1-yl, morpholino, thiomorpholino, hexahydroazepin-1-yl etc.), (47) a 5- to 10-membered aromatic heterocyclic group containing, besides carbon atom, 1 or 2 kinds of 1 to 4 hetero atoms selected from a nitrogen atom, a sulfur atom and an oxygen atom (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), (48) $C_{1-3}$ alkylenedioxy (e.g., methylenedioxy, ethylenedioxy etc.), and (49) $C_{3-7}$ cycloalkyl (e.g., cyclopropyl, cyclobutyl, cyclopentyl, cyclohexyl, cycloheptyl etc.) and the like can be mentioned.

The number of the substituents is 1 to 3.

As the "acyl group" for $R^3$ or $R^4$, an acyl group having 1 to 20 carbon atoms, which is derived from organic carboxylic acid can be mentioned. For example, $C_{1-7}$ alkanoyl groups (e.g., formyl; $C_{1-6}$ alkyl-carbonyl such as acetyl, propionyl, butyryl, isobutyryl, pentanoyl, hexanoyl, heptanoyl and the like; etc.), $C_{6-14}$ aryl-carbonyl groups (e.g., benzoyl, naphthalenecarbonyl etc.), $C_{1-6}$ alkoxy-carbonyl groups (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl etc.), $C_{6-14}$ aryloxycarbonyl groups (e.g., phenoxycarbonyl group), $C_{7-19}$ aralkyl-carbonyl groups (e.g., phenyl-$C_{1-4}$ alkylcarbonyl such as benzylcarbonyl, phenethylcarbonyl, phenylpropylcarbonyl and the like, naphthyl-$C_{1-4}$ alkylcarbonyl such as benzhydrylcarbonyl, naphthylethylcarbonyl and the like, etc.), $C_{7-19}$ aralkyloxy-carbonyl groups (e.g., phenyl-$C_{1-4}$ alkyloxycarbonyl such as benzyloxycarbonyl and the like, etc.), 5- or 6-membered heterocycle-carbonyl group or condensed heterocycle-carbonyl groups thereof (e.g., pyrrolylcarbonyl such as 2- or 3-pyrrolylcarbonyl and the like; pyrazolylcarbonyl such as 3-, 4- or 5-pyrazolylcarbonyl and the like; imidazolylcarbonyl such as 2-, 4- or 5-imidazolylcarbonyl and the like; triazolylcarbonyl such as 1,2,3-triazol-4-ylcarbonyl, 1,2,4-triazol-3-ylcarbonyl and the like; tetrazolylcarbonyl such as 1H- or 2H-tetrazol-5-ylcarbonyl and the like; furylcarbonyl such as 2- or 3-furylcarbonyl and the like; thienylcarbonyl such as 2- or 3-thienylcarbonyl and the like; oxazolylcarbonyl such as 2-, 4- or 5-oxazolylcarbonyl and the like; isoxazolylcarbonyl such as 3-, 4- or 5-isoxazolylcarbonyl and the like; oxadiazolylcarbonyl such as 1,2,3-oxadiazol-4- or 5-ylcarbonyl, 1,2,4-oxadiazol-3- or 5-ylcarbonyl, 1,2,5-oxadiazol-3- or 4-ylcarbonyl, 1,3,4-oxadiazol-2-ylcarbonyl and the like; thiazolylcarbonyl such as 2-, 4- or 5-thiazolylcarbonyl and the like; isothiazolylcarbonyl such as 3-, 4- or 5-isothiazolylcarbonyl and the like; thiadiazolylcarbonyl such as 1,2,3-thiadiazol-4- or 5-ylcarbonyl, 1,2,4-thiadiazol-3- or 5-ylcarbonyl, 1,2,5-thiadiazol-3- or 4-ylcarbonyl, 1,3,4-thiadiazol-2-ylcarbonyl and the like; pyrrolidinylcarbonyl such as 2- or 3-pyrrolidinylcarbonyl and the like; pyridylcarbonyl such as 2-, 3- or 4-pyridylcarbonyl and the like; pyridylcarbonyl wherein nitrogen atom is oxidized such as 2-, 3- or 4-pyridyl-N-oxidocarbonyl and the like; pyridazinylcarbonyl such as 3- or 4-pyridazinylcarbonyl and the like; pyridazinyl wherein one or both nitrogen atoms are oxidized, such as 3-, 4-, 5- or 6-pyridazinyl-N-oxidocarbonyl and the like; pyrimidinylcarbonyl such as 2-, 4- or 5-pyrimidinylcarbonyl and the like; pyrimidinylcarbonyl wherein one or both nitrogen atoms are oxidized, such as 2-, 4-, 5- or 6-pyrimidinyl-N-oxidocarbonyl and the like; pyrazinylcarbonyl; piperidinylcarbonyl such as 2-, 3- or 4-piperidinylcarbonyl and the like; piperazinylcarbonyl; indolylcarbonyl such as 3H-indol-2- or 3-ylcarbonyl and the like; pyranylcarbonyl such as 2-, 3- or 4-pyranylcarbonyl and the like; thiopyranylcarbonyl such as 2-, 3- or 4-thiopyranylcarbonyl and the like; quinolylcarbonyl such as 3-, 4-, 5-, 6-, 7- or 8-quinolylcarbonyl and the like; isoquinolylcarbonyl; pyrido[2,3-d]pyrimidinylcarbonyl (e.g., pyrido[2,3-d]pyrimidin-2-ylcarbonyl); naphthyridinylcarbonyl (e.g., 1,5-naphthyridin-2- or 3-ylcarbonyl) such as 1,5-, 1,6-1,7-, 1,8-, 2,6- or 2,7-naphthyridinylcarbonyl and the like; thieno[2,3-d]pyridylcarbonyl (e.g., thieno[2,3-d]pyridin-3-ylcarbonyl); pyrazinoquinolylcarbonyl (e.g., pyrazino[2,3-b]quinolin-2-ylcarbonyl); a 5- or 6-membered heterocycle-carbonyl group (e.g., chromenylcarbonyl (e.g., 2H-chromen-2- or 3-ylcarbonyl etc.) and the like) containing 1 to 4 hetero atoms such as nitrogen atom (optionally oxidized), oxygen atom, sulfur atom (optionally mono or dioxidized) and the like), a 5- or 6-membered heterocycle-acetyl group (e.g., 5- or 6-membered heterocycle-acetyl group containing 1 to 4 hetero atoms such as nitrogen atom (optionally oxidized), oxygen atom, sulfur atom (optionally mono or dioxidized) and the like), such as 2-pyrrolylacetyl, 3-imidazolylacetyl, 5-isoxazolylacetyl and the like, and the like can be used.

As regards the substituent of acyl group, for example, when the above-mentioned acyl group is an alkanoyl group or alkoxy-carbonyl group, the acyl group is optionally substituted by 1 to 3 alkylthio groups (e.g., $C_{1-4}$ alkylthio such as methylthio, ethylthio, n-propylthio, isopropylthio and the like, and the like), halogen (e.g., fluorine, chlorine, bromine, iodine), alkoxy groups (e.g., $C_{1-6}$ alkoxy such as methoxy, ethoxy, n-propoxy, tert-butoxy, n-hexyloxy and the like, and the like), a nitro group, alkoxy-carbonyl groups (e.g., $C_{1-6}$ alkoxy-carbonyl such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl and the like, and the like), alkylamino group (e.g., mono- or di-$C_{1-6}$ alkylamino such as methylamino, ethylamino, n-propylamino, n-butylamino, tert-butylamino, n-pentylamino, n-hexylamino, dimethylamino, diethylamino, methylethylamino, di-(n-propyl)amino, di-(n-butyl)amino and the like, and the like), alkoxyimino groups (e.g., $C_{1-6}$ alkoxyimino such as methoxyimino, ethoxyimino, n-propoxyimino, tert-butoxyimino, n-hexyloxy-imino and the like, and the like) or hydroxyimino.

When the above-mentioned acyl group is an aryl-carbonyl group, an aryloxy-carbonyl group, an aralkyl-carbonyl group, an aralkyloxycarbonyl group, a 5- or 6-membered heterocycle-carbonyl group or a 5- or 6-membered heterocycle-acetyl group, it is optionally substituted by 1 to 5 (preferably 1 to 3) alkyl groups (e.g., $C_{1-6}$ alkyl such as methyl, ethyl, n-propyl, isopropyl, n-butyl, isobutyl, sec-butyl, tert-butyl, n-pentyl, sec-pentyl, isopentyl, neopentyl, n-hexyl, isohexyl and the like, $C_{3-6}$ cycloalkyl such as cyclohexyl and the like, and the like), alkenyl groups (e.g., $C_{2-6}$ alkenyl such as allyl, isopropenyl, isobutenyl, 1-methylallyl, 2-pentenyl, 2-hexenyl and the like, and the like), alkynyl groups (e.g., $C_{2-6}$ alkynyl such as propargyl, 2-butynyl, 3-butynyl, 3-pentynyl, 3-hexynyl and the like, and the like), alkoxy groups (e.g., $C_{1-6}$ alkoxy such as methoxy, ethoxy, n-propoxy, tert-butoxy, n-hexyloxy and the like, and the like), acyl groups [e.g., $C_{1-7}$ alkanoyl such as formyl, acetyl, propionyl, butyryl, isobutyryl, pentanoyl, hexanoyl, heptanoyl and the like; $C_{6-14}$ arylcarbonyl such as benzoyl, naphthalenecarbonyl and the like; $C_{1-6}$ alkoxy-carbonyl such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl and the like; $C_{6-14}$ aryloxy-carbonyl such as phenoxycarbonyl and the like; $C_{7-19}$ aralkyl-carbonyl such as phenyl-$C_{1-4}$ alkyl-carbonyl (e.g., benzylcarbonyl, phenethylcarbonyl, phenylpropylcarbonyl and the like) and the like; $C_{7-19}$ aralkyloxy-carbonyl such as phenyl-$C_{1-4}$ alkyloxy-carbonyl (e.g., benzyloxycarbonyl and the like) and the like, and the like], nitro, amino, hydroxy, cyano, sulfamoyl, mercapto, halogen (e.g., fluorine, chlorine, bromine, iodine), or alkylthio groups ($C_{1-4}$ alkylthio such as methylthio, ethylthio, n-propylthio, isobutylthio and the like, and the like).

As the "halogen atom" for $R^3$ or $R^4$, fluorine, chlorine, bromine and iodine can be mentioned.

As the "alkyl group" for $R^5$, for example, $C_{1-6}$ alkyl (e.g., methyl, ethyl, propyl, isopropyl, butyl, isobutyl, sec-butyl, tert-butyl, pentyl, hexyl etc.) and the like can be mentioned.

As $R^1$, a "nitrogen-containing monocyclic heterocyclic group optionally condensed with a benzene ring or a heterocycle" (e.g., 5-6-membered aromatic nitrogen-containing monocyclic heterocyclic groups such as thiazolyl, imidazolyl, pyrazolyl, pyridyl, pyrimidinyl, pyridazinyl, pyrazinyl and the like, and the like) optionally substituted by 1 to 3 substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine), (vi) amino group optionally substituted by $C_{1-6}$ alkyl (e.g., methyl, ethyl, propyl, isopropyl, butyl, isobutyl, sec-butyl, tert-butyl, pentyl, hexyl etc.), (vii) oxo and (viii) $C_{1-6}$ alkoxy-carbonyl (e.g., methoxycarbonyl, ethoxycarbonyl, propoxycarbonyl, tert-butoxycarbonyl etc.) is preferable.

As $R^1$, especially, a "nitrogen-containing monocyclic heterocyclic group optionally condensed with a benzene ring or a heterocycle" (e.g., a 5-6-membered aromatic nitrogen-containing monocyclic heterocyclic group such as thiazolyl, imidazolyl, pyrazolyl, pyridyl, pyrimidinyl, pyridazinyl, pyrazinyl and the like, and the like), which is optionally substituted by 1 to 3 substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine), (vi) an amino group optionally substituted by $C_{1-6}$ alkyl (e.g., methyl, ethyl, propyl, isopropyl, butyl, isobutyl, sec-butyl, tert-butyl, pentyl, hexyl etc.) and (vii) oxo, is preferable.

As $R^1$, particularly, a 6-membered nitrogen-containing aromatic heterocyclic group (e.g., pyridyl groups (e.g., 2-, 3- or 4-pyridyl etc.), pyrimidinyl groups (e.g., 2-, 4- or 5-pyrimidinyl etc.), pyridazinyl groups (e.g., 3- or 4-pyridazinyl etc.) etc.) optionally substituted by 1 to 3 substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine) and (vi) an amino group optionally substituted by $C_{1-6}$ alkyl (e.g., methyl, ethyl, propyl, isopropyl, butyl, isobutyl, sec-butyl, tert-butyl, pentyl, hexyl etc.) is preferable, and a pyridyl group optionally substituted by 1 to 3 substituents selected from (i) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine) and (ii) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine) is particularly preferable.

As $R^2$, [1] a $C_{6-14}$ aryl group (e.g., phenyl group) optionally substituted by 1 to 5 (preferably 1 to 3) substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine), (v) acetyl, (vi) $C_{3-7}$ cycloalkyl (e.g., cyclopropyl, cyclobutyl, cyclopentyl, cyclohexyl, cycloheptyl etc.), (vii) $C_{1-6}$ alkylsulfonyl (e.g., methylsulfonyl, ethylsulfonyl etc.), (viii) a $C_{1-6}$ alkyl group substituted by 1 to 3 hydroxy (e.g., hydroxymethyl, hydroxyethyl etc.), (ix) $C_{1-6}$ alkylthio (e.g., methylthio, ethylthio, propylthio, isopropylthio, butylthio, isobutylthio, sec-butylthio, pentylthio, hexylthio etc.) optionally substituted by 1 to 5 (preferably 1 to 3) halogen atoms (e.g., fluorine, chlorine, bromine, iodine) and (x) $C_{1-6}$ alkylsulfinyl (e.g., methylsulfinyl, ethylsulfinyl etc.), [2] a thienyl group optionally substituted by 1 to 3 substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine) and (v) acetyl, or

[3] a pyridyl group optionally substituted by 1 to 4 substituents selected from (i) a halogen atom (e.g., fluorine, chlorine, bromine, iodine), (ii) cyano, (iii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine), (v) acyl (e.g., acetyl), (vi) nitro and (vii) amino is preferable.

Of these, as $R^2$, [1] a $C_{6-14}$ aryl group (e.g., phenyl group) optionally substituted by 1 to 5 (preferably 1 to 3) substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to (preferably 1 to 3) halogen (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine) and (v) acetyl,

[2] a thienyl group optionally substituted by 1 to 3 substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine) and (v) acetyl, or

[3] a pyridyl group optionally substituted by 1 to 4 substituents selected from (i) a halogen atom (e.g., fluorine, chlorine, bromine, iodine), (ii) cyano, (iii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine), (v) acyl (e.g., acetyl), (vi) nitro and (vii) amino is preferable.

Particularly, [1] a phenyl group optionally substituted by 1 to 5 (preferably 1 to 3) substituents selected from (i) a halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine),

[2] a thienyl group optionally substituted by 1 to 3 substituents selected from (i) a halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), or

[3] a pyridyl group optionally substituted by 1 to 4 substituents selected from (i) a halogen atom (e.g., fluorine, chlorine, bromine, iodine) and (ii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine) is preferable.

Of those mentioned above, a preferable embodiment of $R^2$ include [1] a phenyl group optionally substituted by 1 to 5 substituents selected from (i) a halogen atom and (ii) $C_{1-6}$ alkyl optionally substituted by 1 to 5 halogen atoms, [2] a pyridyl group optionally substituted by 1 to 4 substituents selected from lower ($C_{1-6}$) alkyl, a halogen atom, alkoxy ($C_{1-6}$ alkoxy), cyano, acyl (e.g., acetyl), nitro and amino, and the like.

As $R^2$, a phenyl group, a 2-fluorophenyl group, a 2-methylphenyl group, a 2-fluoropyridin-3-yl group, a 3-fluoropyridin-4-yl group, a 2-chloropyridin-3-yl group, a 6-chloropyridin-3-yl group, a 4-methylpyridin-3-yl group, a 2-methylpyridin-3-yl group, a 3-methylpyridin-2-yl group, a 2-trifluoromethylpyridin-3-yl group and a 6'-chloro-2,3'-bipyridin-5-yl group are particularly preferable.

Preferably $R^3$ and $R^4$ are each a hydrogen atom, or one of $R^3$ and $R^4$ is a hydrogen atom and the other is a $C_{1-6}$ alkyl group (e.g., methyl, ethyl, n-propyl, isobutyl etc.), a $C_{1-6}$ alkyl-carbonyl group (e.g., acetyl, propionyl, butyryl, isobutyryl, pentanoyl, hexanoyl, heptanoyl etc.), a halogen atom (e.g., fluorine, chlorine, bromine, iodine), a cyano group or a nitro group. A compound wherein both $R^3$ and $R^4$ are hydrogen atoms is particularly preferable.

As $R^5$, methyl or ethyl is preferable, and methyl is particularly preferable.

The above-mentioned preferable embodiments of the substituents for $R^1$ to $R^5$ may be optionally combined to achieve a preferable embodiment of compound (I).

Of compounds (I), a compound wherein $R^1$ is a 5-6-membered aromatic nitrogen-containing monocyclic heterocyclic group (for example, thiazolyl, imidazolyl, pyrazolyl, pyridyl, pyrimidinyl, pyridazinyl, pyrazinyl and the like) or an imidazo[1,2-a]pyrimidinyl group, which are optionally substituted by 1 to 3 substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine), (vi) amino group optionally substituted by $C_{1-6}$ alkyl (e.g., methyl, ethyl, propyl, isopropyl, butyl, isobutyl, sec-butyl, tert-butyl, pentyl, hexyl etc.) and (vii) $C_{1-6}$ alkoxy-carbonyl (e.g., methoxycarbonyl, ethoxycarbonyl, propoxycarbonyl, tert-butoxycarbonyl etc.);

$R^2$ is [1] a $C_{6-14}$ aryl group (e.g., phenyl group) optionally substituted by 1 to 5 (preferably 1 to 3) substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine), (v) acetyl, (vi) $C_{3-7}$ cycloalkyl (e.g., cyclopropyl, cyclobutyl, cyclopentyl, cyclohexyl, cycloheptyl etc.), (vii) $C_{1-6}$ alkylsulfonyl (e.g., methylsulfonyl, ethylsulfonyl etc.), (viii) a $C_{1-6}$ alkyl group substituted by 1 to 3 hydroxy (e.g., hydroxymethyl, hydroxyethyl etc.), (ix) $C_{1-6}$ alkylthio (e.g., methylthio, ethylthio, propylthio, isopropylthio, butylthio, isobutylthio, sec-butylthio, pentylthio, hexylthio etc.) optionally substituted by 1 to 5 (preferably 1 to 3) halogen atoms (e.g., fluorine, chlorine, bromine, iodine) and (x) $C_{1-6}$ alkylsulfinyl (e.g., methylsulfinyl, ethylsulfinyl etc.),

[2] a thienyl group optionally substituted by 1 to 3 substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine) and (v) acetyl,

[3] a pyridyl group optionally substituted by 1 to 4 substituents selected from (i) a halogen atom (e.g., fluorine, chlorine, bromine, iodine), (ii) cyano, (iii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine), (v) acyl (e.g., acetyl), (vi) nitro and (vii) amino, or

[4] a bipyridyl group optionally substituted by 1 to 3 halogen atoms (e.g., fluorine, chlorine, bromine, iodine);

$R^3$ and $R^4$ are each a hydrogen atom, or one of $R^3$ and $R^4$ is a hydrogen atom and the other is a $C_{1-6}$ alkyl group (e.g., methyl, ethyl, n-propyl, isobutyl etc.), a $C_{1-6}$ alkyl-carbonyl group (e.g., acetyl, propionyl, butyryl, isobutyryl, pentanoyl, hexanoyl, heptanoyl etc.), a halogen atom (e.g., fluorine, chlorine, bromine, iodine), a cyano group or a nitro group;

$R^5$ is methyl or ethyl is preferable, a compound wherein, for example $R^1$ is a pyridyl group optionally substituted by 1 to 3 substituents selected from (i) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine) and (ii) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine), $R^2$ is [1] a phenyl group optionally substituted by 1 to 5 (preferably 1 to 3) substituents selected from (i) a halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine),

[2] a thienyl group optionally substituted by 1 to 3 substituents selected from (i) a halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), or

[3] a pyridyl group optionally substituted by 1 to 4 substituents selected from (i) a halogen atom (e.g., fluorine, chlorine, bromine, iodine) and (ii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), $R^3$ and $R^4$ are each a hydrogen atom, and $R^5$ is methyl is particularly preferable.

As compound (I), N-methyl-1-[5-phenyl-1-(pyridin-3-ylsulfonyl)-1H-pyrrol-3-yl]methanamine, 1-[5-(2-fluorophenyl)-1-(pyridin-3-ylsulfonyl)-1H-pyrrol-3-yl]-N-methylmethanamine, N-methyl-1-[4-methyl-1-(pyridin-3-ylsulfonyl)-5-phenyl-1H-pyrrol-3-yl]methaneamine, N-methyl-1-[1-(pyridin-3-ylsulfonyl)-5-(3-thienyl)-1H-pyrrol-3-yl]methanamine, N-methyl-1-[5-(2-methylphenyl)-1-(pyridin-3-ylsulfonyl)-1H-pyrrol-3-yl]methanamine, 1-[5-(2,4-difluorophenyl)-1-(pyridin-3-ylsulfonyl)-1H-pyrrol-3-yl]-N-methylmethanamine, 1-{5-(2-fluorophenyl)-1-[(6-methylpyridin-3-yl)sulfonyl]-1H-pyrrol-3-yl}-N-methylmethanamine, 1-[4-fluoro-5-phenyl-1-(pyridin-3-ylsulfonyl)-1H-pyrrol-3-yl]-N-methylmethanamine, N-methyl-1-[5-(4-methyl-3-thienyl)-1-(pyridin-3-ylsulfonyl)-1H-pyrrol-3-yl]methanamine, 1-[5-(2-fluoropyridin-3-yl)-1-(pyridin-3-ylsulfonyl)-1H-pyrrol-3-yl]-N-methylmethanamine or a salt thereof is particularly preferable.

As a salt of compound (I), metal salt, ammonium salt, salts with organic bases, salts with inorganic bases, salts with organic acids, salts with basic or acidic amino acids and the like can be mentioned. Preferable examples of metal salt include alkali metal salts such as sodium salt, potassium salt and the like; alkaline earth metal salts such as calcium salt, magnesium salt, barium salt and the like; aluminum salt and the like. Preferable examples of the salt with organic base include a salt with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include a salt with hydrochloric acid, hydrobromic acid, nitric acid, sulfuric acid, phosphoric acid and the like. Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include a salt with arginine, lysin, ornithine and the like. Preferable examples of the salt with acidic amino acid include a salt with aspartic acid, glutamic acid and the like.

Of these, pharmaceutically acceptable salts are preferable. For example, when a compound contains an acidic functional group, inorganic salts such as alkali metal salt (e.g., sodium salt, potassium salt etc.), alkaline earth metal salt (e.g., calcium salt, magnesium salt, barium salt etc.) and the like, ammonium salt and the like; and when a compound contains a basic functional group, for example, salts with inorganic acid such as hydrochloric acid, hydrobromic acid, nitric acid, sulfuric acid, phosphoric acid and the like, or salts with organic acid such as acetic acid, phthalic acid, fumaric acid, oxalic acid, tartaric acid, maleic acid, citric acid, succinic acid, methanesulfonic acid, p-toluenesulfonic acid and the like can be mentioned.

Compound (I) can be produced, for example, according to the methods described in JP application No. 2005-044740, Eur. J. Org. Chem., p. 2283 (2001), J. Med. Chem., vol. 43, p. 1886 (2000), J. Pharm. Pharmacol., vol. 46, p. 740 (1994), WO92/04025, J. Heterocycl. Chem., vol. 25, p. 635 (1988), J. Med. Chem., vol. 14, p. 328 (1971), J. Med. Chem., vol. 35, p. 4195 (1992) or Tetrahedron Lett., vol. 26, p. 4047 (1985), or a method analogous thereto.

The production methods of compound (I) in the present invention are explained.

The compounds (II)-(XXIV) in the formula may form salts, and as such salts, for example, those similar to the salts of compound (I) can be mentioned.

While the compounds obtained in respective steps can be used for the next reaction in the form of a reaction mixture or a crude product, they can also be easily isolated and purified from the reaction mixture by a known separation and purification means, such as recrystallization, distillation, chromatography and the like.

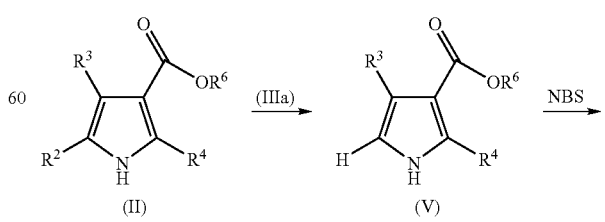

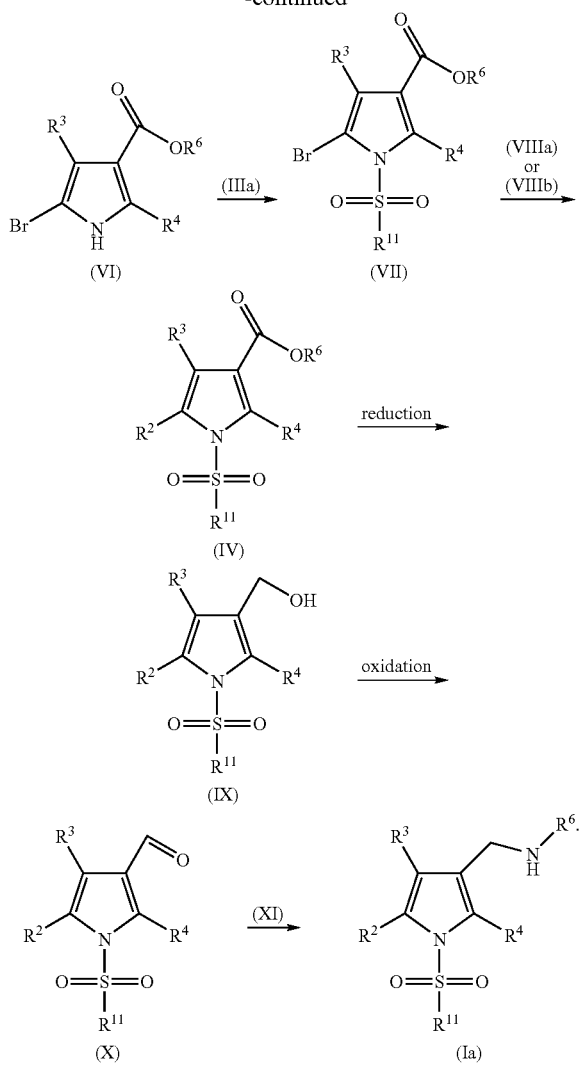

Compound (II) wherein $R^2$, $R^3$ and $R^4$ are as defined above, and $R^6$ is a $C_{1-4}$ alkyl group such as methyl, ethyl, propyl, isopropyl, butyl and the like can be produced according to a method known per se, such as the method described in *Chem. Pharm. Bull.*, vol. 49, p. 1406 (2001), *Tetrahedron Letters,* vol. 35, p. 5989 (1994) and the like or a method analogous thereto.

By reacting compound (II) with a compound represented by the formula (IIIa):

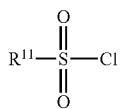

(IIIa)

wherein $R^{11}$ is as defined for $R^1$, or the protecting group described in *Protective Groups in Organic Synthesis*, $3^{rd}$ Ed. Theodora W. Greene, Peter G. M. Wuts, pp. 615-617, Wiley-Interscience (1999) (e.g., phenyl, 4-methylphenyl etc.), compound (IV) (each symbol in the formula is as defined above) can be produced.

This reaction is advantageously carried out using a solvent inert to the reaction. While the solvent is not particularly limited as long as the reaction proceeds, hydrocarbons such as benzene, toluene and the like and ethers such as tetrahydrofuran and the like, amides such as N,N-dimethylformamide, N,N-dimethylacetamide and the like, and the like or a mixed solvent thereof and the like are preferable.

Use of a base is effective for the reaction. As the base, for example, inorganic bases such as sodium hydride, sodium hydroxide, potassium hydroxide and the like, basic salts such as sodium carbonate, potassium carbonate, cesium carbonate, sodium hydrogencarbonate and the like, metal bases such as potassium ethoxide, potassium tert-butoxide, sodium methoxide, sodium ethoxide and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like can be mentioned. The amount of the base to be used is about 1-about 10 mol, preferably about 1-about 5 mol, per 1 mol of compound (II).

The reaction can also be carried out in the co-presence of crown ether. As the crown ether, for example, 15-crown-5-ether, 18-crown-6-ether and the like can be mentioned. The amount of the crown ether to be used is about 1-about 10 mol, preferably about 1-about 5 mol, per 1 mol of compound (II).

While the reaction time varies depending on the reagents and solvent to be used, it is generally about 30 min-about 24 hr, preferably about 30 min-about 8 hr.

The reaction temperature is generally about 0° C.-about 100° C., preferably about 10° C.-about 50° C.

Compound (V) (each symbol in the formula is as defined above) can be produced according to a method known per se, for example, the methods described in *Tetrahedron Letters*, vol. 13, p. 5337 (1972), *Heterocycles*, vol. 7, p. 77 (1977), *Chem. Pharm. Bull.*, vol. 27, p. 2857 (1979), *J. Org. Chem.*, vol. 62, p. 2649 (1997) and the like, or a method analogous thereto.

Compound (VI) (each symbol in the formula is as defined above) can be produced by reacting compound (V) with N-bromosuccinimide (NBS).

N-Bromosuccinimide (NBS) is preferably used in about one equivalent amount relative to compound (V), and the reaction is preferably carried out under an inert gas atmosphere such as nitrogen, argon and the like.

This reaction is advantageously carried out using a solvent inert to the reaction. While the solvent is not particularly limited as long as the reaction proceeds, solvents such as ethers (e.g., tetrahydrofuran, diethyl ether and the like), amides (e.g., N,N-dimethylformamide, N,N-dimethylacetamide and the like) and the like, a mixed solvent thereof and the like are preferable.

While the reaction time varies depending on the reagents and solvent to be used, it is generally about 30 min-about 24 hr, preferably about 5-12 hr.

The reaction temperature is generally about −78° C. to about 25° C., preferably about −78° C. to about 0° C.

Addition of a base is sometimes effective for the reaction. While the base to be used is not limited as long as the reaction proceeds, an organic base such as pyridine, picoline, lutidine and the like, and the like can be mentioned. The amount of the organic base to be used is about 0.001-about 10 equivalents, preferably about 0.001-about 0.1 equivalent, per 1 mol of compound (V).

Compound (VII) (each symbol in the formula is as defined above) can be produced from compound (VI) according to a method similar to the method for producing compound (IV) from compound (II).

Compound (IV) (each symbol in the formula is as defined above) can also be produced by reacting compound (VII) with a compound represented by the formula (VIIIa):

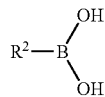
(VIIIa)

or the formula (VIIIb):

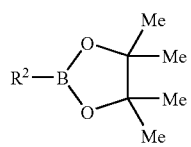
(VIIIb)

wherein $R^2$ is as defined above, according to the method described in *Synthetic Communications*, vol. 11, p. 513 (1981), or a method analogous thereto.

Compound (IX) (each symbol in the formula is as defined above) can be produced by reducing compound (IV) with a reducing agent such as lithium aluminum hydride, diisobutyl aluminum hydride, sodium borohydride, calcium borohydride and the like. As the reducing agent, diisobutyl aluminum hydride is particularly preferable. The amount of the reducing agent to be used is about 0.75-about 10 equivalents, preferably about 1-about 5 equivalents, per 1 mol of compound (IV).

This reaction is advantageously carried out using a solvent inert to the reaction. While the solvent is not particularly limited as long as the reaction proceeds, solvents such as hydrocarbons (e.g., benzene, toluene and the like) and ethers (e.g., tetrahydrofuran, diethyl ether and the like), and the like, a mixed solvent thereof and the like are preferable.

While the reaction time varies depending on the reagents and solvent to be used, it is generally about 30 min-about 24 hr, preferably about 30 min-about 8 hr.

The reaction temperature is generally about −78° C. to about 100° C., preferably about −78° C. to about 25° C.

Compound (X) (each symbol in the formula is as defined above) can be synthesized by reacting compound (IX) with an oxidant such as chromic acid-pyridine complex, pyridinium chlorochromate, manganese dioxide, sulfur trioxide-pyridine complex or tetra-n-propylammonium perruthenate and the like. As the oxidant, manganese dioxide, sulfur trioxide-pyridine complex or tetra-n-propylammonium perruthenate is preferable. The oxidation reaction can be carried out, for example, according to the method described in *Synthesis*, p. 639 (1994).

Compound (Ia) (each symbol in the formula is as defined above) can be produced by subjecting compound (X) and a compound represented by the formula (XI):

$R^5$—$NH_2$ wherein $R^5$ is as defined above, to a reductive amination reaction according to the methods described in *Shin Jikken Kagaku Koza*, Vols. 14-III, pp. 1380-1385 (Maruzen Press).

In addition, compound (Ia) can also be produced by the following method.

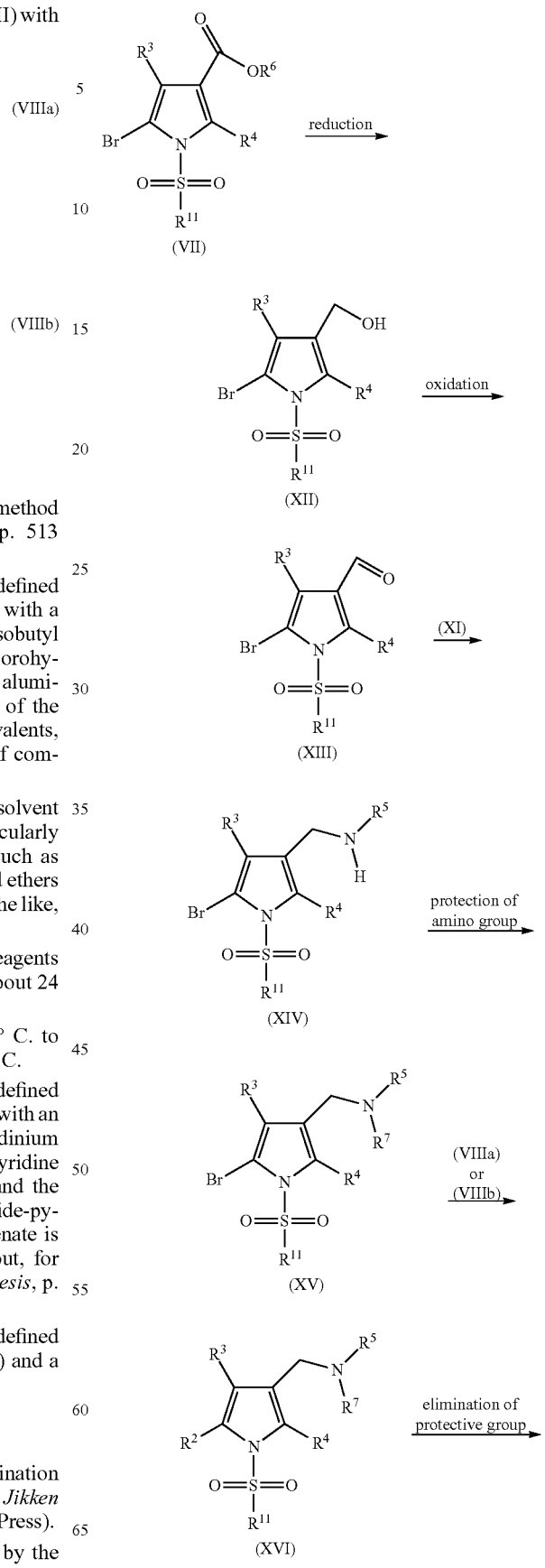

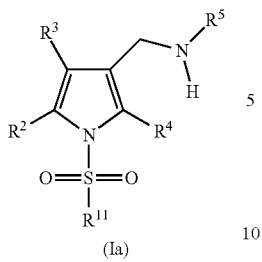

Compound (XII) (each symbol in the formula is as defined above) can be produced from compound (VII) according to a method similar to the method for producing compound (IX) from compound (IV).

Compound (XIII) (each symbol in the formula is as defined above) can be produced from compound (XII) according to a method similar to the method for producing compound (X) from compound (IX).

Compound (XIV) (each symbol in the formula is as defined above) can be produced from compound (XIII) according to a method similar to the method for producing compound (Ia) from compound (X).

Compound (XV) (each symbol in the formula is as defined above and $R^7$ is an amino-protecting group) can be produced by protecting an amino group of compound (XIV). As the amino-protecting group, tert-butylcarbamate group (BOC group), benzylcarbamate group (Cbz group) and the like can be mentioned. The protection reaction can be carried out according to a method known per se, for example, the method described in *Protective Groups in Organic Synthesis*, 3$^{rd}$ Ed., Theodora W. Greene, Peter G. M. Wuts, pp. 494-653, Wiley-Interscience (1999) and the like.

Compound (XVI) (each symbol in the formula is as defined above) can be produced from compound (XV) according to a method similar to the method for producing compound (IV) from compound (VII).

Compound (Ia) (each symbol in the formula is as defined above) can be produced by eliminating the amino-protecting group from compound (XVI) by a method known per se, for example, the method described in *Protective Groups in Organic Synthesis*, 3rd Ed., Theodora W. Greene, Peter G. M. Wuts, pp. 494-653, Wiley-Interscience (1999) and the like.

In addition, compounds (XVI) and (Ia) can also be produced by the following methods.

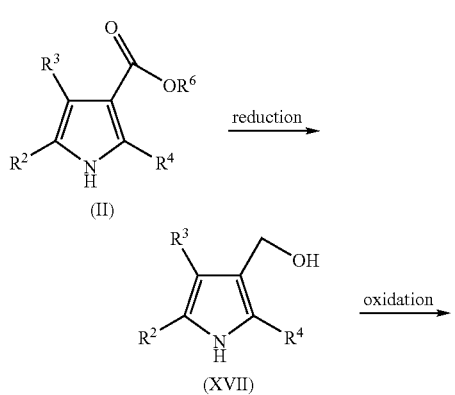

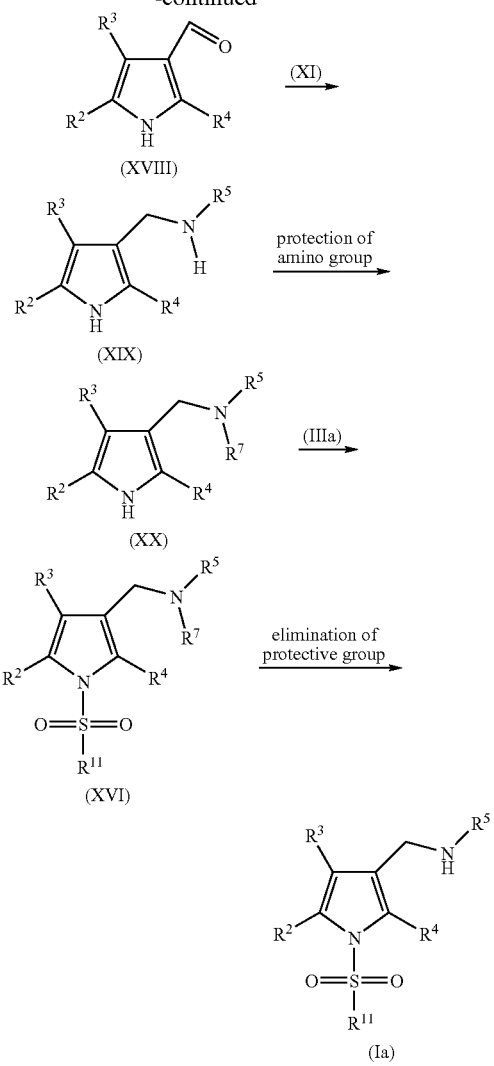

Compound (XVII) (each symbol in the formula is as defined above) can be produced from compound (II) according to a method similar to the method for producing compound (IX) from compound (IV).

Compound (XVIII) (each symbol in the formula is as defined above) can be produced from compound (XVII) according to a method similar to the method for producing compound (X) from compound (IX).

Compound (XIX) (each symbol in the formula is as defined above) can be produced from compound (XVIII) according to a method similar to the method for producing compound (Ia) from compound (X).

Compound (XX) (each symbol in the formula is as defined above) can be produced from compound (XIX) according to a method similar to the method for producing compound (XV) from compound (XIV).

Compound (XVI) (each symbol in the formula is as defined above) can be produced from compound (XX) according to a method similar to the method for producing compound (IV) from compound (II). Furthermore, compound (Ia) can be produced by a method similar to the aforementioned method.

In addition, compounds (XIII), (X) and (Ia) can also be produced by the following methods.

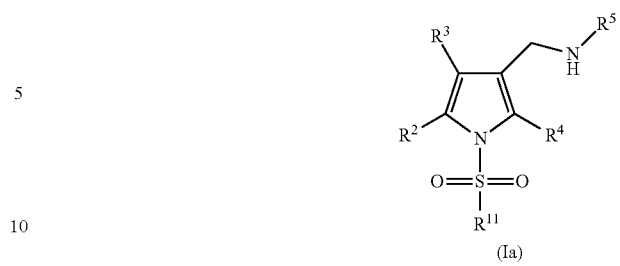

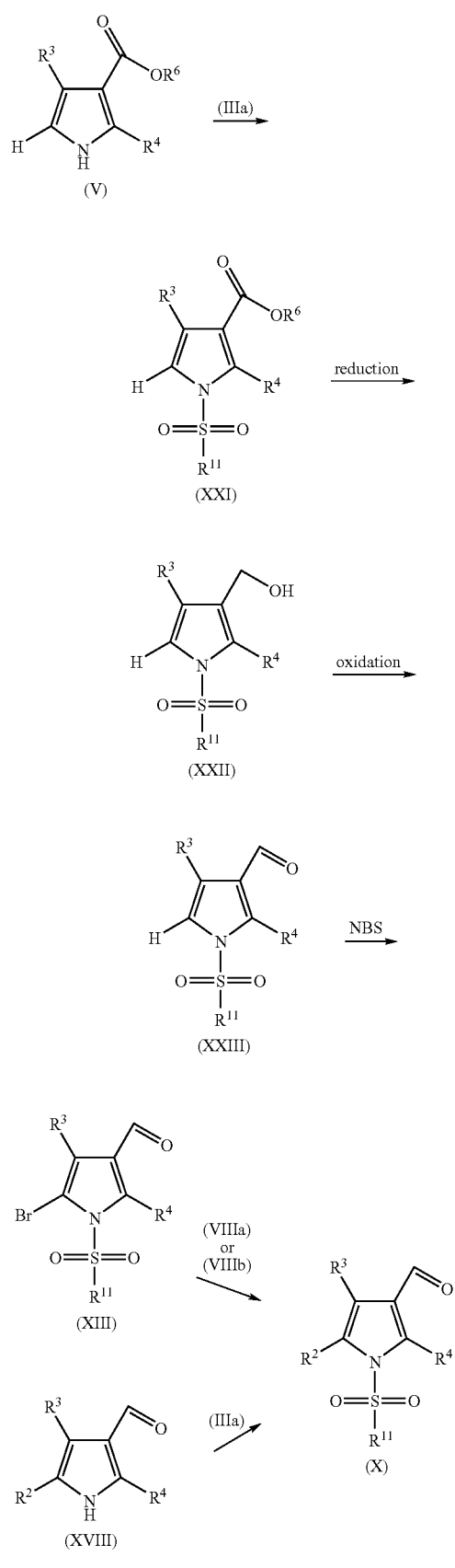

Compound (XXI) (each symbol in the formula is as defined above) can be produced from compound (V) according to a method similar to the method for producing compound (IV) from compound (II).

Compound (XXII) (each symbol in the formula is as defined above) can be produced from compound (XXI) according to a method similar to the method for producing compound (IX) from compound (IV).

Compound (XXIII) (each symbol in the formula is as defined above) can be produced from compound (XXII) according to a method similar to the method for producing compound (X) from compound (IX).

Compound (XIII) (each symbol in the formula is as defined above) can be produced from compound (XXIII) according to a method similar to the method for producing compound (VI) from compound (V).

Compound (X) (each symbol in the formula is as defined above) can be produced from compound (XIII) according to a method similar to the method for producing compound (IV) from compound (VII), or from compound (XVIII) according to a method similar to the method for producing compound (IV) from compound (II). Furthermore, compound (Ia) can be produced according to a method similar to the aforementioned method.

Moreover, compound (XIII) and compound (XVIII) can also be synthesized by the following method, and compound (Ia) can be further produced by a method similar to the aforementioned method.

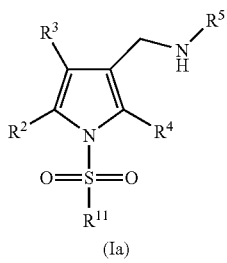

(Ia)

Compound (XXIV) (each symbol in the formula is as defined above) can be produced according to a method known per se, for 5 example, the method described in *J. Org. Chem.*, vol. 55, p. 6317 (1990) and the like, or a method analogous thereto.

Compound (XIII) (each symbol in the formula is as defined above) can be produced from compound (XXIV) according to a method similar to the method for producing compound (IV) from compound (II).

Compound (XVIII) (each symbol in the formula is as defined above) can be produced from compound (XXIV) according to a method similar to the method for producing compound (IV) from compound (VII).

When $R^{11}$ is a group other than the group represented by $R^1$ in each compound, the compound can be converted to compound (I) after deprotection by a method known per se, for example, the method described in *Protective Groups in Organic Synthesis*, 3rd Ed., Theodora W. Greene, Peter G. M. Wuts, pp. 615-617, Wiley-Interscience (1999) and the like, using the formula (III)

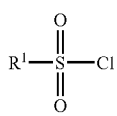

(III)

wherein each symbol in the formula is as defined above, according to a method similar to the method for producing compound (IV) from compound (II).

In each of the aforementioned reactions, when the starting compound has an amino group, a carboxyl group or a hydroxy group as a substituent, a protecting group generally used in peptide chemistry and the like may be introduced into these groups. In this case, by eliminating the protecting group as necessary after the reaction, the objective compound can be obtained. Introduction and elimination of these protecting groups can be performed by a method known per se, for example, the method described in *Protective Groups in Organic Synthesis*, 3rd Ed., Theodora W. Greene, Peter G. M. Wuts, Wiley-Interscience (1999) and the like.

Compound (I) can be isolated and purified by a known means such as phase transfer, concentration, solvent extraction, fractionation, liquid conversion, crystallization, recrystallization, chromatography and the like.

When compound (I) is obtained as a free compound, it can be converted to a desired salt by a method known per se or a method analogous thereto; conversely, when compound (I) is obtained as a salt, it can be converted into a free form or another desired salt by a method known per se or a method analogous thereto.

Compound (I) may be used as a prodrug. The prodrug of compound (I) means a compound which is converted to compound (I) under the physiological condition in the body by a reaction with an enzyme, gastric acid, or the like, that is, a compound which is converted to compound (I) by enzymatic oxidation, reduction, hydrolysis, and the like; a compound which is converted to compound (I) by hydrolysis with gastric acid, and the like.

The prodrug of compound (I) includes a compound wherein the amino group of compound (I) is modified with acyl, alkyl or phosphoryl (e.g., a compound wherein the amino group of compound (I) is modified with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl or t-butyl, etc.); a compound wherein the hydroxy group of compound (I) is modified with acyl, alkyl, phosphoric acid or boric acid (e.g., a compound wherein the hydroxy group of compound (I) is modified with acetyl, palmitoyl, propanoyl, pivaloyl, succinyl, fumaryl, alanyl or dimethylaminomethylcarbonyl, etc.); a compound wherein a carboxyl group of compound (I) is modified to ester or amide (e.g., a compound wherein a carboxyl group of compound (I) is modified to ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester or methylamide, etc.); and the like. These prodrugs can be produced from compound (I) by a method known per se.

In addition, the prodrug of compound (I) may be a compound, which is converted to compound (I) under the physiological conditions, as described in *Pharmaceutical Research and Development*, Vol. 7 (Molecule Design), pp. 163-198 (1990), published by Hirokawa Publishing Co.

When compound (I) contains an optical isomer, a stereoisomer, a regioisomer or a rotamer, either isomer and a mixture of these are also encompassed in compound (I). For example, when compound (I) has an optical isomer, an optical isomer resolved from a racemate is also encompassed in compound (I). These isomers can be obtained as single products according to synthesis and separation methods known per se (concentration, solvent extraction, column chromatography, recrystallization, etc.).

The compound (I) may be a crystal, and both a single crystal and crystal mixtures are encompassed in compound (I). Crystals can be produced by crystallization according to crystallization methods known per se.

The compound (I) may be a solvate (e.g., hydrate etc.) or a non-solvate, both of which are encompassed in the compound (I).

A compound labeled with an isotope (e.g., $^3H$, $^{14}C$, $^{35}S$, $^{125}I$ and the like) is also encompassed in the compound (I).

Compound (I) and a prodrug thereof of the present invention (hereinafter sometimes to be abbreviated as the compound of the present invention) have a proton pump inhibitory effect and effectively suppress gastric acid secretion. In addition, since they show low toxicity (e.g., acute toxicity, chronic toxicity, genetic toxicity, reproductive toxicity, cardiotoxicity, drug interaction, carcinogenicity and the like) and high water-solubility, and are superior in the stability, in vivo kinetics (absorbability, distribution, metabolism, excretion and the like), and efficacy expression, they are useful as pharmaceutical agents.

The compound of the present invention is useful for the treatment or prophylaxis of peptic ulcer (e.g., gastric ulcer, gastric ulcer due to postoperative stress, duodenal ulcer, anastomotic ulcer, ulcer caused by non-steroidal anti-inflammatory agents etc.); Zollinger-Ellison syndrome; gastritis; erosive esophagitis; reflux esophagitis such as erosive reflux esophagitis and the like; symptomatic gastroesophageal reflux disease (symptomatic GERD) such as non-erosive reflux disease or gastroesophageal reflux disease free of esophagitis and the like; functional dyspepsia; gastric cancer (including gastric cancer associated with promoted production of interleukin-1β due to gene polymorphism of interleukin-1); stomach MALT lymphoma; gastric hyperacidity; upper gastrointestinal hemorrhage due to peptic ulcer, acute stress ulcer, hemorrhagic gastritis or invasive stress (e.g. stress caused by major surgery requiring postoperative intensive management, and cerebrovascular disorder, head trauma, multiple organ failure and extensive burn, each requiring intensive treatment) and the like; airway disorders; asthma and the like, pre-anesthetic administration, eradication of *Helicobacter pylori* or eradication assistance and the like, in mammals (e.g., human, simian, sheep, cattle, horse, dog, cat, rabbit, rat, mouse etc.).

As used herein, the above-mentioned reflux esophagitis and symptomatic gastroesophageal reflux disease (symptomatic GERD)) are sometimes collectively referred to simply as GERD.

The content of a compound of the present invention in the pharmaceutical composition of the present invention is about 0.01 to 100% by weight relative to the entire composition. Though subject to change depending on the administration target, administration route, target disease and the like, its dose is about 0.5 to 1,500 mg/day, preferably about 5 to 150 mg/day, based on the active ingredient, when, for example, the compound is orally administered as an anti-ulcer agent to an adult human (60 kg). The compound of the present invention may be administered once daily or in 2 or 3 divided portions per day.

The compound of the present invention shows low toxicity and can be appropriately administered orally or parenterally (e.g., topical, rectal, intravenous administrations and the like) as it is or as a preparation containing a pharmaceutical composition containing a pharmacologically acceptable carrier admixed according to a method known per se, such as tablets (including sugar-coated tablets and film-coated tablets), powder, granule, capsule (including soft capsule), orally disintegrating tablet, orally disintegrating film, liquid, injection, suppository, sustained-release preparation, plaster and the like. Particularly, the compound of the present invention is preferably administered as an oral preparation in the form of tablet, granule, capsule and the like.

The pharmacologically acceptable carrier that may be used to produce the pharmaceutical composition of the present invention includes various organic or inorganic carrier substances in common use as pharmaceutical materials, including excipients, lubricants, binders, disintegrants, water-soluble polymers and basic inorganic salts for solid preparations; and solvents, dissolution aids, suspending agents, isotonizing agents, buffers and soothing agents for liquid preparations and the like. Other ordinary pharmaceutical additives such as preservatives, anti-oxidants, coloring agents, sweetening agents, souring agents, bubbling agents and flavorings may also be used as necessary.

Such "excipients" include, for example, lactose, sucrose, D-mannitol, starch, cornstarch, crystalline cellulose, light silicic anhydride, titanium oxide and the like.

Such "lubricants" include, for example, magnesium stearate, sucrose fatty acid esters, polyethylene glycol, talc, stearic acid and the like.

Such "binders" include, for example, hydroxypropyl cellulose, hydroxypropylmethyl cellulose, crystalline cellulose, starch, polyvinylpyrrolidone, gum arabic powder, gelatin, pullulan, low-substituted hydroxypropyl cellulose and the like.

Such "disintegrants" include (1) crospovidone, (2) what is called super-disintegrants such as croscarmellose sodium (FMC-Asahi Chemical) and carmellose calcium (Gotoku Yakuhin) etc, (3) carboxymethyl starch sodium (e.g., product of Matsutani Chemical), (4) low-substituted hydroxypropyl cellulose (e.g., product of Shin-Etsu Chemical), (5) corn starch, and so forth. Said "crospovidone" may be any crosslinked polymer having the chemical name 1-ethenyl-2-pyrrolidinone homopolymer, including polyvinylpyrrolidone (PVPP) and 1-vinyl-2-pyrrolidinone homopolymer, and is exemplified by Colidon CL (produced by BASF), Polyplasdon XL (produced by ISP), Polyplasdon XL-10 (produced by ISP), Polyplasdon INF-10 (produced by ISP) and the like.

Such "water-soluble polymers" include, for example, ethanol-soluble water-soluble polymers [e.g., cellulose derivatives such as hydroxypropyl cellulose (hereinafter also referred to as HPC) etc, polyvinylpyrrolidone and the like], ethanol-insoluble water-soluble polymers [e.g., cellulose derivatives such as hydroxypropylmethyl cellulose (hereinafter also referred to as HPMC) etc., methyl cellulose, carboxymethyl cellulose sodium and the like, sodium polyacrylate, polyvinyl alcohol, sodium alginate, guar gum and the like] and the like.

Such "basic inorganic salts" include, for example, basic inorganic salts of sodium, potassium, magnesium and/or calcium. Preferred are basic inorganic salts of magnesium and/or calcium. More preferred are basic inorganic salts of magnesium. Such basic inorganic salts of sodium include, for example, sodium carbonate, sodium hydrogencarbonate, disodium hydrogenphosphate and the like. Such basic inorganic salts of potassium include, for example, potassium carbonate, potassium hydrogencarbonate and the like. Such basic inorganic salts of magnesium include, for example, heavy magnesium carbonate, magnesium carbonate, magnesium oxide, magnesium hydroxide, magnesium aluminometasilicate, magnesium silicate, magnesium aluminate, synthetic hydrotalcite $[Mg_6Al_2(OH)_{16}.CO_3.4H_2O]$, and aluminum magnesium hydroxide. Preferred are heavy magnesium carbonate, magnesium carbonate, magnesium oxide, magnesium hydroxide and the like. Such basic inorganic salts of calcium include, for example, precipitated calcium carbonate, calcium hydroxide, etc.

Such "solvents" include, for example, water for injection, alcohol, propylene glycol, macrogol, sesame oil, corn oil, olive oil and the like.

Such "dissolution aids" include, for example, polyethylene glycol, propylene glycol, D-mannitol, benzyl benzoate, ethanol, trisaminomethane, cholesterol, triethanolamine, sodium carbonate, sodium citrate and the like.

Such "suspending agents" include, for example, surfactants such as stearyltriethanolamine, sodium lauryl sulfate, laurylaminopropionic acid, lecithin, benzalkonium chloride, benzethonium chloride, glyceryl monostearate etc; hydrophilic polymers such as polyvinyl alcohol, polyvinylpyrrolidone, carboxymethyl cellulose sodium, methyl cellulose, hydroxymethyl cellulose, hydroxyethyl cellulose, hydroxypropyl cellulose etc., and the like.

Such "isotonizing agents" include, for example, glucose, D-sorbitol, sodium chloride, glycerol, D-mannitol and the like.

Such "buffers" include, for example, buffer solutions of phosphates, acetates, carbonates, citrates etc, and the like.

Such "soothing agents" include, for example, benzyl alcohol and the like.

Such "preservatives" include, for example, p-oxybenzoic acid esters, chlorobutanol, benzyl alcohol, phenethyl alcohol, dehydroacetic acid, sorbic acid and the like.

Such "antioxidants" include, for example, sulfites, ascorbic acid, α-tocopherol and the like.

Such "coloring agents" include, for example, food colors such as Food Color Yellow No. 5, Food Color Red No. 2, Food Color Blue No. 2 etc.; food lake colors, red oxide and the like.

Such "sweetening agents" include, for example, saccharin sodium, dipotassium glycyrrhizinate, aspartame, stevia, thaumatin and the like.

Such "souring agents" include, for example, citric acid (citric anhydride), tartaric acid, malic acid and the like.

Such "bubbling agents" include, for example, sodium bicarbonate and the like.

Such "flavorings" may be synthetic substances or naturally occurring substances, and include, for example, lemon, lime, orange, menthol, strawberry and the like.

The compound of the present invention may be prepared as a preparation for oral administration in accordance with a commonly-known method, by, for example, compression-shaping with a carrier such as an excipient, a disintegrant, a binder, a lubricant, or the like, and subsequently coating the preparation as necessary by a commonly known method for the purpose of taste masking, enteric dissolution or sustained release. For an enteric preparation, an intermediate layer may be provided by a commonly known method between the enteric layer and the drug-containing layer for the purpose of separation of the two layers.

For preparing the compound of the present invention as an orally disintegrating tablet, available methods include, for example, a method in which a core containing crystalline cellulose and lactose is coated with the compound of the present invention and, where necessary, a basic inorganic salt, and then further coated with a coating layer containing a water-soluble polymer to give a composition, which is coated with an enteric coating layer containing polyethylene glycol, further coated with an enteric coating layer containing triethyl citrate, still further coated with an enteric coating layer containing polyethylene glycol, and finally coated with mannitol to give fine granules, which are mixed with additives and shaped.

The above-mentioned "enteric coating layer" includes, for example, a layer consisting of a mixture of one or more kinds from aqueous enteric polymer substrates such as cellulose acetate phthalate (CAP), hydroxypropylmethyl cellulose phthalate, hydroxymethyl cellulose acetate succinate, methacrylic acid copolymers (e.g., Eudragit L30D-55 (trade name; produced by Rohm), Colicoat MAE30DP (trade name; produced by BASF), Polyquid PA30 (trade name; produced by San-yo Chemical) etc.), carboxymethylethyl cellulose, shellac and the like; sustained-release substrates such as methacrylic acid copolymers (e.g., Eudragit NE30D (trade name), Eudragit RL30D (trade name), Eudragit RS30D (trade name), etc.) and the like; water-soluble polymers; plasticizers such as triethyl citrate, polyethylene glycol, acetylated monoglycerides, triacetin, castor oil and the like; and the like, and the like.

The above-mentioned "additive" includes, for example, water-soluble sugar alcohols (e.g., sorbitol, mannitol, maltitol, reduced starch saccharides, xylitol, reduced palatinose, erythritol, etc.), crystalline cellulose (e.g., Ceolas KG 801, Avicel PH 101, Avicel PH 102, Avicel PH 301, Avicel PH 302, Avicel RC-591 (crystalline cellulose carmellose sodium) etc.), low-substituted hydroxypropyl cellulose (e.g., LH-22, LH-32, LH-23, LH-33 (Shin-Etsu Chemical), mixtures thereof etc.) and the like. Furthermore, binders, souring agents, bubbling agents, sweetening agents, flavorings, lubricants, coloring agents, stabilizers, excipients, disintegrants etc. are also used.

The compound of the present invention may be used in combination with 1 to 3 other active ingredients.

Such "other active ingredients" include, for example, anti-*Helicobacter pylori* active substances, imidazole compounds, bismuth salts, quinolone compounds, and so forth.

Such "anti-*Helicobacter pylori* active substances" include, for example, antibiotic penicillins (e.g., amoxicillin, benzylpenicillin, piperacillin, mecillinam, ampicillin, temocillin, bacampicillin, aspoxicillin, sultamicillin, lenampicillin, etc.), antibiotic cefems (e.g., cefixime, cefaclor, etc.), antibiotic macrolides (e.g., erythromycin, clarithromycin, roxithromycin, rokitamycin, flurithromycin, telithromycin, etc.), antibiotic tetracyclines (e.g., tetracycline, minocycline, streptomycin, etc.), antibiotic aminoglycosides (e.g., gentamicin, amikacin, etc.), imipenem and so forth. Of these substances, preferred are antibiotic penicillins, antibiotic macrolides and the like.

Such "imidazole compounds" include, for example, metronidazole, miconazole and the like.

Such "bismuth salts" include, for example, bismuth acetate, bismuth citrate, bismuth subsalicylate and the like.

Such "quinolone compounds" include, for example, ofloxacin, ciploxacin and the like.

For eradication of *Helicobacter pylori*, a compound (I) or a salt thereof of the present invention with antibiotic penicillin (e.g., amoxicillin and the like) and antibiotic erythromycin (e.g., clarithromycin and the like) is preferably used.

For the purpose of eradication of *Helicobacter pylori*, while the compound of the present invention has an anti-*H. pylori* action (bacteriostatic action or eradication action) by itself, it can enhance the antibacterial action of other antibiotics based on the pH controlling action in the stomach and the like, and also provides an assistant effect such as an eradication effect based on the action of the antibiotics to be used in combination.

Such "other active ingredients" and the compound (I) or a salt thereof of the present invention may be mixed, prepared as a single pharmaceutical composition [e.g., tablets, powders, granules, capsules (including soft capsules), liquids, injectable preparations, suppositories, sustained-release preparations, etc.], in accordance with a commonly known method, and used in combination, and may also be prepared as separate preparations and administered to the same subject simultaneously or at a time interval.

In addition, the compound of the present invention may be used in combination with a gastric motility enhancer, a drug acting on lower esophageal sphincter (e.g., temporary lower esophageal sphincter relaxation suppressant etc.), ClC-2 channel opener (intestinal juice secretion enhancer), a histamine H2 receptor antagonist, an antacid, a sedative, a stomachic digestant or a non-steroidal anti-inflammatory drug (NSAID).

As the "gastric motility enhancer", for example, domperidone, metoclopramide, mosapride, itopride, tegaserod and the like can be mentioned.

As the "a drug acting on lower esophageal sphincter", for example, GABA-B receptor agonists such as baclofen, an optically active form thereof and the like, and the like can be mentioned.

As the "ClC-2 channel opener (intestinal juice secretion enhancer)", lubiprostone and the like can be mentioned.

As the "histamine H2 receptor antagonist", cimetidine, ranitidine, famotidine, roxatidine, nizatidine, lafutidine and the like can be mentioned.

As the "antacid", sodium hydrogencarbonate, aluminum hydroxide and the like can be mentioned.

As the "sedatives", diazepam, chlordiazepoxide and the like can be mentioned.

As the "stomachic digestant", gentiana, *swertia japonica*, diastase and the like can be mentioned.

As the "non-steroidal anti-inflammatory drug", for example, aspirin, indomethacin, ibuprofen, mefenamic acid, diclofenac, etodorac, piroxicam, celecoxib and the like can be mentioned.

A gastric motility enhancer, a drug acting on lower esophageal sphincter, a ClC-2 channel opener (intestinal juice secretion enhancer), a histamine H2 receptor antagonist, an antacid, a sedative, a stomachic digestant or a non-steroidal anti-inflammatory drug and compound (I) or a salt thereof of the present invention may be mixed, prepared as a single pharmaceutical composition [e.g., tablets, powders, granules, capsules (including soft capsules), liquids, injections, suppositories, sustained-release preparations, etc.] according to a method known per se for combined use, or may also be prepared as separate preparations and administered to the same subject simultaneously or in a staggered manner.

The compound of the present invention may be used in combination with the following drugs.

(i) proton pump inhibitors, e.g., omeprazole, esomeprazole, pantoprazole, rabeprazole, tenatoprazole, ilaprazole and lansoprazole; (ii) oral antacid mixtures, e.g., Maalox®, Aludrox® and Gaviscon®;

(iii) mucosal protective agents, e.g., polaprezinc, ecabet sodium, rebamipide, teprenone, cetraxate, sucralfate, chloropylline-copper and plaunotol;

(iv) anti-gastric agents, e.g., Anti-gastrin vaccine, itriglumide and Z-360;

(v) 5-$HT_3$ antagonists, e.g., dolasetron, palonosetron, alosetron, azasetron, ramosetron, mitrazapine, granisetron, tropisetron, E-3620, ondansetron and indisetron;

(vi) 5-$HT_4$ agonists, e.g., tegaserod, mosapride, cinitapride and oxtriptane;

(vii) laxatives, e.g., Trifyba®, Fybogel®, Konsyl®, Isogel®, Regulan®, Celevac® and Normacol®;

(viii) $GABA_B$ agonists, e.g., baclofen and AZD-3355;

(ix) $GABA_B$ antagonists, e.g., GAS-360 and SGS-742;

(x) calcium channel blockers, e.g., aranidipine, lacidipine, falodipine, azelnidipine, clinidipine, lomerizine, diltiazem, gallopamil, efonidipine, nisoldipine, amlodipine, lercanidipine, bevantolol, nicardipine, isradipine, benidipine, verapamil, nitrendipine, barnidipine, propafenone, manidipine, bepridil, nifedipine, nilvadipine, nimodipine and fasudil;

(xi) dopamine antagonists, e.g., metoclopramide, domperidone and levosulpiride;

(xii) Tachykinin (NK) antagonists, particularly NK-3, NK-2 and NK-1 antagonists, e.g., nepadutant, saredutant, talnetant, (αR,9R)-7-[3,5-bis(trifluoromethyl)benzyl]-8,9,10,11-tetrahydro-9-methyl-5-(4-methylphenyl)-7H-[1,4] diazocino[2,1-g][1,7]naphthridine-6-13-dione (TAK-637), 5-[[(2R,3S)-2-[(1R)-1-[3,5-bis(trifluoromethyl)phenyl] ethoxy-3-(4-fluorophenyl)-4-morpholinyl]methyl]-1,2-dihydro-3H-1,2,4-triazol-3-one (MK-869), lanepitant, dapitant and 3-[[2-methoxy-5-(trifluoromethoxy)phenyl]methylamino]-2-phenyl-piperidine (2S,3S);

(xiii) nitric oxide synthase inhibitors, e.g., GW-274150, tilarginine, P54, guanidioethyldisulfide and nitroflurbiprofen;

(xiv) vanilloid receptor 1 antagonists, e.g., AMG-517 and GW-705498;

(xv) ghrelin agonists, e.g., capromorelin and TZP-101;

(xvi) AchE release stimulants, e.g., Z-338 and KW-5092.

The above-mentioned drugs (i)-(xvi) and compound (I) or a salt thereof of the present invention may be mixed, prepared as a single pharmaceutical composition [e.g., tablets, powders, granules, capsules (including soft capsules), liquids, injections, suppositories, sustained-release preparations, etc.] according to a method known per se for combined use, or may also be prepared as separate preparations and administered to the same subject simultaneously or in a staggered manner.

EXAMPLES

The present invention is explained in detail in the following by referring to Reference Examples, Examples and Experimental Examples, which are not to be construed as limitative.

In the following Reference Examples and Examples, the "room temperature" generally means about 10° C. to about 35° C., but it is not particularly strictly limited. The mixing ratio of liquids shows a volume ratio. Unless otherwise specified, "%" means weight %. The yield is in mol/mol %. Silica gel column chromatography was performed using silica gel 60 (0.063-0.200 mm) manufactured by MERCK or Fuji Silysia Chemical Ltd. Chromatorex (product name) NH (described as basic silica gel column chromatography). The melting point was measured using Yanagimoto trace melting point measurement apparatus or Buechi trace melting point measurement apparatus (B-545), and shown without amendment. For $^1$H-NMR spectrum, tetramethylsilane was used as the internal standard, and Varian Gemini-200 (200 MHz), Mercury-300 (300 MHz) spectrometer, Bruker AVANCE AV300 (300 MHz) and JNM-AL400 (400 MHz) nuclear magnetic resonance apparatuses JEOL DATUM (JEOL DATUM LTD.) were used for the measurement. The following abbreviations are used for showing the measurement results.

s: singlet, d: doublet, dd: double doublet, dt: double triplet, t: triplet, q: quartet, m: multiplet, br: broad, brs: broad singlet, J: coupling constant, Hz: Hertz.

Reference Example 1

2-bromo-1-(2-fluorophenyl)propan-1-one

To a solution of 2'-fluoropropiophenone (25.0 g) in acetic acid (250 mL) was slowly added bromine (8.4 mL). The mixture was stirred at room temperature for 3 hr, and concentrated under reduced pressure. Water (200 mL) was added to the residue, and the mixture was extracted with diisopropyl ether. The extract was washed with saturated aqueous sodium hydrogencarbonate solution, water and saturated brine, dried over anhydrous magnesium sulfate, filtered and concentrated under reduced pressure to give the title compound as a yellow oil (yield 36.8 g, 97%).

$^1$H-NMR (CDCl$_3$) δ: 1.89-1.91 (3H, m), 5.27-5.34 (1H, m), 7.12-7.19 (1H, m), 7.24-7.30 (1H, m), 7.52-7.59 (1H, m), 7.88-7.93 (1H, m).

Reference Example 2 ethyl 2-cyano-4-oxo-4-phenylbutanoate

Potassium carbonate (13.82 g) was added to ethyl cyanoacetate (37 mL), and the mixture was stirred at 40-45° C. for 45 min. A solution (100 mL) of phenacyl bromide (10.0 g) in acetone was added dropwise over 30 min. After completion of the dropwise addition, the mixture was stirred at room temperature for 18 hr. The reaction mixture was filtered, and the filtrate was concentrated under reduced pressure. Water was added to the residue, and the mixture was extracted with ethyl acetate. The extract was washed with saturated brine, dried over anhydrous sodium sulfate, and concentrated under reduced pressure. Excess ethyl cyanoacetate contained in the obtained oil was evaporated under reduced pressure, and the residue was purified by silica gel column chromatography (eluent:hexane-ethyl acetate=8:1→1:1) to give the title compound as a pale-yellow oil (yield 10.41 g, 90%).

$^1$H-NMR (CDCl$_3$) δ: 1.35 (3H, t, J=7.2 Hz), 3.55 (1H, dd, J=16.0, 5.6 Hz), 3.80 (1H, dd, J=16.0, 7.0 Hz), 4.16 (1H, dd, J=7.0, 5.6 Hz), 4.31 (2H, q, J=7.2 Hz), 7.40-7.70 (3H, m), 7.90-8.00 (2H, m).

Reference Example 3 methyl 2-cyano-4-(2-fluorophenyl)-3-methyl-4-oxobutanoate

To a solution of methyl cyanoacetate (15.5 mL) and diisopropylethylamine (64 mL) in tetrahydrofuran (110 mL) was added a solution of 2-bromo-1-(2-fluorophenyl)propan-1-one (36.8 g) in tetrahydrofuran (160 mL), and the mixture was stirred at 70° C. for 20 hr. The reaction mixture was allowed to cool to room temperature, the insoluble material was filtered off, and the filtrate was concentrated under reduced pressure. The residue was purified by silica gel column chromatography (eluent:hexane-ethyl acetate=5:1) to give the title compound as a brown oil (yield 31.9 g, 80%).

$^1$H-NMR (CDCl$_3$) δ: 1.42-1.46 (3H, m), 3.82-3.85 (4H, m), 3.99-4.17 (1H, m), 7.14-7.22 (1H, m), 7.25-7.31 (1H, m), 7.55-7.63 (1H, m), 7.85-7.91 (1H, m).

Reference Example 4 ethyl 2-cyano-4-(2-fluorophenyl)-4-oxobutanoate

To a solution of 2'-fluoroacetophenone (28.6 g) in ethyl acetate (400 mL) was added copper (II) bromide (92.6 g), and the mixture was heated under reflux for 4 hr. The reaction mixture was allowed to cool to room temperature and the insoluble material was filtered off. The filtrate was concentrated under reduced pressure to give crude 2-bromo-1-(2-fluorophenyl)ethanone (yield 90.5 g) as an oil. Potassium carbonate (88 g) was added to ethyl cyanoacetate (168 g), and the mixture was stirred at 45° C. for 1 hr. A solution (360 mL) of crude 2-bromo-1-(2-fluorophenyl)ethanone (90.5 g) in acetone was added dropwise over 20 min. After completion of the dropwise addition, the mixture was stirred at the same temperature for 1 hr. Water (300 mL) and ethyl acetate (300 mL) were added to the reaction mixture, and the mixture was extracted with ethyl acetate. The extract was washed with 10% aqueous sodium dihydrogen phosphate solution and saturated brine, dried over anhydrous sodium sulfate, and concentrated under reduced pressure. Excess ethyl cyanoacetate contained in the obtained oil was evaporated under reduced pressure and the residue was purified by silica gel column chromatography (eluent:hexane-ethyl acetate=20:1→4:1) to give the title compound as an oil (yield 64.0 g, about 100%).

$^1$H-NMR (CDCl$_3$) δ: 1.35 (3H, t, J=7.2 Hz), 3.55-3.80 (2H, m), 4.11 (1H, t, J=6.0 Hz), 4.24-4.34 (2H, m), 7.15-7.29 (2H, m), 7.55-7.62 (1H, m), 7.94 (1H, dt, J=7.5, 1.8 Hz).

Reference Example 5 ethyl 2-cyano-4-oxo-4-[(2-trifluoromethyl)phenyl]butanoate

2'-(Trifluoromethyl)acetophenone (10.0 g) was dissolved in chloroform (30 mL) and diethyl ether (30 mL), a solution of bromine (8.50 g) in chloroform (20 mL) was added dropwise while maintaining the reaction temperature at not higher than 25° C. After the dropwise addition, the mixture was stirred at room temperature for 1 hr, water was added to the reaction mixture and the mixture was extracted with chloroform. The extract was washed with saturated brine, dried over anhydrous magnesium sulfate, concentration under reduced pressure to give crude 2-bromo-1-(2-trifluoromethylphenyl)ethanone. Potassium carbonate (13.82 g) was added to ethyl cyanoacetate (44.44 g), and the mixture was stirred at 45° C. for 1 hr. A solution of crude 2-bromo-1-(2-trifluoromethylphenyl)ethanone in acetone (100 mL) was added dropwise. After completion of the dropwise addition, the mixture was stirred at the same temperature for 1 hr, and stirred overnight at room temperature. The reaction mixture was filtered, and the filtrate was concentrated under reduced pressure. Water was added to the residue, and the mixture was extracted with ethyl acetate. The extract was washed with saturated brine, dried over anhydrous magnesium sulfate, and concentrated under reduced pressure. Excess ethyl cyanoacetate contained in the obtained oil was evaporated under reduced pressure and the residue was purified by silica gel column chromatography (eluent:hexane-ethyl acetate=9:1→7:1) to give the title compound as an oil (yield 10.43 g, from 2'-(trifluoromethyl)acetophenone, yield 66%).

$^1$H-NMR (CDCl$_3$) δ: 1.36 (3H, t, J=7.2 Hz), 3.34-3.46 (1H, m), 3.59-3.70 (1H, m), 4.08-4.22 (1H, m), 4.32 (2H, q, J=7.2 Hz), 7.57-7.80 (4H, m).

Reference Example 6 ethyl 2-chloro-5-phenyl-1H-pyrrole-3-carboxylate

To a solution (60 mL) of ethyl 2-cyano-4-oxo-4-phenylbutanoate (5.0 g) in tetrahydrofuran was blown in hydrogen chloride (28 g) under ice-cooling, and the mixture was stirred at room temperature for 3 hr. Then, nitrogen was blown in to remove excess hydrogen chloride. The reaction mixture was concentrated under reduced pressure, and the residue was purified by silica gel column chromatography (eluent:hexane-ethyl acetate=6:1) to give the title compound as a pale-yellow solid (yield 4.24 g, 79%).

$^1$H-NMR (CDCl$_3$) δ: 1.37 (3H, t, J=6.8 Hz), 4.33 (2H, q, J=6.8 Hz), 6.87 (1H, d, J=3.2 Hz), 7.20-7.60 (5H, m), 8.79 (1H, br).

Reference Example 7 ethyl 2-chloro-5-(2-fluorophenyl)-1H-pyrrole-3-carboxylate

A mixture of ethyl 2-cyano-4-(2-fluorophenyl)-4-oxobutanoate (19.3 g) and 4 mol/L hydrogen chloride-ethyl acetate solution (100 mL) was stirred at room temperature for 18 hr. The reaction mixture was concentrated under reduced pressure, and the residue was purified by silica gel column chromatography (eluent:hexane-ethyl acetate=10:1→3:1) to give the title compound as a brown solid (yield 8.76 g, 53%).

$^1$H-NMR (CDCl$_3$) δ: 1.36-1.41 (3H, m), 4.33 (2H, q, J=7.2 Hz), 6.99-7.00 (1H, m), 7.09-7.26 (3H, m), 7.55-7.61 (1H, m), 9.08 (1H, brs).

Reference Example 8 methyl 2-chloro-5-(2-fluorophenyl)-4-methyl-1H-pyrrole-3-carboxylate

To a solution of methyl 2-cyano-4-(2-fluorophenyl)-3-methyl-4-oxobutanoate (31.0 g) in ethyl acetate (30 mL) was added 4 mol/L hydrogen chloride-ethyl acetate solution (150 mL), and the mixture was stirred at room temperature for 2 days. Water (200 mL) was added to the reaction mixture, and the mixture was extracted with ethyl acetate. The extract was washed twice with water, and then washed with saturated aqueous sodium hydrogencarbonate solution, dried over anhydrous sodium sulfate, filtered, and concentrated under reduced pressure. The residue was recrystallized from ethyl acetate to give the title compound as white crystals (yield 19.3 g, 58%).

$^1$H-NMR (CDCl$_3$) δ: 2.33 (3H, s), 3.86 (3H, s), 7.12-7.42 (4H, m), 8.53 (1H, brs).

Reference Example 9 ethyl 5-phenyl-1H-pyrrole-3-carboxylate

To a solution (50 mL) of ethyl 2-chloro-5-phenyl-1H-pyrrole-3-carboxylate (8.5 g) in ethanol was added 10% palladium carbon (50% containing water, 0.5 g), and the mixture was stirred under a hydrogen atmosphere at room temperature for 24 hr. The reaction mixture was filtered, and the filtrate was concentrated under reduced pressure. The residue was purified by silica gel column chromatography (eluent: hexane-ethyl acetate=9:1→1:1) to give the title compound as a colorless solid (yield 4.50 g, 62%).

$^1$H-NMR (CDCl$_3$) δ: 1.36 (3H, t, J=7.2 Hz), 4.31 (2H, q, J=7.2 Hz), 6.91 (1H, m), 7.20-7.70 (6H, m), 8.77 (1H, br).

Reference Example 10 ethyl 5-(2-fluorophenyl)-1H-pyrrole-3-carboxylate

To a solution (80 mL) of ethyl 2-chloro-5-(2-fluorophenyl)-1H-pyrrole-3-carboxylate (8.6 g) in ethanol was added 10% palladium carbon (50% containing water, 0.86 g), and the mixture was stirred under a hydrogen atmosphere at room temperature for 36 hr. The reaction mixture was filtered, and the filtrate was concentrated under reduced pressure. The residue was dissolved in ethanol (70 mL), 10% palladium carbon (50% containing water, 0.90 g) was added, and the mixture was stirred under a hydrogen atmosphere at room temperature for 60 hr. The reaction mixture was filtered, and the filtrate was concentrated under reduced pressure. The residue was purified by silica gel column chromatography (eluent:hexane-ethyl acetate=10:1→5:1) to give the title compound as a brown solid (yield 1.37 g, 18%).

$^1$H-NMR (CDCl$_3$) δ: 1.67 (3H, t, J=7.2 Hz), 4.31 (2H, q, J=7.2 Hz), 7.03-7.05 (1H, m), 7.08-7.25 (3H, m), 7.49-7.50 (1H, m), 7.58-7.66 (1H, m), 9.22 (1H, brs).

Reference Example 11 methyl 5-(2-fluorophenyl)-4-methyl-1H-pyrrole-3-carboxylate

To a solution of methyl 2-chloro-5-(2-fluorophenyl)-4-methyl-1H-pyrrole-3-carboxylate (10.2 g) in methanol (200 mL) was added 10% palladium carbon (50% containing water, 1.28 g), and the mixture was stirred under a hydrogen atmosphere at room temperature for 20 hr. The reaction mixture was filtered, and the filtrate was concentrated under reduced pressure. A saturated aqueous sodium hydrogencarbonate solution (100 mL) was added to the residue, and the mixture was extracted with ethyl acetate. The extract was washed with saturated aqueous sodium hydrogencarbonate solution, water and saturated brine, dried over anhydrous sodium sulfate, filtered, and concentrated under reduced pressure. Recrystallization of the residue from ethyl acetate-hexane gave the title compound as white crystals (yield 6.70 g, 76%).

$^1$H-NMR (CDCl$_3$) δ: 2.40 (3H, s), 3.82 (3H, s), 7.12-7.33 (3H, m), 7.42-7.49 (2H, m), 8.67 (1H, brs)

Reference Example 12 ethyl 5-[(2-trifluoromethyl)phenyl]-1H-pyrrole-3-carboxylate

By a similar operation as in Reference Examples 7 and 9 and using ethyl 2-cyano-4-oxo-4-[(2-trifluoromethyl)phenyl]butanoate, the title compound was obtained as colorless crystals. More specifically, a mixture of ethyl 2-cyano-4-[(2-trifluoromethyl)phenyl]-4-oxobutanoate (10.2 g) and 4 mol/L hydrogen chloride-ethyl acetate solution (100 mL) was stirred at room temperature for 18 hr. The reaction mixture was concentrated under reduced pressure, and the residue was purified by silica gel column chromatography (eluent:hexane-ethyl acetate=10:1→3:1) to give ethyl 2-chloro-5-[(2-trifluoromethyl)phenyl]-1H-pyrrole-3-carboxylate as a brown solid (yield 6.37 g, 59%). This was dissolved in ethanol (120 mL), 10% palladium carbon (50% containing water, 0.5 g) was added, and the mixture was stirred under a hydrogen atmosphere at room temperature for 24 hr. The reaction mixture was filtered, and the filtrate was concentrated under reduced pressure. The residue was purified by silica gel column chromatography (eluent:hexane-ethyl acetate=9:1→1:1) to give the title compound as a colorless solid (yield 2.89 g, 51%).

$^1$H-NMR (CDCl$_3$) δ: 1.36 (3H, t, J=7.2 Hz), 4.31 (2H, q, J=7.2 Hz), 6.81 (1H, s), 7.42-7.61 (5H, m), 8.69 (1H, br).

Reference Example 13

(5-phenyl-1H-pyrrol-3-yl)methanol

A solution (100 mL) of ethyl 5-phenyl-1H-pyrrole-3-carboxylate (2.16 g) in tetrahydrofuran was cooled to −78° C., and a 1.5 mol/L solution (24 mL) of diisobutylaluminum hydride in toluene was added dropwise over 10 min. The mixture was further stirred at −78° C. for 1 hr, water (2 mL) was added dropwise over 2 min, and the mixture was further stirred at room temperature for 1 hr. The reaction mixture was filtered using celite and anhydrous magnesium sulfate, and concentrated under reduced pressure to give the title compound as a pale-red powder (yield 1.51 g, 87%).

$^1$H-NMR (DMSO-d$_6$) δ: 4.34 (2H, d, J=5.4 Hz), 4.60 (1H, t, J=5.4 Hz), 6.45-6.46 (1H, m), 6.74 (1H, br), 7.11-7.15 (1H, m), 7.31-7.35 (2H, m), 7.57-7.59 (2H, m), 11.05 (1H, s).

Reference Example 14

[5-(2-fluorophenyl)-4-methyl-1H-pyrrol-3-yl]methanol

By a similar operation as in Reference Example 13 and using methyl 5-(2-fluorophenyl)-4-methyl-1H-pyrrole-3-carboxylate (1.63 g) and a solution (15 mL) of 1.5 mol/L diisobutylaluminum hydride in toluene, the title compound was obtained as white crystals (yield 1.18 g, 82%).

$^1$H-NMR (CDCl$_3$) δ: 1.30 (1H, t, J=4.8 Hz), 2.25 (3H, s), 4.61 (2H, d, J=4.8 Hz), 6.87 (1H, d, J=3.3 Hz), 7.10-7.28 (3H, m), 7.44-7.50 (1H, m), 8.40 (1H, brs).

Reference Example 15

5-phenyl-1H-pyrrole-3-carbaldehyde

To a solution (45 mL) of (5-phenyl-1H-pyrrol-3-yl)methanol (1.51 g) in acetonitrile were added tetra-n-propylammonium perruthenate (0.46 g), N-methylmorpholine N-oxide (2.36 g) and molecular sieves 4A powder (4.5 g), and the mixture was stirred at room temperature for 1.5 hr. The reaction mixture was filtered through celite, and the filtrate was concentrated under reduced pressure. The residue was purified by silica gel column chromatography (eluent: hexane-ethyl acetate=4:1→1:1) to give the title compound as a pale-yellow powder (yield 0.92 g, 62%).

$^1$H-NMR (CDCl$_3$) δ: 6.95 (1H, m), 7.29-7.32 (1H, m), 7.40-7.44 (2H, m), 7.50-7.52 (3H, m), 9.02 (1H, br), 9.84 (1H, s).

Reference Example 16

5-(2-fluorophenyl)-4-methyl-1H-pyrrole-3-carbaldehyde

By a similar operation as in Reference Example 15 and using [5-(2-fluorophenyl)-4-methyl-1H-pyrrol-3-yl]methanol (1.17 g), tetra-n-propylammonium perruthenate (101 mg), N-methylmorpholine N-oxide (1.01 g) and molecular sieves 4A powder (572 mg), the title compound was obtained as pale-pink crystals (yield 0.67 g, 58%).

$^1$H-NMR (CDCl$_3$) δ: 2.45 (3H, s), 7.14-7.36 (3H, m), 7.44-7.50 (2H, m), 8.82 (1H, brs), 9.92 (1H, s).

Reference Example 17

5-(2-fluorophenyl)-1H-pyrrole-3-carbaldehyde

A solution (220 mL) of ethyl 5-(2-fluorophenyl)-1H-pyrrole-3-carboxylate (11.6 g) in tetrahydrofuran was cooled to −78° C., and a 1.5 mol/L solution (100 mL) of diisobutylaluminum hydride in toluene was added dropwise over 10 min. The mixture was stirred at −78° C. for 1 hr and water (10 mL) was added dropwise over 2 min. The mixture was allowed to warm to room temperature and the mixture was stirred for 2 hr. The reaction mixture was filtered by adding celite and anhydrous magnesium sulfate and concentrated under reduced pressure to give a pale-yellow oil (yield 8.3 g). To a solution (220 mL) of the obtained pale-yellow oil (8.30 g) in acetonitrile were added tetra-n-propylammonium perruthenate (1.75 g), N-methylmorpholine N-oxide (13.5 g) and molecular sieves 4A powder (5 g), and the mixture was stirred at room temperature for 1.5 hr. The reaction mixture was filtered through celite, and the filtrate was concentrated under reduced pressure. The residue was purified by silica gel column chromatography (eluent:hexane-ethyl acetate=7:3→1:1) to give the title compound as yellow crystals (yield 5.6 g, 60%).

$^1$H-NMR (CDCl$_3$) δ: 7.07-7.28 (4H, m), 7.52-7.54 (1H, m), 7.61-7.67 (1H, m), 9.49 (1H, brs), 9.86 (1H, s).

Reference Example 18

5-[2-(trifluoromethyl)phenyl]-1H-pyrrole-3-carbaldehyde

A solution (28 mL) of ethyl 5-[2-(trifluoromethyl)phenyl]-1H-pyrrole-3-carboxylate (1.38 g) in tetrahydrofuran was cooled to −78° C., and a 1.5 mol/L solution (13 mL) of diisobutylaluminum hydride in toluene was added dropwise over 10 min. The mixture was further stirred at −78° C. for 1 hr, and water (3 mL) was added dropwise over 2 min. The mixture was allowed to warm to room temperature and the mixture was further stirred for 1 hr. The reaction mixture was filtered by adding celite and anhydrous magnesium sulfate, and the filtrate was concentrated under reduced pressure to give a pale-yellow oil (yield 1.14 g). The obtained oil (1.14 g) was dissolved in acetonitrile (50 mL), and tetra-n-propylammonium perruthenate (0.26 g), N-methylmorpholine N-oxide (1.32 g) and molecular sieves 4A powder (5 g) were added to this solution. The mixture was stirred at room temperature for 1.5 hr. The reaction mixture was filtered through celite, and the filtrate was concentrated under reduced pressure. The residue was purified by silica gel column chromatography (eluent: hexane-ethyl acetate=4:1→1:1) to give the title compound as colorless crystals (yield 0.71 g, 61%).

$^1$H-NMR (CDCl$_3$) δ: 6.79-6.81 (1H, m), 7.46-7.78 (5H, m), 9.13 (1H, br), 9.82 (1H, s).

Reference Example 19 methyl 1H-pyrrole-3-carboxylate

To a suspension of potassium tert-butoxide (17.9 g) in tetrahydrofuran (200 mL) was added dropwise a solution of p-toluenesulfonylmethyl isocyanide (25.2 g) and methyl acrylate (11.8 mL) in tetrahydrofuran (200 mL) over 30 min. The reaction mixture was stirred at room temperature for 1 hr, water was added, and the mixture was extracted with ethyl acetate. The extract was washed with saturated aqueous sodium hydrogencarbonate solution, water and saturated brine, dried over anhydrous magnesium sulfate, filtered, and concentrated under reduced pressure. The residue was purified by silica gel column chromatography (eluent:hexane-ethyl acetate=4:1) to give the title compound as a white solid (yield 6.56 g, 41%).

$^1$H-NMR (CDCl$_3$) δ: 3.82 (3H, s), 6.15 (1H, m), 6.75 (1H, m), 7.43 (1H, m), 8.50 (1H, brs).

Reference Example 20 methyl 4-methyl-1H-pyrrole-3-carboxylate

By a similar operation as in Reference Example 19 and using p-toluenesulfonylmethyl isocyanide (94.6 g), methyl crotonate (48.5 g) and potassium tert-butoxide (76.7 g), the title compound was obtained as a pale-yellow solid (yield 16.8 g, 25%).

$^1$H-NMR (CDCl$_3$) δ: 2.29 (3H, s), 3.80 (3H, s), 6.53-6.54 (1H, m), 7.36-7.38 (1H, m), 8.25 (1H, brs).

Reference Example 21 ethyl 2-methyl-1H-pyrrole-3-carboxylate

Vinyl acetate (13.4 g) was added dropwise over 2 hr to bromine (25 g) under ice-cooling with stirring. The reaction mixture was further stirred at the same temperature for 1 hr. Ethyl 3-oxobutanoate (18.5 g) was added, and 25% aqueous ammonia solution (44 mL) was added dropwise over 1 hr. The reaction mixture was further stirred at room temperature for 30 min, water was added and the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=19:

1→3:1) and recrystallized from hexane to give the title compound as a colorless solid (yield 7.56 g, 35%).
$^1$H-NMR (CDCl$_3$) δ: 1.32-1.37 (3H, m), 2.53 (3H, s), 4.24-4.31 (2H, m), 6.55-6.58 (2H, m), 8.13 (1H, br).

Reference Example 22 methyl 5-bromo-1H-pyrrole-3-carboxylate

A solution (30 mL) of methyl 1H-pyrrole-3-carboxylate (3.06 g) in tetrahydrofuran was cooled to −78° C., N-bromosuccinimide (4.38 g) and then pyridine (3 drops) were added, and the mixture was stirred at the same temperature for 1 hr. Water was added to the reaction mixture, and the mixture was extracted with ethyl acetate. The extract was washed with saturated aqueous sodium hydrogencarbonate solution, water and saturated brine, dried over anhydrous sodium sulfate, and concentrated under reduced pressure. The residue was purified by silica gel column chromatography (eluent:hexane-ethyl acetate=5:1) to give the title compound as a pale-yellow solid (yield 3.08 g, 62%).
$^1$H-NMR (CDCl$_3$) δ: 3.81 (3H, s), 6.58 (1H, m), 7.36 (1H, m), 8.60 (1H, brs).

Reference Example 23 methyl 5-bromo-4-methyl-1H-pyrrole-3-carboxylate

By a similar operation as in Reference Example 22 and using methyl 4-methyl-1H-pyrrole-3-carboxylate (1.0 g) and N-bromosuccinimide (1.28 g), the title compound was obtained as a pale-yellow solid (yield 489 mg, 31%).
$^1$H-NMR (CDCl$_3$) δ: 2.23 (3H, s), 3.80 (3H, s), 7.37 (1H, d, J=3.0 Hz), 8.40 (1H, brs).

Reference Example 24 ethyl 5-bromo-2-methyl-1H-pyrrole-3-carboxylate

To a solution of ethyl 2-methyl-1H-pyrrole-3-carboxylate (1.53 g) in tetrahydrofuran (20 mL) was added N-bromosuccinimide (1.78 g) at −78° C., and the mixture was stirred at the same temperature for 30 min. Water and diethyl ether were added to extract the reaction mixture. The extract was washed with saturated brine, dried over anhydrous magnesium sulfate, and concentrated under reduced pressure at 5° C. or below. The residue was washed with hexane to give the title compound as a colorless solid (yield 2.26 g, 97%).
$^1$H-NMR (CDCl$_3$) δ: 1.30-1.35 (3H, m), 2.51 (3H, s), 4.22-4.29 (2H, m), 6.50 (1H, s), 8.01 (1H, br).

Reference Example 25

2-hydroxy-5-pyrimidinesulfonic acid

Fuming sulfuric acid (containing 25% sulfur dioxide, 100 mL) was cooled to 0° C., and 2-aminopyrimidine (25 g) was gradually added over 1 hr. The mixture was heated to 180° C. and stirred for 40 hr. After cooling to room temperature, the mixture was poured into ice (1 kg). The precipitate was collected by filtration and recrystallized from water to give the title compound (yield 25.6 g, 55%).
$^1$H-NMR (DMSO-d$_6$) δ: 6.20-7.20 (2H, m), 8.71 (2H, s).

Reference Example 26

2-chloro-5-pyrimidinesulfonyl chloride

A mixture of 2-hydroxy-5-pyrimidinesulfonic acid (12.8 g) and phosphorus pentachloride (37.8 g) was stirred at 180° C. for 4 hr. After cooling to room temperature, toluene (200 mL) was added, and the insoluble material was filtered off. The filtrate was washed with ice water, dried over anhydrous magnesium sulfate, and the solvent was evaporated under reduced pressure. The residue was stood in a freezer for one day to give the title compound as a pale-yellow solid (yield 14.8 g, 96%).
$^1$H-NMR (CDCl$_3$) δ: 9.19 (2H, s)

Reference Example 27

6-chloropyridazine-3-thiol

To a suspension (88 mL) of sodium hydrogensulfide (3.78 g) in ethanol was added 3,6-dichloropyridazine (5.0 g), and the mixture was refluxed for 1 hr. The solvent was evaporated under reduced pressure, and water (12.5 mL) was added. The mixture was adjusted to about pH 9 with 2 mol/L sodium hydroxide solution, and the precipitate was filtered off. The filtrate was adjusted to about pH 2 with 6 mol/L hydrochloric acid and the precipitate was collected by filtration to give the title compound as a yellow solid (yield 4.74 g, 96%).
$^1$H-NMR (CDCl$_3$) δ: 6.99 (1H, d, J=9.6 Hz), 7.60 (1H, d, J=9.6 Hz).

Reference Example 28

6-chloropyridazine-3-sulfonyl fluoride

To a mixture cooled to −20° C. of methanol (10 mL) and water (10 mL) were added potassium hydrogenfluoride (16 g) and 6-chloropyridazine-3-thiol (2.37 g). After stirring at the same temperature for 20 min, chlorine was blown in for 30 min. Ice water (20 mL) was added and the precipitate was collected by filtration. The precipitate was extracted with ethyl acetate and water. The extract was washed with saturated brine, and dried over anhydrous magnesium sulfate. The solvent was evaporated under reduced pressure to allow crystallization, and the crystals were washed with hexane to give the title compound as a gray solid (yield 1.68 g, 53%).
$^1$H-NMR (CDCl$_3$) δ: 7.86-7.89 (1H, m), 8.17-8.19 (1H, m).

Reference Example 29 pyridin-3-ylsulfonyl chloride hydrochloride

A mixture of 3-pyridinesulfonic acid (50.0 g), phosphorus pentachloride (80.0 g) and phosphorus oxychloride (100 mL) was stirred at 120° C. for 8 hr. Under a nitrogen atmosphere, the mixture was cooled to room temperature, and chloroform (dehydrated, 330 mL) was added. Hydrogen chloride was blown in, and the precipitated crystals were collected by filtration and washed with chloroform (dehydrated) to give the title compound as a white solid (yield 54.7 g, 81%).
$^1$H-NMR (DMSO-d$_6$) δ: 8.03-8.07 (1H, m), 8.68 (1H, d, J=8.1 Hz), 8.87 (1H, d, J=5.7 Hz), 9.01 (1H, s).

Reference Example 30

6-methoxypyridin-3-ylsulfonyl chloride

5-Amino-2-methoxypyridine (1.24 g) was dissolved in acetic acid (8.3 mL), and the mixture was stirred under ice-cooling. Concentrated hydrochloric acid (8.3 mL) was added, and an aqueous solution (5 mL) of sodium nitrite (689 mg) was added dropwise over 15 min while keeping the inside temperature at not higher than 10° C. The reaction mixture was stirred for 10 min, and gradually added at 5° C. to a mixture of cuprous chloride (280 mg) and acetic acid (17 mL) saturated in advance with sulfur dioxide gas. The mixture was allowed to gradually warm to room temperature until the generation of gas stopped. The reaction mixture was concentrated to about 5 mL under reduced pressure, and the precipitate was collected by filtration to give the title compound (yield 1.0 g, 51%) as crude crystals. This compound was used for the next reaction without purification.

Reference Example 31

6-chloropyridin-3-ylsulfonyl chloride

Under ice-cooling, thionyl chloride (12 mL) was added dropwise over 1 hr to water (70 mL) and the mixture was stirred at room temperature for 12 hr to give a sulfur dioxide-containing solution. Separately, under ice-cooling, 5-amino-2-chloropyridine (5.0 g) was added to concentrated hydrochloric acid (40 mL) and the mixture was stirred. An aqueous solution (12.5 mL) of sodium nitrite (2.88 g) was added dropwise while keeping the inside temperature at not higher than 5° C., and the mixture was further stirred for 15 min. The reaction mixture was gradually added at 5° C. to the above-mentioned sulfur dioxide-containing solution added with cuprous chloride (70 mg). Under ice-cooling, the mixture was further stirred for 30 min. The precipitate was collected by filtration, and washed with water and ethanol to give the title compound (yield 4.79 g, 58%).
$^1$H-NMR (CDCl$_3$) δ: 7.60-7.63 (1H, m), 8.24-8.27 (1H, m), 9.03-9.04 (1H, m).

Reference Example 32

2-chloro-3-pyridinesulfonyl chloride

Under ice-cooling, thionyl chloride (24 mL) was added dropwise over 1 hr to water (140 mL) and the mixture was stirred at room temperature for 12 hr to give a sulfur dioxide-containing solution. Separately, under ice-cooling, 3-amino-2-chloropyridine (10 g) was added to concentrated hydrochloric acid (80 mL) and the mixture was stirred. An aqueous solution (25 mL) of sodium nitrite (5.75 g) was added dropwise while keeping the inside temperature at not higher than 5° C., and the mixture was further stirred for 15 min. The reaction mixture was gradually added at 5° C. to the above-mentioned sulfur dioxide-containing solution added with cuprous chloride (140 mg). Under ice-cooling, the mixture was further stirred for 30 min, and the precipitate was collected by filtration and washed with water and ethanol to give the title compound (yield 6.99 g, 42%).
$^1$H-NMR (CDCl$_3$) δ: 7.54-7.56 (1H, m), 8.46-8.48 (1H, m), 8.71-8.73 (1H, m).

Reference Example 33

6-chloro-5-methylpyridine-3-amine

Reduced iron (793 mg) was added to an aqueous solution (25 mL) of ammonium chloride (1.27 g), and the mixture was stirred at room temperature for 5 min. A solution (10 mL) of 2-chloro-3-methyl-5-nitropyridine (816 mg) in methanol was added dropwise over 10 min. The reaction mixture was stirred at 40° C. for 20 min and at 50° C. for 1.5 hr and further refluxed for 1 hr. The reaction mixture was filtered through celite, and celite was washed with methanol. Methanol was mostly removed by concentration under reduced pressure, and saturated aqueous sodium hydrogencarbonate solution was added. The mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=19:1→7:3) to give the title compound as a solid (yield 280 mg, 42%).
$^1$H-NMR (CDCl$_3$) δ: 3.62 (2H, br), 6.88-6.89 (1H, m), 7.70-7.71 (1H, m).

Reference Example 34

6-chloro-5-methylpyridine-3-sulfonyl chloride

Under ice-cooling, thionyl chloride (0.6 mL) was added dropwise over 30 min to water (3.4 mL). The mixture was stirred at room temperature for 12 hr to give a sulfur dioxide-containing solution. Separately, under ice-cooling, 6-chloro-5-methylpyridine-3-amine (278 mg) was added to concentrated hydrochloric acid (6 mL) and the mixture was stirred. An aqueous solution (2 mL) of sodium nitrite (148 mg) was added dropwise while keeping the inside temperature at not higher than 5° C., and the mixture was further stirred for 15 min. The reaction mixture was gradually added at 5° C. to the above-mentioned sulfur dioxide-containing solution added with cuprous chloride (5 mg). Under ice-cooling, the mixture was further stirred for 30 min, and the precipitate was collected by filtration and washed with water to give the title compound as a pale-yellow solid (yield 271 mg, 62%).
$^1$H-NMR (CDCl$_3$) δ: 2.54 (3H, s), 8.15 (1H, s), 8.86 (1H, s).

Reference Example 35

2-pyridinesulfonyl chloride

Under ice-cooling, 2-mercaptopyridine (2.0 g) was added to sulfuric acid (50 mL) and the mixture was stirred. Sodium hypochlorite solution (chlorine content 5%, 126 mL) was added dropwise over 1.5 hr, and the mixture was further stirred at the same temperature for 30 min. The reaction mixture was diluted with water (100 mL), and extracted with dichloromethane. The extract was washed with saturated brine, dried over anhydrous magnesium sulfate, and concentrated under reduced pressure to give the title compound as a colorless oil (yield 2.45 g, 77%).
$^1$H-NMR (CDCl$_3$) δ: 7.69-7.71 (1H, m), 8.06-8.14 (2H, m), 8.83-8.85 (1H, m).

Reference Example 36

Ethyl 1-[(2-chloro-5-pyrimidine)sulfonyl]-5-phenyl-1H-pyrrole-3-carboxylate

Ethyl 5-phenyl-1H-pyrrole-3-carboxylate (1.60 g) was dissolved in tetrahydrofuran (50 mL), sodium hydride (60% in oil, 446 mg) was added and the mixture was stirred at room temperature for 15 min. 15-Crown-5 (2.24 mL) was added and the mixture was further stirred at the same temperature for 15 min. 2-Chloro-5-pyrimidinesulfonyl chloride (2.06 g) was added and the reaction mixture was stirred at room temperature for 1 hr. Water was added, and the mixture was extracted with ethyl acetate. The extract was washed with water and saturated brine, dried over anhydrous magnesium sulfate, and concentrated under reduced pressure. The residue was purified by silica gel column chromatography (eluent:

hexane-ethyl acetate=19:1→7:3) to give the title compound as a yellow oil (yield 2.03 g, 70%).

¹H-NMR (CDCl₃) δ: 1.35-1.39 (3H, m), 4.30-4.37 (2H, m), 6.64 (1H, s), 7.22-7.26 (2H, m), 7.37-7.51 (3H, m), 8.04 (1H, s), 8.37 (2H, s).

Reference Example 37 ethyl 1-[(2-methyl-5-pyrimidine)sulfonyl]-5-phenyl-1H-pyrrole-3-carboxylate

Under a nitrogen atmosphere, tetrakis(triphenylphosphine)palladium (87 mg) and 2 mol/L trimethylaluminum-hexane solution (1.5 mL) were added to a solution of ethyl 1-[(2-chloro-5-pyrimidine)sulfonyl]-5-phenyl-1H-pyrrole-3-carboxylate (588 mg) in tetrahydrofuran (20 mL) with stirring. The mixture was stirred at room temperature for 15 min and 2 mol/L trimethylaluminum-hexane solution (1 mL) was added. After stirring at the same temperature for 20 min, ice water (100 mL) and ammonium chloride (2.0 g) were added, and the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=19:1→1:1) to give the title compound as a pale-yellow oil (yield 350 mg, 63%).

¹H-NMR (CDCl₃) δ: 1.34-1.39 (3H, m), 2.77 (3H, s), 4.29-4.36 (2H, m), 6.61 (1H, s), 7.21-7.26 (2H, m), 7.37-7.49 (3H, m), 8.06 (1H, s), 8.41 (2H, s).

Reference Example 38 ethyl 1-[(2-amino-5-pyrimidine)sulfonyl]-5-phenyl-1H-pyrrole-3-carboxylate 7 mol/L ammonia-methanol solution (1.0 mL) was added to a solution of ethyl 1-[(2-chloro-5-pyrimidine)sulfonyl]-5-phenyl-1H-pyrrole-3-carboxylate (392 mg) in tetrahydrofuran (10 mL) with stirring. The mixture was stirred at room temperature for 20 min, saturated aqueous sodium hydrogencarbonate solution was added, and the mixture was extracted with ethyl acetate. The extract was washed with saturated brine, dried over anhydrous magnesium sulfate, and concentrated under reduced pressure to give the title compound as a colorless solid (yield 373 mg, about 100%).

¹H-NMR (CDCl₃) δ: 1.34-1.39 (3H, m), 4.28-4.36 (2H, m), 5.60 (2H, br), 6.59 (1H, s), 7.26-7.46 (5H, m), 8.02-8.03 (3H, m).

Reference Example 39 ethyl 1-(imidazo[1,2-a]pyrimidin-6-ylsulfonyl)-5-phenyl-1H-pyrrole-3-carboxylate A mixture of ethyl 1-[(2-amino-5-pyrimidine)sulfonyl]-5-phenyl-1H-pyrrole-3-carboxylate (373 mg), 2-bromo-1,1-diethoxyethane (394 mg) and acetic acid (20 mL) was stirred in a microwave reaction apparatus at 130° C. for 30 min. After cooling to room temperature, the solvent was evaporated under reduced pressure. Saturated aqueous sodium hydrogencarbonate solution was added to the residue, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=19:1→ethyl acetate) to give the title compound as a brown solid (yield 157 mg, 40%).

¹H-NMR (CDCl₃) δ: 1.35-1.40 (3H, m), 4.30-4.37 (2H, m), 6.61 (1H, s), 7.17-7.49 (2H, m), 7.26-7.49 (4H, m), 7.94 (1H, s), 7.99 (1H, s), 8.11 (1H, s), 8.38 (1H, s).

Reference Example 40 ethyl 5-phenyl-1-(pyridazin-3-ylsulfonyl)-1H-pyrrole-3-carboxylate

Ethyl 5-phenyl-1H-pyrrole-3-carboxylate (1.06 g) was dissolved in tetrahydrofuran (30 mL), sodium hydride (60% in oil, 300 mg) was added and the mixture was stirred at room temperature for 15 min. 15-Crown-5 (1.52 mL) was added and the mixture was further stirred at the same temperature for 15 min. 6-Chloropyridazine-3-sulfonyl fluoride (1.28 g) was added and the reaction mixture was stirred at room temperature for 30 min. Hydrazine (1.60 g) was added and the reaction mixture was stirred at room temperature for 15 min. Saturated aqueous sodium hydrogencarbonate solution was added, and the mixture was extracted with ethyl acetate. The extract was washed with water and saturated brine, dried over anhydrous magnesium sulfate, and concentrated under reduced pressure. The residue was dissolved in tetrahydrofuran (30 mL), manganese dioxide (75% chemically treated product, 5.0 g) was added, and the mixture was stirred at room temperature for 10 min. The reaction mixture was filtered through celite, and celite was washed with ethyl acetate. The filtrate was concentrated under reduced pressure, and the residue was purified by silica gel column chromatography (eluent:hexane-ethyl acetate=19:1→1:1) to give the title compound (yield 613 mg, yield 24% (containing impurity)).

¹H-NMR (CDCl₃) δ: 1.34-1.39 (3H, m), 4.29-4.36 (2H, m), 6.61 (1H, s), 7.11-7.22 (2H, m), 7.24-7.51 (5H, m), 8.20 (1H, s), 9.28-9.30 (1H, s).

Reference Example 41 methyl 5-bromo-1-(phenylsulfonyl)-1H-pyrrole-3-carboxylate

Sodium hydride (60% in oil, 1.1 g) was washed with hexane, and suspended in N,N-dimethylformamide (50 mL). A solution (10 mL) of methyl 5-bromo-1H-pyrrole-3-carboxylate (5.0 g) in N,N-dimethylformamide was added to the suspension at 0° C. After stirring at 0° C. for 30 min, a solution of benzenesulfonyl chloride (3.3 mL) in N,N-dimethylformamide (5 mL) was added, and the reaction mixture was stirred at room temperature for 1 hr. Water was added, and the mixture was extracted with ethyl acetate. The extract was washed with saturated aqueous sodium hydrogencarbonate solution, water and saturated brine, dried over anhydrous sodium sulfate, and concentrated under reduced pressure. The residue was purified by silica gel column chromatography (eluent: hexane-ethyl acetate=5:1) to give the title compound as a colorless solid (yield 8.5 g, 99%).

¹H-NMR (CDCl₃) δ: 3.83 (3H, s), 6.68 (1H, d, J=2.1 Hz), 7.55-7.60 (2H, m), 7.67-7.72 (1H, m), 7.96-7.99 (2H, m), 8.08 (1H, d, J=2.1 Hz).

Reference Example 42 methyl 5-bromo-4-methyl-1-(phenylsulfonyl)-1H-pyrrole-3-carboxylate

Sodium hydride (60% in oil, 202 mg) was washed with hexane and suspended in N,N-dimethylformamide (10 mL). A solution (10 mL) of methyl 5-bromo-4-methyl-1H-pyrrole- 3-carboxylate (1.0 g) in N,N-dimethylformamide was added dropwise at −78° C. After completion of the dropwise addition, the reaction mixture was stirred at room temperature for 30 min and added dropwise to an ice-cooled solution (10 mL) of benzenesulfonyl chloride (0.71 mL) in N,N-dimethylformamide. After completion of the dropwise addition, the reaction mixture was stirred at room temperature for 1 hr, and concentrated under reduced pressure. The residue was recrystallized from ethyl acetate-hexane to give the title compound as a brown solid (yield 1.13 g, 69%).

$^1$H-NMR (CDCl$_3$) δ: 2.11 (3H, s), 3.79 (3H, s), 7.45-7.70 (3H, m), 7.85-7.95 (2H, m), 8.06 (1H, s).

Reference Example 43 ethyl 2-methyl-1-(phenylsulfonyl)-1H-pyrrole-3-carboxylate

By a similar operation as in Reference Example 41 and using ethyl 2-methyl-1H-pyrrole-3-carboxylate (8.81 g), sodium hydride (60% in oil, 2.58 g) and benzenesulfonyl chloride (7.8 mL), the title compound was obtained as white crystals (yield 14.3 g, 85%).

$^1$H-NMR (CDCl$_3$) δ: 1.31 (3H, t, J=7.2 Hz), 2.62 (3H, s), 4.24 (2H, q, J=7.2 Hz), 6.63 (1H, d, J=3.3 Hz), 7.30 (1H, d, J=3.3 Hz), 7.51-7.57 (2H, m), 7.62-7.68 (1H, m), 7.81-7.84 (2H, m).

Reference Example 44 ethyl 5-bromo-2-methyl-1-(pyridin-3-ylsulfonyl)-1H-pyrrole-3-carboxylate

Ethyl 5-bromo-2-methyl-1H-pyrrole-3-carboxylate (2.26 g) was dissolved in tetrahydrofuran (100 mL), sodium hydride (60% in oil, 1.16 g) was added and the mixture was stirred at room temperature for 15 min. 15-Crown-5 (5.90 mL) was added and the mixture was further stirred at the same temperature for 15 min. 3-Pyridinesulfonyl chloride hydrochloride (3.13 g) was added and the reaction mixture was stirred at room temperature for 1 hr. Saturated aqueous sodium hydrogencarbonate solution was added, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=19:1→7:3) to give the title compound as a yellow oil (yield 2.31 g, 64%).

$^1$H-NMR (CDCl$_3$) δ: 1.24-1.34 (3H, m), 2.94 (3H, s), 4.23-4.30 (2H, m), 6.69 (1H, s), 7.51-7.55 (1H, m), 8.17-8.21 (1H, m), 8.88-8.91 (1H, m), 9.14 (1H, m).

Reference Example 45 ethyl 2-methyl-5-phenyl-1-(pyridin-3-ylsulfonyl)-1H-pyrrole-3-carboxylate

A suspension of ethyl 5-bromo-2-methyl-1-(pyridin-3-ylsulfonyl)-1H-pyrrole-3-carboxylate (2.26 g), phenylboronic acid (1.54 g), dichloro[bis(triphenylphosphine)]palladium (211 mg) and sodium carbonate (1.91 g) in 1,2-dimethoxyethane (20 mL)-water (10 mL) was stirred at 80° C. for 40 min. After cooling, the reaction mixture was filtered through celite, and celite was washed with ethyl acetate. The organic layer was separated from the filtrate, washed with water and saturated brine, dried over anhydrous magnesium sulfate, and concentrated under reduced pressure. The residue was purified by silica gel column chromatography (eluent:hexane-ethyl acetate=9:1→6:4) to give the title compound as a colorless oil (yield 2.39 g, about 100%).

$^1$H-NMR (CDCl$_3$) δ: 1.30-1.34 (3H, m), 2.92 (3H, s), 4.23-4.30 (2H, m), 6.59 (1H, s), 7.23-7.39 (4H, m), 7.50-7.68 (2H, m), 8.22-8.25 (1H, m), 8.61-8.62 (1H, m), 8.75-8.77 (1H, m).

Reference Example 46

[5-bromo-1-(phenylsulfonyl)-1H-pyrrol-3-yl]methanol

A solution (80 mL) of methyl 5-bromo-1-(phenylsulfonyl)-1H-pyrrole-3-carboxylate (7.1 g) in tetrahydrofuran was cooled to −78° C., a 1.5 mol/L solution (42 mL) of diisobutylaluminum hydride in toluene was added dropwise over 30 min and the mixture was further stirred at −78° C. for 1 hr. 1 mol/L hydrochloric acid (20 mL) was added to the reaction mixture, and the mixture was extracted with ethyl acetate. The extract was washed with saturated aqueous sodium hydrogencarbonate solution, water and saturated brine, dried over anhydrous sodium sulfate, and concentrated under reduced pressure to give the title compound as a brown oil (yield 7.1 g, about 100%).

$^1$H-NMR (CDCl$_3$) δ: 1.62 (1H, brs), 4.51 (2H, s), 6.33-6.34 (1H, m), 7.44-7.45 (1H, m), 7.51-7.57 (2H, m), 7.62-7.68 (1H, m), 7.93-7.97 (2H, m).

Reference Example 47

[2-methyl-1-(phenylsulfonyl)-1H-pyrrol-3-yl]methanol

By a similar operation as in Reference Example 13 and using ethyl 2-methyl-1-(phenylsulfonyl)-1H-pyrrole-3-carboxylate (8.05 g) and 1.5 mol/L diisobutylaluminum hydride toluene solution (55 mL), the title compound was obtained as white crystals (yield 6.61 g, 96%).

$^1$H-NMR (CDCl$_3$) δ: 1.37 (1H, brs), 2.29 (3H, s), 4.42 (2H, brs), 6.29 (1H, d, J=3.6 Hz), 7.30 (1H, d, J=3.6 Hz), 7.49-7.55 (2H, m), 7.58-7.64 (1H, m), 7.78-7.81 (2H, m).

Reference Example 48

5-bromo-1-(phenylsulfonyl)-1H-pyrrole-3-carbaldehyde

To a solution (80 mL) of [5-bromo-1-(phenylsulfonyl)-1H-pyrrol-3-yl]methanol (7.1 g) in acetonitrile were added tetra-n-propylammonium perruthenate (0.63 g), N-methylmorpholine N-oxide hydrate (4.2 g) and molecular sieves 4A powder (3.5 g), and the mixture was stirred at room temperature for 2 hr. The reaction mixture was filtered, and the filtrate was concentrated under reduced pressure. Water was added to the residue, and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=4:1) to give the title compound as a colorless solid (yield 4.6 g, 71%).

$^1$H-NMR (CDCl$_3$) δ: 6.73 (1H, d, J=2.1 Hz), 7.57-7.63 (2H, m), 7.70-7.75 (1H, m), 7.98-8.02 (2H, m), 8.10 (1H, d, J=2.1 Hz), 9.77 (1H, s).

Reference Example 49

5-bromo-4-methyl-1-(phenylsulfonyl)-1H-pyrrole-3-carbaldehyde

By a similar reaction as in Reference Example 17 and using methyl 5-bromo-4-methyl-1-(phenylsulfonyl)-1H-pyrrole-3-carboxylate, the title compound was obtained as a colorless solid (1.78 g, 54%).
$^1$H-NMR (CDCl$_3$) δ: 2.14 (3H, s), 7.50-7.62 (3H, m), 7.91-7.96 (2H, m), 8.04 (1H, s), 9.77 (1H, s).

Reference Example 50

4-methyl-5-phenyl-1H-pyrrole-3-carbaldehyde

A suspension of 5-bromo-4-methyl-1-(phenylsulfonyl)-1H-pyrrole-3-carbaldehyde (1.78 g), phenylboronic acid (1.37 g), dichloro[bis(triphenylphosphine)]palladium (0.19 g) and sodium carbonate (1.72 g) in 1,2-dimethoxyethane (30 mL)-water (10 mL) was stirred at 100° C. for 1 hr. 8 mol/L aqueous sodium hydroxide solution (15 mL) was added, and the mixture was stirred at 90° C. for 3 hr. After cooling, the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=9:1→1:1), and the obtained solid was washed with hexane to give the title compound as a pale-yellow solid (yield 815 mg, 69%).
$^1$H-NMR (CDCl$_3$) δ: 2.47 (3H, s), 7.34-7.48 (6H, m), 8.58 (1H, br), 9.91 (1H, s).

Reference Example 51

2-methyl-1-(phenylsulfonyl)-1H-pyrrole-3-carbaldehyde

To a mixture of [2-methyl-1-(phenylsulfonyl)-1H-pyrrol-3-yl]methanol (6.35 g), dimethyl sulfoxide (50 mL) and triethylamine (25 mL) was added sulfur trioxide-pyridine complex (4.57 g), and the mixture was stirred at room temperature for 12 hr. Saturated aqueous sodium hydrogencarbonate solution was added to the reaction mixture, and the mixture was extracted with ethyl acetate. The extract was washed with saturated aqueous sodium hydrogencarbonate solution, water and saturated brine, dried over anhydrous sodium sulfate, filtered, and concentrated under reduced pressure. The residue was purified by silica gel column chromatography (eluent:hexane-ethyl acetate=2:1) to give a white title compound (yield 5.27 g, 84%).
$^1$H-NMR (CDCl$_3$) δ: 2.62 (3H, s), 6.65 (1H, d, J=3.6 Hz), 7.35 (1H, d, J=3.6 Hz), 7.55-7.61 (2H, m), 7.66-7.71 (1H, m), 7.85-7.88 (2H, m), 9.89 (1H, s).

Reference Example 52

2-methyl-1H-pyrrole-3-carbaldehyde

To a solution of 2-methyl-1-(phenylsulfonyl)-1H-pyrrole-3-carbaldehyde (4.59 g) in tetrahydrofuran (20 mL) and methanol (5 mL) was added 8 mol/L aqueous sodium hydroxide solution (2.5 mL) at 0° C., and the reaction mixture was stirred at the same temperature for 30 min. Water was added to the reaction mixture, and the mixture was extracted with ethyl acetate. The extract was washed with saturated aqueous sodium hydrogencarbonate solution, water and saturated brine, dried over anhydrous sodium sulfate, filtered, and concentrated under reduced pressure. The residue was purified by silica gel column chromatography (eluent:hexane-ethyl acetate=2:1) to give the title compound as a white solid (yield 1.06 g, 54%).
$^1$H-NMR (CDCl$_3$) δ: 2.56 (3H, s), 6.58-6.59 (1H, m), 6.65-6.67 (1H, m), 8.52 (1H, brs), 9.89 (1H, s).

Reference Example 53

2-methyl-1-(pyridin-3-ylsulfonyl)-1H-pyrrole-3-carbaldehyde

By a similar reaction as in Reference Example 44 and using 2-methyl-1H-pyrrole-3-carbaldehyde (1.10 g), sodium hydride (60% in oil, 1.20 g), 15-crown-5 (6.0 mL) and pyridin-3-ylsulfonyl chloride hydrochloride (3.22 g), the title compound was obtained as white crystals (yield 1.10 g, 44%).
$^1$H-NMR (CDCl$_3$) δ: 2.66 (3H, s), 6.68 (1H, d, J=3.9 Hz), 7.34 (1H, d, J=3.9 Hz), 7.51-7.55 (1H, m), 8.09-8.13 (1H, m), 8.89-8.91 (1H, m), 9.10-9.11 (1H, m), 9.90 (1H, s).

Reference Example 54

5-bromo-2-methyl-1-(pyridin-3-ylsulfonyl)-1H-pyrrole-3-carbaldehyde

To a solution of 2-methyl-1-(pyridin-3-ylsulfonyl)-1H-pyrrole-3-carbaldehyde (974 mg) in N,N-dimethylformamide (10 mL) was added N-bromosuccinimide (1.17 g) at 0° C., and the mixture was stirred at room temperature for 1 hr. Water was added to the reaction mixture, and the mixture was extracted with ethyl acetate. The extract was washed with saturated aqueous sodium hydrogencarbonate solution, water and saturated brine, dried over anhydrous magnesium sulfate, filtered, and concentrated under reduced pressure. The residue was purified by silica gel column chromatography (eluent:hexane-ethyl acetate=2:1) to give the title compound as white crystals (yield 675 mg, 53%).
$^1$H-NMR (CDCl$_3$) δ: 2.89 (3H, s), 6.18 (1H, s), 7.53-7.57 (1H, m), 8.21-8.26 (1H, m), 8.91-8.93 (1H, m), 9.17-9.18 (1H, m), 9.92 (1H, s).

Reference Example 55

5-phenyl-1-(pyridin-3-ylsulfonyl)-1H-pyrrole-3-carbaldehyde

Under an argon atmosphere, 5-phenyl-1H-pyrrole-3-carbaldehyde (342 mg) was dissolved in absolute tetrahydrofuran (20 mL) and sodium hydride (60% in oil, 240 mg) was added while stirring at room temperature. After stirring at the same temperature for 15 min, 15-crown-5 (1.21 mL) was added, and the mixture was further stirred at the same temperature for 15 min. Pyridin-3-ylsulfonyl chloride hydrochloride (642 mg) was added, and the mixture was further stirred at the same temperature for 30 min. The reaction mixture was diluted with ethyl acetate, washed successively with saturated aqueous sodium hydrogencarbonate solution and saturated brine, and dried over anhydrous magnesium sulfate. The solvent was evaporated under reduced pressure and the residue was purified by silica gel column chromatography (eluent: hexane-ethyl acetate=19:1→1:1) to give the title compound as a brown solid (yield 470 mg, 75%).

$^1$H-NMR (CDCl$_3$) δ: 6.60 (1H, d, J=1.8 Hz), 7.15-7.19 (2H, m), 7.25-7.37 (3H, m), 7.42-7.48 (1H, m), 7.53-7.57 (1H, m), 8.13 (1H, d, J=1.8 Hz), 8.49-8.50 (1H, m), 8.74-8.76 (1H, m), 9.90 (1H, s).

Reference Example 56

1-[(6-methoxypyridin-3-yl)sulfonyl]-5-phenyl-1H-pyrrole-3-carbaldehyde

Under an argon atmosphere, 5-phenyl-1H-pyrrole-3-carbaldehyde (171 mg) was dissolved in absolute tetrahydrofuran (20 mL), and sodium hydride (60% in oil, 200 mg) was added at room temperature while stirring. After stirring at the same temperature for 15 min, 15-crown-5 (1.01 mL) was added, and the mixture was further stirred at the same temperature for 15 min. 6-Methoxypyridin-3-ylsulfonyl chloride (623 mg) was added, and the mixture was stirred at the same temperature for 1 hr. The reaction mixture was diluted with ethyl acetate, washed successively with saturated aqueous sodium hydrogencarbonate solution and saturated brine, and dried over anhydrous magnesium sulfate. The solvent was evaporated under reduced pressure and the residue was purified by silica gel column chromatography (eluent:hexane-ethyl acetate=19:1→1:1) to give the title compound as an oil (yield 59 mg, 17%).
$^1$H-NMR (CDCl$_3$) δ: 3.95 (3H, s), 6.59-6.62 (2H, m), 7.19-7.44 (6H, m), 8.08-8.10 (2H, m), 9.88 (1H, s).

Reference Example 57

1-(6-chloropyridin-3-ylsulfonyl)-5-phenyl-1H-pyrrole-3-carbaldehyde

Under an argon atmosphere, 5-phenyl-1H-pyrrole-3-carbaldehyde (514 mg) was dissolved in absolute tetrahydrofuran (15 mL), and sodium hydride (60% in oil, 180 mg) was added at room temperature while stirring. After stirring at the same temperature for 15 min, 15-crown-5 (0.90 mL) was added, and the mixture was further stirred at the same temperature for 15 min. 6-Chloropyridin-3-ylsulfonyl chloride (827 mg) was added, and the mixture was further stirred at the same temperature for 1 hr. The reaction mixture was diluted with ethyl acetate, washed successively with saturated aqueous sodium hydrogencarbonate solution and saturated brine, and dried over anhydrous magnesium sulfate. The solvent was evaporated under reduced pressure and the residue was purified by silica gel column chromatography (eluent:hexane-ethyl acetate=19:1→7:3) to give the title compound as an oil (yield 762 mg, 73%).
$^1$H-NMR (CDCl$_3$) δ: 6.62 (1H, s), 7.19-7.49 (7H, m), 8.09 (1H, s), 8.24-8.26 (1H, m), 8.90 (1H, s).

Reference Example 58

1-(2-chloropyridin-3-ylsulfonyl)-5-phenyl-1H-pyrrole-3-carbaldehyde

By a reaction under similar conditions as in Reference Example 55 and using 5-phenyl-1H-pyrrole-3-carbaldehyde (514 mg), sodium hydride (60% in oil, 180 mg), 15-crown-5 (0.90 mL) and 2-chloro-3-pyridinesulfonyl chloride (716 mg), the title compound was obtained as an amorphous form (yield 716 mg, 69%).

$^1$H-NMR (CDCl$_3$) δ: 6.64 (1H, s), 6.70-6.90 (1H, m), 7.05-7.08 (2H, m), 7.15-7.18 (2H, m), 7.26-7.32 (1H, m), 7.55-7.59 (1H, m), 8.26 (1H, s), 8.44-8.46 (1H, m), 9.94 (1H, s).

Reference Example 59

1-(2-chloropyrimidin-5-ylsulfonyl)-5-phenyl-1H-pyrrole-3-carbaldehyde

By a reaction under similar conditions as in Reference Example 55 and using 5-phenyl-1H-pyrrole-3-carbaldehyde (342 mg), sodium hydride (60% in oil, 120 mg), 15-crown-5 (0.60 mL) and 2-chloro-5-pyrimidinesulfonyl chloride (554 mg), the title compound was obtained as a yellow solid (yield 390 mg, 56%).
$^1$H-NMR (CDCl$_3$) δ: 6.68 (1H, s), 7.22-7.26 (2H, m), 7.39-7.52 (3H, m), 8.09 (1H, s), 8.35 (2H, s), 9.91 (1H, s).

Reference Example 60

1-[(6-chloro-5-methylpyridin-3-yl)sulfonyl]-5-phenyl-1H-pyrrole-3-carbaldehyde

By a reaction under similar conditions as in Reference Example 55 and using 5-phenyl-1H-pyrrole-3-carbaldehyde (171 mg), sodium hydride (60% in oil, 60 mg), 15-crown-5 (0.30 mL) and 6-chloro-5-methylpyridine-3-sulfonyl chloride (270 mg), the title compound was obtained as a solid (yield 244 mg, 68%).
$^1$H-NMR (CDCl$_3$) δ: 2.27 (3H, s), 6.62 (1H, s), 7.20-7.26 (3H, m), 7.35-7.49 (3H, m), 8.09 (1H, s), 8.13 (1H, m), 9.90 (1H, s).

Reference Example 61

2-methyl-5-phenyl-1-(pyridin-3-ylsulfonyl)-1H-pyrrole-3-carbaldehyde

A solution (15 mL) of ethyl 2-methyl-5-phenyl-1-(pyridin-3-ylsulfonyl)-1H-pyrrole-3-carboxylate (980 mg) in tetrahydrofuran was cooled to −78° C., a 1.5 mol/L solution (5.3 mL) of diisobutylaluminum hydride in toluene was added dropwise over 10 min., and the mixture was warmed to 0° C. over 2 hr. Water (100 mL) and ethyl acetate (20 mL) were added, and the mixture was stirred at room temperature for 30 min. The reaction mixture was filtered through celite, and the organic layer was collected, washed with saturated brine, dried over anhydrous sodium sulfate, and concentrated under reduced pressure. The residue was dissolved in acetonitrile solution (25 mL), tetra-n-propylammonium perruthenate (93 mg), N-methylmorpholine N-oxide hydrate (466 mg) and molecular sieves 4A powder (500 mg) were added, and the mixture was stirred at room temperature for 2 hr. The reaction mixture was concentrated under reduced pressure, and ethyl acetate (30 mL) was added to the residue. The mixture was filtered through celite, and celite was washed with ethyl acetate. The filtrate was concentrated under reduced pressure, and the residue was purified by silica gel column chromatography (eluent: hexane-ethyl acetate=19:1→1:1) to give the title compound as a yellow oil (yield 235 mg, 27%).
$^1$H-NMR (CDCl$_3$) δ: 2.93 (3H, s), 6.51 (1H, s), 7.18-7.42 (6H, m), 7.59-7.64 (1H, m), 8.60 (1H, s), 8.77-8.79 (1H, m), 10.03 (1H, s).

Reference Example 62

1-[(2-methyl-5-pyrimidine)sulfonyl]-5-phenyl-1H-pyrrole-3-carbaldehyde

Under a nitrogen atmosphere, a solution of ethyl 1-[(2-methyl-5-pyrimidine)sulfonyl]-5-phenyl-1H-pyrrole-3-carboxylate (280 mg) in tetrahydrofuran (20 mL) was cooled to −78° C., a 1.5 mol/L solution (3.0 mL) of diisobutylaluminum hydride in toluene was added while stirring. After stirring at the same temperature for 15 min, the mixture was allowed to warm to −40° C. over 30 min. Water (50 mL) was added, and after stirring at the same temperature for 5 min, the mixture was allowed to warm to 0° C. over 10 min. Ethyl acetate (30 mL) was added, and after stirring at the same temperature for 15 min, the mixture was stirred at room temperature for 20 min. A gel-like mixture was filtered through celite, and celite was washed with ethyl acetate. The organic layer was separated from the filtrate, washed with saturated brine, dried over anhydrous magnesium sulfate, and concentrated under reduced pressure. The residue was dissolved in tetrahydrofuran (50 mL), manganese dioxide (75% chemically treated product, 3.0 g) was added, and the mixture was stirred at room temperature for 1 hr. The reaction mixture was filtered through celite, and celite was washed with ethyl acetate. The filtrate was concentrated under reduced pressure and the residue was purified by silica gel column chromatography (eluent: hexane-ethyl acetate=19:1→1:1) to give the title compound as a pale-yellow solid (yield 150 mg, 61%).

$^1$H-NMR (CDCl$_3$) δ: 2.78 (3H, s), 6.64 (1H, s), 7.21-7.26 (2H, m), 7.36-7.51 (3H, m), 8.10 (1H, s), 8.40 (2H, s), 9.90 (1H, s).

Reference Example 63

5-(2-fluorophenyl)-1-(pyridin-3-ylsulfonyl)-1H-pyrrole-3-carbaldehyde

To a solution (96 mL) of 5-(2-fluorophenyl)-1H-pyrrole-3-carbaldehyde (475 mg) in tetrahydrofuran was added sodium hydride (60% in oil, 503 mg) at room temperature and the mixture was stirred for 30 min. 15-Crown-5 (2.77 g) was added dropwise and the mixture was stirred for 30 min. Pyridine-3-sulfonyl chloride hydrochloride (1.35 g) was added, and the mixture was further stirred for 3 hr. The reaction mixture was diluted with saturated brine, and the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=7:3→2:3) and crystallized from diisopropyl ether-ethyl acetate (4:1) to give the title compound as colorless crystals (yield 680 mg, 82%).

$^1$H-NMR (CDCl$_3$) δ: 6.68 (1H, d, J=1.8 Hz), 6.99-7.05 (1H, m), 7.16-7.19 (2H, m), 7.35-7.39 (1H, m), 7.45-7.51 (1H, m), 7.69-7.73 (1H, m), 8.14 (1H, d, J=1.8 Hz), 8.58-8.59 (1H, m), 8.81-8.83 (1H, m), 9.91 (1H, s).

Reference Example 64

1-(pyridin-3-ylsulfonyl)-5-[2-(trifluoromethyl)phenyl]-1H-pyrrole-3-carbaldehyde To a solution (36 mL) of 5-[2-(trifluoromethyl)phenyl]-1H-pyrrole-3-carbaldehyde (240 mg) in tetrahydrofuran was added sodium hydride (60% in oil, 201 mg) at room temperature and the mixture was stirred for 30 min. 15-Crown-5 (1.11 g) was added dropwise and the mixture was stirred for 30 min. Pyridine-3-sulfonyl chloride hydrochloride (537 mg) was added, and the mixture was further stirred for 3 hr. The reaction mixture was diluted with saturated brine, and the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=4:1→2:3) and crystallized from diisopropyl ether to give the title compound as colorless crystals (yield 380 mg, about 100%).

$^1$H-NMR (CDCl$_3$) δ: 6.69 (1H, d, J=1.8 Hz), 7.34-7.38 (1H, m), 7.44-7.48 (1H, m), 7.61-7.69 (4H, m), 8.16 (1H, d, J=1.8 Hz), 8.45 (1H, d, J=2.4 Hz), 8.81 (1H, m), 9.91 (1H, s).

Reference Example 65

4-methyl-5-phenyl-1-(pyridin-3-ylsulfonyl)-1H-pyrrole-3-carbaldehyde

4-Methyl-5-phenyl-1H-pyrrole-3-carbaldehyde (185 mg) was dissolved in tetrahydrofuran (10 mL), sodium hydride (60% in oil, 60 mg) was added and the mixture was stirred at room temperature for 15 min. 15-Crown-5 (0.30 mL) was added and the mixture was further stirred at the same temperature for 15 min. 3-Pyridinesulfonyl chloride hydrochloride (231 mg) was added and the reaction mixture was stirred at room temperature for 1 hr. Water was added, and the mixture was extracted with ethyl acetate. The extract was washed with water and saturated brine, dried over anhydrous magnesium sulfate, and concentrated under reduced pressure. The residue was purified by silica gel column chromatography (eluent:hexane-ethyl acetate=19:1→1:1) to give the title compound as a colorless solid (yield 172 mg, 53%).

$^1$H-NMR (CDCl$_3$) δ: 2.03 (3H, s), 7.01-7.04 (2H, m), 7.26-7.55 (5H, m), 8.07 (1H, s), 8.47 (1H, m), 8.75-8.78 (1H, m), 9.97 (1H, s).

Reference Example 66

4-methyl-5-phenyl-1-(pyridin-2-ylsulfonyl)-1H-pyrrole-3-carbaldehyde

By a reaction under similar conditions as in Reference Example 65 and using 4-methyl-5-phenyl-1H-pyrrole-3-carbaldehyde (185 mg), sodium hydride (60% in oil, 60 mg), 15-crown-5 (0.30 mL) and 2-pyridinesulfonyl chloride (231 mg) instead of 3-pyridinesulfonyl chloride hydrochloride, the title compound was obtained as an amorphous form (yield 262 mg, 80%).

$^1$H-NMR (CDCl$_3$) δ: 2.03 (3H, s), 6.92-6.95 (2H, m), 7.21-7.49 (5H, m), 7.65-7.69 (1H, m), 8.14 (1H, s), 8.64-8.65 (1H, m), 9.98 (1H, s).

Reference Example 67

1-[(1,2-dimethyl-1H-imidazol-4-yl)sulfonyl]-4-methyl-5-phenyl-1H-pyrrole-3-carbaldehyde By a reaction under similar conditions as in Reference Example 65 and using 4-methyl-5-phenyl-1H-pyrrole-3-carbaldehyde (185 mg), sodium hydride (60% in oil, 60 mg), 15-crown-5 (0.30 mL) and (1,2-dimethyl-1H-imidazol-4-yl)sulfonyl chloride (253 mg), the title compound was obtained as a colorless solid (yield 294 mg, 86%).

¹H-NMR (CDCl₃) δ: 2.05 (3H, s), 2.33 (3H, s), 3.40 (3H, s), 6.48 (1H, s), 7.11-7.14 (2H, m), 7.26-7.41 (3H, m), 8.08 (1H, s), 9.93 (1H, s).

Reference Example 68

1-[(5-chloro-1,3-dimethyl-1H-pyrazol-4-yl)sulfonyl]-4-methyl-5-phenyl-1H-pyrrole-3-carbaldehyde By a reaction under similar conditions as in Reference Example 65 and using 4-methyl-5-phenyl-1H-pyrrole-3-carbaldehyde (185 mg), sodium hydride (60% in oil, 60 mg), 15-crown-5 (0.30 mL) and (5-chloro-1,3-dimethyl-1H-pyrazol-4-yl)sulfonyl chloride (298 mg), the title compound was obtained as an oil (yield 379 mg, about 100%).
¹H-NMR (CDCl₃) δ: 1.74 (3H, s), 2.04 (3H, s), 3.69 (3H, s), 7.04-7.07 (2H, m), 7.28-7.38 (3H, m), 8.09 (1H, s), 9.96 (1H, s).

Reference Example 69

1-[(2,4-dimethyl-1,3-thiazol-5-yl)sulfonyl]-4-methyl-5-phenyl-1H-pyrrole-3-carbaldehyde By a reaction under similar conditions as in Reference Example 65 and using 4-methyl-5-phenyl-1H-pyrrole-3-carbaldehyde (185 mg), sodium hydride (60% in oil, 60 mg), 15-crown-5 (0.30 mL) and (2,4-dimethyl-1,3-thiazol-5-yl)sulfonyl chloride (275 mg), the title compound was obtained as an oil (yield 27.8 mg, 8%).
¹H-NMR (CDCl₃) δ: 2.05 (3H, s), 2.10 (3H, s), 2.59 (3H, s), 7.07-7.10 (2H, m), 7.31-7.40 (3H, m), 8.02 (1H, s), 9.96 (1H, s).

Reference Example 70

5-(2-fluorophenyl)-4-methyl-1-(pyridin-3-ylsulfonyl)-1H-pyrrole-3-carbaldehyde

By a similar operation as in Reference Example 65 and using 5-(2-fluorophenyl)-4-methyl-1H-pyrrole-3-carbaldehyde (301 mg), sodium hydride (60% in oil, 179 mg), 15-crown-5 (0.88 mL) and pyridin-3-ylsulfonyl chloride hydrochloride (476 mg), the title compound was obtained as white crystals (yield 440 mg, 87%).
¹H-NMR (CDCl₃) δ: 2.02 (3H, s), 6.98-7.04 (1H, m), 7.13-7.24 (2H, m), 7.33-7.38 (1H, m), 7.43-7.51 (1H, m), 7.65-7.69 (1H, m), 8.09 (1H, s), 8.54-8.55 (1H, m), 8.80-8.82 (1H, m), 9.98 (1H, s).

Reference Example 71

1-[5-bromo-1-(phenylsulfonyl)-1H-pyrrol-3-yl]-N-methylmethanamine

To a solution (60 mL) of 5-bromo-1-(phenylsulfonyl)-1H-pyrrole-3-carbaldehyde (3.5 g) in methanol were added methylammonium chloride (7.5 g) and sodium cyanoborohydride (2.4 g), and the mixture was stirred at room temperature for 1 hr. The reaction mixture was concentrated under reduced pressure, saturated aqueous sodium hydrogencarbonate solution was added to the residue, and the mixture was extracted with ethyl acetate. The extract was washed with saturated aqueous sodium hydrogencarbonate solution, water and saturated brine, dried over anhydrous sodium sulfate, and concentrated under reduced pressure to give the title compound as a brown oil (yield 4.4 g, about 100%).
¹H-NMR (CDCl₃) δ: 2.47 (3H, s), 2.98 (1H, brs), 3.66 (2H, s), 6.35 (1H, d, J=2.4 Hz), 7.51-7.57 (3H, m), 7.61-7.68 (1H, m), 7.93-7.97 (2H, m).

Reference Example 72 tert-butyl{[5-bromo-1-(phenylsulfonyl)-1H-pyrrol-3-yl]methyl}methylcarbamate

To a solution of 1-[5-bromo-1-(phenylsulfonyl)-1H-pyrrol-3-yl]-N-methylmethanamine (4.4 g) in ethyl acetate (60 mL) was added di-tert-butyl bicarbonate (2.8 mL), and the mixture was stirred at room temperature for 14 hr. Saturated aqueous sodium hydrogencarbonate solution was added to the reaction mixture, and the mixture was extracted with ethyl acetate. The extract was washed with aqueous sodium hydrogencarbonate solution and saturated brine, dried over anhydrous sodium sulfate, and concentrated under reduced pressure. The residue was purified by silica gel column chromatography (eluent:hexane-ethyl acetate=4:1) to give the title compound as a colorless oil (yield 3.4 g, 73%).
¹H-NMR (CDCl₃) δ: 1.48 (9H, s), 2.79 (3H, brs), 4.17 (2H, brs), 6.24 (1H, brs), 7.35 (1H, brs), 7.51-7.57 (2H, m), 7.62-7.68 (1H, m), 7.90-7.94 (2H, m).

Reference Example 73 tert-butyl[(5-bromo-1H-pyrrol-3-yl)methyl]methylcarbamate tert-Butyl{[5-bromo-1-(phenylsulfonyl)-1H-pyrrol-3-yl]methyl}methylcarbamate (1.0 g) was dissolved in a mixed solvent of tetrahydrofuran (15 mL) and methanol (5 mL), and 8 mol/L aqueous sodium hydroxide solution (1.5 mL) was added dropwise at not more than 10° C. After stirring at the same temperature for 4 hr, water was added to the residue and the mixture was extracted with ethyl acetate. The extract was washed with saturated brine, dried over anhydrous sodium sulfate, and concentrated under reduced pressure. The residue was purified by basic silica gel column chromatography (eluent:hexane-ethyl acetate=9:1→4:1) to give the title compound as a pale-yellow oil (yield 410 mg, 61%).
¹H-NMR (CDCl₃) δ: 1.48 (9H, s), 2.79 (3H, s), 4.17 (2H, s), 6.09 (1H, brs), 6.64 (1H, brs), 8.07 (1H, br).

Reference Example 74 tert-butyl{[5-bromo-1-(pyridin-3-ylsulfonyl)-1H-pyrrol-3-yl]methyl}methylcarbamate To a suspension (10 mL) of sodium hydride (60% in oil, 204 mg) in tetrahydrofuran was added a solution (3 mL) of tert-butyl[(5-bromo-1H-pyrrol-3-yl)methyl]methylcarbamate (410 mg) in N,N-dimethylformamide at 0° C., and 15-crown-5 (938 mg) and pyridin-3-ylsulfonyl chloride hydrochloride (456 mg) were added at the same temperature. After stirring at room temperature for 2 hr, water was added to the reaction mixture, and the mixture was extracted with ethyl acetate. The extract was washed with saturated aqueous sodium hydrogencarbonate solution, water and saturated brine, dried over anhydrous sodium sulfate, and concentrated under reduced pressure. The residue was purified by silica gel column chromatography (eluent:hexane-ethyl acetate=8:1→3:1) to give the title compound as a pale-yellow powder (yield 522 mg, 85%).

¹H-NMR (CDCl₃) δ: 1.47 (9H, s), 2.80 (3H, brs), 4.18 (2H, brs), 6.28 (1H, brs), 7.35 (1H, brs), 7.48-7.52 (1H, m), 8.18-8.22 (1H, m), 8.85-8.88 (1H, m), 9.12-9.13 (1H, m).

Reference Example 75 tert-butyl{[1-(2-chloro-3-pyridinesulfonyl)-5-phenyl-1H-pyrrol-3-yl]methyl}methylcarbamate 1-(2-Chloro-3-pyridinesulfonyl)-5-phenyl-1H-pyrrole-3-carbaldehyde (443 mg) was dissolved in absolute tetrahydrofuran (5 mL), a 2 mol/L solution (0.74 mL) of methylamine in tetrahydrofuran was added, and the mixture was stirred at room temperature for 30 min. The reaction mixture was added to a solution of sodium borohydride (97 mg) in methanol (2.5 mL), and the mixture was stirred at the same temperature for 20 min. The reaction mixture was diluted with ethyl acetate, washed successively with saturated aqueous sodium hydrogencarbonate solution, water and saturated brine and dried over anhydrous magnesium sulfate, and the solvent was evaporated under reduced pressure. The residue was dissolved in tetrahydrofuran (20 mL), di-tert-butyl bicarbonate (1.40 g), sodium hydrogencarbonate (0.54 g) and water (13 mL) were added, and the mixture was stirred at room temperature for 20 min. The reaction mixture was diluted with ethyl acetate, washed successively with saturated aqueous sodium hydrogencarbonate solution, water and saturated brine and dried over anhydrous magnesium sulfate, and the solvent was evaporated under reduced pressure. The residue was purified by silica gel column chromatography (eluent: hexane-ethyl acetate=19:1→3:1) to give the title compound as a solid (yield 361 mg, 61%).
¹H-NMR (CDCl₃) δ: 1.47 (9H, s), 2.87 (3H, s), 4.29 (2H, s), 6.30-6.32 (1H, m), 6.95-7.00 (1H, m), 7.06-7.33 (5H, m), 7.51-7.56 (2H, m), 8.38-8.41 (1H, m).

Reference Example 76 tert-butyl{[1-(6-chloro-5-methyl-3-pyridinesulfonyl)-5-phenyl-1H-pyrrol-3-yl]methyl}methylcarbamate 1-[(6-Chloro-5-methylpyridin-3-yl)sulfonyl]-5-phenyl-1H-pyrrole-3-carbaldehyde (244 mg) was dissolved in absolute tetrahydrofuran (6.8 mL), a 2 mol/L solution (0.34 mL) of methylamine in tetrahydrofuran was added, and the mixture was stirred at room temperature for 4 hr. The reaction mixture was added to a solution of sodium borohydride (51 mg) in methanol (3 mL), and the mixture was stirred at the same temperature for 3 min. di-tert-Butyl bicarbonate (654 mg) was added, and water (5 mL) and sodium hydrogencarbonate (420 mg) were added 3 min later. The mixture was further stirred at room temperature for 30 min, water was added to the reaction mixture, and the mixture was extracted with ethyl acetate. The extract was washed with saturated brine, dried over anhydrous magnesium sulfate, and the solvent was evaporated under reduced pressure. The residue was purified by silica gel column chromatography (eluent:hexane-ethyl acetate=19:1→3:1) to give the title compound as an oil (yield 247 mg, 77%).
¹H-NMR (CDCl₃) δ: 1.47 (9H, s), 2.28 (3H, s), 2.82 (3H, s), 4.24-4.28 (2H, m), 6.15 (1H, s), 7.23-7.42 (7H, m), 8.15 (1H, s).

Reference Example 77 tert-butyl({[1-(6-chloropyridin-3-yl)sulfonyl]-5-phenyl-1H-pyrrol-3-yl}methyl)methylcarbamate 1-[(6-Chloropyridin-3-yl)sulfonyl]-5-phenyl-1H-pyrrole-3-carbaldehyde (1.27 g) was dissolved in absolute tetrahydrofuran (20 mL), a 2 mol/L solution (2.1 mL) of methylamine in tetrahydrofuran was added, and the mixture was stirred at room temperature for 30 min. The reaction mixture was added to a solution of sodium borohydride (277 mg) in methanol (10 mL), and the mixture was stirred at the same temperature for 20 min. The reaction mixture was diluted with ethyl acetate, washed successively with saturated aqueous sodium hydrogencarbonate solution, water and saturated brine and dried over anhydrous magnesium sulfate. di-tert-Butyl bicarbonate (3.99 g) was added, and the solvent was evaporated under reduced pressure. The residue was dissolved in tetrahydrofuran (30 mL), sodium hydrogencarbonate (1.53 g) and water (36 mL) was added, and the mixture was stirred at room temperature for 30 min. The reaction mixture was diluted with ethyl acetate, washed successively with saturated aqueous sodium hydrogencarbonate solution, water and saturated brine, and dried over anhydrous magnesium sulfate. The solvent was evaporated under reduced pressure and the residue was purified by silica gel column chromatography (eluent:hexane-ethyl acetate=19:1→3:1) to give the title compound as a solid (yield 544 mg, 32%).
¹H-NMR (CDCl₃) δ: 1.47 (9H, s), 2.82 (3H, s), 4.23 (2H, s), 6.16 (1H, s), 7.23-7.49 (8H, m), 8.28 (1H, s).

Reference Example 78 tert-butyl methyl({[1-(6-methylpyridin-3-yl)sulfonyl]-5-phenyl-1H-pyrrol-3-yl}methyl)carbamate Under an argon atmosphere, a mixture of tert-butyl({[1-(6-chloropyridin-3-yl)sulfonyl]-5-phenyl-1H-pyrrol-3-yl}methyl)methylcarbamate (100 mg), methylboronic acid (14 mg), tetrakis(triphenylphosphine)palladium (25 mg), potassium carbonate (90 mg) and dioxane (3 mL) was stirred at 80° C. for 24 hr. Methylboronic acid (14 mg) and tetrakis(triphenylphosphine)palladium (25 mg) were added, and the mixture was stirred at 90° C. for 24 hr. Methylboronic acid (14 mg), tetrakis(triphenylphosphine)palladium (25 mg), potassium carbonate (90 mg) and dioxane (2 mL) were added, and the mixture was stirred at 90° C. for 24 hr. The reaction mixture was diluted with ethyl acetate, washed successively with saturated aqueous sodium hydrogencarbonate solution, water and saturated brine, and dried over anhydrous magnesium sulfate. The solvent was evaporated under reduced pressure and the residue was purified by silica gel column chromatography (eluent:hexane-ethyl acetate=19:1→1:1) to give the title compound as an oil (yield 85.8 mg, 36%).
¹H-NMR (CDCl₃) δ: 1.46 (9H, s), 2.58 (3H, s), 2.81 (3H, s), 4.20-4.23 (2H, m), 6.13 (1H, s), 7.07-7.10 (1H, m), 7.24-7.42 (7H, m), 8.39 (1H, s).

Reference Example 79 tert-butyl methyl{[1-(pyridin-3-ylsulfonyl)-5-(3-thienyl)-1H-pyrrol-3-yl]methyl}carbamate Under an argon atmosphere, a suspension of tert-butyl{[5-bromo-1-(pyridin-3-ylsulfonyl)-1H-pyrrol-3-yl]methyl}methylcarbamate (232 mg), 3-thienylboronic acid (138 mg), tetrakis(triphenylphosphine)palladium (31.3 mg) and sodium carbonate (175 mg) in 1,2-dimethoxyethane (10 mL) and water (5 mL) was stirred at 105° C. for 1 hr. The reaction mixture was allowed to cool to room temperature, water was added to the reaction mixture, and the mixture was extracted with ethyl acetate. The extract was washed with saturated aqueous sodium hydrogencarbonate solution, water and saturated brine, dried over anhydrous sodium sulfate, and concentrated under reduced pressure. The residue was purified by silica gel column chromatography (eluent:hexane-ethyl acetate=1:1) to give the title compound as a pale-yellow oil (yield 189 mg, 81%).

$^1$H-NMR (CDCl$_3$) δ: 1.47 (9H, s), 2.82 (3H, brs), 4.22 (2H, brs), 6.17 (1H, brs), 7.04-7.06 (1H, m), 7.16-7.17 (1H, m), 7.25-7.32 (3H, m), 7.57-7.61 (1H, m), 8.56 (1H, d, J=2.4 Hz), 8.71-8.73 (1H, m).

Reference Example 80 tert-butyl{[5-(4-fluorophenyl)-1-(pyridin-3-ylsulfonyl)-1H-pyrrol-3-yl]methyl}methylcarbamate By a similar operation as in Reference Example 79 and using tert-butyl{[5-bromo-1-(pyridin-3-ylsulfonyl)-1H-pyrrol-3-yl]methyl}methylcarbamate (300 mg), (4-fluorophenyl)boronic acid (195 mg), tetrakis(triphenylphosphine)palladium (40 mg) and sodium carbonate (222 mg), the title compound was obtained as a pale-yellow oil (yield 293 mg, 94%).

$^1$H-NMR (CDCl$_3$) δ: 1.47 (9H, s), 2.81 (3H, brs), 4.22 (2H, brs), 6.12 (1H, brs), 7.00-7.06 (2H, m), 7.18-7.31 (4H, m), 7.56-7.60 (1H, m), 8.54-8.55 (1H, m), 8.73-8.75 (1H, m).

Reference Example 81 tert-butyl methyl{[5-(2-methylphenyl)-1-(pyridin-3-ylsulfonyl)-1H-pyrrol-3-yl]methyl}carbamate By a similar operation as in Reference Example 79 and using tert-butyl{[5-bromo-1-(pyridin-3-ylsulfonyl)-1H-pyrrol-3-yl]methyl}methylcarbamate (300 mg), (2-methylphenyl)boronic acid (190 mg), tetrakis(triphenylphosphine)palladium (40 mg) and sodium carbonate (222 mg), the title compound was obtained as a pale-yellow oil (yield 210 mg, 68%). More specifically, a suspension of tert-butyl{[5-bromo-1-(pyridin-3-ylsulfonyl)-1H-pyrrol-3-yl]methyl}methylcarbamate (300 mg), (2-methylphenyl)boronic acid (190 mg), tetrakis(triphenylphosphine)palladium (40 mg) and sodium carbonate (222 mg) in 1,2-dimethoxyethane (10 mL) and water (7.5 mL) was stirred at 105° C. for 18 hr. The reaction mixture was allowed to cool to room temperature, water was added to the reaction mixture, and the mixture was extracted with ethyl acetate. The extract was washed with saturated aqueous sodium hydrogencarbonate solution, water and saturated brine, dried over anhydrous sodium sulfate, and concentrated under reduced pressure. The residue was purified by silica gel column chromatography (eluent:hexane-ethyl acetate=7:1→3:1) to give the title compound as a pale-yellow oil (yield 210 mg, 68%).

$^1$H-NMR (CDCl$_3$) δ: 1.47 (9H, s), 1.92 (3H, s), 2.84 (3H, brs), 4.26 (2H, brs), 6.07 (1H, d, J=1.2 Hz), 6.87-6.89 (1H, m), 7.09-7.19 (2H, m), 7.26-7.35 (3H, m), 7.58-7.62 (1H, m), 8.54-8.55 (1H, m), 8.75-8.77 (1H, m).

Reference Example 82 tert-butyl{[5-(4-fluoro-2-methylphenyl)-1-(pyridin-3-ylsulfonyl)-1H-pyrrol-3-yl]methyl}methylcarbamate By a similar operation as in Reference Example 79 and using tert-butyl{[5-bromo-1-(pyridin-3-ylsulfonyl)-1H-pyrrol-3-yl]methyl}methylcarbamate (300 mg), (4-fluoro-2-methylphenyl)boronic acid (215 mg), tetrakis(triphenylphosphine)palladium (40 mg) and sodium carbonate (222 mg), the title compound was obtained as a pale-yellow oil (yield 216 mg, 67%).

$^1$H-NMR (CDCl$_3$) δ: 1.47 (9H, s), 1.92 (3H, s), 2.84 (3H, brs), 4.25 (2H, brs), 6.05 (1H, br), 6.79-6.91 (3H, m), 7.30-7.35 (2H, m), 7.61-7.65 (1H, m), 8.58-8.59 (1H, m), 8.77-8.79 (1H, m).

Reference Example 83 tert-butyl methyl{[5-(4-methyl-3-thienyl)-1-(pyridin-3-ylsulfonyl)-1H-pyrrol-3-yl]methyl}carbamate By a similar operation as in Reference Example 79 and using tert-butyl{[5-bromo-1-(pyridin-3-ylsulfonyl)-1H-pyrrol-3-yl]methyl}methylcarbamate (300 mg), (4-methyl-3-thienyl)boronic acid (198 mg), tetrakis(triphenylphosphine)palladium (40 mg) and sodium carbonate (222 mg), the title compound was obtained as a pale-yellow oil (yield 200 mg, 64%). More specifically, a suspension of tert-butyl{[5-bromo-1-(pyridin-3-ylsulfonyl)-1H-pyrrol-3-yl]methyl}methylcarbamate (300 mg), (4-methyl-3-thienyl)boronic acid (198 mg), tetrakis(triphenylphosphine)palladium (40 mg) and sodium carbonate (222 mg) in 1,2-dimethoxyethane (10 mL) and water (7.5 mL) was stirred at 105° C. for 18 hr. The reaction mixture was allowed to cool to room temperature, water was added to the reaction mixture, and the mixture was extracted with ethyl acetate. The extract was washed with saturated aqueous sodium hydrogencarbonate solution, water and saturated brine, dried over anhydrous sodium sulfate, and concentrated under reduced pressure. The residue was purified by silica gel column chromatography (eluent:hexane-ethyl acetate=6:1→3:1) to give the title compound as a pale-yellow oil (yield 200 mg, 64%).

$^1$H-NMR (CDCl$_3$) δ: 1.47 (9H, s), 1.81 (3H, s), 2.83 (3H, brs), 4.26 (2H, brs), 6.10 (1H, br), 6.90 (1H, br), 7.02-7.03 (1H, m), 7.26-7.35 (2H, m), 7.61-7.65 (1H, m), 8.58-8.59 (1H, m), 8.75-8.77 (1H, m).

Reference Example 84 tert-butyl{[5-(3-cyanophenyl)-1-(pyridin-3-ylsulfonyl)-1H-pyrrol-3-yl]methyl}methylcarbamate By a similar operation as in Reference Example 79 and using tert-butyl{[5-bromo-1-(pyridin-3-ylsulfonyl)-1H-pyrrol-3-yl]methyl}methylcarbamate (300 mg), (3-cyanophenyl)boronic acid (205 mg), tetrakis(triphenylphosphine)palladium (40 mg) and sodium carbonate (222 mg), the title compound was obtained as a pale-yellow oil (yield 298 mg, 94%).

$^1$H-NMR (CDCl$_3$) δ: 1.47 (9H, s), 2.81 (3H, brs), 4.22 (2H, brs), 6.21 (1H, br), 7.31-7.35 (2H, m), 7.46-7.69 (6H, m), 8.56 (1H, d, J=1.8 Hz), 8.76-8.78 (1H, m)

Reference Example 85 tert-butyl{[5-(2-chlorophenyl)-1-(pyridin-3-ylsulfonyl)-1H-pyrrol-3-yl]methyl}methylcarbamate By a similar operation as in Reference Example 79 and using tert-butyl{[5-bromo-1-(pyridin-3-ylsulfonyl)-1H-pyrrol-3-yl]methyl}methylcarbamate (300 mg), (2-chlorophenyl)boronic acid (218 mg), tetrakis(triphenylphosphine)palladium (40 mg) and sodium carbonate (222 mg), the title compound was obtained as a pale-blue oil (yield 171 mg, 53%).

¹H-NMR (CDCl₃) δ: 1.47 (9H, s), 2.84 (3H, brs), 4.26 (2H, brs), 6.20 (1H, d, J=1.8 Hz), 7.26-7.36 (6H, m), 7.65-7.71 (1H, m), 8.58-8.59 (1H, m), 8.75-8.79 (1H, m).

Reference Example 86 tert-butyl{[5-(2,4-difluorophenyl)-1H-pyrrol-3-yl]methyl}methylcarbamate

By a similar operation as in Reference Example 79 and using tert-butyl{[5-bromo-1-(pyridin-3-ylsulfonyl)-1H-pyrrol-3-yl]methyl}methylcarbamate (300 mg), (2,4-difluorophenyl)boronic acid (198 mg), tetrakis(triphenylphosphine)palladium (40 mg) and sodium carbonate (220 mg), the title compound was obtained as a colorless oil (yield 113 mg, 50%).
¹H-NMR (CDCl₃) δ: 1.50 (9H, s), 2.84 (3H, brs), 4.30 (2H, brs), 6.49 (1H, br), 6.78-6.92 (3H, m), 7.48-7.58 (1H, m), 8.78 (1H, br).

Reference Example 87 tert-butyl{[5-(2,5-difluorophenyl)-1H-pyrrol-3-yl]methyl}methylcarbamate

By a similar operation as in Reference Example 79 and using tert-butyl{[5-bromo-1-(pyridin-3-ylsulfonyl)-1H-pyrrol-3-yl]methyl}methylcarbamate (300 mg), (2,5-difluorophenyl)boronic acid (220 mg), tetrakis(triphenylphosphine)palladium (40 mg) and sodium carbonate (220 mg), the title compound was obtained as a colorless oil (yield 135 mg, 60%).
¹H-NMR (CDCl₃) δ: 1.50 (9H, s), 2.84 (3H, brs), 4.30 (2H, brs), 6.56 (1H, br), 6.77-6.85 (2H, m), 7.00-7.08 (1H, m), 7.20-7.26 (1H, m), 8.90 (1H, br).

Reference Example 88 tert-butyl{[5-(4-chloro-2-fluorophenyl)-1H-pyrrol-3-yl]methyl}methylcarbamate

By a similar operation as in Reference Example 79 and using tert-butyl{[5-bromo-1-(pyridin-3-ylsulfonyl)-1H-pyrrol-3-yl]methyl}methylcarbamate (300 mg), (4-chloro-2-fluorophenyl)boronic acid (243 mg), tetrakis(triphenylphosphine)palladium (40 mg) and sodium carbonate (220 mg), the title compound was obtained as a colorless oil (yield 127 mg, 54%).
¹H-NMR (CDCl₃) δ: 1.50 (9H, s), 2.84 (3H, s), 4.30 (2H, s), 6.55 (1H, br), 6.80 (1H, br), 7.11-7.15 (2H, m), 7.46-7.52 (1H, m), 8.82 (1H, br).

Reference Example 89 tert-butyl{[5-(2,4-difluorophenyl)-1-(pyridin-3-ylsulfonyl)-1H-pyrrol-3-yl]methyl}methylcarbamate By a similar operation as in Reference Example 44 and using tert-butyl{[5-(2,4-difluorophenyl)-1H-pyrrol-3-yl]methyl}methylcarbamate (113 mg), sodium hydride (60% in oil, 51 mg), 15-crown-5 (0.21 mL) and pyridine-3-ylsulfonyl chloride hydrochloride (113 mg), the title compound was obtained as a pale-yellow oil (yield 110 mg, 68%).
¹H-NMR (CDCl₃) δ: 1.46 (9H, s), 2.82 (3H, brs), 4.24 (2H, brs), 6.19 (1H, br), 6.77-6.92 (2H, m), 7.11-7.19 (1H, m), 7.33-7.37 (2H, m), 7.68-7.72 (1H, m), 8.62 (1H, d, J=2.4 Hz), 8.77-8.79 (1H, m).

Reference Example 90 tert-butyl{[5-(2,5-difluorophenyl)-1-(pyridin-3-ylsulfonyl)-1H-pyrrol-3-yl]methyl}methylcarbamate By a similar operation as in Reference Example 44 and using tert-butyl{[5-(2,5-difluorophenyl)-1H-pyrrol-3-yl]methyl}methylcarbamate (135 mg), sodium hydride (60% in oil, 60 mg), 15-crown-5 (0.25 mL) and pyridin-3-ylsulfonyl chloride hydrochloride (135 mg), the title compound was obtained as a colorless oil (yield 105 mg, 54%).
¹H-NMR (CDCl₃) δ: 1.50 (9H, s), 2.82 (3H, s), 4.23 (2H, brs), 6.24 (1H, br), 6.89-7.13 (4H, m), 7.33-7.39 (2H, m), 7.71-7.75 (1H, m), 8.67 (1H, d, J=2.4 Hz), 8.78-8.80 (1H, m).

Reference Example 91 tert-butyl{[5-(4-chloro-2-fluorophenyl)-1-(pyridin-3-ylsulfonyl)-1H-pyrrol-3-yl]methyl}methylcarbamate By a similar operation as in Reference Example 44 and using tert-butyl{[5-(4-chloro-2-fluorophenyl)-1H-pyrrol-3-yl]methyl}methylcarbamate (127 mg), sodium hydride (60% in oil, 54 mg), 15-crown-5 (0.22 mL) and pyridin-3-ylsulfonyl chloride hydrochloride (120 mg), the title compound was obtained as a colorless oil (yield 103 mg, 57%).
¹H-NMR (CDCl₃) δ: 1.46 (9H, s), 2.81 (3H, s), 4.23 (2H, brs), 6.21 (1H, brs), 7.08-7.15 (4H, m), 7.32-7.38 (2H, m), 7.69-7.73 (1H, m), 8.64 (1H, d, J=2.4 Hz), 8.77-8.79 (1H, m).

Reference Example 92 tert-butyl{[5-(3-fluorophenyl)-1-(pyridin-3-ylsulfonyl)-1H-pyrrol-3-yl]methyl}methylcarbamate By a similar operation as in Reference Example 79 and using tert-butyl{[5-bromo-1-(pyridin-3-ylsulfonyl)-1H-pyrrol-3-yl]methyl}methylcarbamate (300 mg), (3-fluorophenyl)boronic acid (195 mg), tetrakis(triphenylphosphine)palladium (40 mg) and sodium carbonate (222 mg), the title compound was obtained as a pale-yellow oil (yield 280 mg, 90%).
¹H-NMR (CDCl₃) δ: 1.47 (9H, s), 2.81 (3H, brs), 4.22 (2H, brs), 6.16 (1H, brs), 6.93-7.11 (3H, m), 7.27-7.32 (3H, m), 7.59-7.63 (1H, m), 8.58 (1H, d, J=2.1 Hz), 8.73-8.75 (1H, m).

Reference Example 93 tert-butyl{[5-bromo-2-methyl-1-(pyridin-3-ylsulfonyl)-1H-pyrrol-3-yl]methyl}methylcarbamate 5-Bromo-2-methyl-1-(pyridin-3-ylsulfonyl)-1H-pyrrole-3-carbaldehyde (565 mg) was dissolved in tetrahydrofuran (2 mL) and methanol (2 mL), a 40% solution (1.5 mL) of methylamine methanol was added at room temperature and the mixture was stirred for 30 min. Sodium borohydride (130 mg) was added to the reaction mixture at room temperature and the mixture was stirred for 15 min. The reaction mixture was concentrated under reduced pressure, a saturated aqueous sodium hydrogencarbonate solution was added to the residue, and the mixture was extracted with ethyl acetate. The extract was washed with saturated aqueous sodium hydrogencarbonate solution, water and saturated brine, dried over anhydrous sodium sulfate, and the solvent was evaporated under reduced pressure. The residue was dissolved in ethyl acetate (6 mL), di-tert-butyl bicarbonate (0.45 mL) was added, and the mixture was stirred at room temperature for 1 hr. To the reaction mixture was added 1 mol/L hydrochloric acid (10 mL), and the mixture was further stirred for 15 min. The reaction mixture was neutralized with saturated aqueous sodium hydrogencarbonate solution, and extracted with ethyl acetate. The extract was washed with saturated aqueous sodium hydrogencarbonate solution, water and saturated brine, dried over anhydrous sodium sulfate, and the solvent was evaporated under reduced pressure. The residue was purified by silica gel column chromatography (eluent:hexane-ethyl acetate=4:1→1:1) to give a mixture of the title compound and 5-bromo-2-methyl-1-(pyridin-3-ylsulfonyl)-1H-pyrrole-3-carbaldehyde. The mixture was dissolved in tetrahydrofuran (5 mL), a 2 mol/L solution (4 mL) of methylamine in tetrahydrofuran was added, and the mixture was stirred at room temperature for 12 hr. To the reaction mixture was added a solution of sodium borohydride (131 mg) in methanol (1 mL), and the mixture was stirred for 1 hr. The reaction mixture was concentrated under reduced pressure, a saturated aqueous sodium hydrogencarbonate solution was added to the residue, and the mixture was extracted with ethyl acetate. The extract was washed with saturated aqueous sodium hydrogencarbonate solution, water and saturated brine, dried over anhydrous sodium sulfate, and the solvent was evaporated under reduced pressure. The residue was dissolved in ethyl acetate (6 mL), di-tert-butyl bicarbonate (0.45 mL) was added, and the mixture was stirred at room temperature for 1 hr. Saturated aqueous sodium hydrogencarbonate solution was added to the reaction mixture, and the mixture was extracted with ethyl acetate. The extract was washed with saturated aqueous sodium hydrogencarbonate solution, water and saturated brine, dried over anhydrous sodium sulfate, and the solvent was evaporated under reduced pressure. The residue was purified by silica gel column chromatography (eluent:hexane-ethyl acetate=2:1) to give the title compound as a yellow oil (yield 384 mg, 50%).

$^1$H-NMR (CDCl$_3$) δ: 1.46 (9H, s), 2.49 (3H, s), 2.71 (3H, brs), 4.15 (2H, brs), 6.24 (1H, brs), 7.47-7.52 (1H, m), 8.13-8.17 (1H, m), 8.84-8.86 (1H, m), 9.07-9.08 (1H, m).

Reference Example 94

2-bromo-1-(2,6-difluorophenyl)ethanone

To a solution of 1-(2,6-difluorophenyl)ethanone (10.0 g) in diethyl ether (50 mL) was added anhydrous aluminum chloride (86 mg) and the mixture was stirred for 5 min. Bromine (3.3 mL) was added dropwise at 10-15° C. After stirring at room temperature for 2 hr, the mixture was poured into water, and the mixture was extracted with ethyl acetate. The obtained organic layer was washed with saturated brine, dried over anhydrous magnesium sulfate, concentrated under reduced pressure to give the title compound as a pale-yellow oil (yield 15.2 g, about 100%).

$^1$H-NMR (CDCl$_3$) δ: 4.37 (2H, s), 6.97-7.04 (2H, m), 7.43-7.53 (1H, m).

Reference Example 95 ethyl 2-cyano-4-(2,6-difluorophenyl)-4-oxobutanoate

To a solution of ethyl cyanoacetate (7.24 g) and diisopropylethylamine (19.9 g) in tetrahydrofuran (30 mL) was added dropwise a solution of 2-bromo-1-(2,6-difluorophenyl)ethanone (15.16 g) in tetrahydrofuran (15 mL) at 10-15° C. The mixture was stirred at room temperature for 12 hr. The reaction mixture was filtered, and the obtained filtrate was concentrated under reduced pressure. The residue was dissolved in ethyl acetate, washed successively with water, 1 mol/L hydrochloric acid and saturated brine, dried over anhydrous magnesium sulfate, and concentrated under reduced pressure. The residue was purified by silica gel column chromatography (eluent:hexane-ethyl acetate=4:1→3:2) to give the title compound as a pale-green oil (yield 13.8 g, 81%).

$^1$H-NMR (CDCl$_3$) δ: 1.35 (3H, t, J=7.1 Hz), 3.44-3.53 (1H, m), 3.63-3.72 (1H, m), 4.13-4.18 (1H, m), 4.31 (2H, q, J=7.1 Hz), 6.95-7.05 (2H, m), 7.44-7.54 (1H, m).

Reference Example 96 methyl 2-cyano-4-(4-cyclohexylphenyl)-4-oxobutanoate

4-Cyclohexylacetophenone (10.0 g) was dissolved in chloroform (30 mL) and diethyl ether (30 mL), and bromine (8.70 g) was slowly added dropwise. After completion of the dropwise addition, the reaction mixture was stirred at room temperature for 1 hr, diluted with water and extracted with chloroform. The extract was washed with water, dried over anhydrous magnesium sulfate, and concentrated under reduced pressure to give crude 2-bromo-1-(5-cyclohexylpyridin-2-yl)ethanone (15.8 g) as an oil. This was dissolved in tetrahydrofuran (20 mL), and added dropwise to a mixture of methyl cyanoacetate (4.95 g), diisopropylethylamine (16.2 g) and tetrahydrofuran (50 mL). The reaction mixture was stirred at room temperature for 20 hr, the insoluble material was filtered off, and the filtrate was concentrated under reduced pressure. The residue was dissolved in ethyl acetate, washed with saturated brine, dried over anhydrous magnesium sulfate, and concentrated under reduced pressure. The residue was purified by silica gel column chromatography (eluent: hexane-ethyl acetate=4:1→3:1) to give the title compound as an oil (yield 12.1 g, 82%).

$^1$H-NMR (CDCl$_3$) δ: 1.20-1.51 (5H, m), 1.70-1.90 (5H, m), 2.51-2.64 (1H, m), 3.47-3.73 (1H, m), 3.58-3.88 (1H, m), 3.85 (3H, s), 4.09-4.19 (1H, m), 7.32 (2H, d, J=8.1 Hz), 7.89 (2H, d, J=8.1 Hz).

Reference Example 97 ethyl 2-chloro-5-(2,6-difluorophenyl)-1H-pyrrole-3-carboxylate

A solution (14 mL) of ethyl 2-cyano-4-(2,6-difluorophenyl)-4-oxobutanoate (13.83 g) in ethyl acetate was added dropwise to 4 mol/L hydrogen chloride-ethyl acetate solution (100 mL) at 10-15° C. The mixture was stirred at room temperature for 12 hr, and concentrated under reduced pressure. The residue was purified by silica gel column chromatography (eluent:hexane-ethyl acetate=9:1→8:2) to give the title compound as yellow crystals (yield 10.0 g, 68%).

$^1$H-NMR (CDCl$_3$) δ: 1.38 (3H, t, J=7.2 Hz), 4.34 (2H, q, J=7.2 Hz), 6.95-7.04 (2H, m), 7.14-7.23 (2H, m), 9.20 (1H, br).

Reference Example 98 methyl 2-chloro-5-(4-cyclohexylphenyl)-1H-pyrrole-3-carboxylate

14% Hydrogen chloride-1,4-dioxane solution (50 mL) was added to methyl 2-cyano-4-(4-cyclohexylphenyl)-4-oxobutanoate (12.1 g) and the mixture was stirred at room temperature for 8 hr and concentrated under reduced pressure. The residue was dissolved in ethyl acetate, washed with saturated brine, dried over anhydrous magnesium sulfate, and concentrated under reduced pressure. The residue was crystallized from diisopropyl ether and collected by filtration to give a nearly 1:1 mixture (3.41 g) of the title compound and methyl 2-amino-5-(4-cyclohexylphenyl)-3-furoate. The filtrate was concentrated under reduced pressure, and the residue was purified by silica gel column chromatography (eluent: hexane-ethyl acetate=7:2) to give the title compound as crystals (yield 0.64 g, 5%).

$^1$H-NMR (CDCl$_3$) δ: 1.22-1.48 (5H, m), 1.71-1.91 (5H, m), 2.46-2.58 (1H, m), 3.86 (3H, s), 6.81 (1H, d, J=3.2 Hz), 7.23 (2H, d, J=8.3 Hz), 7.36 (2H, d, J=8.3 Hz), 8.67 (1H, brs).

Reference Example 99 methyl 2-chloro-4-fluoro-5-phenyl-1H-pyrrole-3-carboxylate

To a suspension of methyl 2-chloro-5-phenyl-1H-pyrrole-3-carboxylate (4.66 g) synthesized from methyl cyanoacetate and phenacyl bromide in the same manner as in Reference Example 95 and Reference Example 97 in acetonitrile (200 mL) was added 2,6-dichloro-N-fluoropyridinium triflate (6.26 g) over 10 min under ice-cooling. The reaction mixture was stirred at the same temperature for 2 hr and at room temperature for 2 hr, and concentrated under reduced pressure. A saturated aqueous sodium hydrogencarbonate solution was added to the residue, and the mixture was extracted with ethyl acetate. The extract was dried over magnesium sulfate, and concentrated under reduced pressure. The residue was purified by silica gel column chromatography (eluent: hexane-ethyl acetate=19:1→7:3) to give the title compound as a pale-yellow solid (yield 815 mg, 16%). More specifically, to a solution of methyl cyanoacetate (41 g) and diisopropylethylamine (117 g) in tetrahydrofuran (2600 mL) was added dropwise a solution of phenacyl bromide (75 g) in tetrahydrofuran (370 mL). The mixture was stirred at room temperature for 12 hr. The reaction mixture was filtered, and the obtained filtrate was concentrated under reduced pressure. The residue was dissolved in ethyl acetate, washed successively with 1 mol/L hydrochloric acid, water and saturated brine, dried over anhydrous sodium sulfate, and concentrated under reduced pressure. The residue was washed with diethyl ether to give methyl 2-cyano-4-phenyl-4-oxobutanoate as a brown oil (yield 77.4 g, 95%). To a solution (125 mL) of ethyl 2-cyano-4-(2,6-difluorophenyl)-4-oxobutanoate (25 g) in ethyl acetate was added dropwise 4 mol/L hydrogen chloride-ethyl acetate solution (25 mL). The mixture was stirred at room temperature for 18 hr, and concentrated under reduced pressure. Water was added to the residue, and the mixture was extracted with ethyl acetate. The organic layer was washed with 6% aqueous sodium hydrogencarbonate solution and saturated brine, dried over anhydrous sodium sulfate, and concentrated under reduced pressure. The residue was washed with diisopropyl ether to give methyl 2-chloro-5-phenyl-1H-pyrrole-3-carboxylate as colorless crystals (yield 10.0 g, 37%). The title compound was synthesized from the thus-obtained methyl 2-chloro-5-phenyl-1H-pyrrole-3-carboxylate.

$^1$H-NMR (CDCl$_3$) δ: 3.90 (3H, s), 7.26-7.32 (1H, m), 7.40-7.60 (4H, m), 8.29 (1H, br).

Reference Example 100 ethyl 5-(2,6-difluorophenyl)-1H-pyrrole-3-carboxylate

To a solution of ethyl 2-chloro-5-(2,6-difluorophenyl)-1H-pyrrole-3-carboxylate (9.82 g) in ethanol (200 mL) was added 10% palladium carbon (50% containing water, 4.91 g), and the mixture was stirred under a hydrogen atmosphere at 40° C. for 72 hr. The reaction mixture was filtered, and the filtrate was concentrated under reduced pressure. The residue was purified by silica gel column chromatography (eluent: hexane-ethyl acetate=4:1) to give the title compound as colorless crystals (yield 3.80 g, 24%).

$^1$H-NMR (CDCl$_3$) δ: 1.37 (3H, t, J=7.2 Hz), 4.32 (2H, q, J=7.2 Hz), 6.94-7.04 (2H, m), 7.11-7.21 (1H, m), 7.24-7.27 (1H, m), 7.54-7.55 (1H, m) 9.37 (1H, br).

Reference Example 101 methyl 5-(4-cyclohexylphenyl)-1H-pyrrole-3-carboxylate

To a solution of a nearly 1:1 mixture (3.41 g) of methyl 2-chloro-5-(4-cyclohexylphenyl)-1H-pyrrole-3-carboxylate and methyl 2-amino-5-(4-cyclohexylphenyl)-3-furoate in methanol (30 mL) and ethyl acetate (10 mL) was added 10% palladium carbon (50% containing water, 0.34 g), and the mixture was stirred under a hydrogen atmosphere at 50° C. for 14 hr. The reaction mixture was filtered, and the filtrate was concentrated under reduced pressure. The residue was purified by silica gel column chromatography (eluent:hexane-ethyl acetate=3:1→2:1) to give the title compound as crystals (yield 1.25 g, 41%).

$^1$H-NMR (CDCl$_3$) δ: 1.19-1.50 (5H, m), 1.73-1.93 (5H, m), 2.43-2.57 (1H, m), 3.84 (3H, s), 6.86 (1H, s), 7.24 (2H, d, J=8.3 Hz), 7.41 (2H, d, J=8.3 Hz), 7.45 (1H, dd, J=3.0, 1.7 Hz), 8.73 (1H, brs).

Reference Example 102 methyl 4-fluoro-5-phenyl-1H-pyrrole-3-carboxylate

Methyl 2-chloro-4-fluoro-5-phenyl-1H-pyrrole-3-carboxylate (0.92 mg), 10% palladium carbon (50% containing water, 0.20 g) and triethylamine (0.56 mL) were suspended in methanol (30 mL), and the mixture was stirred under a hydrogen atmosphere at room temperature for 2 hr. The reaction mixture was filtered through celite, and the insoluble material was washed with ethyl acetate. The filtrate was concentrated under reduced pressure and the residue was purified by silica gel column chromatography (eluent:hexane-ethyl acetate=19:1→1:1) to give the title compound as a colorless solid (yield 0.69 g, 87%).

$^1$H-NMR (CDCl$_3$) δ: 3.87 (3H, s), 7.24-7.31 (2H, m), 7.39-7.46 (2H, m), 7.51-7.54 (2H, m), 8.32 (1H, br).

Reference Example 103

[5-(2,6-difluorophenyl)-1H-pyrrol-3-yl]methanol

A solution (35 mL) of ethyl 5-(2,6-difluorophenyl)-1H-pyrrole-3-carboxylate (3.35 g) in tetrahydrofuran was cooled to −50° C., and a 1.5 mol/L solution (30 mL) of diisobutylaluminum hydride in toluene was added dropwise by small portions. The mixture was stirred at the same temperature for 1 hr, water was added to the reaction mixture, and the mixture was stirred at room temperature for 1 hr. The reaction mixture was diluted with ethyl acetate, celite and anhydrous magnesium sulfate were added and the mixture was further stirred for 15 min. The suspension was filtrated, and the obtained filtrate was concentrated under reduced pressure to give the title compound as pale-red crystals (yield 2.70 g, 97%).

$^1$H-NMR (CDCl$_3$) δ: 1.46 (1H, br), 4.64 (2H, s), 6.88-7.02 (4H, m), 7.06-7.16 (1H, m), 9.07 (1H, br).

Reference Example 104

[5-(4-cyclohexylphenyl)-1H-pyrrol-3-yl]methanol

To a solution of methyl 5-(4-cyclohexylphenyl)-1H-pyrrole-3-carboxylate (3.0 g) in absolute tetrahydrofuran (40 mL) was added dropwise a 1.5 mol/L solution (21.0 mL) of diisobutylaluminum hydride in toluene at −78° C. The mixture was further stirred at the same temperature for 2 hr. To the reaction mixture was added 1 mol/L hydrochloric acid, and the mixture was diluted with ethyl acetate. The insoluble material was filtered off through celite, and the filtrate was extracted with ethyl acetate. The extract was washed with saturated brine, dried over anhydrous magnesium sulfate, and concentrated under reduced pressure. The residue was purified by silica gel column chromatography (eluent:hexane-ethyl acetate=1:1) to give the title compound as crystals (yield 1.07 g, 40%).

$^1$H-NMR (CDCl$_3$) δ: 1.16-1.50 (5H, m), 1.69-1.93 (5H, m), 2.45-2.55 (1H, m), 4.60 (2H, s), 6.45-6.51 (1H, m), 6.81-6.86 (1H, m), 7.21 (2H, d, J=8.3 Hz), 7.39 (2H, d, J=8.3 Hz), 8.30 (1H, br), 1H not detected.

Reference Example 105

5-(2,6-difluorophenyl)-1H-pyrrole-3-carbaldehyde

To a solution (26 mL) of [5-(2,6-difluorophenyl)-1H-pyrrol-3-yl]methanol (2.56 g) in acetonitrile were added tetra-n-propylammonium perruthenate (430 mg), N-methylmorpholine N-oxide (2.15 g) and molecular sieves 4A powder (5 g), and the mixture was stirred at room temperature for 2 hr. The reaction mixture was diluted with ethyl acetate (60 mL) and filtered through celite. The filtrate was concentrated under reduced pressure. The residue was purified by silica gel column chromatography (eluent:hexane-ethyl acetate=1:1) to give the title compound as pale-red crystals (yield 1.94 g, 77%).

$^1$H-NMR (CDCl$_3$) δ: 6.97-7.06 (2H, m), 7.16-7.24 (1H, m), 7.28-7.31 (1H, m), 7.56-7.58 (1H, m), 9.55 (1H, br), 9.88 (1H, s).

Reference Example 106

5-(4-cyclohexylphenyl)-1H-pyrrole-3-carbaldehyde

To a solution (35 mL) of [5-(4-cyclohexylphenyl)-1H-pyrrol-3-yl]methanol (1.00 g) in acetonitrile were added tetra-n-propylammonium perruthenate (115 mg), N-methylmorpholine N-oxide (0.60 g) and molecular sieves 4A powder (1.15 g) under ice-cooling. The mixture was stirred at room temperature for 1.5 hr, and the reaction mixture was suspended in ethyl acetate, and filtered through celite. The filtrate was concentrated under reduced pressure, and the residue was purified by silica gel column chromatography (eluent:hexane-ethyl acetate=2:1) to give the title compound as crystals (yield 0.53 g, 53%).

$^1$H-NMR (CDCl$_3$) δ: 1.17-1.49 (5H, m), 1.70-1.95 (5H, m), 2.45-2.58 (1H, m), 6.89 (1H, s), 7.25 (2H, d, J=8.1 Hz), 7.43 (2H, d, J=8.1 Hz), 7.47 (1H, s), 8.99 (1H, brs), 9.82 (1H, s).

Reference Example 107

1H-pyrrole-3-carbaldehyde

To a suspension of sodium hydride (13.7 g) in tetrahydrofuran (450 mL) was added dropwise pyrrole (17.4 g) under ice-cooling. The reaction mixture was stirred at the same temperature for 1.5 hr, and triisopropylsilyl chloride (50.0 g) was added dropwise at the same temperature. The mixture was further stirred at below 10° C. for 1.5 hr, ice water was added and the mixture was extracted with diethyl ether. The extract was washed with water, dried over anhydrous sodium sulfate, and concentrated under reduced pressure. A solution of the residue (57.7 g) in dichloromethane (30 mL) was added at once to a suspension of (chloromethylene)dimethylammonium chloride (36.5 g) in dichloromethane (500 mL) at 0° C. The reaction mixture was refluxed for 30 min and cooled to 0° C. The resulting solid was collected by filtration, and washed with diethyl ether. The obtained solid was dissolved in water (50 mL), a 1 mol/L aqueous sodium hydroxide solution (500 mL) was added at room temperature, and the mixture was stirred for 2 hr. The reaction mixture was extracted with chloroform and ethyl acetate. The extract was dried over anhydrous sodium sulfate, and concentrated under reduced pressure. The residue was washed with diisopropyl ether to give the title compound as pale-brown crystals (yield 9.4 g, 38%).

$^1$H-NMR (CDCl$_3$) δ: 6.68-6.70 (1H, m), 6.83-6.86 (1H, m), 7.45-7.47 (1H, m), 9.00-9.20 (1H, m), 9.82 (1H, s).

Reference Example 108

2-chloro-2,2-difluoro-1-(2-methylphenyl)ethanone

Magnesium (flake, 6.2 g) was suspended in diethyl ether (10 mL), and iodine (small amount) was added and a solution of 2-bromotoluene (43.26 g) in diethyl ether (100 mL) were slowly added dropwise. After stirring at room temperature for 1 hr, the reaction mixture was added dropwise to a solution of chlorodifluoroacetic acid (10.0 g) in diethyl ether (100 mL) at −10° C., and the mixture was stirred at 0° C. for 1 hr. Saturated aqueous ammonium chloride solution was added to the reaction mixture, and the mixture was extracted with diethyl ether. The extract was washed with saturated brine, dried over magnesium sulfate, and concentrated under reduced pressure. The residue was distilled under reduced pressure (boiling point: 81-82° C./12-13 mmHg) to give the title compound as a pale-yellow oil (yield 4.9 g, 31%).

$^1$H-NMR (CDCl$_3$) δ: 2.54 (3H, s), 7.29-7.36 (2H, m), 7.47-7.53 (1H, m), 7.89-7.92 (1H, m).

Reference Example 109

2,2-difluoro-2-iodo-1-(2-methylphenyl)ethanone

To a suspension of zinc (1.6 g) in acetonitrile (40 mL) were added trimethylsilyl chloride (3.1 mL) and 2-chloro-2,2-difluoro-1-(2-methylphenyl)ethanone (4.0 g), and the mixture was stirred at 55° C. for 3 hr. The reaction mixture was allowed to cool to room temperature, iodine (3.5 g) was added, and the mixture was further stirred for 2 hr. Water was added to the reaction mixture, and the mixture was extracted with diethyl ether. The extract was washed with aqueous sodium hydrogen sulfite solution, aqueous sodium hydrogencarbonate solution and saturated brine, dried over anhydrous sodium sulfate, and concentrated under reduced pressure. The residue was purified by basic silica gel column chromatography (eluent: hexane) to give the title compound as a yellow oil (yield 2.6 g, 46%).

$^1$H-NMR (CDCl$_3$) δ: 2.51 (3H, s), 7.26-7.35 (2H, m), 7.46-7.51 (1H, m), 7.91-7.94 (1H, m).

Reference Example 110

2,2-difluoro-4-iodo-1-(2-methylphenyl)-4-trimethyl-silylbutan-1-one

Under a nitrogen atmosphere, to a mixture of tetrakis(triphenylphosphine)palladium (0.52 g) and vinyltrimethylsilane (1.9 mL) was added 2,2-difluoro-2-iodo-1-(2-methylphenyl)ethanone (2.6 g), and the mixture was stirred at room temperature for 2 hr. Diethyl ether was added to the reaction mixture, the insoluble material was filtered off, and the filtrate was concentrated under reduced pressure. The residue was purified by basic silica gel column chromatography (eluent: hexane) to give the title compound as a colorless oil (yield 2.6 g, 74%).

$^1$H-NMR (CDCl$_3$) δ: 0.21 (9H, s), 2.50 (3H, s), 2.70-2.89 (2H, m), 3.19-3.24 (1H, m), 7.27-7.32 (2H, m), 7.42-7.48 (1H, m), 7.89-7.92 (1H, m).

Reference Example 111

3-fluoro-2-(2-methylphenyl)-1H-pyrrole

To a solution (20 mL) of 2,2-difluoro-4-iodo-1-(2-methylphenyl)-4-trimethylsilylbutan-1-one (2.5 g) in tetrahydrofuran was added 28% aqueous ammonia solution (6 mL), and the mixture was stirred at room temperature for 14 hr. The reaction mixture was extracted with ethyl acetate. The extract was washed with saturated brine, dried over anhydrous magnesium sulfate, and concentrated under reduced pressure. The residue was dissolved in acetonitrile (15 mL) and water (8 mL), and potassium fluoride (0.75 g) was added. The reaction mixture was stirred at 60° C. for 3 hr, and concentrated under reduced pressure. The residue was extracted with ethyl acetate. The extract was washed with saturated aqueous sodium hydrogencarbonate solution, water and saturated brine, dried over anhydrous magnesium sulfate, and concentrated under reduced pressure. The residue was purified by silica gel column chromatography (eluent:hexane-ethyl acetate=20:1) to give the title compound as a pale-yellow oil (yield 0.87 g, 78%).

$^1$H-NMR (CDCl$_3$) δ: 2.39 (3H, d, J=1.5 Hz), 6.06-6.08 (1H, m), 6.60-6.63 (1H, m), 7.19-7.33 (4H, m), 7.71 (1H, brs).

Reference Example 112

5-bromo-1H-pyrrole-3-carbaldehyde

A solution of 1H-pyrrole-3-carbaldehyde (19.1 g) in tetrahydrofuran (300 mL) was cooled to −70° C., and a solution of N-bromosuccinimide (35.8 g) in N,N-dimethylformamide (100 mL) was added dropwise. After stirring at the same temperature for 1 hr, the mixture was raised to −10° C. over 2 hr and further stirred for 30 min. Ice water was added to the reaction mixture at 0° C., and the mixture was allowed to warm to room temperature and extracted with ethyl acetate. The extract was washed with 10% aqueous citric acid solution, 6% aqueous sodium hydrogencarbonate solution and saturated brine, dried over anhydrous sodium sulfate, and concentrated under reduced pressure. The crystals obtained as a residue were washed with diisopropyl ether to give the title compound as colorless crystals (yield 17.7 g, 51%).

$^1$H-NMR (CDCl$_3$) δ: 6.65-6.66 (1H, m), 7.37-7.38 (1H, m), 8.80 (1H, br), 9.70 (1H, s).

Reference Example 113

5-(2-methylphenyl)-1H-pyrrole-3-carbaldehyde

5-Bromo-1H-pyrrole-3-carbaldehyde (100 mg), 2-methylphenylboronic acid (94 mg) and sodium carbonate (146 mg) were suspended in a mixed solvent of 1,2-dimethoxyethane (5 mL) and water (2 mL), and the mixture was sufficiently degassed under a nitrogen atmosphere. Tetrakis(triphenylphosphine)palladium (33 mg) was added, and the mixture was further degassed and refluxed at 105° C. for 24 hr. The reaction mixture was allowed to cool to room temperature, and the mixture was extracted with water and ethyl acetate. The extract was washed with saturated brine, dried over anhydrous sodium sulfate, and concentrated under reduced pressure. The residue was purified by silica gel column chromatography (eluent:hexane-ethyl acetate=8:1→3:1) to give the title compound as colorless crystals (yield 72 mg, 68%).

$^1$H-NMR (CDCl$_3$) δ: 2.44 (3H, s), 6.75-6.77 (1H, m), 7.23-7.36 (4H, m), 7.50-7.51 (1H, m), 8.75 (1H, br), 9.85 (1H, s).

Reference Example 114

4-chloro-5-(2-fluorophenyl)-1H-pyrrole-3-carbaldehyde

To a solution (15 mL) of 5-(2-fluorophenyl)-1H-pyrrole-3-carbaldehyde (1.0 g) in N,N-dimethylformamide was added N-chlorosuccinimide (0.71 g) at 0° C., and the mixture was stirred at 60° C. for 2 hr. The mixture was cooled to room temperature, water was added and the mixture was extracted with ethyl acetate. The extract was washed with saturated brine, dried over anhydrous sodium sulfate, and the solvent was evaporated under reduced pressure. The residue was purified by silica gel column chromatography (eluent:hexane-ethyl acetate=8:1→3:1) to give the title compound as a yellow powder (yield 0.55 g, 46%).

$^1$H-NMR (CDCl$_3$) δ: 7.15-7.40 (3H, m), 7.52 (1H, d, J=3.6 Hz), 7.97-8.03 (1H, m), 9.24 (1H, br), 9.96 (1H, s).

Reference Example 115

4-fluoro-5-(2-fluorophenyl)-1H-pyrrole-3-carbaldehyde

To a solution (60 mL) of 5-(2-fluorophenyl)-1H-pyrrole-3-carbaldehyde (3.1 g) in tetrahydrofuran was added 2,6-dichloro-N-fluoropyridinium triflate (5.6 g) at 0° C., and the mixture was stirred at the same temperature for 2 hr. Saturated aqueous sodium hydrogencarbonate solution was added to the reaction mixture, and the mixture was extracted with ethyl acetate. The extract was washed with saturated aqueous sodium hydrogencarbonate solution, water and saturated brine, dried over anhydrous sodium sulfate, and concentrated under reduced pressure. The residue was purified by silica gel column chromatography (eluent:hexane-ethyl acetate=2:1) to give the title compound as white crystals (yield 0.43 g, 13%).

$^1$H-NMR (CDCl$_3$) δ: 7.11-7.30 (4H, m), 7.80-7.87 (1H, m), 9.14 (1H, brs), 9.88 (1H, s).

Reference Example 116

4-fluoro-5-(2-methylphenyl)-1H-pyrrole-3-carbaldehyde

Sodium hydride (0.40 g) was washed twice with hexane and suspended in tetrahydrofuran (10 mL). A solution of 3-fluoro-2-(2-methylphenyl)-1H-pyrrole (0.86 g) in tetrahydrofuran (3 mL) was added at 0° C., and the mixture was stirred at the same temperature for 30 min. A solution (2 mL) of triisopropylsilyl trifluoroacetate (2.7 mL) in tetrahydrofuran was added at 0° C., and the mixture was stirred at the same temperature for 15 min. Ice water was added to the reaction mixture, and the mixture was extracted with ethyl acetate. The extract was washed with saturated aqueous sodium hydrogencarbonate solution, water and saturated brine, dried over anhydrous sodium sulfate, and concentrated under reduced pressure. The residue was dissolved in tetrahydrofuran (10 mL) and acetonitrile (2 mL), (chloromethylene)dimethylammonium chloride (1.6 g) was added, and the mixture was heated under reflux for 2 hr, and concentrated under reduced pressure. The residue was dissolved in tetrahydrofuran (2 mL), 1 mol/L aqueous sodium hydroxide solution (20 mL) was added, and the mixture was stirred at room temperature for 1 hr. The reaction mixture was extracted with ethyl acetate. The extract was washed with saturated aqueous sodium hydrogencarbonate solution, water and saturated brine, dried over anhydrous sodium sulfate, and concentrated under reduced pressure. The residue was purified by silica gel column chromatography (eluent:hexane-ethyl acetate=2:1) to give the title compound as a yellow oil (yield 0.48 g, 48%).
$^1$H-NMR (CDCl$_3$) δ: 2.38 (3H, s), 7.23-7.32 (5H, m), 8.38 (1H, brs), 9.87 (1H, s).

Reference Example 117

5-nitro-3-(trifluoromethyl)pyridin-2-ol

2-Hydroxy-3-(trifluoromethyl)pyridine (3.0 g) was added to conc. sulfuric acid (18 mL) under ice-cooling, and the mixture was stirred at the same temperature for 5 min. Fuming nitric acid (90-95%, 7 mL) was added dropwise over 5 min, and the mixture was allowed to return to room temperature over 2 hr, heated to 50° C. and stirred for 3 hr. After cooling to room temperature, the reaction mixture was poured into ice (200 g), and the mixture was extracted with ethyl acetate. The extract was washed with saturated brine, dried over anhydrous magnesium sulfate, and concentrated under reduced pressure. The precipitate was washed with diisopropyl ether to give the title compound as a solid (yield 2.7 g, 69%).
$^1$H-NMR (CDCl$_3$) δ: 8.65-8.67 (1H, m), 8.80-8.81 (1H, m), 1H not detected.

Reference Example 118

2-chloro-5-nitro-3-(trifluoromethyl)pyridine

A mixture of 5-nitro-3-(trifluoromethyl)pyridin-2-ol (2.65 g), phosphorus pentachloride (3.17 g) and phosphorus oxychloride (1.5 mL) was stirred at 90° C. for 3 hr. After cooling to room temperature, the reaction mixture was poured into ice, and the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=19:1→3:1) to give the title compound as a yellow oil (yield 2.21 g, 77%).
$^1$H-NMR (CDCl$_3$) δ: 8.79-8.81 (1H, m), 9.40-9.41 (1H, m).

Reference Example 119

6-chloro-5-(trifluoromethyl)pyridine-3-amine

Reduced iron (1.3 g) and ammonium chloride (2.1 g) were added to water (40 mL), and the mixture was stirred at room temperature for 5 min. A solution of 2-chloro-5-nitro-3-(trifluoromethyl)pyridine (1.8 g) in methanol (40 mL) was added, and the mixture was stirred at room temperature for 1 hr. Reduced iron (2.3 g) was added, and the mixture was further stirred at the same temperature for 3 hr. The reaction mixture was filtered through celite, and celite was washed with ethyl acetate. The filtrate was extracted with ethyl acetate, and the extract was washed with saturated brine, dried over anhydrous magnesium sulfate, and concentrated under reduced pressure. The residue was purified by silica gel column chromatography (eluent:hexane-ethyl acetate=19:1→1:1) to give the title compound as a solid (yield 1.0 g, 65%).
$^1$H-NMR (CDCl$_3$) δ: 7.29 (1H, m), 7.99 (1H, m), 2H not detected.

Reference Example 120

6-chloro-5-(trifluoromethyl)pyridine-3-sulfonyl chloride

Under ice-cooling, thionyl chloride (4 mL) was added dropwise over 20 min to water (27 mL). The mixture was stirred at room temperature for 12 hr to give a sulfur dioxide-containing solution. Separately, 6-chloro-5-(trifluoromethyl) pyridine-3-amine (1.14 g) was added to concentrated hydrochloric acid (9 mL) with stirring under ice-cooling, and concentrated hydrochloric acid (9 mL) was further added. A solution of sodium nitrite (0.44 g) in water (6 mL) was added dropwise over 10 min. The reaction mixture was gradually added at 5° C. to the above-mentioned sulfur dioxide-containing solution added with cuprous chloride (15 mg). Under ice-cooling, the mixture was further stirred for 30 min, and the precipitate was collected by filtration and washed with water. The obtained precipitate was purified by silica gel column chromatography (eluent:hexane-ethyl acetate=19:1→9:1) to give the title compound as an orange solid (yield 437 mg, 27%).
$^1$H-NMR (CDCl$_3$) δ: 8.58 (1H, m), 9.18 (1H, m).

Reference Example 121

6-chloro-2-methylpyridine-3-sulfonyl chloride

Under ice-cooling, thionyl chloride (4 mL) was added dropwise to water (24 mL) over 20 min. The mixture was stirred at room temperature for 12 hr to give a sulfur dioxide-containing solution. Separately, to the concentrated hydrochloric acid (6 mL) was added 5-amino-2-chloro-6-methylpyridine (1.0 g) with stirring under ice-cooling, and a solution of sodium nitrite (0.5 g) in water (2 mL) was added dropwise over 10 min. The reaction mixture was gradually added at 5° C. to the above-mentioned sulfur dioxide-containing solution added with cuprous chloride (10 mg). Under ice-cooling, the mixture was further stirred for 30 min, and the precipitate was collected by filtration, and washed with water to give the title compound as a pale-yellow solid (yield 1.1 g, 67%).
$^1$H-NMR (CDCl$_3$) δ: 2.99 (3H, s), 7.41 (1H, dd, J=8.7, 0.9 Hz), 8.26 (1H, d, J=8.4 Hz).

Reference Example 122 ethyl 1-[(5-bromopyridin-3-yl)sulfonyl]-5-phenyl-1H-pyrrole-3-carboxylate

By a similar reaction as in Reference Example 40 and using 5-bromo-6-chloropyridine-3-sulfonyl chloride (3.49 g), the title compound was obtained as a yellow solid (yield 1.63 g, 38%).

¹H-NMR (CDCl₃) δ: 1.35-1.39 (3H, m), 4.29-4.37 (2H, m), 6.60 (1H, s), 7.18-7.20 (2H, m), 7.35-7.51 (4H, m), 8.06 (1H, s), 8.45 (1H, s), 8.78 (1H, s).

Reference Example 123 ethyl 5-phenyl-1-{[5-(trifluoromethyl)pyridin-3-yl]sulfonyl}-1H-pyrrole-3-carboxylate By a similar reaction as in Reference Example 40 and using 6-chloro-5-(trifluoromethyl)pyridine-3-sulfonyl chloride (413 mg), the title compound was obtained as a colorless solid (yield 191 mg, 35%).
¹H-NMR (CDCl₃) δ: 1.37 (3H, t, J=7.2 Hz), 4.33 (2H, dd, J=14.4, 7.2 Hz), 6.61 (1H, s), 7.16-7.18 (2H, m), 7.33-7.45 (3H, m), 7.65 (1H, s), 8.09 (1H, s), 8.75 (1H, s), 8.98 (1H, s).

Reference Example 124 ethyl 1-[(2-methylpyridin-3-yl)sulfonyl]-5-phenyl-1H-pyrrole-3-carboxylate

By a similar reaction as in Reference Example 40 and using 6-chloro-2-methylpyridine-3-sulfonyl chloride (543 mg), the title compound was obtained as a red oil (yield 135 mg, 18%).
¹H-NMR (CDCl₃) δ: 1.35-1.40 (3H, m), 2.47 (3H, s), 4.33 (2H, dd, J=14.1, 6.9 Hz), 6.59 (1H, d, J=1.8 Hz), 6.82-7.49 (7H, m), 8.21 (1H, d, J=2.1 Hz), 8.51 (1H, dd, J=4.8, 1.8 Hz).

Reference Example 125 methyl 4-fluoro-5-phenyl-1-(pyridin-3-ylsulfonyl)-1H-pyrrole-3-carboxylate

By a similar reaction as in Reference Example 36 and using methyl 4-fluoro-5-phenyl-1H-pyrrole-3-carboxylate (172 mg), the title compound was obtained as a colorless solid (yield 206 mg, 73%). More specifically, to a solution of methyl 4-fluoro-5-phenyl-1H-pyrrole-3-carboxylate (172 mg) in tetrahydrofuran (10 mL) was added sodium hydride (60% in oil, 94 mg), and the mixture was stirred for 15 min. 15-Crown-5 (0.48 mL) was added, and the mixture was further stirred for 15 min. Pyridine-3-sulfonyl chloride hydrochloride (219 mg) was added and the mixture was stirred for 30 min. Water was added, and the mixture was extracted with ethyl acetate. The organic layer was washed with water and saturated brine, dried over anhydrous magnesium sulfate, and concentrated under reduced pressure. The residue was purified by silica gel column chromatography (eluent:hexane-ethyl acetate=19:1→1:1) to give the title compound as a colorless solid (yield 206 mg, 73%).
¹H-NMR (CDCl₃) δ: 3.89 (3H, s), 7.17-7.20 (2H, m), 7.26-7.55 (5H, m), 7.95 (1H, d, J=4.8 Hz), 8.50-8.51 (1H, m), 8.76-8.78 (1H, m).

Reference Example 126

1-[(5-bromopyridin-3-yl)sulfonyl]-5-phenyl-1H-pyrrole-3-carbaldehyde

By a similar reaction as in Reference Example 62 and using ethyl 1-[(5-bromopyridin-3-yl)sulfonyl]-5-phenyl-1H-pyrrole-3-carboxylate (1.63 g), the title compound was obtained as a pale-yellow solid (yield 1.18 g, 80%).
¹H-NMR (CDCl₃) δ: 6.63 (1H, s), 7.17-7.20 (2H, m), 7.36-7.39 (2H, m), 7.50-7.52 (2H, m), 8.10 (1H, s), 8.46 (1H, s), 8.79-8.80 (1H, m), 9.91 (1H, s).

Reference Example 127

5-phenyl-1-{[5-(trifluoromethyl)pyridin-3-yl]sulfonyl}-1H-pyrrole-3-carbaldehyde By a similar reaction as in Reference Example 62 and using ethyl 5-phenyl-1-{[(5-trifluoromethyl)pyridin-3-yl]sulfonyl}-1H-pyrrole-3-carboxylate (190 mg), the title compound was obtained as a colorless solid (yield 138 mg, 83%).
¹H-NMR (CDCl₃) δ: 6.64 (1H, d, J=1.5 Hz), 7.15-7.18 (2H, m), 7.33-7.38 (2H, m), 7.44-7.47 (1H, m), 7.63-7.64 (1H, m), 8.14 (1H, d, J=1.5 Hz), 8.76 (1H, d, J=2.1 Hz), 9.00 (1H, d, J=1.5 Hz), 9.92 (1H, s).

Reference Example 128

1-[(2-methylpyridin-3-yl)sulfonyl]-5-phenyl-1H-pyrrole-3-carbaldehyde

By a similar reaction as in Reference Example 62 and using ethyl 1-[(2-methylpyridin-3-yl)sulfonyl]-5-phenyl-1H-pyrrole-3-carboxylate (364 mg), the title compound was obtained as an orange solid (yield 182 mg, 57%).
¹H-NMR (CDCl₃) δ: 2.47 (3H, s), 6.62 (1H, d, J=1.8 Hz), 6.83-6.90 (1H, m), 7.02-7.04 (2H, m), 7.16-7.31 (3H, m), 7.39-7.42 (1H, m), 8.24 (1H, s), 8.52-8.54 (1H, m), 9.93 (1H, s).

Reference Example 129

4-fluoro-5-phenyl-1-(pyridin-3-ylsulfonyl)-1H-pyrrole-3-carbaldehyde

Under a nitrogen atmosphere, a solution of methyl 4-fluoro-5-phenyl-1-(pyridin-3-ylsulfonyl)-1H-pyrrole-3-carboxylate (200 mg) in tetrahydrofuran (10 mL) was cooled to −78° C., and a 1.5 mol/L solution (1.85 mL) of diisobutylaluminum hydride in toluene was added with stirring. After stirring at the same temperature for 15 min, the mixture was raised to 0° C. over 1.5 hr. Water (20 mL) was added, and the mixture was stirred at the same temperature for 5 min. After stirring, ethyl acetate (20 mL) was added, and the mixture was stirred for 15 min, and then stirred at room temperature for 20 min. The reaction mixture was filtered through celite, and celite was washed with ethyl acetate. The filtrate was extracted with ethyl acetate. The extract was washed with saturated brine, dried over anhydrous magnesium sulfate, and concentrated under reduced pressure. The residue was dissolved in tetrahydrofuran (10 mL), manganese dioxide (75% chemically treated product, 1.0 g) was added, and the mixture was stirred at room temperature for 16 hr. The reaction mixture was filtered through celite, and celite was washed with ethyl acetate. The filtrate was concentrated under reduced pressure and the residue was purified by silica gel column chromatography (eluent:hexane-ethyl acetate=19:1→1:2) to give the title compound as a colorless solid (yield 123 mg, 67%).
¹H-NMR (CDCl₃) δ: 7.17-7.20 (2H, m), 7.26-7.57 (5H, m), 7.96 (1H, d, J=4.8 Hz), 8.50-8.51 (1H, m), 8.76-8.80 (1H, m), 9.92 (1H, s).

Reference Example 130

5-(2,6-difluorophenyl)-1-(pyridin-3-ylsulfonyl)-1H-pyrrole-3-carbaldehyde

To a solution of 5-(2,6-difluorophenyl)-1H-pyrrole-3-carbaldehyde (420 mg) in tetrahydrofuran (42 mL) was added sodium hydride (60% in oil, 244 mg) at room temperature and the mixture was stirred for 30 min. 15-Crown-5 (1.34 g) was added dropwise and the mixture was stirred for 30 min. 3-Pyridylsulfonyl chloride hydrochloride (565 mg) was added, and the mixture was further stirred for 1 hr. The reaction mixture was diluted with saturated brine, and the mixture was extracted with ethyl acetate. The obtained extract was washed with water and saturated brine, dried over anhydrous magnesium sulfate, and concentrated under reduced pressure. The residue was purified by silica gel column chromatography (eluent:hexane-ethyl acetate=7:3→1:1), and crystallized from diisopropyl ether to give the title compound as colorless crystals (yield 590 mg, 84%).

$^1$H-NMR (CDCl$_3$) δ: 6.76 (1H, d, J=1.9 Hz), 6.90-6.95 (2H, m), 7.40-7.52 (2H, m), 7.77-7.81 (1H, m), 8.18 (1H, d, J=1.9 Hz), 8.65-8.66 (1H, m), 8.85-8.87 (1H, m), 9.91 (1H, s).

Reference Example 131

5-(4-cyclohexylphenyl)-1-(pyridin-3-ylsulfonyl)-1H-pyrrole-3-carbaldehyde

Sodium hydride (60% in oil, 68 mg) was added to a solution of 5-(4-cyclohexylphenyl)-1H-pyrrole-3-carbaldehyde (0.17 g) in tetrahydrofuran (12 mL) at room temperature. The mixture was stirred for 20 min, 3-pyridinesulfonyl chloride (0.19 g) was added, and the mixture was stirred at room temperature for 3 hr. The reaction mixture was poured into ice water, and the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=3:2→2:1) to give the title compound as crystals (yield 0.26 g, 97%).

$^1$H-NMR (CDCl$_3$) δ: 1.21-1.53 (5H, m), 1.73-1.98 (5H, m), 2.50-2.60 (1H, m), 6.57 (1H, d, J=1.9 Hz), 7.03-7.09 (2H, m), 7.13-7.29 (3H, m), 7.48 (1H, ddd, J=8.3, 2.0, 1.9 Hz), 8.11 (1H, d, J=1.9 Hz), 8.49 (1H, d, J=2.3 Hz), 8.73 (1H, dd, J=4.8, 1.6 Hz), 9.89 (1H, s).

Reference Example 132

1-[(6-chloropyridin-3-yl)sulfonyl]-5-(2-fluorophenyl)-1H-pyrrole-3-carbaldehyde

By a similar reaction as in Reference Example 65 and using 5-(2-fluorophenyl)-1H-pyrrole-3-carbaldehyde (893 mg) and 6-chloropyridine-3-sulfonyl chloride (1.30 g), the title compound was obtained as a pale-red solid (yield 1.14 g, 66%). More specifically, 5-(2-fluorophenyl)-1H-pyrrole-3-carbaldehyde (893 mg) was dissolved in tetrahydrofuran (10 mL), sodium hydride (60% in oil, 226 mg) was added and the mixture was stirred at room temperature for 15 min. 15-Crown-5 (1.1 mL) was added and the mixture was further stirred at the same temperature for 15 min. 6-Chloropyridine-3-sulfonyl chloride (1.30 g) was added. The reaction mixture was stirred at room temperature for 15 min. Water was added, and the mixture was extracted with ethyl acetate. The extract was washed with water and saturated brine, dried over anhydrous magnesium sulfate, and concentrated under reduced pressure. The residue was purified by silica gel column chromatography (eluent:hexane-ethyl acetate=19:1→3:2) to give the title compound as a pale-red solid (yield 1.14 g, 66%).

$^1$H-NMR (CDCl$_3$) δ: 6.71 (1H, d, J=9.0 Hz), 7.05 (1H, t, J=9.0 Hz), 7.19-7.23 (2H, m), 7.38 (1H, d, J=8.4 Hz), 7.45-7.53 (1H, m), 7.63-7.67 (1H, m), 8.11 (1H, d, J=1.8 Hz), 8.33 (1H, d, J=2.7 Hz), 9.91 (1H, s).

Reference Example 133

5-(2-fluorophenyl)-1-[(6-methylpyridin-3-yl)sulfonyl]-1H-pyrrole-3-carbaldehyde

Under an argon atmosphere, a mixture of 1-[(6-chloropyridin-3-yl)sulfonyl]-5-(2-fluorophenyl)-1H-pyrrole-3-carbaldehyde (365 mg), methylboronic acid (90 mg), tetrakis(triphenylphosphine)palladium (116 mg), potassium carbonate (691 mg) and 1,4-dioxane (25 mL) was stirred at 80° C. for 3 days. The reaction mixture was poured into saturated aqueous sodium hydrogencarbonate solution, and the mixture was extracted with ethyl acetate. The extract was washed with saturated brine, dried over magnesium sulfate, and concentrated under reduced pressure. The residue was purified by silica gel column chromatography (eluent:hexane-ethyl acetate=19:1→1:1) to give the title compound as a yellow solid (yield 134 mg, 39%).

$^1$H-NMR (CDCl$_3$) δ: 2.64 (3H, s), 6.67 (1H, d, J=1.8 Hz), 7.04 (1H, t, J=8.4 Hz), 7.17-7.21 (3H, m), 7.45-7.50 (1H, m), 7.58 (1H, dd, J=8.7, 3.6 Hz), 8.12 (1H, d, J=1.8 Hz), 8.45 (1H, d, J=2.4 Hz), 9.89 (1H, s).

Reference Example 134

5-(2-fluorophenyl)-1-(pyridin-2-ylsulfonyl)-1H-pyrrole-3-carbaldehyde

By a similar reaction as in Reference Example 65 and using 5-(2-fluorophenyl)-1H-pyrrole-3-carbaldehyde (190 mg) and pyridine-2-sulfonyl chloride (231 mg), the title compound was obtained as a pale-red solid (yield 183 mg, 55%).

$^1$H-NMR (CDCl$_3$) δ: 6.67 (1H, d, J=1.8 Hz), 6.97 (1H, t, J=8.7 Hz), 7.07-7.10 (2H, m), 7.36-7.42 (1H, m), 7.52-7.55 (2H, m), 7.76-7.82 (1H, m), 8.23 (1H, d, J=1.5 Hz), 8.67 (1H, d, J=4.5 Hz), 9.92 (1H, s).

Reference Example 135

5-(2-fluorophenyl)-1-[(1-methyl-1H-pyrazol-4-yl)sulfonyl]-1H-pyrrole-3-carbaldehyde By a similar operation as in Reference Example 65 and using 5-(2-fluorophenyl)-1H-pyrrole-3-carbaldehyde (189 mg) and 1-methyl-1H-pyrazole-4-sulfonyl chloride (217 mg), the title compound was obtained as yellow crystals (yield 217 mg, 65%).

$^1$H-NMR (CDCl$_3$) δ: 3.85 (3H, s), 6.67 (1H, d, J=1.8 Hz), 7.04-7.11 (1H, m), 7.17-7.22 (1H, m), 7.25-7.35 (3H, m), 7.43-7.50 (1H, m), 8.06 (1H, d, J=1.5 Hz), 9.86 (1H, s).

Reference Example 136

5-(2-methylphenyl)-1-(pyridin-3-ylsulfonyl)-1H-pyrrole-3-carbaldehyde

To a solution of 5-(2-methylphenyl)-1H-pyrrole-3-carbaldehyde (371 mg) in tetrahydrofuran (10 mL) were added sodium hydride (60% in oil, 288 mg) and 15-crown-5 (1.32 g) at room temperature. After stirring for 5 min, a suspension of pyridine-3-sulfonyl chloride hydrochloride (642 mg) in N,N-dimethylformamide (5 mL) was added at the same temperature. After stirring for 15 min, ice water was added, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=6:1→3:1) to give the title compound as a red oil (yield 521 mg, 80%).

$^1$H-NMR (CDCl$_3$) δ: 1.82 (3H, s), 6.56 (1H, d, J=1.5 Hz), 6.87-6.90 (1H, m), 7.11-7.19 (2H, m), 7.30-7.39 (2H, m), 7.56-7.60 (1H, m), 8.15 (1H, d, J=1.5 Hz), 8.52-8.53 (1H, m), 8.80-8.82 (1H, m), 9.92 (1H, s).

Reference Example 137

4-chloro-5-(2-fluorophenyl)-1-(pyridin-3-ylsulfonyl)-1H-pyrrole-3-carbaldehyde

A suspension of sodium hydride (60% in oil, 216 mg) in tetrahydrofuran (5 mL) was cooled to 0° C., a solution of 4-chloro-5-(2-fluorophenyl)-1H-pyrrole-3-carbaldehyde (335 mg) in tetrahydrofuran (5 mL), 15-crown-5 (991 mg), and pyridine-3-sulfonyl chloride hydrochloride (482 mg) were added at 10° C. or below. After stirring for 15 min, water was added, and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=4:1→2:1) to give the title compound as a yellow powder (yield 429 mg, 78%).

$^1$H-NMR (CDCl$_3$) δ: 7.02-7.08 (1H, m), 7.19-7.29 (2H, m), 7.37-7.41 (1H, m), 7.50-7.57 (1H, m), 7.68-7.72 (1H, m), 8.15 (1H, s), 8.54-8.55 (1H, m), 8.83-8.86 (1H, m), 9.97 (1H, s).

Reference Example 138

4-fluoro-5-(2-fluorophenyl)-1-(pyridin-3-ylsulfonyl)-1H-pyrrole-3-carbaldehyde

Sodium hydride (60% in oil, 0.25 g) was washed twice with hexane and suspended in tetrahydrofuran (10 mL). A solution (5 mL) of 4-fluoro-5-(2-fluorophenyl)-1H-pyrrole-3-carbaldehyde (0.43 g) in tetrahydrofuran was added at 0° C., and the mixture was stirred at the same temperature for 30 min. 15-Crown-5 (1.3 mL) and 3-pyridinesulfonyl chloride hydrochloride (0.68 g) were added at 0° C., and the mixture was stirred at the same temperature for 1 hr. Water was added to the reaction mixture, and the mixture was extracted with ethyl acetate. The extract was washed with saturated aqueous sodium hydrogencarbonate solution, water and saturated brine, dried over anhydrous sodium sulfate, and concentrated under reduced pressure. The residue was purified by silica gel column chromatography (eluent:hexane-ethyl acetate=1:1) to give the title compound as pale-yellow crystals (yield 0.55 g, 76%).

$^1$H-NMR (CDCl$_3$) δ: 7.02-7.08 (1H, m), 7.20-7.31 (2H, m), 7.36-7.41 (1H, m), 7.48-7.55 (1H, m), 7.67-7.71 (1H, m), 8.00 (1H, d, J=5.1 Hz), 8.55-8.56 (1H, m), 8.83-8.85 (1H, m), 9.93 (1H, s).

Reference Example 139

4-fluoro-5-(2-methylphenyl)-1-(pyridin-3-ylsulfonyl)-1H-pyrrole-3-carbaldehyde

Sodium hydride (60% in oil, 0.11 g) was washed twice with hexane and suspended in tetrahydrofuran (10 mL). A solution (5 mL) of 4-fluoro-5-(2-methylphenyl)-1H-pyrrole-3-carbaldehyde (0.45 g) in tetrahydrofuran was added at 0° C., and the mixture was stirred at the same temperature for 15 min. A solution (2 mL) of 15-crown-5 (0.56 mL) and 3-pyridinesulfonyl chloride (0.44 g) in tetrahydrofuran was added at 0° C., and the mixture was stirred at the same temperature for 30 min. Water was added to the reaction mixture, and the mixture was extracted with ethyl acetate. The extract was washed with saturated aqueous sodium hydrogencarbonate solution, water and saturated brine, dried over anhydrous magnesium sulfate, and concentrated under reduced pressure. The residue was purified by silica gel column chromatography (eluent:hexane-ethyl acetate=1:1) to give the title compound as pale-yellow crystals (yield 0.59 g, 77%).

$^1$H-NMR (CDCl$_3$) δ: 1.77 (3H, s), 7.02-7.04 (1H, m), 7.17-7.23 (2H, m), 7.29-7.34 (1H, m), 7.37-7.42 (1H, m), 7.54-7.58 (1H, m), 8.00 (1H, d, J=4.5 Hz), 8.49-8.50 (1H, m), 8.81-8.83 (1H, m), 9.92 (1H, s).

Reference Example 140

2-chloro-5-(2,6-difluorophenyl)-1-(pyridin-3-ylsulfonyl)-1H-pyrrole-3-carbaldehyde To a solution of 5-(2,6-difluorophenyl)-1-(pyridin-3-ylsulfonyl)-1H-pyrrole-3-carbaldehyde (250 mg) in tetrahydrofuran (10 mL) and N,N-dimethylformamide (10 mL) was added N-chlorosuccinimide (1.06 g) and the mixture was stirred for 15 hr. Water was added to the reaction mixture, and the mixture was extracted with ethyl acetate. The extract was washed with saturated aqueous sodium hydrogencarbonate solution and saturated brine, dried over anhydrous magnesium sulfate, and concentrated under reduced pressure. The residue was purified by silica gel column chromatography (eluent:hexane-ethyl acetate=7:3→1:1) to give the title compound as a pale-yellow oil (yield 160 mg, 58%).

$^1$H-NMR (CDCl$_3$) δ: 6.74 (1H, s), 7.00-7.05 (2H, m), 7.42-7.56 (2H, m), 8.10-8.14 (1H, m), 8.91 (1H, dd, J=4.9, 1.5 Hz), 9.07 (1H, d, J=2.1 Hz), 9.92 (1H, s).

Reference Example 141

2-chloro-5-(2-fluorophenyl)-1-(pyridin-3-ylsulfonyl)-1H-pyrrole-3-carbaldehyde

To a solution of 5-(2-fluorophenyl)-1-(pyridin-3-ylsulfonyl)-1H-pyrrole-3-carbaldehyde (331 mg) in N,N-dimethylformamide (33 mL) was added N-chlorosuccinimide (268 mg) and the mixture was stirred at 60° C. for 1 hr. A saturated aqueous sodium hydrogencarbonate solution was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=7:3→1:1) to give the title compound as a colorless oil (yield 250 mg, 68%).

$^1$H-NMR (CDCl$_3$) δ: 6.65 (1H, s), 7.13-7.35 (3H, m), 7.45-7.55 (2H, m), 8.09-8.13 (1H, m), 8.90-9.03 (2H, m), 9.92 (1H, s).

Reference Example 142 tert-butyl({1-[(5-bromopyridin-3-yl)sulfonyl]-5-phenyl-3-yl-1H-pyrrol-3-yl}methyl)methylcarbamate 1-[(5-Bromopyridin-3-yl)sulfonyl]-5-phenyl-1H-pyrrole-3-carbaldehyde (1.18 g) was dissolved in absolute tetrahydrofuran (15 mL), a 2 mol/L solution (4.6 mL) of methylamine in tetrahydrofuran was added, and the mixture was stirred at room temperature for 16 hr. The reaction mixture was added to a solution of sodium borohydride (341 mg) in methanol (6 mL), and the mixture was stirred at the same temperature for 5 min. di-tert-Butyl bicarbonate (3.87 g) was added, and water (15 mL) and sodium hydrogencarbonate (1.26 g) were added 5 min later. The mixture was further stirred at room temperature for 30 min, water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=19:1→1:1), and fractions showing Rf values of 0.63, 0.30 and 0.075 (eluent:hexane-ethyl acetate=3:1) by TLC analysis were collected and concentrated under reduced pressure. The residue was dissolved in tetrahydrofuran (30 mL), manganese dioxide (75% chemically treated product, 3.0 g) was added, and the mixture was stirred at room temperature for 2 hr. The reaction mixture was filtered through celite, and celite was washed with ethyl acetate. The filtrate was concentrated under reduced pressure, and the residue was purified by silica gel column chromatography (eluent:hexane-ethyl acetate=19:1→1:1) to give the title compound as a colorless oil (yield 733 mg, 48%).
$^1$H-NMR (CDCl$_3$) δ: 1.47 (9H, s), 2.82 (3H, s), 4.23 (2H, m), 6.16 (1H, s), 7.21-7.56 (7H, m), 8.44 (1H, s), 8.76 (1H, s).

Reference Example 143 tert-butyl{[5-(2,4-dimethylphenyl)-1-(pyridin-3-ylsulfonyl)-1H-pyrrol-3-yl]methyl}methylcarbamate By a similar operation as in Reference Example 79 and using tert-butyl{[5-bromo-1-(pyridin-3-ylsulfonyl)-1H-pyrrol-3-yl]methyl}methylcarbamate (300 mg), (4-fluorophenyl)boronic acid (209 mg), tetrakis(triphenylphosphine)palladium (40 mg) and sodium carbonate (222 mg), the title compound was obtained as a pale-yellow oil (yield 177 mg, 56%).
$^1$H-NMR (CDCl$_3$) δ: 1.46 (9H, s), 1.89 (3H, s), 2.36 (3H, s), 2.83 (3H, s), 4.25 (2H, brs), 6.03-6.04 (1H, m), 6.76 (1H, d, J=8.1 Hz), 6.92-6.95 (1H, m), 7.00 (1H, brs), 7.26-7.33 (2H, m), 7.61-7.65 (1H, m), 8.56-8.57 (1H, m), 8.75-8.77 (1H, m).

Reference Example 144 tert-butyl{[5-(2-formylphenyl)-1-(pyridin-3-ylsulfonyl)-1H-pyrrol-3-yl]methyl}methylcarbamate tert-Butyl{[5-bromo-1-(pyridin-3-ylsulfonyl)-1H-pyrrol-3-yl]methyl}methylcarbamate (430 mg) was dissolved in toluene (10 mL), and the mixture was sufficiently degassed. Dicyclohexyl(2',6'-dimethoxybiphenyl-2-yl)phosphine (66 mg) and tris(dibenzylideneacetone)dipalladium (0) (37 mg) were added at room temperature. The mixture was stirred for 30 min with deaeration, and a 2 mol/L aqueous sodium carbonate solution (1.2 mL) and (2-formylphenyl)boronic acid (180 mg) were added. After further stirring at room temperature for 15 min, the mixture was heated to 120° C. over 1 hr, and further stirred for 16 hr. The reaction mixture was cooled to room temperature, water was added and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=4:1→1:1) to give the title compound as a yellow oil (yield 218 mg, 48%).
$^1$H-NMR (CDCl$_3$) δ: 1.47 (9H, s), 2.86 (3H, s), 4.27 (2H, brs), 6.23 (1H, brs), 7.09-7.11 (1H, m), 7.28-7.33 (1H, m), 7.43 (1H, d, J=1.2 Hz), 7.53-7.61 (3H, m), 7.96-7.99 (1H, m), 8.49-8.50 (1H, m), 8.75-8.77 (1H, m), 9.61-9.62 (1H, m).

Reference Example 145 tert-butyl methyl{[5-[4-(methylsulfonyl)phenyl]-1-(pyridin-3-ylsulfonyl)-1H-pyrrol-3-yl]methyl}carbamate A mixture of tert-butyl{[5-bromo-1-(pyridin-3-ylsulfonyl)-1H-pyrrol-3-yl]methyl}methylcarbamate (430 mg), 4-(methanesulfonyl)phenylboronic acid (300 mg), tetrakis(triphenylphosphine)palladium (115 mg), sodium carbonate (320 mg), 1,2-dimethoxyethane (10 mL) and water (10 mL) was stirred under a nitrogen atmosphere at 80° C. for 14 hr. The reaction mixture was allowed to cool to room temperature, filtered through celite, and the filtrate was extracted with ethyl acetate. The extract was washed with saturated brine, dried over anhydrous magnesium sulfate, and concentrated under reduced pressure. The residue was purified by silica gel column chromatography (eluent:hexane-ethyl acetate=2:1→1:2) to give the title compound as an oil (yield 275 mg, 64%).
$^1$H-NMR (CDCl$_3$) δ: 1.26 (9H, s), 2.79 (3H, s), 3.13 (3H, s), 4.22 (2H, s), 6.26 (1H, s), 7.26-7.37 (2H, m), 7.44-7.71 (3H, m), 7.93 (2H, d, J=8.3 Hz), 8.58 (1H, d, J=2.1 Hz), 8.76 (1H, dd, J=4.9, 1.5 Hz).

Reference Example 146 tert-butyl({5-[2-(hydroxymethyl)phenyl]-1-(pyridin-3-ylsulfonyl)-1H-pyrrol-3-yl}methyl)methylcarbamate tert-Butyl{[5-(2-formylphenyl)-1-(pyridin-3-ylsulfonyl)-1H-pyrrol-3-yl]methyl}methylcarbamate (218 mg) was dissolved in tetrahydrofuran (2 mL), and sodium borohydride (24 mg) and methanol (1 mL) were added at 0° C. After stirring at the same temperature for 30 min, water was added, and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=1:1→1:3) to give the title compound as a colorless oil (yield 132 mg, 60%).
$^1$H-NMR (CDCl$_3$) δ: 1.46 (9H, s), 2.10-2.15 (1H, m), 2.85 (3H, s), 4.25 (2H, brs), 4.30-4.38 (2H, m), 6.12 (1H, d, J=1.5 Hz), 6.69-6.72 (1H, m), 7.13-7.18 (1H, m), 7.30-7.35 (2H, m), 7.44-7.49 (1H, m), 7.59-7.62 (2H, m), 8.50 (1H, d, J=2.4 Hz), 8.76-8.78 (1H, m).

Reference Example 147

5-mesityl-1H-pyrrole-3-carbaldehyde

A mixture of 5-bromo-1H-pyrrole-3-carbaldehyde (0.87 g), 2,4,6-trimethylphenylboronic acid (3.28 g), cesium carbonate (13.0 g), tri-tert-butylphosphine (0.10 g), tris(dibenzylideneacetone)dipalladium (0) (0.23 g) and mesitylene (200 mL) was stirred with heating under reflux for 5 hr. Water was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=3:1) to give the title compound as a brown amorphous form (yield 0.30 g, 28%).

$^1$H-NMR (CDCl$_3$) δ: 2.11 (6H, s), 2.32 (3H, s), 6.51-6.52 (1H, m), 6.93 (2H, s), 7.47-7.49 (1H, m), 9.82 (1H, s), 1H not detected.

Reference Example 148

5-[2-(methylthio)phenyl]-1H-pyrrole-3-carbaldehyde

5-Bromo-1H-pyrrole-3-carbaldehyde (174 mg), [2-(methylthio)phenyl]boronic acid (202 mg) and sodium carbonate (254 mg) were suspended in a mixed solvent of 1,2-dimethoxyethane (5 mL) and water (2 mL), and the mixture was sufficiently degassed under a nitrogen atmosphere. Tetrakis(triphenylphosphine)palladium (58 mg) was added, and the mixture was further degassed and stirred at 105° C. for 16 hr. The reaction mixture was allowed to cool to room temperature, water was added and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=9:1→4:1) to give the title compound as pale-yellow crystals (yield 150 mg, 69%).

$^1$H-NMR (CDCl$_3$) δ: 2.38 (3H, s), 6.94-6.95 (1H, m), 7.21-7.31 (2H, m), 7.39-7.42 (1H, m), 7.48-7.53 (2H, m), 9.85 (1H, s), 9.95 (1H, br).

Reference Example 149

5-(2-bromophenyl)-1H-pyrrole-3-carbaldehyde

By a similar operation as in Reference Example 148 and using 5-bromo-1H-pyrrole-3-carbaldehyde (870 mg), (2-bromophenyl)boronic acid (1.20 g), sodium carbonate (1.27 g) and tetrakis(triphenylphosphine)palladium (289 mg), the title compound was obtained as colorless crystals (yield 396 mg, 32%).

$^1$H-NMR (CDCl$_3$) δ: 6.94-6.95 (1H, m), 7.16-7.22 (1H, m), 7.34-7.39 (1H, m), 7.49-7.54 (2H, m), 7.63-7.66 (1H, m), 9.28 (1H, br), 9.85 (1H, s).

Reference Example 150

5-[2-(methylsulfinyl)phenyl]-1H-pyrrole-3-carbaldehyde

To a solution of 5-[2-(methylthio)phenyl]-1H-pyrrole-3-carbaldehyde (200 mg) in ethyl acetate (10 mL) was added 3-chloroperbenzoic acid (238 mg) under ice-cooling. After stirring at room temperature for 1 hr, a saturated sodium thiosulfate aqueous solution was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent:ethyl acetate) to give the title compound as a pale-pink powder (yield 160 mg, 75%).

$^1$H-NMR (CDCl$_3$) δ: 2.64 (3H, s), 7.04-7.06 (1H, m), 7.35-7.41 (1H, m), 7.57-7.64 (2H, m), 7.72-7.82 (2H, m), 9.86 (1H, s), 12.35 (1H, br).

Reference Example 151

5-[2-(methylsulfonyl)phenyl]-1H-pyrrole-3-carbaldehyde

To a solution of 5-[2-(methylthio)phenyl]-1H-pyrrole-3-carbaldehyde (100 mg) in ethyl acetate (5 mL) was added 3-chloroperbenzoic acid (318 mg) under ice-cooling. After stirring at room temperature for 3 hr, a saturated sodium thiosulfate aqueous solution was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=1:1→1:3) to give the title compound as pale-yellow crystals (yield 88.9 mg, 78%).

$^1$H-NMR (CDCl$_3$) δ: 2.77 (3H, s), 6.94-6.96 (1H, m), 7.54-7.60 (2H, m), 7.67-7.73 (2H, m), 8.20-8.24 (1H, m), 9.88 (1H, s), 10.60 (1H, s).

Reference Example 152

5-(2-fluorophenyl)-4-iodo-1H-pyrrole-3-carbaldehyde 5-(2-Fluorophenyl)-1H-pyrrole-3-carbaldehyde (2.0 g) was dissolved in N,N-dimethylformamide (60 mL), N-iodosuccinimide (2.38 g) was added and the mixture was stirred at for 12 hr. Water was added to the reaction mixture and the mixture was extracted with ethyl acetate. The extract was washed successively with a saturated aqueous sodium hydrogencarbonate solution, a 3% aqueous potassium hydrogensulfate solution and saturated brine, dried over anhydrous sodium sulfate, and concentrated under reduced pressure. The residue was purified by silica gel column chromatography (eluent:hexane-ethyl acetate=7:3→1:1) to give the title compound as a pale-brown powder (yield 450 mg, 14%).

$^1$H-NMR (CDCl$_3$) δ: 7.16-7.30 (2H, m), 7.37-7.44 (1H, m), 7.63 (1H, d, J=3.4 Hz), 7.81-7.86 (1H, m), 9.24 (1H, br), 9.81 (1H, s).

Reference Example 153

5-mesityl-1-(pyridin-3-ylsulfonyl)-1H-pyrrole-3-carbaldehyde

To a solution of 5-mesityl-1H-pyrrole-3-carbaldehyde (0.36 g) in tetrahydrofuran (20 mL) was added sodium hydride (60% in oil, 0.14 g) under ice-cooling, and the mixture was stirred at room temperature for 0.5 hr. A solution of 15-crown-5 (0.75 g) in tetrahydrofuran (3 mL) was added and, after stirring for 5 min, pyridin-3-ylsulfonyl chloride (0.45 g) was added under ice-cooling. The reaction mixture was stirred at room temperature for 0.5 hr, a saturated aqueous sodium hydrogencarbonate solution was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=10:1→2:1) to give the title compound as a pale-brown amorphous form (yield 0.38 g, 62%).

$^1$H-NMR (CDCl$_3$) δ: 1.63 (6H, s), 2.35 (3H, s), 6.48 (1H, d, J=1.5 Hz), 6.83 (2H, s), 7.26-7.35 (1H, m), 7.60-7.64 (1H, m), 8.17 (1H, dd, J=1.5, 0.9 Hz), 8.56 (1H, d, J=2.1 Hz), 8.83 (1H, dd, J=4.5, 1.5 Hz), 9.90 (1H, s).

Reference Example 154

5-[2-(methylthio)phenyl]-1-(pyridin-3-ylsulfonyl)-1H-pyrrole-3-carbaldehyde

To a suspension of sodium hydride (60% in oil, 40 mg) in tetrahydrofuran (3 mL) were added a solution of 5-[2-(methylthio)phenyl]-1H-pyrrole-3-carbaldehyde (150 mg) in tetrahydrofuran (5 mL), 15-crown-5 (182 mg) and pyridin-3-ylsulfonyl chloride (135 mg) under ice-cooling. After stirring at room temperature for 2 hr, water was added and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=4:1→2:1) to give the title compound as colorless crystals (yield 170 mg, 69%).

$^1$H-NMR (CDCl$_3$) δ: 2.05 (3H, s), 6.68 (1H, d, J=2.1 Hz), 6.97-6.99 (1H, m), 7.17-7.31 (3H, m), 7.40-7.45 (1H, m), 7.65-7.70 (1H, m), 8.16 (1H, d, J=2.1 Hz), 8.45-8.46 (1H, m), 8.75-8.77 (1H, m), 9.90 (1H, s).

Reference Example 155

5-(2-bromophenyl)-1-(pyridin-3-ylsulfonyl)-1H-pyrrole-3-carbaldehyde

By a similar operation as in Reference Example 154 and using sodium hydride (60% in oil, 91.0 mg), 5-(2-bromophenyl)-1H-pyrrole-3-carbaldehyde (396 mg), 15-crown-5 (418 mg) and pyridin-3-ylsulfonyl chloride (309 mg), the title compound was obtained as a pale-yellow solid (yield 560 mg, 91%).

$^1$H-NMR (CDCl$_3$) δ: 6.66 (1H, d, J=1.5 Hz), 7.31-7.40 (4H, m), 7.48-7.52 (1H, m), 7.66-7.71 (1H, m), 8.15 (1H, d, J=1.8 Hz), 8.55 (1H, d, J=2.7 Hz), 8.82-8.84 (1H, m), 9.92 (1H, s).

Reference Example 156

5-[2-(methylsulfonyl)phenyl]-1-(pyridin-3-ylsulfonyl)-1H-pyrrole-3-carbaldehyde

By a similar operation as in Reference Example 154 and using sodium hydride (60% in oil, 40 mg), 5-[2-(methylsulfonyl)phenyl]-1H-pyrrole-3-carbaldehyde (88.9 mg), 15-crown-5 (94.4 mg) and pyridin-3-ylsulfonyl chloride (69.7 mg), the title compound was obtained as a colorless amorphous form (yield 72.0 mg, 52%).

$^1$H-NMR (CDCl$_3$) δ: 2.87 (3H, s), 6.67 (1H, d, J=1.8 Hz), 7.37-7.48 (2H, m), 7.72-7.76 (3H, m), 8.02-8.05 (1H, m), 8.14 (1H, d, J=1.8 Hz), 8.50 (1H, d, J=2.7 Hz), 8.81-8.83 (1H, m), 9.89 (1H, s).

Reference Example 157

2-[4-formyl-1-(pyridin-3-ylsulfonyl)-1H-pyrrole-2-yl]benzonitrile

A suspension of 5-(2-bromophenyl)-1-(pyridin-3-ylsulfonyl)-1H-pyrrole-3-carbaldehyde (102 mg), zinc cyanide (61.0 mg) and tetrakis(triphenylphosphine)palladium (60.0 mg) in N,N-dimethylformamide (2 mL) was heated (100 W, 4 min 30 sec) using a microwave focused chemical synthesis reactor manufactured by CEM, water was added to the reaction mixture and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=4:1→2:1) to give the title compound as a pale-yellow oil (yield 97.4 mg, 63%).

$^1$H-NMR (CDCl$_3$) δ: 6.79 (1H, d, J=1.8 Hz), 7.41-7.51 (2H, m), 7.58-7.78 (4H, m), 8.17 (1H, d, J=1.5 Hz), 8.45 (1H, d, J=2.7 Hz), 8.84-8.86 (1H, m), 9.91 (1H, s).

Reference Example 158

5-(2-fluorophenyl)-4-iodo-1-(pyridin-3-ylsulfonyl)-1H-pyrrole-3-carbaldehyde

To a solution (42 mL) of 5-(2-fluorophenyl)-4-iodo-1H-pyrrole-3-carbaldehyde (400 mg) in tetrahydrofuran was added sodium hydride (60% in oil, 102 mg) at room temperature and the mixture was stirred for 30 min. 15-Crown-5 (560 mg) was added dropwise and the mixture was stirred for 30 min. Pyridin-3-ylsulfonyl chloride (340 mg) was added, and the mixture was further stirred for 1 hr. The reaction mixture was diluted with saturated brine and the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=3:2→1:1) and crystallized from diisopropyl ether to give the title compound as colorless crystals (yield 540 mg, 93%).

$^1$H-NMR (CDCl$_3$) δ: 7.01-7.07 (1H, m), 7.12-7.17 (1H, m), 7.23-7.28 (1H, m), 7.37-7.41 (1H, m), 7.50-7.58 (1H, m), 7.69-7.73 (1H, m), 8.21 (1H, s), 8.54-8.54 (1H, m), 8.85 (1H, dd, J=4.9, 1.5 Hz), 9.85 (1H, s).

Reference Example 159

5-(2,6-dimethylphenyl)-1-(pyridin-3-ylsulfonyl)-1H-pyrrole-3-carbaldehyde

A mixture of 5-bromo-1H-pyrrole-3-carbaldehyde (0.87 g), 2,6-dimethylphenylboronic acid (4.50 g), cesium carbonate (13.0 g), tri-tert-butylphosphine (0.10 g), tris(dibenzylideneacetone)dipalladium (0) (0.23 g) and mesitylene (200 mL) was stirred with heating under reflux for 5 hr. Water was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=3:1) to give a brown oil (0.48 g). To a solution of the oil in tetrahydrofuran (20 mL) was added sodium hydride (60% in oil, 0.19 g) under ice-cooling, and the mixture was stirred at room temperature for 0.5 hr. A solution of 15-crown-5 (1.06 g) in tetrahydrofuran (3 mL) was added, and the mixture was stirred for 5 min. Pyridin-3-ylsulfonyl chloride (0.64 g) was added under ice-cooling. The reaction mixture was stirred at room temperature for 0.5 hr, a saturated aqueous sodium hydrogencarbonate solution was added, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=2:1) to give the title compound as a pale-brown oil (yield 0.42 g, 25%).

$^1$H-NMR (CDCl$_3$) δ: 1.66 (6H, s), 6.52 (1H, d, J=2.1 Hz), 6.70 (2H, d, J=7.5 Hz), 7.25-7.34 (2H, m), 7.56-7.60 (1H, m), 8.19 (1H, d, J=1.5 Hz), 8.53 (1H, d, J=1.8 Hz), 8.81-8.83 (1H, m), 9.91 (1H, s).

Reference Example 160

2-bromo-5-(2-fluorophenyl)-1-(pyridin-3-ylsulfonyl)-1H-pyrrole-3-carbaldehyde 5-(2-Fluorophenyl)-1-(pyridin-3-ylsulfonyl)-1H-pyrrole-3-carbaldehyde (330 mg) was dissolved in N,N-dimethylformamide (30 mL), N-bromosuccinimide (356 mg) was added and the mixture was stirred at 80° C. for 2 hr. The reaction mixture was allowed to cool, a saturated aqueous sodium hydrogencarbonate solution was added, and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=7:3) and crystallized from diisopropyl ether to give the title compound as colorless crystals (yield 270 mg, 66%).

$^1$H-NMR (CDCl$_3$) δ: 6.70 (1H, s), 7.12-7.26 (2H, m), 7.29-7.35 (1H, m), 7.44-7.52 (2H, m), 8.07-8.11 (1H, m), 8.89 (1H, dd, J=4.9, 1.5 Hz), 9.01-9.02 (1H, m), 9.86 (1H, s).

Reference Example 161

2-(2-fluorophenyl)-4-formyl-1-(pyridin-3-ylsulfonyl)-1H-pyrrole-3-carbonitrile 5-(2-Fluorophenyl)-4-iodo-1-(pyridin-3-ylsulfonyl)-1H-pyrrole-3-carbaldehyde (489 mg), copper (I) cyanide (480 mg), tris(dibenzylideneacetone)dipalladium (0) (49 mg) and 1,1'-bis(diphenylphosphino)ferrocene (89 mg) were mixed in 1,4-dioxane (20 mL), and the mixture was heated under reflux for 3 hr. The reaction mixture was allowed to cool, diluted with ethyl acetate, and filtered. The obtained filtrate was washed with a saturated aqueous sodium hydrogencarbonate solution and saturated brine, dried over anhydrous magnesium sulfate, and concentrated under reduced pressure. The residue was purified by silica gel column chromatography (eluent:hexane-ethyl acetate=2:3→3:7) to give the title compound as a colorless oil (yield 380 mg, about 100%).

$^1$H-NMR (CDCl$_3$) δ: 7.06-7.12 (1H, m), 7.24-7.32 (2H, m), 7.40-7.45 (1H, m), 7.55-7.63 (1H, m), 7.70-7.74 (1H, m), 8.19 (1H, s), 8.57 (1H, d, J=1.9 Hz), 8.88 (1H, dd, J=4.8, 1.6 Hz), 9.97 (1H, s).

Reference Example 162

5-(2-fluorophenyl)-3-formyl-1-(pyridin-3-ylsulfonyl)-1H-pyrrole-2-carbonitrile

2-Bromo-5-(2-fluorophenyl)-1-(pyridin-3-ylsulfonyl)-1H-pyrrole-3-carbaldehyde (340 mg), copper (I) cyanide (400 mg), tris(dibenzylideneacetone)dipalladium (0) (40 mg), 1,1'-bis(diphenylphosphino)ferrocene (70 mg) were mixed in 1,4-dioxane (30 mL), and the mixture was heated under reflux for 24 hr. The reaction mixture was allowed to cool, diluted with ethyl acetate, and filtered. The obtained filtrate was washed with a saturated aqueous sodium hydrogencarbonate solution and saturated brine, dried over anhydrous magnesium sulfate, and concentrated under reduced pressure. The residue was purified by silica gel column chromatography (eluent:hexane-ethyl acetate=3:2) and crystallized from diisopropyl ether to give the title compound as colorless crystals (yield 169 mg, 57%).

$^1$H-NMR (CDCl$_3$) δ: 6.72 (1H, s), 7.12-7.18 (1H, m), 7.24-7.28 (2H, m), 7.50-7.60 (2H, m), 8.10-8.14 (1H, m), 8.82 (1H, d, J=2.4 Hz), 8.92 (1H, dd, J=4.9, 1.5 Hz), 10.09 (1H, s).

Reference Example 163 tert-butyl({5-bromo-1-[(6-methoxypyridin-3-yl)sulfonyl]-1H-pyrrol-3-yl}methyl)methylcarbamate Sodium hydride (60% in oil, 433 mg) was washed twice with hexane, and suspended in tetrahydrofuran (20 mL). A solution of tert-butyl[(5-bromo-1H-pyrrol-3-yl)methyl]methylcarbamate (2.66 g) in tetrahydrofuran (10 mL) was added to the suspension at 0° C., and a solution of 15-crown-5 (2.20 mL) and 6-methoxypyridin-3-ylsulfonyl chloride (2.29 g) in tetrahydrofuran (5 mL) was added at the same temperature. After stirring at room temperature for 30 min, water was added to the reaction mixture, and the mixture was extracted with ethyl acetate. The extract was washed with a saturated aqueous sodium hydrogencarbonate solution, water and saturated brine, dried over anhydrous sodium sulfate, and concentrated under reduced pressure. The residue was purified by basic silica gel column chromatography (eluent:hexane-ethyl acetate=6:1) to give the title compound as a brown oil (yield 4.02 g, 95%).

$^1$H-NMR (CDCl$_3$) δ: 1.47 (9H, s), 2.79 (3H, brs), 4.01 (3H, s), 4.17 (2H, brs), 6.25 (1H, brs), 6.82 (1H, d, J=9.0 Hz), 7.32 (1H, brs), 7.94-7.98 (1H, m), 8.77-8.78 (1H, m).

Reference Example 164 tert-butyl{[5-(4-cyanophenyl)-1-(pyridin-3-ylsulfonyl)-1H-pyrrol-3-yl]methyl}methylcarbamate By a similar operation as in Reference Example 79 and using tert-butyl{[5-bromo-1-(pyridin-3-ylsulfonyl)-1H-pyrrol-3-yl]methyl}methylcarbamate (430 mg), (4-cyanophenyl)boronic acid (176 mg), sodium carbonate (254 mg) and tetrakis(triphenylphosphine)palladium (57.8 mg), the title compound was obtained as a pale-yellow oil (yield 382 mg, 84%).

$^1$H-NMR (CDCl$_3$) δ: 1.46 (9H, s), 2.79 (3H, s), 4.21 (2H, brs), 6.23 (1H, brs), 7.28-7.34 (2H, m), 7.39-7.43 (2H, m), 7.59-7.66 (3H, m), 8.55 (1H, d, J=2.1 Hz), 8.74-8.76 (1H, m).

Reference Example 165 tert-butyl{[5-(5-cyano-2-fluorophenyl)-1-(pyridin-3-ylsulfonyl)-1H-pyrrol-3-yl]methyl}methylcarbamate By a similar operation as in Reference Example 79 and using tert-butyl{[5-bromo-1-(pyridin-3-ylsulfonyl)-1H-pyrrol-3-yl]methyl}methylcarbamate (430 mg), (5-cyano-2-fluorophenyl)boronic acid (198 mg), sodium carbonate (254 mg) and tetrakis(triphenylphosphine)palladium (57.8 mg), the title compound was obtained as a pale-yellow oil (yield 28.9 mg, 6%).

$^1$H-NMR (CDCl$_3$) δ: 1.46 (9H, s), 2.82 (3H, s), 4.24 (2H, brs), 6.28 (1H, brs), 7.21 (1H, t, J=8.7 Hz), 7.35-7.42 (2H, m), 7.49-7.52 (1H, m), 7.69-7.73 (2H, m), 8.66 (1H, d, J=2.4 Hz), 8.81-8.83 (1H, m).

Reference Example 166 tert-butyl{[5-(2-fluoro-5-methoxyphenyl)-1-(pyridin-3-ylsulfonyl)-1H-pyrrol-3-yl]methyl}methylcarbamate tert-Butyl{[5-bromo-1-(pyridin-3-ylsulfonyl)-1H-pyrrol-3-yl]methyl}methylcarbamate (431 mg), (2-fluoro-5-methoxyphenyl)boronic acid (256 mg), sodium hydrogencarbonate (253 mg) and tetrakis(triphenylphosphine)palladium (174 mg) were added to a degassed mixture of 1,2-dimethoxyethane (8 mL) and water (2 mL), and the mixture was stirred under a nitrogen atmosphere at 90° C. for 1 hr. The reaction mixture was allowed to cool, a saturated aqueous sodium hydrogencarbonate solution was added, and the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=1:1) to give the title compound as a colorless oil (yield 475 mg, about 100%).

$^1$H-NMR (CDCl$_3$) δ: 1.47 (9H, s), 2.83 (3H, s), 3.78 (3H, s), 4.24 (2H, s), 6.22 (1H, d, J=1.1 Hz), 6.69-6.71 (1H, m), 6.90-6.98 (2H, m), 7.72-7.36 (2H, m), 7.69-7.73 (1H, m), 8.65 (1H, d, J=2.3 Hz), 8.77 (1H, dd, J=4.9, 1.5 Hz).

Reference Example 167 tert-butyl{[5-(2-fluoro-3-formylphenyl)-1-(pyridin-3-ylsulfonyl)-1H-pyrrol-3-yl]methyl}methylcarbamate By a similar operation as in Reference Example 79 and using tert-butyl{[5-bromo-1-(pyridin-3-ylsulfonyl)-1H-pyrrol-3-yl]methyl}methylcarbamate (430 mg), (2-fluoro-3-formylphenyl)boronic acid (252 mg), sodium carbonate (254 mg) and tetrakis(triphenylphosphine)palladium (173 mg), the title compound was obtained as a pale-yellow oil (yield 250 mg, 53%).

$^1$H-NMR (CDCl$_3$) δ: 1.47 (9H, s), 2.83 (3H, s), 4.25 (2H, brs), 6.28 (1H, brs), 7.26-7.46 (4H, m), 7.68-7.72 (1H, m), 7.92-7.97 (1H, m), 8.61 (1H, d, J=2.1 Hz), 8.77-8.79 (1H, m), 10.30 (1H, s).

Reference Example 168 tert-butyl{[5-(3-acetyl-2-fluorophenyl)-1-(pyridin-3-ylsulfonyl)-1H-pyrrol-3-yl]methyl}methylcarbamate By a similar operation as in Reference Example 79 and using tert-butyl{[5-bromo-1-(pyridin-3-ylsulfonyl)-1H-pyrrol-3-yl]methyl}methylcarbamate (430 mg), (3-acetyl-2-fluorophenyl)boronic acid (273 mg), sodium carbonate (254 mg), and tetrakis(triphenylphosphine)palladium (173 mg), the title compound was obtained as a pale-yellow oil (yield 443 mg, 91%).

$^1$H-NMR (CDCl$_3$) δ: 1.47 (9H, s), 2.59 (3H, d, J=5.4 Hz), 2.83 (3H, s), 4.25 (2H, brs), 6.24 (1H, brs), 7.19-7.36 (4H, m), 7.66-7.70 (1H, m), 7.90-7.96 (1H, m), 8.60 (1H, d, J=2.4 Hz), 8.76-8.78 (1H, m).

Reference Example 169 tert-butyl{[5-(2-fluoropyridin-3-yl)-1-(pyridin-3-ylsulfonyl)-1H-pyrrol-3-yl]methyl}methylcarbamate A suspension of tert-butyl{[5-bromo-1-(pyridin-3-ylsulfonyl)-1H-pyrrol-3-yl]methyl}methylcarbamate (430 mg), (2-fluoropyridin-3-yl)boronic acid (221 mg), sodium carbonate (254 mg) and tetrakis(triphenylphosphine)palladium (173 mg) in 1,2-dimethoxyethane (10 mL) and water (5 mL) was stirred at 105° C. for 1 hr. The reaction mixture was cooled to room temperature. Water was added to the reaction mixture and the mixture was extracted with ethyl acetate. The extract was washed with saturated brine, dried over anhydrous sodium sulfate and concentrated under reduced pressure. The residue was purified by silica gel column chromatography (eluent:hexane-ethyl acetate=6:1→1:1) to give the title compound as a pale-yellow oil (yield 310 mg, 69%).

$^1$H-NMR (CDCl$_3$) δ: 1.46 (9H, s), 2.82 (3H, s), 4.23 (2H, brs), 6.29 (1H, brs), 7.23-7.27 (1H, m), 7.34-7.39 (2H, m), 7.66-7.73 (2H, m), 8.25-8.27 (1H, m), 8.66 (1H, d, J=2.4 Hz), 8.78-8.80 (1H, m).

Reference Example 170 tert-butyl{[5-(3-fluoropyridin-4-yl)-1-(pyridin-3-ylsulfonyl)-1H-pyrrol-3-yl]methyl}methylcarbamate tert-Butyl{[5-bromo-1-(pyridin-3-ylsulfonyl)-1H-pyrrol-3-yl]methyl}methylcarbamate (215 mg), (3-fluoropyridin-4-yl)boronic acid hydrate (120 mg), sodium hydrogencarbonate (126 mg) and tetrakis(triphenylphosphine)palladium (87 mg) were added to a degassed mixture of 1,2-dimethoxyethane (8 mL) and water (2 mL), and the mixture was stirred under a nitrogen atmosphere at 80° C. for 3 hr. The reaction mixture was allowed to cool, a saturated aqueous sodium hydrogencarbonate solution was added, and the mixture was extracted with ethyl acetate. The extract was washed with saturated brine, dried over anhydrous magnesium sulfate, and concentrated under reduced pressure. The residue was purified by basic silica gel column chromatography (eluent:hexane-ethyl acetate=1:1) to give the title compound as a pale-yellow oil (yield 60 mg, 27%).

$^1$H-NMR (CDCl$_3$) δ: 1.47 (9H, s), 2.61 (3H, s), 4.24 (2H, s), 6.35 (1H, s), 7.22-7.26 (1H, m), 7.35-7.40 (2H, m), 7.71-7.75 (1H, m), 8.47 (1H, d, J=4.8 Hz), 8.50 (1H, d, J=1.3 Hz), 8.70 (1H, d, J=2.1 Hz), 8.81 (1H, dd, J=4.8, 1.6 Hz).

Reference Example 171 tert-butyl{[5-(2-chloropyridin-3-yl)-1-(pyridin-3-ylsulfonyl)-1H-pyrrol-3-yl]methyl}methylcarbamate tert-Butyl{[5-bromo-1-(pyridin-3-ylsulfonyl)-1H-pyrrol-3-yl]methyl}methylcarbamate (431 mg), (2-chloropyridin-3-yl)boronic acid (237 mg), sodium hydrogencarbonate (126 mg) and tetrakis(triphenylphosphine)palladium (87 mg) were added to a degassed mixture of 1,2-dimethoxyethane (8 mL) and water (2 mL), and the mixture was stirred under a nitrogen atmosphere at 100° C. for 3 hr. The reaction mixture was allowed to cool, a saturated aqueous sodium hydrogencarbonate solution was added, and the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=1:1→1:4) to give the title compound as a colorless oil (yield 280 mg, 60%).

$^1$H-NMR (CDCl$_3$) δ: 1.47 (9H, s), 2.84 (3H, s), 4.27 (2H, s), 6.30 (1H, s), 7.30-7.39 (3H, m), 7.65-7.73 (2H, m), 8.43-8.45 (1H, m), 8.67 (1H, d, J=2.3 Hz), 8.80 (1H, dd, J=4.9, 1.5 Hz).

Reference Example 172 tert-butyl{[5-(6-chloropyridin-3-yl)-1-(pyridin-3-ylsulfonyl)-1H-pyrrol-3-yl]methyl}methylcarbamate

Reference Example 173 tert-butyl{[5-(6'-chloro-2,3'-bipyridin-5-yl)-1-(pyridin-3-ylsulfonyl)-1H-pyrrol-3-yl]methyl}methylcarbamate tert-Butyl{[5-bromo-1-(pyridin-3-ylsulfonyl)-1H-pyrrol-3-yl]methyl}methylcarbamate (431 mg), (6-chloropyridin-3-yl)boronic acid (237 mg), sodium hydrogencarbonate (252 mg) and tetrakis(triphenylphosphine)palladium (87 mg) were added to a degassed mixture of 1,2-dimethoxyethane (8 mL) and water (2 mL), and the mixture was stirred under a nitrogen atmosphere at 90° C. for 3 hr. The reaction mixture was allowed to cool, a saturated aqueous sodium hydrogencarbonate solution was added, and the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=1:1→3:7), and fractions showing Rf value of 0.6 (eluent:hexane-ethyl acetate=1:1) were collected to give the title compound of Reference Example 172 as a colorless oil (yield 100 mg, 22%). Then, fractions showing Rf value of 0.4 (eluent:hexane-ethyl acetate=1:1) were collected to give the title compound of Reference Example 173 as a pale-yellow powder (yield 100 mg, 19%).

Reference Example 172 $^1$H-NMR (CDCl$_3$) δ: 1.47 (9H, s), 2.81 (3H, s), 4.23 (2H, s), 6.24 (1H, s), 7.23-7.38 (3H, m), 7.59-7.63 (1H, m), 7.72 (1H, dd, J=8.3, 2.3 Hz), 8.14 (1H, d, J=2.3 Hz), 8.64 (1H, d, J=2.3 Hz), 8.78 (1H, dd, J=4.7, 1.7 Hz). Reference Example 173 $^1$H-NMR (CDCl$_3$) δ: 1.47 (9H, s), 2.82 (3H, s), 4.24 (2H, s), 6.29 (1H, s), 7.31-7.37 (2H, m), 7.47 (1H, d, J=8.3 Hz), 7.64-7.68 (1H, m), 7.76-7.86 (2H, m), 8.38 (1H, dd, J=8.5, 2.5 Hz), 8.51 (1H, d, J=1.9 Hz), 8.63 (1H, d, J=2.3 Hz), 8.77 (1H, dd, J=4.9, 1.5 Hz), 9.04 (1H, d, J=2.3 Hz).

Reference Example 174 tert-butyl({5-(2-fluoropyridin-3-yl)-1-[(6-methoxypyridin-3-yl)sulfonyl]-1H-pyrrol-3-yl}methyl)methylcarbamate By a similar operation as in Reference Example 79 and using tert-butyl({5-bromo-1-[(6-methoxypyridin-3-yl)sulfonyl]-1H-pyrrol-3-yl}methyl)methylcarbamate (463 mg), (2-fluoropyridin-3-yl)boronic acid (172 mg), sodium carbonate (260 mg) and tetrakis(triphenylphosphine)palladium (176 mg), the title compound was obtained as a pale-yellow oil (yield 293 mg, 45%).

$^1$H-NMR (CDCl$_3$) δ: 1.47 (9H, s), 2.83 (3H, brs), 3.97 (3H, s), 4.23 (2H, brs), 6.28 (1H, s), 6.69-6.72 (1H, m), 7.26-7.36 (2H, m), 7.49-7.53 (1H, m), 7.75-7.80 (1H, m), 8.22-8.23 (1H, m), 8.26-8.27 (1H, m).

Reference Example 175 tert-butyl({5-[2-fluoro-3-(hydroxymethyl)phenyl]-1-(pyridin-3-ylsulfonyl)-1H-pyrrol-3-yl}methyl)methylcarbamate To a solution of tert-butyl{[5-(2-fluoro-3-formylphenyl)-1-(pyridin-3-ylsulfonyl)-1H-pyrrol-3-yl]methyl}-methylcarbamate (388 mg) in tetrahydrofuran (8 mL) were added under ice-cooling, sodium borohydride (41.3 mg) and methanol (3 mL). After stirring at the same temperature for 30 min, water was added to the reaction mixture and the mixture was extracted with ethyl acetate. The extract was washed with saturated brine, dried over anhydrous sodium sulfate, and concentrated under reduced pressure. The residue was purified by basic silica gel column chromatography (eluent: hexane-ethyl acetate=2:1→1:2) to give the title compound as a colorless oil (yield 238 mg, 61%).

$^1$H-NMR (CDCl$_3$) δ: 1.46 (9H, s), 2.83 (3H, s), 4.24 (2H, brs), 4.65 (2H, brs), 6.19 (1H, brs), 7.15-7.19 (2H, m), 7.34-7.38 (2H, m), 7.51-7.55 (1H, m), 7.73-7.76 (1H, m), 8.40-8.41 (1H, m), 8.75-8.77 (1H, m), 1H not detected.

Reference Example 176 tert-butyl({5-[2-fluoro-3-(1-hydroxyethyl)phenyl]-1-(pyridin-3-ylsulfonyl)-1H-pyrrol-3-yl}methyl)methylcarbamate By a similar operation as in Reference Example 175 and using tert-butyl{[5-(3-acetyl-2-fluorophenyl)-1-(pyridin-3-ylsulfonyl)-1H-pyrrol-3-yl]methyl}methylcarbamate (443 mg), the title compound was obtained as a pale-yellow amorphous form (yield 318 mg, 71%).

$^1$H-NMR (CDCl$_3$) δ: 1.47 (9H, s), 1.50 (3H, d, J=6.3 Hz), 2.83 (3H, s), 4.25 (2H, brs), 5.06 (1H, q, J=6.3 Hz), 6.20 (1H, brs), 7.09-7.22 (2H, m), 7.34-7.38 (2H, m), 7.59-7.64 (1H, m), 7.72-7.76 (1H, m), 8.40 (1H, d, J=2.4 Hz), 8.75-8.78 (1H, m), 1H not detected.

Reference Example 177 tert-butyl{[5-(2-fluoro-3-methoxyphenyl)-1-(pyridin-3-ylsulfonyl)-1H-pyrrol-3-yl]methyl}methylcarbamate tert-Butyl{[5-bromo-1-(pyridin-3-ylsulfonyl)-1H-pyrrol-3-yl]methyl}methylcarbamate (431 mg), (2-fluoro-3-methoxyphenyl)boronic acid (256 mg), sodium hydrogencarbonate (253 mg) and tetrakis(triphenylphosphine)palladium (88 mg) were added to a mixture of 1,2-dimethoxyethane (8 mL) and water (2 mL), and the mixture was stirred under a nitrogen atmosphere 100° C. for 2 hr. The reaction mixture was allowed to cool, a saturated aqueous sodium hydrogencarbonate solution was added, and the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=1:1) to give the title compound as a colorless oil (yield 475 mg, about 100%).

$^1$H-NMR (CDCl$_3$) δ: 1.46 (9H, s), 2.82 (3H, s), 3.90 (3H, s), 4.24 (2H, s), 6.21 (1H, d, J=1.5 Hz), 6.72-6.79 (1H, m), 7.00-7.09 (2H, m), 7.32-7.36 (2H, m), 7.69-7.73 (1H, m), 8.63 (1H, d, J=2.3 Hz), 8.76 (1H, dd, J=4.9, 1.5 Hz).

Reference Example 178 tert-butyl{[5-(2-fluoro-6-methoxyphenyl)-1-(pyridin-3-ylsulfonyl)-1H-pyrrol-3-yl]methyl}methylcarbamate tert-butyl{[5-bromo-1-(pyridin-3-ylsulfonyl)-1H-pyrrol-3-yl]methyl}methylcarbamate (431 mg), (2-fluoro-6-methoxyphenyl)boronic acid (256 mg), sodium hydrogencarbonate (253 mg) and tetrakis(triphenylphosphine)palladium (176 mg) were added to a mixture of 1,2-dimethoxyethane (8 mL) and water (2 mL), and the mixture was stirred under a nitrogen atmosphere at 100° C. for 20 hr. The reaction mixture was allowed to cool, a saturated aqueous sodium hydrogencarbonate solution was added, and the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=1:1) to give the title compound as a colorless oil (yield 100 mg, 21%).

$^1$H-NMR (CDCl$_3$) δ: 1.46 (9H, s), 2.85 (3H, s), 3.58 (3H, s), 4.26 (2H, s), 6.17 (1H, d, J=1.9 Hz), 6.64-6.70 (2H, m), 7.31-7.39 (3H, m), 7.71-7.75 (1H, m), 8.60 (1H, d, J=1.9 Hz), 8.76 (1H, dd, J=4.9, 1.5 Hz).

Reference Example 179

2-[4-(difluoromethoxy)phenyl]-4,4,5,5-tetramethyl-1,3,2-dioxaborolane

A solution (10 mL) of 1-bromo-4-(difluoromethoxy)benzene (500 mg), 4,4,4',4',5,5,5',5'-octamethyl-2,2'-bi-1,3,2-dioxaborolane (654 mg), potassium acetate (660 mg) and 1,1'-bis(diphenylphosphino)ferrocene dichloropalladium (73.2 mg) in dimethylformamide was stirred at 80° C. for 3 hr. The reaction mixture was cooled to room temperature, diluted with ethyl acetate and filtered through celite. The filtrate was washed with water and saturated brine, dried over anhydrous sodium sulfate, and concentrated under reduced pressure. The residue was purified by silica gel column chromatography (eluent:hexane-ethyl acetate=19:1→8:1) to give the title compound as a pale-yellow oil (yield 348 mg, 58%).

$^1$H-NMR (CDCl$_3$) δ: 1.35 (12H, s), 6.54 (1H, t, J=73.5 Hz), 7.09 (2H, d, J=7.8 Hz), 7.81 (2H, d, J=7.8 Hz).

Reference Example 180 tert-butyl({5-[4-(difluoromethoxy)phenyl]-1-(pyridin-3-ylsulfonyl)-1H-pyrrol-3-yl}methyl)methylcarbamate tert-Butyl{[5-bromo-1-(pyridin-3-ylsulfonyl)-1H-pyrrol-3-yl]methyl}methylcarbamate (430 mg), 2-[4-(difluoromethoxy)phenyl]-4,4,5,5-tetramethyl-1,3,2-dioxaborolane (348 mg), sodium carbonate (254 mg) and tetrakis(triphenylphosphine)palladium (174 mg) were suspended in dimethoxyethane (10 mL) and water (4 mL), and the mixture was stirred under a nitrogen atmosphere at 105° C. for 1 hr. The reaction mixture was allowed to cool to room temperature, water was added, and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=4:1→2:1) to give the title compound as a pale-yellow oil (yield 550 mg, quantitative yield).

$^1$H-NMR (CDCl$_3$) δ: 1.46 (9H, s), 2.80 (3H, s), 4.21 (2H, brs), 6.13 (1H, brs), 6.57 (1H, t, J=73.2 Hz), 7.06-7.09 (2H, m), 7.21-7.31 (4H, m), 7.55-7.59 (1H, m), 8.54 (1H, d, J=2.4 Hz), 8.71-8.73 (1H, m).

Reference Example 181 tert-butyl methyl{[5-(4-methylpyridin-3-yl)-1-(pyridin-3-ylsulfonyl)-1H-pyrrol-3-yl]methyl}carbamate tert-Butyl{[5-bromo-1-(pyridin-3-ylsulfonyl)-1H-pyrrol-3-yl]methyl}methylcarbamate (431 mg), (4-methylpyridin-3-yl)boronic acid (206 mg), sodium hydrogencarbonate (253 mg) and tetrakis(triphenylphosphine)palladium (87 mg) were added to a degassed mixture of 1,2-dimethoxyethane (8 mL) and water (2 mL), and the mixture was stirred under a nitrogen atmosphere at 80° C. for 6 hr. The reaction mixture was allowed to cool, a saturated aqueous sodium hydrogencarbonate solution was added, and the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=1:1→0:1) to give the title compound as a colorless oil (yield 230 mg, 52%).

$^1$H-NMR (CDCl$_3$) δ: 1.47 (9H, s), 2.11 (3H, s), 2.85 (3H, s), 4.27 (2H, s), 6.15 (1H, s), 7.18 (1H, d, J=4.9 Hz), 7.34-7.39 (2H, m), 7.58-7.62 (1H, m), 7.94 (1H, s), 8.49 (1H, d, J=5.3 Hz), 8.64 (1H, d, J=2.3 Hz), 8.80 (1H, dd, J=4.9, 1.5 Hz).

Reference Example 182

3-bromo-2-methylpyridine

2-Methylpyridine (46.6 g) was added dropwise to aluminum chloride (200 g) and the mixture was stirred at 100° C. To a mixture was added dropwise bromine (40.0 g) at the same temperature over 1 hr, and the mixture was further stirred for 30 min. After cooling, the reaction mixture was poured into ice water, concentrated hydrochloric acid was added until the mixture was acidified. The obtained solution was washed with ethyl acetate, and the aqueous layer was basified with a 8 mol/L aqueous sodium hydroxide solution. After extraction with diethyl ether, the extract was washed with saturated brine, dried over anhydrous sodium sulfate, and concentrated under reduced pressure. The residue was purified by silica gel column chromatography (eluent: hexane-diethyl ether=10:1) to give the title compound as a colorless oil (yield 5.09 g, 12%).

$^1$H-NMR (CDCl$_3$) δ: 2.67 (3H, s), 6.98-7.03 (1H, m), 7.78-7.82 (1H, m), 8.40-8.44 (1H, m).

Reference Example 183 tert-butyl methyl{[5-(2-methylpyridin-3-yl)-1-(pyridin-3-ylsulfonyl)-1H-pyrrol-3-yl]methyl}carbamate To a solution of 3-bromo-2-methylpyridine (504 mg) in diethyl ether (15 mL) was added a 1.62 mol/L solution (2 mL) of n-butyl lithium in hexane at −78° C., and the mixture was stirred at the same temperature for 15 min. Thereto was added triisopropoxyborane (1.22 mL) at the same temperature, and the obtained mixture was stirred at 0° C. for 1 hr. Methanol (2 mL) was added to the reaction mixture, and the mixture was concentrated under reduced pressure. tert-Butyl({5-bromo-1-[(pyridin-3-yl)sulfonyl]-1H-pyrrol-3-yl}methyl)methylcarbamate (432 mg), sodium carbonate (1.15 g), tetrakis(triphenylphosphine)palladium (174 mg), 1,2-dimethoxyethane (20 mL) and water (10 mL) was added to the residue, and the mixture was stirred under a nitrogen atmosphere at 105° C. for 1 hr. The reaction mixture was allowed to cool to room temperature, water was added, and the mixture was extracted with ethyl acetate. The extract was washed with a saturated aqueous sodium hydrogencarbonate solution, water and saturated brine, dried over anhydrous magnesium sulfate, and concentrated under reduced pressure. The residue was purified by basic silica gel column chromatography (eluent:hexane-ethyl acetate=1:1) to give the title compound as a brown oil (yield 282 mg, 22%).

¹H-NMR (CDCl₃) δ: 1.47 (9H, s), 2.09 (3H, s), 2.85 (3H, s), 4.27 (2H, brs), 6.14 (1H, brs), 7.10-7.14 (1H, m), 7.26-7.38 (3H, m), 7.56-7.60 (1H, m), 8.54-8.56 (1H, m), 8.60-8.61 (1H, m), 8.78-8.80 (1H, m).

Reference Example 184

6-methylnicotinamide

A mixture of methyl 6-methylnicotinate (13.9 g) and 28% aqueous ammonia (140 mL) was stirred at room temperature for 4 hr. The reaction mixture was concentrated under reduced pressure, and the residue was recrystallized from ethanol to give the title compound as a white solid (yield 8.98 g, 72%).

¹H-NMR (CDCl₃) δ: 2.63 (3H, s), 5.60-6.20 (2H, brm), 7.25-7.28 (1H, m), 8.04-8.07 (1H, m), 8.90 (1H, d, J=2.1 Hz).

Reference Example 185

6-methylpyridine-3-amine

Bromine (1.0 mL) was added to a 4 mol/L aqueous sodium hydroxide solution (60 mL) at 0° C., and the mixture was stirred at the same temperature for 15 min. 6-Methylnicotinamide (2.4 g) was added to the obtained solution over 10 min, and the mixture was stirred at room temperature for 30 min and further stirred at 75° C. for 4 hr. The reaction mixture was allowed to cool to room temperature, and extracted with ethyl acetate:THF=2:1. The extract was washed with a small amount of saturated brine, dried over anhydrous magnesium sulfate, and concentrated under reduced pressure. Recrystallization of the residue from ethyl acetate-hexane gave the title compound as a pale-yellow solid (yield 0.93 g, 49%).

¹H-NMR (CDCl₃) δ: 2.43 (3H, s), 3.54 (2H, brs), 6.89-6.95 (2H, m), 7.99-8.01 (1H, m).

Reference Example 186

6-methylpyridin-3-ylsulfonyl chloride

To a mixture of 6-methylpyridine-3-amine (449 mg) and concentrated hydrochloric acid (5 mL) was added a solution of sodium nitrite (857 mg) in water (2 mL) at 0° C., and the mixture was stirred at the same temperature for 10 min. To the mixture was added a solution of concentrated hydrochloric acid (2.5 mL), copper sulfate (69 mg) and sodium hydrogen sulfite (5.08 g) in water (8 mL) at 0° C., and the mixture was stirred at room temperature for 30 min. The reaction mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=10:1) to give the title compound as a pale-yellow solid (yield 0.12 g, 15%).

¹H-NMR (CDCl₃) δ: 2.73 (3H, s), 7.40-7.43 (1H, m), 8.16-8.20 (1H, m), 9.11-9.12 (1H, m).

Reference Example 187 tert-butyl({5-bromo-1-[(6-methylpyridin-3-yl)sulfonyl]-1H-pyrrol-3-yl}methyl)methylcarbamate To a solution of tert-butyl[(5-bromo-1H-pyrrol-3-yl)methyl]methylcarbamate (207 mg) in tetrahydrofuran (30 mL) was added sodium hydride (60% in oil, 31 mg) at 0° C., and the mixture was stirred at the same temperature for 10 min. A solution (3 mL) of 15-crown-5 (0.16 mL) and 6-methylpyridin-3-ylsulfonyl chloride (117 mg) in tetrahydrofuran was added at the same temperature. After stirring at room temperature for 30 min, water was added to the reaction mixture, and the mixture was extracted with ethyl acetate. The extract was washed with a saturated aqueous sodium hydrogencarbonate solution, water and saturated brine, dried over anhydrous sodium sulfate, and concentrated under reduced pressure. The residue was purified by silica gel column chromatography (eluent:hexane-ethyl acetate=4:1) to give the title compound as a brown oil (yield 213 mg, 79%).

¹H-NMR (CDCl₃) δ: 1.47 (9H, s), 2.66 (3H, s), 2.79 (3H, s), 4.17 (2H, brs), 6.26 (1H, brs), 7.26-7.33 (2H, m), 8.03-8.07 (1H, m), 9.01-9.02 (1H, m).

Reference Example 188 tert-butyl({5-(2-fluoropyridin-3-yl)-1-[(6-methylpyridin-3-yl)sulfonyl]-1H-pyrrol-3-yl}methyl)methylcarbamate A suspension of tert-butyl({5-bromo-1-[(6-methylpyridin-3-yl)sulfonyl]-1H-pyrrol-3-yl}methyl)methylcarbamate (206 mg), (2-fluoropyridin-3-yl)boronic acid (80 mg), sodium carbonate (119 mg) and tetrakis(triphenylphosphine)palladium (80 mg) in 1,2-dimethoxyethane (5 mL) and water (2.5 mL) was stirred under a nitrogen atmosphere at 105° C. for 1 hr. The reaction mixture was allowed to cool to room temperature, water was added to the reaction mixture, and the mixture was extracted with ethyl acetate. The extract was washed with a saturated aqueous sodium hydrogencarbonate solution, water and saturated brine, dried over anhydrous sodium sulfate, and concentrated under reduced pressure. The residue was purified by silica gel column chromatography (eluent:hexane-ethyl acetate=1:1) to give the title compound as a pale-yellow oil (yield 87 mg, 41%).

¹H-NMR (CDCl₃) δ: 1.46 (9H, s), 2.62 (3H, m), 2.82 (3H, s), 4.23 (2H, brs), 6.29 (1H, s), 7.18-7.27 (2H, m), 7.33 (1H, s), 7.54-7.57 (1H, m), 7.72-7.75 (1H, m), 8.26-8.27 (1H, m), 8.53 (1H, s).

Reference Example 189

5-(2-fluoropyridin-3-yl)-1-(phenylsulfonyl)-1H-pyrrole-3-carbaldehyde

5-Bromo-1-(phenylsulfonyl)-1H-pyrrole-3-carbaldehyde (3.15 g), (2-fluoropyridin-3-yl)boronic acid (2.83 g), sodium hydrogencarbonate (2.53 g) and tetrakis(triphenylphosphine)palladium (870 mg) were added to a degassed mixture of 1,2-dimethoxyethane (80 mL) and water (20 mL), and the mixture was stirred under a nitrogen atmosphere at 80° C. for 5 hr. The reaction mixture was allowed to cool, a saturated aqueous sodium hydrogencarbonate solution was added, and the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=4:1→2:3) to give the title compound as a colorless oil (yield 2.25 g, 68%).

¹H-NMR (CDCl₃) δ: 6.71 (1H, d, J=1.7 Hz), 7.24-7.28 (1H, m), 7.42-7.48 (4H, m), 7.62-7.68 (1H, m), 7.70-7.76 (1H, m), 8.14 (1H, d, J=1.9 Hz), 8.28-8.31 (1H, m), 9.90 (1H, s).

Reference Example 190

5-(2-fluoropyridin-3-yl)-1H-pyrrole-3-carbaldehyde 5-(2-Fluoropyridin-3-yl)-1-(phenylsulfonyl)-1H-pyrrole-3-carbaldehyde (2.25 g) was dissolved in methanol (20 mL) and tetrahydrofuran (20 mL), a 8 mol/L aqueous sodium hydroxide solution (20 mL) was added dropwise at room temperature and the mixture was stirred for 1 hr. The reaction mixture was diluted with saturated brine, and the mixture was extracted with ethyl acetate. The extract was washed with saturated brine, dried over anhydrous magnesium sulfate, and concentrated under reduced pressure. Ethyl acetate was added to the residue and insoluble crystals were collected by filtration to give the title compound as pale-brown crystals (yield 1.03 g, 79%).

$^1$H-NMR (DMSO-d$_6$) δ: 6.99 (1H, d, J=1.5 Hz), 7.43-7.48 (1H, m), 7.88 (1H, s), 8.12-8.15 (1H, m), 8.27-8.34 (1H, m), 9.77 (1H, s), 12.28 (1H, brs).

Reference Example 191

4-chloro-5-(2-fluoropyridin-3-yl)-1H-pyrrole-3-carbaldehyde 5-(2-Fluoropyridin-3-yl)-1H-pyrrole-3-carbaldehyde (610 mg) was dissolved in N,N-dimethylformamide (20 mL), N-chlorosuccinimide (641 mg) was added and the mixture was stirred at 80° C. for 40 min. After cooling, water was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=3:2→1:1) to give the title compound as a colorless powder (yield 320 mg, 44%).

$^1$H-NMR (DMSO-d$_6$) δ: 7.49-7.54 (1H, m), 7.86 (1H, d, J=2.3 Hz), 8.12-8.19 (1H, m), 8.30-8.32 (1H, m), 9.80 (1H, s), 12.48 (1H, brs).

Reference Example 192

4-chloro-5-(2-fluoropyridin-3-yl)-1-(pyridin-3-ylsulfonyl)-1H-pyrrole-3-carbaldehyde To a solution (20 mL) of 4-chloro-5-(2-fluoropyridin-3-yl)-1H-pyrrole-3-carbaldehyde (270 mg) in tetrahydrofuran was added sodium hydride (60% in oil, 100 mg) at room temperature and the mixture was stirred for 30 min. 15-Crown-5 (530 mg) was added dropwise and the mixture was stirred for 30 min. 3-Pyridylsulfonyl chloride (321 mg) was added, and the mixture was further stirred for 1 hr. The reaction mixture was diluted with saturated brine, and the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=1:1→1:4), and crystallized from diethyl ether to give the title compound as colorless crystals (yield 358 mg, 81%).

$^1$H-NMR (CDCl$_3$) δ: 7.35-7.39 (1H, m), 7.42-7.46 (1H, m), 7.69-7.73 (1H, m), 7.76-7.82 (1H, m), 8.14 (1H, s), 8.39-8.41 (1H, m), 8.64 (1H, dd, J=2.5 Hz, 0.6 Hz), 8.89 (1H, dd, J=4.8 Hz, 1.6 Hz), 9.97 (1H, s).

Reference Example 193 tributyl(2-thienyl)stannane

A solution (10 mL) of 2-bromothiophene (1.0 g) in tetrahydrofuran was cooled to −70° C., and a 1.6 mol/L solution (4.2 mL) of n-butyllithium in hexane was added dropwise. After stirring at the same temperature for 30 min, tributyltin chloride (2.1 g) was added dropwise. After further stirring for 1 hr, water was added to the reaction mixture, and the mixture was extracted with ethyl acetate. The extract was washed with saturated brine, dried over anhydrous sodium sulfate, and concentrated under reduced pressure. The residual oil (2.4 g) containing the title compound was used for the next step without purification.

Reference Example 194 tert-butyl methyl{[1-(pyridin-3-ylsulfonyl)-5-(2-thienyl)-1H-pyrrol-3-yl]methyl}carbamate To a solution of crude tributyl(2-thienyl)stannane (1.1 g) and tert-butyl{[5-bromo-1-(pyridin-3-ylsulfonyl)-1H-pyrrol-3-yl]methyl}methylcarbamate (430 mg) in toluene was added tetrakis(triphenylphosphine)palladium (116 mg), and the mixture was stirred under a nitrogen atmosphere at 120° C. for 1 hr. The reaction mixture was allowed to cool to room temperature and the solvent was evaporated under reduced pressure. The residue was purified by basic silica gel column chromatography (eluent:hexane-ethyl acetate=4:1) to give the title compound as a pale-yellow oil (yield 315 mg, 73%).

$^1$H-NMR (CDCl$_3$) δ: 1.47 (9H, s), 2.83 (3H, s), 4.22 (2H, brs), 6.25 (1H, brs), 7.04-7.07 (1H, m), 7.16-7.17 (1H, m), 7.27-7.31 (2H, m), 7.36-7.37 (1H, m), 7.62-7.66 (1H, m), 8.58-8.59 (1H, m), 8.71-8.73 (1H, m).

Reference Example 195

3-methyl-2-(tributylstannyl)pyridine

A solution (10 mL) of 2-bromo-3-methylpyridine (1.0 g) in tetrahydrofuran was cooled to −70° C., and a 1.6 mol/L solution (4.0 mL) of n-butyllithium in hexane was added dropwise. After stirring at the same temperature for 15 min, tributyltin chloride (2.2 g) was added dropwise. After further stirring for 1 hr, water was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent: hexane-ethyl acetate=19:1) to give the title compound as a colorless oil (yield 1.75 g, 79%).

$^1$H-NMR (CDCl$_3$) δ: 0.85-0.95 (9H, m), 1.11-1.17 (6H, m), 1.29-1.37 (6H, m), 1.49-1.57 (6H, m), 2.36 (3H, s), 6.99-7.03 (1H, m), 7.31-7.34 (1H, m), 8.52-8.54 (1H, m).

Reference Example 196 tert-butyl methyl{[5-(3-methylpyridin-2-yl)-1-(pyridin-3-ylsulfonyl)-1H-pyrrol-3-yl]methyl}carbamate A solution of 3-methyl-2-(tributylstannyl)pyridine (1.0 g), tert-butyl{[5-bromo-1-(pyridin-3-ylsulfonyl)-1H-pyrrol-3-yl]methyl}methylcarbamate (563 mg) and tetrakis(triphenylphosphine)palladium (454 mg) in toluene was stirred under a nitrogen atmosphere at 120° C. for 30 hr. The mixture was cooled to room temperature and the solvent was evaporated under reduced pressure. The residue was purified by basic silica gel column chromatography (eluent:hexane-ethyl acetate=4:1) to give the title compound as a colorless oil (yield 129 mg, 22%).

$^1$H-NMR (CDCl$_3$) δ: 1.45 (9H, s), 2.80 (3H, brs), 4.25 (2H, brs), 6.26 (1H, brs), 7.23-7.27 (2H, m), 7.39-7.44 (1H, m), 7.60 (1H, d, J=6.9 Hz), 7.99-8.03 (1H, m), 8.36 (1H, d, J=4.5 Hz), 8.78-8.80 (1H, m), 8.86-8.87 (1H, m).

Reference Example 197 tert-butyl{[5-{2-fluoro-3-[(hydroxyimino)methyl]phenyl}-1-(pyridin-3-ylsulfonyl)-1H-pyrrol-3-yl]methyl}methylcarbamate To a solution (3 mL) of tert-butyl{[5-(2-fluoro-3-formylphenyl)-1-(pyridin-3-ylsulfonyl)-1H-pyrrol-3-yl]methyl}methylcarbamate (182 mg) in 2-propanol were added hydroxylamine hydrochloride (40 mg) and sodium acetate (47 mg). After stirring at room temperature for 3 hr, saturated aqueous sodium hydrogencarbonate solution was added to the reaction mixture and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=8:1→3:1) to give the title compound as a pale-yellow oil (yield 150 mg, 80%).

$^1$H-NMR (CDCl$_3$) δ: 1.46 (9H, s), 2.82 (3H, s), 4.24 (2H, s), 6.22 (1H, s), 7.15-7.19 (2H, m), 7.31-7.35 (2H, m), 7.67-7.71 (1H, m), 7.76-7.85 (1H, m), 8.27 (1H, s), 8.63 (1H, d, J=2.1 Hz), 8.76-8.78 (1H, m), 1H not detected.

Reference Example 198 tert-butyl{[5-(3-cyano-2-fluorophenyl)-1-(pyridin-3-ylsulfonyl)-1H-pyrrol-3-yl]methyl}methylcarbamate To a solution (5 mL) of tert-butyl{[5-{2-fluoro-3-[(hydroxyimino)methyl]phenyl}-1-(pyridin-3-ylsulfonyl)-1H-pyrrol-3-yl]methyl}methylcarbamate (150 mg) in tetrahydrofuran were added triethylamine (93 mg) and methanesulfonyl chloride (84 mg) at room temperature. The reaction mixture was stirred at 70° C. for 8 hr, and cooled to room temperature. Water was added and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=8:1→3:1) to give the title compound as a pale-yellow oil (yield 106 mg, 73%).

$^1$H-NMR (CDCl$_3$) δ: 1.46 (9H, s), 2.82 (3H, s), 4.24 (2H, s), 6.28 (1H, brs), 7.25-7.40 (3H, m), 7.48-7.53 (1H, m), 7.66-7.70 (2H, m), 8.62 (1H, d, J=2.7 Hz), 8.80-8.82 (1H, m).

Reference Example 199 tert-butyl{[5-(4-bromo-3-thienyl)-1-(pyridin-3-ylsulfonyl)-1H-pyrrol-3-yl]methyl}methylcarbamate By a similar operation as in Reference Example 79 and using tert-butyl{[5-bromo-1-(pyridin-3-ylsulfonyl)-1H-pyrrol-3-yl]methyl}methylcarbamate (430 mg), (4-bromo-3-thienyl)boronic acid (248 mg), sodium carbonate (254 mg) and tetrakis(triphenylphosphine)palladium (116 mg), the title compound was obtained as a pale-yellow oil (yield 470 mg, 92%).

$^1$H-NMR (CDCl$_3$) δ: 1.47 (9H, s), 2.84 (3H, brs), 4.26 (2H, brs), 6.21-6.22 (1H, m), 7.18-7.19 (1H, m), 7.30-7.39 (3H, m), 7.63-7.67 (1H, m), 8.57-8.58 (1H, m), 8.74-8.76 (1H, m).

Reference Example 200 tert-butyl{[5-(4-cyano-3-thienyl)-1-(pyridin-3-ylsulfonyl)-1H-pyrrol-3-yl]methyl}methylcarbamate To a solution (5 mL) of tert-butyl{[5-(4-bromo-3-thienyl)-1-(pyridin-3-ylsulfonyl)-1H-pyrrol-3-yl]methyl}methylcarbamate (470 mg) in N,N-dimethylformamide were added zinc cyanide (215 mg) and tetrakis(triphenylphosphine)palladium (212 mg) and the mixture was sufficiently degassed. The mixture was stirred with heating at 120° C. for 18 hr and cooled to room temperature. Water and ethyl acetate were added and the mixture was filtered through celite. The filtrate was concentrated under reduced pressure and the residue was extracted with ethyl acetate. The extract was washed with saturated brine, dried over anhydrous sodium sulfate, and concentrated under reduced pressure. The residue was purified by silica gel column chromatography (eluent:hexane-ethyl acetate=4:1→2:1) to give the title compound as a pale-yellow oil (yield 297 mg, 71%).

$^1$H-NMR (CDCl$_3$) δ: 1.47 (9H, s), 2.83 (3H, brs), 4.25 (2H, brs), 6.34-6.35 (1H, m), 7.35-7.39 (2H, m), 7.48 (1H, br), 7.65-7.68 (1H, m), 7.87 (1H, d, J=3.0 Hz), 8.53-8.54 (1H, m), 8.78-8.79 (1H, m).

Example 1

N-methyl-1-[5-phenyl-1-(pyridin-3-ylsulfonyl)-1H-pyrrol-3-yl]methanamine Dihydrochloride 5-Phenyl-1-(pyridin-3-ylsulfonyl)-1H-pyrrole-3-carbaldehyde (230 mg) was dissolved in absolute tetrahydrofuran (10 mL), a 2 mol/L solution (1 mL) of methylamine in tetrahydrofuran was added, and the mixture was stirred at room temperature for 2 hr. The reaction mixture was added to a solution of sodium borohydride (76 mg) in methanol (5 mL), and the mixture was stirred at the same temperature for 20 min. The reaction mixture was diluted with ethyl acetate, washed successively with a saturated aqueous sodium hydrogencarbonate solution, water and saturated brine, and dried over anhydrous magnesium sulfate. The solvent was evaporated under reduced pressure and the residue was purified by silica gel column chromatography (eluent:ethyl acetate-methanol=1:0→1:1) and further by HPLC(ODS, 0.1% trifluoroacetic acid-containing water-0.1% trifluoroacetic acid-containing acetonitrile=97:3→0.1% trifluoroacetic acid-containing acetonitrile) to give trifluoroacetate of the title compound. The obtained trifluoroacetate was neutralized with a saturated aqueous sodium hydrogencarbonate solution, extracted with ethyl acetate, washed successively with a saturated aqueous sodium hydrogencarbonate solution, water and saturated brine, and dried over anhydrous magnesium sulfate. The solvent was evaporated under reduced pressure. The residue was dissolved in ethyl acetate (5 mL), a 4 mol/L hydrogen chloride-ethyl acetate solution (1 mL) and ethanol (5 mL) were added, and the mixture was concentrated under reduced pressure and crystallized from ethyl acetate-ethanol to give the title compound (yield 85 mg, 29%).

$^1$H-NMR (DMSO-d$_6$) δ: 2.50 (3H, s), 3.97-4.00 (2H, s), 6.50 (1H, s), 7.14-7.16 (2H, m), 7.35-7.45 (3H, m), 7.62-7.70 (1H, m), 7.78-7.83 (2H, m), 8.47-8.48 (1H, m), 8.84-8.86 (1H, m), 9.08 (2H, br), 1H not detected.

Example 2

1-{1-[(6-methoxypyridin-3-yl)sulfonyl]-5-phenyl-1H-pyrrol-3-yl}-N-methylmethanamine Hydrochloride 1-[(6-Methoxypyridin-3-yl)sulfonyl]-5-phenyl-1H-pyrrole-3-carbaldehyde (59 mg) was dissolved in absolute tetrahydrofuran (5 mL), a 2 mol/L solution (0.25 mL) of methylamine in tetrahydrofuran was added, and the mixture was stirred at room temperature for 3 hr. The reaction mixture was added to a solution of sodium borohydride (19 mg) in methanol (2 mL), and the mixture was stirred at the same temperature for 20 min. The reaction mixture was diluted with ethyl acetate, washed successively with water and saturated brine, and dried over anhydrous magnesium sulfate. The solvent was evaporated under reduced pressure and the residue was purified by silica gel column chromatography (eluent:ethyl acetate-methanol=1:0→1:1) to give a free salt (48 mg) of the title compound. The obtained free salt was dissolved in ethyl acetate (2 mL), a 4 mol/L hydrogen chloride-ethyl acetate solution (3 mL) was added, and the mixture was left standing at room temperature for 30 min. The precipitated crystals were collected by filtration, washed with ethyl acetate to give the title compound (yield 39 mg, 58%).

$^1$H-NMR (DMSO-$d_6$) δ: 2.50 (3H, s), 3.90 (3H, s), 3.98 (2H, s), 6.45 (1H, s), 6.91-6.94 (1H, m), 7.16-7.18 (2H, m), 7.36-7.45 (3H, m), 7.59-7.63 (1H, m), 7.72 (1H, s), 8.09-8.10 (1H, m), 8.91 (2H, br).

Example 3

N-methyl-1-{1-[6-(methylamino)pyridin-3-ylsulfonyl]-5-phenyl-1H-pyrrol-3-yl}methanamine dihydrochloride By a similar reaction as in Example 2 and using 1-(6-chloro-3-pyridinesulfonyl)-5-phenyl-1H-pyrrole-3-carbaldehyde (100 mg), the title compound was obtained (yield 58 mg, 47%).

$^1$H-NMR (DMSO-$d_6$) δ: 2.50 (3H, s), 2.78 (3H, s), 3.95-3.99 (2H, m), 6.39-6.42 (2H, m), 7.20-7.23 (3H, m), 7.35-7.43 (3H, m), 7.63 (1H, s), 7.82-7.85 (2H, m), 9.00 (2H, br), 1H not detected.

Example 4

N-methyl-1-{1-[2-(methylamino)pyridin-3-ylsulfonyl]-5-phenyl-1H-pyrrol-3-yl}methanamine dihydrochloride 1-(2-Chloropyridin-3-ylsulfonyl)-5-phenyl-1H-pyrrole-3-carbaldehyde (173 mg) was dissolved in tetrahydrofuran (10 mL), a 2 mol/L solution (1.25 mL) of methylamine in tetrahydrofuran was added, and the mixture was stirred at room temperature for 12 hr. The reaction mixture was added to a solution (2 mL) of sodium borohydride (76 mg) in methanol, and the mixture was stirred at room temperature for 20 min. A saturated aqueous sodium hydrogencarbonate solution was added, and the mixture was extracted with ethyl acetate. The extract was washed with saturated brine, dried over anhydrous magnesium sulfate, and concentrated under reduced pressure. The residue was purified by silica gel column chromatography (eluent:ethyl acetate→ethyl acetate-methanol=1:4) to give a free salt of the title compound. To a solution (3 mL) of the obtained free salt in ethanol was added a 4 mol/L hydrogen chloride-ethyl acetate solution (1 mL). The solvent was evaporated under reduced pressure, and the residue was recrystallized from ethanol to give the title compound (yield 126 mg, 59%).

$^1$H-NMR (DMSO-$d_6$) δ: 2.50 (3H, s), 2.77 (3H, d, J=4.5 Hz), 3.95-3.99 (2H, m), 4.80 (1H, br), 6.28-6.30 (1H, m), 6.41-6.47 (2H, m), 7.10-7.19 (3H, m), 7.32-7.44 (3H, m), 7.88 (1H, s), 8.25-8.27 (1H, m), 9.19 (2H, br).

Example 5

N-methyl-1-{1-[2-(methylamino)pyrimidin-3-ylsulfonyl]-5-phenyl-1H-pyrrol-3-yl}methanamine hydrochloride By a similar reaction as in Example 2 and using 1-(2-chloropyrimidin-5-ylsulfonyl)-5-phenyl-1H-pyrrole-3-carbaldehyde (100 mg), the title compound was obtained (yield 64 mg, 57%).

$^1$H-NMR (DMSO-$d_6$) δ: 2.50 (3H, s), 2.80-2.82 (3H, s), 3.98 (2H, s), 6.47 (1H, s), 7.23-7.26 (2H, m), 7.39-7.43 (3H, m), 7.66-7.67 (1H, m), 7.96-7.97 (1H, m), 8.11-8.12 (1H, m), 8.48-8.52 (1H, m), 8.97 (2H, br)

Example 6

N-methyl-1-[2-methyl-5-phenyl-1-(pyridin-3-ylsulfonyl)-1H-pyrrol-3-yl]methanamine dihydrochloride By a similar reaction as in Example 2 and using 2-methyl-5-phenyl-1-(pyridin-3-ylsulfonyl)-1H-pyrrole-3-carbaldehyde (235 mg), an ethanol (1 equivalent) adduct of the title compound was obtained as a solid (yield 110 mg, 39%).

$^1$H-NMR (DMSO-$d_6$) δ: 1.06 (3H, t, J=7.2 Hz), 2.43-2.50 (6H, m), 3.44 (2H, dd, J=14.1, 7.2 Hz), 3.91-3.94 (2H, m), 6.47 (1H, s), 7.21-7.43 (2H, m), 7.36-7.41 (3H, m), 7.56-7.63 (1H, m), 7.82-7.88 (1H, m), 8.53 (1H, s), 8.87-8.93 (3H, m), 2H not detected.

Example 7

N-methyl-1-[1-(2-methylpyrimidin-5-ylsulfonyl)-5-phenyl-1H-pyrrol-3-yl]-methanamine dihydrochloride 1-[(2-Methyl-5-pyrimidine)sulfonyl]-5-phenyl-1H-pyrrole-3-carbaldehyde (148 mg) was dissolved in absolute tetrahydrofuran (10 mL), a 2 mol/L solution (1.25 mL) of methylamine in tetrahydrofuran was added, and the mixture was stirred overnight at room temperature. The reaction mixture was added to a solution of sodium borohydride (95 mg) in methanol (3.0 mL), and the mixture was stirred at the same temperature for 20 min. The reaction mixture was diluted with ethyl acetate, washed with saturated brine, dried over anhydrous magnesium sulfate, and the solvent was evaporated under reduced pressure. The residue was dissolved in tetrahydrofuran (20 mL), di-tert-butyl bicarbonate (0.55 g), sodium hydrogencarbonate (0.25 g) and water (10 mL) were added, and the mixture was stirred at room temperature for 30 min. The reaction mixture was diluted with ethyl acetate, washed successively with a saturated aqueous sodium hydrogencarbonate solution and saturated brine, dried over anhydrous magnesium sulfate, and the solvent was evaporated under reduced pressure. The residue was dissolved in tetrahydrofuran (20 mL), manganese dioxide (75% chemically treated product, 1.5 g) was added, and the mixture was stirred at room temperature for 1 hr. The reaction mixture was filtered through celite, and celite was washed with ethyl acetate.

The filtrate was concentrated under reduced pressure, and the residue was purified by silica gel column chromatography (eluent:hexane-ethyl acetate=19:1→1:1) to give an oil. The obtained oil was dissolved in ethanol (1 mL), a 4 mol/L hydrogen chloride-ethyl acetate solution (1 mL) was added and the mixture was stirred at room temperature for 3 hr. The solvent was evaporated under reduced pressure to give a solid (67 mg). Recrystallization from ethanol gave the title compound as a colorless solid (yield 34 mg, 18%).

$^1$H-NMR (DMSO-$d_6$) δ: 2.53 (3H, s), 2.70 (3H, s), 3.98 (2H, s), 6.50 (1H, s), 7.18-7.20 (2H, m), 7.38-7.47 (3H, m), 7.76-7.77 (1H, m), 8.59 (2H, s), 8.88 (2H, br), 1H not detected.

Example 8

1-[5-(2-fluorophenyl)-1-(pyridin-3-ylsulfonyl)-1H-pyrrol-3-yl]-N-methylmethanamine fumarate 5-(2-Fluorophenyl)-1-(pyridin-3-ylsulfonyl)-1H-pyrrole-3-carbaldehyde (1.52 g) was dissolved in methanol (30 mL), a 40% methylamine methanol solution (3.57 g) was added at room temperature and the mixture was stirred for 30 min. Sodium borohydride (523 mg) was added at room temperature and the mixture was stirred for 10 min. 1 mol/L Hydrochloric acid (50 mL) was added and the mixture was stirred for 5 min. The reaction mixture was basified with a saturated aqueous sodium hydrogencarbonate solution, and the mixture was extracted with ethyl acetate. The extract was washed with saturated brine, dried over anhydrous sodium sulfate, and concentrated under reduced pressure. The residue was purified by basic silica gel column chromatography (eluent: ethyl acetate-methanol=1:0→7:3) to give a free salt of the title compound as a pale-yellow oil (yield 1.30 g). The obtained free salt (750 mg) was dissolved in ethyl acetate (30 mL), a solution of fumaric acid (278 mg) in methanol (3 mL) was added dropwise at room temperature. After stirring for 30 min, the obtained crystals were collected by filtration, and washed with ethyl acetate to give the title compound as colorless crystals (yield 912 mg, 74%).

$^1$H-NMR (DMSO-$d_6$) δ: 2.43 (3H, s), 3.87 (2H, s), 6.47 (2H, s), 6.49 (1H, d, J=1.8 Hz), 7.07-7.13 (1H, m), 7.19-7.26 (2H, m), 7.49-7.56 (1H, m), 7.59-7.64 (1H, m), 7.74 (1H, d, J=1.8 Hz), 7.86-7.90 (1H, m), 8.56-8.57 (1H, m), 8.87-8.89 (1H, m), 3H not detected.

melting point 201-203° C.

Example 9

N-methyl-1-{1-(pyridin-3-ylsulfonyl)-5-[2-(trifluoromethyl)phenyl]-1H-pyrrol-3-yl}methanamine dihydrochloride 1-(Pyridin-3-ylsulfonyl)-5-[2-(trifluoromethyl)phenyl]-1H-pyrrole-3-carbaldehyde (340 mg) was dissolved in ethanol (34 mL), a 40% methylamine methanol solution (695 mg) was added at room temperature and the mixture was stirred for 30 min. Sodium borohydride (102 mg) was added at room temperature and the mixture was stirred for 10 min. 1 mol/L Hydrochloric acid (10 mL) was added and the mixture was stirred for 5 min. The reaction mixture was basified with a saturated aqueous sodium hydrogencarbonate solution, and the mixture was extracted with ethyl acetate. The extract was washed with saturated brine, dried over anhydrous sodium sulfate, and concentrated under reduced pressure. The residue was purified by basic silica gel column chromatography (eluent: ethyl acetate-methanol=1:0→7:3) and dissolved in ethyl acetate (5 mL). A 4 mol/L hydrogen chloride-ethyl acetate solution (1 mL) was added and the mixture was concentrated under reduced pressure. The residue was crystallized from ethyl acetate to give the title compound as pale-red crystals (yield 288 mg, 69%).

$^1$H-NMR (DMSO-$d_6$) δ: 2.47 (3H, t, J=5.5 Hz), 4.00 (2H, t, J=5.5 Hz), 6.60 (1H, d, J=1.8 Hz), 7.18-7.21 (1H, m), 7.63-7.81 (4H, m), 7.91-8.00 (2H, m), 8.58 (1H, d, J=1.8 Hz), 8.90-8.92 (1H, m), 9.48-9.57 (2H, m), 1H not detected.

Example 10

N-methyl-1-[4-methyl-5-phenyl-1-(pyridin-3-ylsulfonyl)-1H-pyrrol-3-yl]methanamine dihydrochloride By a similar reaction as in Example 2 and using 4-methyl-5-phenyl-1-(pyridin-3-ylsulfonyl)-1H-pyrrole-3-carbaldehyde (171 mg), the title compound was obtained (yield 110 mg, 50%).

$^1$H-NMR (DMSO-$d_6$) δ: 1.79 (3H, s), 2.57 (3H, s), 3.96-4.00 (2H, m), 6.98-7.01 (2H, m), 7.36-7.43 (3H, m), 7.55-7.60 (1H, m), 7.79-7.82 (2H, m), 8.43-8.44 (1H, m), 8.84-8.86 (1H, m), 9.13 (2H, br), 1H not detected.

Example 11

N-methyl-1-[4-methyl-5-phenyl-1-(pyridin-2-ylsulfonyl)-1H-pyrrol-3-yl]methanamine hydrochloride 4-Methyl-5-phenyl-1-(pyridin-2-ylsulfonyl)-1H-pyrrole-3-carbaldehyde (262 mg) was dissolved in tetrahydrofuran (10 mL), a 2 mol/L solution (1.0 mL) of methylamine in tetrahydrofuran was added, and the mixture was stirred at room temperature for 4 hr. The reaction mixture was added to a solution (5 mL) of sodium borohydride (76 mg) in methanol, and the mixture was stirred at room temperature for 20 min. Water was added, and the mixture was extracted with ethyl acetate. The extract was washed with water and saturated brine, dried over anhydrous magnesium sulfate, and concentrated under reduced pressure. The residue was purified by silica gel column chromatography (eluent:ethyl acetate-methanol=1:0→1:1) and further by HPLC (ODS, 0.1% trifluoroacetic acid-containing water-0.1% trifluoroacetic acid-containing acetonitrile=9:1→0.1% trifluoroacetic acid-containing acetonitrile) to give trifluoroacetate of the title compound. The obtained trifluoroacetate was neutralized with a saturated aqueous sodium hydrogencarbonate solution, extracted with ethyl acetate, washed successively with a saturated aqueous sodium hydrogencarbonate solution, water and saturated brine, and dried over anhydrous magnesium sulfate. The solvent was evaporated under reduced pressure. The residue was dissolved in ethyl acetate (3 mL), a 4 mol/L solution (2 mL) of hydrogen chloride in ethyl acetate was added. After allowing to stand at room temperature for 30 min, the precipitate was collected by filtration and washed with ethyl acetate to give the title compound (yield 141 mg, 47%).

$^1$H-NMR (DMSO-$d_6$) δ: 1.79 (3H, s), 2.59 (3H, s), 4.01 (2H, s), 6.88-6.90 (2H, m), 7.27-7.45 (4H, m), 7.71-7.74 (2H, m), 7.95-7.99 (1H, m), 8.68-8.70 (1H, m), 8.88 (2H, br).

Example 12

1-{1-[(1,2-dimethyl-1H-imidazol-4-yl)sulfonyl]-4-methyl-5-phenyl-1H-pyrrol-3-yl}-N-methylmethanamine dihydrochloride 1-[(1,2-Dimethyl-1H-imidazol-4-yl)sulfonyl]-4-methyl-5-phenyl-1H-pyrrole-3-carbaldehyde (294 mg) was dissolved in tetrahydrofuran (5 mL), a 2 mol/L solution (1.0 mL) of methylamine in tetrahydrofuran was added, and the mixture was stirred at room temperature for 1 hr. The mixture was heated to 40° C., and the mixture was further stirred for 4 hr. The reaction mixture was added to a solution (5 mL) of sodium borohydride (76 mg) in methanol, and the mixture was stirred at room temperature for 1 hr. Water was added, and the mixture was extracted with ethyl acetate. The extract was washed with water and saturated brine, dried over anhydrous magnesium sulfate, and concentrated under reduced pressure. The residue was purified by basic silica gel column chromatography (eluent:hexane-ethyl acetate=9:1→0:1) to give a free salt of the title compound. To a solution (3 mL) of the obtained free salt in ethyl acetate was added a 4 mol/L hydrogen chloride-ethyl acetate solution (1 mL). After allowing to stand at room temperature for 30 min, the precipitate was collected by filtration, and washed with ethyl acetate to give the title compound (yield 196 mg, 53%).

$^1$H-NMR (DMSO-$d_6$) δ: 1.79 (3H, s), 2.25 (3H, s), 2.60 (3H, m), 3.45 (3H, s), 3.95-3.99 (2H, m), 4.86 (1H, br), 6.99-7.01 (2H, m), 7.13 (1H, s), 7.32-7.39 (3H, m), 7.59 (1H, s), 8.96 (2H, br).

Example 13

1-{1-[(5-chloro-1,3-dimethyl-1H-pyrazol-4-yl)sulfonyl]-4-methyl-5-phenyl-1H-pyrrol-3-yl}-N-methylmethanamine hydrochloride By a similar reaction as in Example 12 and using 1-[(5-chloro-1,3-dimethyl-1H-pyrazol-4-yl)sulfonyl]-4-methyl-5-phenyl-1H-pyrrole-3-carbaldehyde (378 mg), the title compound was obtained as a solid (yield 238 mg, 55%).

$^1$H-NMR (DMSO-$d_6$) δ: 1.67 (3H, s), 1.79 (3H, s), 2.58 (3H, s), 3.67 (3H, s), 3.99 (2H, s), 6.97-6.99 (2H, m), 7.33-7.41 (3H, m), 7.73 (1H, s), 8.90 (2H, br).

Example 14

1-{1-[(1,3-dimethyl-1H-pyrazol-4-yl)sulfonyl]-4-methyl-5-phenyl-1H-pyrrol-3-yl}-N-methylmethanamine hydrochloride Using 1-[(5-chloro-1,3-dimethyl-1H-pyrazol-4-yl)sulfonyl]-4-methyl-5-phenyl-1H-pyrrole-3-carbaldehyde (295 mg), a free salt (297 mg) of the compound of Example 13 was obtained as an oil. The obtained oil was dissolved in toluene (10 mL) and methanol (10 mL), 10% palladium carbon (50% containing water, 30 mg) and 20% sodium ethoxide-ethanol solution (309 mg) were added, and the mixture was stirred at under a hydrogen atmosphere at room temperature for 24 hr. The reaction mixture was filtered, and the filtrate was concentrated under reduced pressure. The residue was dissolved in ethyl acetate solution (5 mL) and a 4 mol/L hydrogen chloride-ethyl acetate solution (1 mL) was added. After allowing to stand at room temperature for 30 min, the precipitate was collected by filtration, and washed with ethyl acetate to give the title compound (yield 221 mg, 72%).

$^1$H-NMR (DMSO-$d_6$) δ: 1.80 (3H, s), 1.90 (3H, s), 2.59 (3H, m), 3.63 (3H, s), 3.99 (2H, s), 6.99-7.02 (2H, m), 7.35-7.40 (3H, m), 7.51 (1H, s), 7.66 (1H, s), 8.87 (2H, br).

Example 15

1-{1-[(2,4-dimethyl-1,3-thiazol-5-yl)sulfonyl]-4-methyl-5-phenyl-1H-pyrrol-3-yl}-N-methylmethanamine trifluoroacetate To a solution (1 mL) of 1-[(2,4-dimethyl-1,3-thiazol-5-yl)sulfonyl]-4-methyl-5-phenyl-1H-pyrrole-3-carbaldehyde (27.7 mg) in tetrahydrofuran was added a 2 mol/L solution (0.1 mL) of methylamine in tetrahydrofuran, and the mixture was stirred at room temperature for 2 hr. The reaction mixture was added to a solution (1 mL) of sodium borohydride (7.6 mg) in methanol, and the mixture was stirred at room temperature for 20 min. Water was added to the reaction mixture, and the mixture was extracted with ethyl acetate. The extract was washed with a saturated aqueous sodium hydrogencarbonate solution, water and saturated brine, dried over anhydrous magnesium sulfate, and concentrated under reduced pressure. The residue was purified by HPLC (ODS, 0.1% trifluoroacetic acid-containing water-0.1% trifluoroacetic acid-containing acetonitrile (97:3)→0.1% trifluoroacetic acid-containing acetonitrile alone), and triturated with diisopropyl ether to give the title compound as a solid (yield 12.1 mg, 33%).

$^1$H-NMR (DMSO-$d_6$) δ: 1.80 (3H, s), 2.06 (3H, s), 2.58 (3H, s), 2.62 (3H, s), 4.03 (2H, s), 7.05-7.07 (2H, m), 7.37-7.44 (3H, m), 7.67 (1H, s), 8.62 (2H, br).

Example 16

[5-(2-fluorophenyl)-4-methyl-1-(pyridin-3-ylsulfonyl)-1H-pyrrol-3-yl]-N-methylmethanamine hydrochloride To a solution of 5-(2-fluorophenyl)-4-methyl-1-(pyridin-3-ylsulfonyl)-1H-pyrrole-3-carbaldehyde (382 mg) in methanol (5 mL) and tetrahydrofuran (2 mL) was added a 40% methylamine methanol solution (1.1 mL), and the mixture was stirred at room temperature for 4 hr. Sodium borohydride (51 mg) was added to the reaction mixture, and the mixture was further stirred for 15 min. The reaction mixture was concentrated under reduced pressure. A saturated aqueous sodium hydrogencarbonate solution (50 mL) was added to the residue, and the mixture was extracted with ethyl acetate. The extract was washed with a saturated aqueous sodium hydrogencarbonate solution, water and saturated brine, dried over anhydrous sodium sulfate, and the solvent was evaporated under reduced pressure. The residue was purified by basic silica gel column chromatography (eluent: ethyl acetate) to give a free salt of the title compound (yield 342 mg). To a solution of the obtained free salt (336 mg) in ethanol (5 mL) was added a 4 mol/L hydrogen chloride-ethyl acetate solution (5.0 mL), and the mixture was stirred at room temperature for 30 min. The reaction mixture was concentrated under reduced pressure, and the residue was recrystallized from ethanol to give the title compound as white crystals (yield 197 mg, 46%).

$^1$H-NMR (DMSO-$d_6$) δ: 1.76 (3H, s), 2.59 (3H, t, J=5.4 Hz), 4.01 (2H, t, J=5.4 Hz), 7.03-7.08 (1H, m), 7.21-7.28 (2H, m), 7.51-7.64 (2H, m), 7.82-7.86 (2H, m), 8.53 (1H, d, J=2.4 Hz), 8.80-8.89 (3H, m).

Example 17

1-[1-(2-chloropyridin-3-ylsulfonyl)-5-phenyl-1H-pyrrol-3-yl]-N-methylmethanamine hydrochloride To a solution (3 mL) of tert-butyl{[1-(2-chloro-3-pyridinesulfonyl)-5-phenyl-1H-pyrrol-3-yl]
methyl}methylcarbamate (70 mg) in ethyl acetate was added a 4 mol/L hydrogen chloride-ethyl acetate solution (1 mL), and the mixture was stirred at room temperature for 3 hr. The solvent was evaporated under reduced pressure, and the residue was crystallized from ethanol-ethyl acetate to give the title compound (yield 29 mg, 49%).

¹H-NMR (DMSO-d₆) δ: 2.56 (3H, s), 4.04 (2H, s), 6.48 (1H, s), 6.99-7.02 (2H, m), 7.25-7.36 (4H, m), 7.66-7.69 (1H, m), 7.83 (1H, s), 8.60-8.62 (1H, m), 8.79 (2H, br).

Example 18

5-({4-[(methylamino)methyl]-2-phenyl-1H-pyrrol-1-yl}sulfonyl)pyrimidine-2-amine

To a solution (4 mL) of 1-(2-chloropyrimidin-5-ylsulfonyl)-5-phenyl-1H-pyrrole-3-carbaldehyde (139 mg) in tetrahydrofuran was added a 0.5 mol/L ammonia-dioxane solution (4 mL). After stirring at room temperature for 1 hr, a saturated aqueous sodium hydrogencarbonate solution was added, and the mixture was extracted with ethyl acetate. The extract was washed with saturated brine, dried over anhydrous magnesium sulfate, and concentrated under reduced pressure. The residue was dissolved in a tetrahydrofuran (5 mL), a 2 mol/L solution (0.75 mL) of methylamine in tetrahydrofuran was added, and the mixture was stirred overnight at room temperature. The reaction mixture was added to a solution (2 mL) of sodium borohydride (38 mg) in methanol, and the mixture was stirred at room temperature for 5 min. A saturated aqueous sodium hydrogencarbonate solution was added to the reaction mixture, and the mixture was extracted with ethyl acetate. The extract was washed with saturated brine, dried over anhydrous magnesium sulfate, and concentrated under reduced pressure. The residue was purified by HPLC (ODS, 0.1% trifluoroacetic acid-containing water-0.1% trifluoroacetic acid-containing acetonitrile=9:1→0.1% trifluoroacetic acid-containing acetonitrile) to give trifluoroacetate of the title compound. The obtained trifluoroacetate was neutralized with a saturated aqueous sodium hydrogencarbonate solution, extracted with ethyl acetate, washed successively with a saturated aqueous sodium hydrogencarbonate solution, water and saturated brine, and dried over anhydrous magnesium sulfate. The solvent was evaporated under reduced pressure and crystallized crystals were washed with diisopropyl ether to give the title compound as a colorless solid (yield 23 mg, 17%).

¹H-NMR (DMSO-d₆) δ: 2.27 (3H, s), 3.52 (2H, s), 6.31 (1H, s), 7.26-7.40 (6H, m), 7.94 (2H, br), 8.00 (2H, s), 1H not detected.

Example 19

1-[(imidazo[1,2-a]pyrimidin-6-ylsulfonyl)-5-phenyl-1H-pyrrol-3-yl]-N-methylmethanamine dihydrochloride Under a nitrogen atmosphere, a solution of ethyl 1-(imidazo[1,2-a]pyrimidin-6-ylsulfonyl)-5-phenyl-1H-pyrrole-3-carboxylate (242 mg) in tetrahydrofuran (10 mL) was cooled to −78° C., a 1.5 mol/L solution (2.0 mL) of diisobutylaluminum hydride in toluene was added with stirring. After stirring at the same temperature for 1 hr, the mixture was warmed to −20° C. over 1 hr. Water (30 mL) was added and, after stirring at the same temperature for 5 min, the mixture was allowed to warm to 0° C. over 10 min. Ethyl acetate (20 mL) was added and, after stirring at the same temperature for 15 min, the mixture was stirred at room temperature for 20 min. The reaction mixture in a gel state was filtered through celite, and celite was washed with ethyl acetate. The organic layer was separated from the filtrate, washed with saturated brine, dried over anhydrous magnesium sulfate, and concentrated under reduced pressure. The residue was dissolved in tetrahydrofuran (50 mL), manganese dioxide (75% chemically treated product, 2.0 g) was added, and the mixture was stirred at room temperature for 2 hr. The reaction mixture was filtered through celite, and celite was washed with ethyl acetate. The filtrate was concentrated under reduced pressure, the residue was dissolved in absolute tetrahydrofuran (5 mL), a 2 mol/L solution (0.6 mL) of methylamine in tetrahydrofuran was added, and the mixture was stirred at room temperature for 2 hr. The reaction mixture was added to a solution of sodium borohydride (45 mg) in methanol (2 mL), and the mixture was stirred at the same temperature for 20 min. The reaction mixture was diluted with ethyl acetate, washed with saturated brine, dried over anhydrous magnesium sulfate, and the solvent was evaporated under reduced pressure. The residue was dissolved in tetrahydrofuran (10 mL), di-tert-butyl bicarbonate (0.22 g), sodium hydrogencarbonate (84 mg) and water (5 mL) were added, and the mixture was stirred at room temperature for 30 min. The reaction mixture was diluted with ethyl acetate, washed with saturated brine, dried over anhydrous magnesium sulfate, and the solvent was evaporated under reduced pressure. The residue was dissolved in tetrahydrofuran (20 mL), manganese dioxide (75% chemically treated product, 1.0 g) was added, and the mixture was stirred at room temperature for 2 days. The reaction mixture was filtered through celite, and celite was washed with ethyl acetate. The filtrate was concentrated under reduced pressure, and the residue was purified by silica gel column chromatography (eluent:hexane-ethyl acetate=19:1→0:1) to give an oil. The obtained oil was dissolved in ethanol (1 mL), and a 4 mol/L hydrogen chloride-ethyl acetate solution (1 mL) was added. After stirring at room temperature for 2 hr, the solvent was evaporated under reduced pressure, and the residue was triturated with ethyl acetate-ethanol to give the title compound as a brown solid (yield 8.5 mg, 3%).

¹H-NMR (DMSO-d₆) δ: 2.50 (3H, s), 4.02-4.05 (2H, m), 6.49 (1H, s), 7.16-7.19 (2H, m), 7.32-7.44 (3H, m), 7.79 (1H, s), 7.92-7.99 (2H, m), 8.29-8.30 (1H, m), 8.97 (2H, br), 9.23-9.24 (1H, m), 1H not detected.

Example 20

N-methyl-1-[5-phenyl-1-(pyridazin-3-ylsulfonyl)-1H-pyrrol-3-yl]methanamine fumarate Under a nitrogen atmosphere, a solution of ethyl 5-phenyl-1-(pyridazin-3-ylsulfonyl)-1H-pyrrole-3-carboxylate (567 mg) in tetrahydrofuran (16 mL) was cooled to −78° C., a 1.5 mol/L solution (6.4 mL) of diisobutylaluminum hydride in toluene was added with stirring. The reaction mixture warmed to −20° C. over 1 hr. Water (75 mL) was added, and after stirring at the same temperature for 5 min, the mixture was allowed to warm to 0° C. over 10 min. Ethyl acetate (75 mL) was added, and after stirring at the same temperature for 15 min, the mixture was stirred at room temperature for 20 min. The reaction mixture was filtered through celite, and celite was washed with ethyl acetate. The organic layer was separated from the filtrate, washed with saturated brine, dried over anhydrous magnesium sulfate, and concentrated under reduced pressure. The residue was dissolved in tetrahydrofuran (30 mL), manganese dioxide (75% chemically treated product, 5.0 g) was added, and the mixture was stirred at room temperature for 1 hr. The reaction mixture was filtered through celite, and celite was washed with ethyl acetate. The filtrate was concentrated under reduced pressure and the residue was dissolved in absolute tetrahydrofuran (15 mL). A 2 mol/L solution (1.5 mL) of methylamine in tetrahydrofuran was added, and the mixture was stirred overnight at room temperature. The reaction mixture was added to a solution of sodium borohydride (66 mg) in methanol (5 mL), and the mixture was stirred at the same temperature for 20 min. A saturated aqueous sodium hydrogencarbonate solution was added to the reaction mixture, and the mixture was extracted with ethyl acetate. The extract was washed with saturated brine, dried over anhydrous magnesium sulfate, and the solvent was evaporated under reduced pressure. The residue was purified by HPLC (ODS, 0.1% trifluoroacetic acid-containing water-0.1% trifluoroacetic acid-containing acetonitrile=9:1→0.1% trifluoroacetic acid-containing acetonitrile) to give trifluoroacetate of the title compound. The obtained trifluoroacetate was neutralized with a saturated aqueous sodium hydrogencarbonate solution, extracted with ethyl acetate, washed successively with a saturated aqueous sodium hydrogencarbonate solution, water and saturated brine, and dried over anhydrous magnesium sulfate. The solvent was evaporated under reduced pressure to give a free salt (59 mg) of the title compound. The obtained free salt (59 mg) was dissolved in methanol (2 mL) and ethyl acetate (2 mL), and fumaric acid (21 mg) was added. The solvent was evaporated under reduced pressure, and recrystallization from ethyl acetate-methanol gave the title compound as a pale-yellow solid (yield 41 mg, 6%).

$^1$H-NMR (DMSO-$d_6$) δ: 2.42 (3H, s), 3.82 (2H, s), 6.41 (1H, s), 6.47 (2H, s), 7.09-7.12 (2H, m), 7.29-7.38 (3H, m), 7.63 (1H, s), 7.80-7.83 (1H, m), 7.91-7.96 (1H, m), 9.48-9.50 (1H, m), 3H not detected.

Example 21

N-methyl-1-[1-(5-methyl-3-pyridinesulfonyl)-5-phenyl-1H-pyrrol-3-yl]methanamine fumarate To a solution (5 mL) of tert-butyl{[1-(6-chloro-5-methyl-3-pyridinesulfonyl)-5-phenyl-1H-pyrrol-3-yl]methyl}methylcarbamate (237 mg) in tetrahydrofuran was added hydrazine (160 mg) at room temperature with stirring. After stirring at the same temperature for 3 hr, a saturated aqueous sodium hydrogencarbonate solution was added, and the mixture was extracted with ethyl acetate. The extract was washed with water and saturated brine, dried over anhydrous magnesium sulfate, and concentrated under reduced pressure. The residue was dissolved in tetrahydrofuran (30 mL), manganese dioxide (75% chemically treated product, 1.0 g) was added, and the mixture was stirred at room temperature for 10 min. The reaction mixture was filtered through celite, and celite was washed with ethyl acetate. The filtrate was concentrated under reduced pressure, and the residue was purified by silica gel column chromatography (eluent: hexane-ethyl acetate=19:1→1:1) to give an oil. The obtained oil was dissolved in ethanol (2 mL), and a 4 mol/L hydrogen chloride-ethyl acetate solution (1 mL) was added. After stirring at room temperature for 2 hr, the solvent was evaporated under reduced pressure, a saturated aqueous sodium hydrogencarbonate solution was added, and the mixture was extracted with ethyl acetate. The extract was washed with water and saturated brine, dried over anhydrous magnesium sulfate, and concentrated under reduced pressure. The residue (93 mg) was dissolved in ethanol (3 mL), and fumaric acid (29 mg) was added. After allowing to stand at room temperature for 30 min, the precipitated crystals were collected by filtration and washed with methanol to give the title compound as a colorless solid (yield 91 mg, 40%).

$^1$H-NMR (DMSO-$d_6$) δ: 2.27 (3H, s), 2.38 (3H, s), 3.75 (2H, s), 6.37 (1H, s), 6.47 (2H, s), 7.15-7.17 (2H, m), 7.36-7.45 (4H, m), 7.58 (1H, s), 8.28 (1H, s), 8.68 (1H, s), 3H not detected.

Example 22

5-({4-[(methylamino)methyl]-2-phenyl-1H-pyrrol-1-yl}sulfonyl)pyridin-2-ol hydrochloride tert-Butyl{[1-(6-chloro-3-pyridinesulfonyl)-5-phenyl-1H-pyrrol-3-yl]methyl}methylcarbamate (175 mg) was dissolved in tetrahydrofuran (10 mL), a 8 mol/L aqueous sodium hydroxide solution (3.8 mL) was added, and the mixture was stirred at 50° C. for 2 days. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=19:1→0:1) to give a free salt of the title compound. To a solution (1 mL) of the obtained free salt in ethanol was added a 4 mol/L hydrogen chloride-ethyl acetate solution (2 mL). After stirring at room temperature for 4 hr, the solvent was evaporated under reduced pressure, and the residue was crystallized from ethanol-ethyl acetate to give the title compound (yield 40 mg, 27%).

$^1$H-NMR (DMSO-$d_6$) δ: 2.50 (3H, s), 3.97-4.01 (2H, m), 6.32-6.36 (1H, m), 6.47 (1H, s), 7.20-7.23 (4H, m), 7.37-7.48 (3H, m), 7.66 (1H, s), 8.94 (2H, br), 12.35 (1H, br).

Example 23

5-({4-[(methylamino)methyl]-2-phenyl-1H-pyrrol-1-yl}sulfonyl)pyridine-2-carbonitrile hydrochloride Under an argon atmosphere, a mixture of tert-butyl{[1-(6-chloro-3-pyridinesulfonyl)-5-phenyl-1H-pyrrol-3-yl]methyl}methylcarbamate (100 mg), zinc (II) cyanide (51 mg), tetrakis(triphenylphosphine)palladium (50 mg) and N,N-dimethylformamide (4 mL) was stirred at 100° C. for 2 hr. The reaction mixture was diluted with ethyl acetate, washed successively with a saturated aqueous sodium hydrogencarbonate solution, water and saturated brine and dried over anhydrous magnesium sulfate, and the solvent was evaporated under reduced pressure. The residue was purified by silica gel column chromatography (eluent:hexane-ethyl acetate=19:1→7:3) to give an oil. The obtained oil was dissolved in ethyl acetate (2 mL), and a 4 mol/L hydrogen chloride-ethyl acetate solution (2 mL) was added. After stirring at room temperature for 1 hr, the solvent was evaporated under reduced pressure, and the residue was crystallized from ethanol to give the title compound (yield 57 mg, 68%).

$^1$H-NMR (DMSO-$d_6$) δ: 2.50 (3H, s), 3.98 (2H, s), 6.52 (1H, s), 7.15-7.17 (2H, m), 7.37-7.47 (3H, m), 7.79 (1H, s), 8.04-8.07 (1H, m), 8.22-8.24 (1H, m), 8.61-8.62 (1H, m), 9.03 (2H, br).

Example 24

N-methyl-1-{1-[(6-methylpyridin-3-yl)sulfonyl]-5-phenyl-1H-pyrrol-3-yl}methanamine dihydrochloride tert-Butyl({[1-(6-methylpyridin-3-yl)sulfonyl]-5-phenyl-1H-pyrrol-3-yl}methyl)methylcarbamate (113 mg) was dissolved in ethanol (2 mL), a 4 mol/L hydrogen chloride-ethyl acetate solution (1 mL) was added, and the mixture was stirred at room temperature for 1 hr. The solvent was concentrated under reduced pressure, and the residue was recrystallized from ethanol to give the title compound (yield 40 mg, 38%).

$^1$H-NMR (DMSO-$d_6$) δ: 2.50-2.53 (6H, m), 3.97-3.99 (2H, m), 6.46 (1H, s), 7.16-7.18 (2H, m), 7.38-7.44 (4H, m), 7.65-7.75 (2H, m), 8.34 (1H, s), 8.98 (2H, br), 1H not detected.

Example 25

N-methyl-1-[1-(pyridin-3-ylsulfonyl)-5-(3-thienyl)-1H-pyrrol-3-yl]methanamine hydrochloride By a similar operation as in Example 24 and using tert-butyl{[1-(pyridin-3-ylsulfonyl)-5-(3-thienyl)-1H-pyrrol-3-yl]methyl}methylcarbamate (182 mg), the title compound was obtained as colorless crystals (yield 64 mg, 41%).
$^1$H-NMR (CDCl$_3$) δ: 2.60 (3H, s), 3.98 (2H, brs), 6.57 (1H, brs), 7.00 (1H, brd, J=4.5 Hz), 7.16 (1H, brs), 7.26-7.31 (2H, m), 7.70 (2H, brs), 8.61 (1H, brs), 8.73 (1H, brs), 9.86 (2H, brs).

Example 26

1-[5-(4-fluorophenyl)-1-(pyridin-3-ylsulfonyl)-1H-pyrrol-3-yl]-N-methylmethanamine dihydrochloride tert-Butyl{[5-(4-fluorophenyl)-1-(pyridin-3-ylsulfonyl)-1H-pyrrol-3-yl]methyl}methylcarbamate (293 mg) was dissolved in dichloromethane (1 mL), trifluoroacetic acid (1 mL) was added at 0° C., and the mixture was stirred at room temperature for 3 hr. The reaction solution was basified by adding dropwise to a 6% aqueous sodium hydrogencarbonate solution, and the mixture was extracted with ethyl acetate. The organic layer was washed with saturated brine, dried over anhydrous sodium sulfate, and concentrated under reduced pressure. The residue was purified by basic silica gel column chromatography (eluent:hexane-ethyl acetate=1:1→1:9) to give a free salt of the title compound as a pale-yellow oil. The obtained free salt was dissolved in ethyl acetate (5 mL), a 4 mol/L hydrogen chloride-ethyl acetate solution (1 mL) was added, and the mixture was concentrated under reduced pressure. The residue was recrystallized from ethyl acetate-ethanol to give the title compound as colorless crystals (yield 110 mg, 40%).
$^1$H-NMR (DMSO-$d_6$) δ: 2.47-2.51 (3H, m), 3.97 (2H, t, J=6.0 Hz), 6.52-6.53 (1H, m), 7.15-7.26 (4H, m), 7.57-7.61 (1H, m), 7.79-7.85 (2H, m), 8.00 (1H, d, J=2.4 Hz), 8.85-8.87 (1H, m), 9.22 (2H, br), 1H not detected.

Example 27

N-methyl-1-[5-(2-methylphenyl)-1-(pyridin-3-ylsulfonyl)-1H-pyrrol-3-yl]methanamine dihydrochloride By a similar operation as in Example 26 and using tert-butyl methyl{[5-(2-methylphenyl)-1-(pyridin-3-ylsulfonyl)-1H-pyrrol-3-yl]methyl}carbamate (210 mg), the title compound was obtained as colorless crystals (yield 67 mg, 34%). More specifically, tert-butyl methyl{[5-(2-methylphenyl)-1-(pyridin-3-ylsulfonyl)-1H-pyrrol-3-yl]methyl}carbamate (210 mg) was dissolved in dichloromethane (2 mL), trifluoroacetic acid (1 mL) was added at 0° C., and the mixture was stirred at room temperature for 2 hr. The reaction solution was basified by adding dropwise to a 6% aqueous sodium hydrogencarbonate solution, and the mixture was extracted with ethyl acetate. The organic layer was washed with saturated brine, dried over anhydrous sodium sulfate, and concentrated under reduced pressure. The residue was purified by basic silica gel column chromatography (eluent:hexane-ethyl acetate=1:1→1:9) to give a free salt of the title compound as a pale-yellow oil. The obtained free salt was dissolved in ethyl acetate (5 mL), a 4 mol/L hydrogen chloride-ethyl acetate solution (1 mL) was added, and the mixture was concentrated under reduced pressure. The residue was recrystallized from ethyl acetate-ethanol to give the title compound as colorless crystals (yield 67 mg, 34%).
$^1$H-NMR (DMSO-$d_6$) δ: 1.80 (3H, s), 2.49-2.53 (3H, m), 4.00 (2H, t, J=5.4 Hz), 6.46 (1H, d, J=2.4 Hz), 6.83 (1H, d, J=7.8 Hz), 7.13-7.22 (2H, m), 7.33-7.39 (1H, m), 7.59-7.63 (1H, m), 7.80-7.85 (2H, m), 8.46 (1H, d, J=2.4 Hz), 8.88-8.90 (1H, m), 9.27 (2H, br), 1H not detected.
melting point 196-200° C.

Example 28

1-[5-(4-fluoro-2-methylphenyl)-1-(pyridin-3-ylsulfonyl)-1H-pyrrol-3-yl]-N-methylmethanamine dihydrochloride By a similar operation as in Example 26 and using tert-butyl{[5-(4-fluoro-2-methylphenyl)-1-(pyridin-3-ylsulfonyl)-1H-pyrrol-3-yl]methyl}methylcarbamate (216 mg), the title compound was obtained as colorless crystals (yield 81 mg, 40%).
$^1$H-NMR (DMSO-$d_6$) δ: 1.80 (3H, s), 2.49-2.51 (3H, m), 4.00 (2H, t, J=6.0 Hz), 6.47 (1H, d, J=2.1 Hz), 6.85-6.90 (1H, m), 6.98-7.12 (2H, m), 7.61-7.65 (1H, m), 7.81-7.88 (2H, m), 8.51 (1H, d, J=2.7 Hz), 8.89-8.91 (1H, m), 9.29 (2H, br), 1H not detected.

Example 29

N-methyl-1-[5-(4-methyl-3-thienyl)-1-(pyridin-3-ylsulfonyl)-1H-pyrrol-3-yl]methanamine dihydrochloride By a similar operation as in Example 26 and using tert-butyl methyl{[5-(4-methyl-3-thienyl)-1-(pyridin-3-ylsulfonyl)-1H-pyrrol-3-yl]methyl}carbamate (200 mg), the title compound was obtained as colorless crystals (yield 125 mg, 67%). More specifically, tert-butyl methyl{[5-(4-methyl-3-thienyl)-1-(pyridin-3-ylsulfonyl)-1H-pyrrol-3-yl]methyl}carbamate (200 mg) was dissolved in dichloromethane (1 mL), trifluoroacetic acid (1 mL) was added at 0° C., and the mixture was stirred at room temperature for 1 hr. The reaction solution was basified by adding dropwise to a 6% aqueous sodium hydrogencarbonate solution, and the mixture was extracted with ethyl acetate. The organic layer was washed with saturated brine, dried over anhydrous sodium sulfate, and concentrated under reduced pressure. The residue was purified by basic silica gel column chromatography (eluent:hexane-ethyl acetate=1:1→1:9) to give a free salt of the title compound as a pale-yellow oil. The obtained free salt was dissolved in ethyl acetate (5 mL), a 4 mol/L hydrogen chloride-ethyl acetate solution (1 mL) was added, and the mixture was concentrated under reduced pressure. The residue was recrystallized from ethyl acetate-ethanol to give the title compound as colorless crystals (yield 125 mg, 67%).
$^1$H-NMR (DMSO-$d_6$) δ: 1.71 (3H, s), 2.49-2.51 (3H, m), 3.98 (2H, t, J=5.7 Hz), 6.49 (1H, d, J=2.1 Hz), 7.16-7.23 (2H, m), 7.58-7.62 (1H, m), 7.79-7.86 (2H, m), 8.50-8.51 (1H, m), 8.87-8.89 (1H, m), 9.30 (2H, br), 1H not detected.
melting point 178-181° C.

Example 30

3-[4-[(methylamino)methyl]-1-(pyridin-3-ylsulfonyl)-1H-pyrrole-2-yl]benzonitrile hydrochloride By a similar operation as in Example 26 and using tert-butyl{[5-(3-cyanophenyl)-1-(pyridin-3-ylsulfonyl)-1H-pyrrol-3-yl]methyl}methylcarbamate (298 mg), the title compound was obtained as colorless crystals (yield 132 mg, 52%).

$^1$H-NMR (DMSO-$d_6$) δ: 2.48-2.51 (3H, m), 3.98 (2H, brs), 6.65 (1H, d, J=1.8 Hz), 7.51-7.65 (4H, m), 7.85-7.95 (3H, m), 8.55 (1H, d, J=2.4 Hz), 8.88-8.90 (1H, m), 9.25 (2H, br).

Example 31

1-[5-(2-chlorophenyl)-1-(pyridin-3-ylsulfonyl)-1H-pyrrol-3-yl]-N-methylmethanamine dihydrochloride By a similar operation as in Example 26 and using tert-butyl{[5-(2-chlorophenyl)-1-(pyridin-3-ylsulfonyl)-1H-pyrrol-3-yl]methyl}methylcarbamate (171 mg), the title compound was obtained as colorless crystals (yield 74 mg, 46%).

$^1$H-NMR (DMSO-$d_6$) δ: 2.50 (3H, br), 4.01 (2H, t, J=6.0 Hz), 5.40 (1H, br), 6.55 (1H, d, J=2.1 Hz), 7.13-7.16 (1H, m), 7.35-7.40 (1H, m), 7.47-7.51 (2H, m), 7.61-7.65 (1H, m), 7.84-7.93 (2H, m), 8.57 (1H, d, J=2.1 Hz), 8.89-8.91 (1H, m), 9.23 (2H, br).

Example 32

1-[5-(2,4-difluorophenyl)-1-(pyridin-3-ylsulfonyl)-1H-pyrrol-3-yl]-N-methylmethanamine dihydrochloride By a similar operation as in Example 26 and using tert-butyl{[5-(2,4-difluorophenyl)-1-(pyridin-3-ylsulfonyl)-1H-pyrrol-3-yl]methyl}methylcarbamate (110 mg), the title compound was obtained as colorless crystals (yield 58 mg, 56%).

$^1$H-NMR (DMSO-$d_6$) δ: 2.48-2.51 (3H, m), 3.98 (2H, t, J=5.7 Hz), 6.62 (1H, d, J=1.8 Hz), 7.13-7.17 (2H, m), 7.28-7.36 (1H, m), 7.62-7.66 (1H, m), 7.86-7.95 (2H, m), 8.61 (1H, d, J=2.4 Hz), 8.89-8.91 (1H, m), 9.31 (2H, br), 1H not detected.

Example 33

1-[5-(2,5-difluorophenyl)-1-(pyridin-3-ylsulfonyl)-1H-pyrrol-3-yl]-N-methylmethanamine hydrochloride By a similar operation as in Example 26 and using tert-butyl{[5-(2,5-difluorophenyl)-1-(pyridin-3-ylsulfonyl)-1H-pyrrol-3-yl]methyl}methylcarbamate (105 mg), the title compound was obtained as colorless crystals (yield 39 mg, 43%).

$^1$H-NMR (DMSO-$d_6$) δ: 2.50-2.51 (3H, m), 3.99 (2H, brs), 6.62 (1H, d, J=1.8 Hz), 7.00-7.06 (1H, m), 7.27-7.44 (2H, m), 7.63-7.67 (1H, m), 7.86 (1H, br), 7.94-7.97 (1H, m), 8.65 (1H, d, J=2.7 Hz), 8.90-8.92 (1H, m), 9.08 (2H, m).

Example 34

1-[5-(4-chloro-2-fluorophenyl)-1-(pyridin-3-ylsulfonyl)-1H-pyrrol-3-yl]-N-methylmethanamine dihydrochloride By a similar operation as in Example 26 and using tert-butyl{[5-(4-chloro-2-fluorophenyl)-1-(pyridin-3-ylsulfonyl)-1H-pyrrol-3-yl]methyl}methylcarbamate (103 mg), the title compound was obtained as colorless crystals (yield 32 mg, 33%).

$^1$H-NMR (DMSO-$d_6$) δ: 2.47-2.52 (3H, m), 3.97 (2H, t, J=6.0 Hz), 5.10 (1H, br), 6.64 (1H, brs), 7.15 (1H, t, J=7.8 Hz), 7.34-7.36 (1H, m), 7.50-7.53 (1H, m), 7.62-7.67 (1H, m), 7.88 (1H, brs), 7.95-7.98 (1H, m), 8.64 (1H, d, J=2.4 Hz), 8.90 (1H, d, J=4.8 Hz), 9.33 (2H, br).

Example 35

1-[5-(3-fluorophenyl)-1-(pyridin-3-ylsulfonyl)-1H-pyrrol-3-yl]-N-methylmethanamine hydrochloride tert-Butyl{[5-(3-fluorophenyl)-1-(pyridin-3-ylsulfonyl)-1H-pyrrol-3-yl]methyl}methylcarbamate (280 mg) was dissolved in ethyl acetate (3 mL), a 4 mol/L hydrogen chloride-ethyl acetate solution (6 mL) was added, and the mixture was stirred at room temperature for 16 hr. The reaction solution was basified by adding dropwise to a 6% aqueous sodium hydrogencarbonate solution, and the mixture was extracted with ethyl acetate. The organic layer was washed with saturated brine, dried over anhydrous sodium sulfate, and concentrated under reduced pressure. The residue was purified by basic silica gel column chromatography (eluent:ethyl acetate-hexane=1:1→9:1) to give a free salt of the title compound as a pale-yellow oil. The obtained free salt was dissolved in ethyl acetate, a 4 mol/L hydrogen chloride-ethyl acetate solution was added, and the mixture was concentrated under reduced pressure. The residue was crystallized from ethyl acetate and hexane, and recrystallized from ethyl acetate-ethanol to give the title compound as colorless crystals (yield 84 mg, 35%).

$^1$H-NMR (DMSO-$d_6$) δ: 2.49-2.51 (3H, m), 3.97 (2H, s), 6.57 (1H, d, J=1.8 Hz), 6.98-7.02 (2H, m), 7.27-7.33 (1H, m), 7.40-7.47 (1H, m), 7.58-7.62 (1H, m), 7.80-7.87 (2H, m), 8.54 (1H, d, J=2.7 Hz), 8.86-8.88 (1H, m), 9.06 (2H, br).

Example 36

1-[5-(2-fluorophenyl)-2-methyl-1-(pyridin-3-ylsulfonyl)-1H-pyrrol-3-yl]-N-methylmethanamine fumarate A suspension of tert-butyl{[5-bromo-2-methyl-1-(pyridin-3-ylsulfonyl)-1H-pyrrol-3-yl]methyl}methylcarbamate (369 mg), (2-fluorophenyl)boronic acid (234 mg), sodium carbonate (265 mg) and tetrakis(triphenylphosphine)palladium (48.9 mg) in 1,2-dimethoxyethane (15 mL) and water (7.5 mL) was stirred at 105° C. for 12 hr. The reaction mixture was allowed to cool to room temperature, water was added and the mixture was extracted with ethyl acetate. The extract was washed with a saturated aqueous sodium hydrogencarbonate solution, water and saturated brine, dried over anhydrous magnesium sulfate, filtered, and concentrated under reduced pressure. The residue was purified by silica gel column chromatography (eluent:hexane-ethyl acetate=1:4) to give an oil. The obtained oil was dissolved in ethanol (5 mL), a 4 mol/L hydrogen chloride-ethyl acetate solution (2 mL) was added, and the mixture was stirred at room temperature for 4 hr. The reaction mixture was concentrated under reduced pressure, and the residue was neutralized by adding a saturated aqueous sodium hydrogencarbonate solution (50 mL). The mixture was extracted with ethyl acetate, and the extract was washed with a saturated aqueous sodium hydrogencarbonate solution, water and saturated brine, dried over anhydrous sodium sulfate, and the solvent was evaporated under reduced pressure. The residue was purified by basic silica gel column chromatography (eluent:ethyl acetate), and further by HPLC (ODS, 0.1% trifluoroacetic acid-containing water-0.1% trifluoroacetic acid-containing acetonitrile=9:1→0.1% trifluoroacetic acid-containing acetonitrile) to give trifluoroacetate of the title compound. The obtained trifluoroacetate was neutralized with a saturated aqueous sodium hydrogencarbonate solution, and the mixture was extracted with ethyl acetate. The extract was washed successively with a saturated aqueous sodium hydrogencarbonate solution, water and saturated brine, and dried over anhydrous magnesium sulfate. The solvent was evaporated under reduced pressure to give a free salt of the title compound (yield 65 mg). The free salt (62 mg) was dissolved in ethyl acetate (2 mL), a solution of fumaric acid (17 mg) in methanol (2 mL) was added, and the mixture was stirred for 10 min. The reaction mixture was concentrated under reduced pressure, and the residue was recrystallized from ethanol to give the title compound as white crystals (yield 25 mg, 7%).

$^1$H-NMR (DMSO-$d_6$) δ: 2.35 (3H, s), 2.40 (3H, s), 3.75 (2H, s), 6.46 (3H, s), 7.20-7.28 (3H, s), 7.44-7.52 (1H, m), 7.63-7.67 (1H, m), 7.88-7.92 (1H, m), 8.61 (1H, d, J=2.4 Hz), 8.88-8.90 (1H, m), 3H not detected.

Example 37

N-methyl-1-(5-phenyl-1-{[5-(trifluoromethyl)pyridin-3-yl]sulfonyl}-1H-pyrrol-3-yl)methanamine hydrochloride To a solution of 5-phenyl-1-{[5-(trifluoromethyl)pyridin-3-yl]sulfonyl}-1H-pyrrole-3-carbaldehyde (137 mg) in absolute tetrahydrofuran (5 mL) was added at room temperature, a 2 mol/L solution (0.36 mL) of methylamine in tetrahydrofuran was added, and the mixture was stirred for 16 hr. Sodium borohydride (27 mg) and methanol (2 mL) were added, and the mixture was stirred at the same temperature for 2 min. A saturated aqueous sodium hydrogencarbonate solution was added to the reaction mixture, and the mixture was extracted with ethyl acetate. The extract was washed with saturated brine, dried over anhydrous magnesium sulfate, and concentrated under reduced pressure. The residue was dissolved in tetrahydrofuran (5 mL), di-tert-butyl bicarbonate (218 mg), water (2 mL) and sodium hydrogencarbonate (84 mg) were added, and the mixture was stirred at room temperature for 30 min. Water was added to the reaction mixture, and the mixture was extracted with ethyl acetate. The extract was washed with saturated brine, dried over anhydrous magnesium sulfate, and concentrated under reduced pressure. The residue was dissolved in tetrahydrofuran (20 mL), manganese dioxide (75% chemically treated product, 1.0 g) was added, and the mixture was stirred at room temperature for 3 hr. The reaction mixture was filtered through celite, and celite was washed with ethyl acetate. The filtrate was concentrated under reduced pressure, and the residue was purified by silica gel column chromatography (eluent:hexane-ethyl acetate=19:1→1:1), fractions containing a material showing Rf value of 0.46 (eluent:hexane-ethyl acetate=3:1) by TLC analysis were collected and concentrated under reduced pressure. The residue was dissolved in ethanol (1 mL), and a 4 mol/L hydrogen chloride-ethyl acetate solution (1 mL) was added. After stirring at room temperature for 2 hr, the solvent was evaporated under reduced pressure. The residue was purified by HPLC (ODS, 0.1% trifluoroacetic acid-containing water-0.1% trifluoroacetic acid-containing acetonitrile=97:3→0.1% trifluoroacetic acid-containing acetonitrile) to give trifluoroacetate of the title compound. The obtained trifluoroacetate was neutralized with a saturated aqueous sodium hydrogencarbonate solution, extracted with ethyl acetate, washed successively with a saturated aqueous sodium hydrogencarbonate solution, water and saturated brine and dried over anhydrous magnesium sulfate, and concentrated under reduced pressure. The residue was dissolved in ethyl acetate (1 mL), a 4 mol/L hydrogen chloride-ethyl acetate solution (1 mL) was added, and the mixture was concentrated under reduced pressure. Recrystallization from ethanol gave the title compound (yield 23 mg, 15%).

$^1$H-NMR (DMSO-$d_6$) δ: 2.50 (3H, s), 3.97 (2H, s), 6.49 (1H, s), 7.13-7.15 (2H, m), 7.37-7.48 (3H, m), 7.80-7.87 (2H, m), 8.72 (2H, br), 8.86 (1H, s), 9.33 (1H, s).

Example 38

N-methyl-1-{1-[(2-methylpyridin-3-yl)sulfonyl]-5-phenyl-1H-pyrrol-3-yl}methanamine dihydrochloride By a similar reaction as in Example 12 and using 1-[(2-methylpyridin-3-yl)sulfonyl]-5-phenyl-1H-pyrrole-3-carbaldehyde (180 mg), the title compound was obtained as a solid (yield 110 mg, 48%).

$^1$H-NMR (DMSO-$d_6$) δ: 2.37 (3H, s), 2.53-2.57 (3H, m), 4.02-4.10 (2H, m), 6.51 (1H, d, J=1.8 Hz), 7.01 (2H, d, J=6.9 Hz), 7.11-7.35 (4H, m), 7.44-7.46 (1H, m), 7.84 (1H, d, J=2.1 Hz), 8.61-8.62 (1H, m), 9.07 (2H, br), 1H not detected.

Example 39

1-[5-(2,6-difluorophenyl)-1-(pyridin-3-ylsulfonyl)-1H-pyrrol-3-yl]-N-methylmethanamine fumarate 5-(2,6-Difluorophenyl)-1-(pyridin-3-ylsulfonyl)-1H-pyrrole-3-carbaldehyde (250 mg) was added to a mixture of a 40% methylamine methanol solution (560 mg) and methanol (5 mL) at room temperature, and the mixture was stirred for 30 min. Sodium borohydride (41 mg) was added to the reaction mixture and the mixture was stirred for 10 min. The reaction mixture was concentrated under reduced pressure at 30° C. The residue was extracted with a saturated aqueous sodium hydrogencarbonate solution and ethyl acetate. The extract was washed with saturated brine, dried over anhydrous magnesium sulfate, and concentrated under reduced pressure. The residue was purified by basic silica gel column chromatography (eluent:ethyl acetate), dissolved in ethanol (5 mL), and a solution of fumaric acid (84 mg) in ethanol (5 mL) was added to allow crystallization to give the title compound as colorless crystals (yield 229 mg, 67%).

$^1$H-NMR (DMSO-$d_6$) δ: 2.43 (3H, s), 3.85 (2H, s), 6.48 (2H, s), 6.57 (1H, d, J=1.7 Hz), 7.12-7.18 (2H, m), 7.55-7.66 (2H, m) 7.81 (1H, d, J=1.7 Hz), 7.93-7.97 (1H, m), 8.61 (1H, d, J=2.1 Hz), 8.90 (1H, dd, J=4.7, 1.5 Hz), 3H not detected.

Example 40

1-[5-(4-cyclohexylphenyl)-1-(pyridin-3-ylsulfonyl)-1H-pyrrol-3-yl]-N-methylmethanamine dihydrochloride To a solution of 5-(4-cyclohexylphenyl)-1-(pyridin-3-ylsulfonyl)-1H-pyrrole-3-carbaldehyde (0.78 g) in methanol (20 mL) were added methylammonium chloride (1.61 g) and sodium cyanoborohydride (0.49 g), and the mixture was stirred at room temperature for 16 hr. The reaction mixture was concentrated under reduced pressure, a saturated aqueous sodium hydrogencarbonate solution was added to the residue, and the mixture was extracted with ethyl acetate. The extract was washed with saturated brine, dried over anhydrous magnesium sulfate, and concentrated under reduced pressure. The residue was purified by basic silica gel column chromatography (eluent:hexane-ethyl acetate=3:2→0:1) to give an oil (0.39 g). The oil was dissolved in ethyl acetate (3 mL), a 4 mol/L hydrogen chloride-ethyl acetate solution (1.5 mL) was added, and the mixture was concentrated under reduced pressure. Crystallization from methanol-ethyl acetate gave the title compound as crystals (yield 0.41 g, 43%).

$^1$H-NMR (DMSO-$d_6$) δ: 1.20-1.46 (5H, m), 1.68-1.88 (5H, m), 2.45-2.59 (1H, m), 2.48 (3H, s), 3.97 (2H, d, J=5.3 Hz), 6.48 (1H, s), 7.04 (2H, d, J=8.1 Hz), 7.20 (2H, d, J=8.1 Hz), 7.51-7.57 (1H, m), 7.73-7.79 (2H, m), 8.43 (1H, s), 8.83 (1H, d, J=4.7 Hz), 9.17 (2H, s), 1H not detected.

Example 41

1-[4-fluoro-5-phenyl-1-(pyridin-3-ylsulfonyl)-1H-pyrrol-3-yl]-N-methylmethanamine dihydrochloride By a similar reaction as in Example 12 and using 4-fluoro-5-phenyl-1-(pyridin-3-ylsulfonyl)-1H-pyrrole-3-carbaldehyde (121 mg), the title compound was obtained as a colorless solid (yield 30.7 mg, 20%). More specifically, 4-fluoro-5-phenyl-1-(pyridin-3-ylsulfonyl)-1H-pyrrole-3-carbaldehyde (121 mg) was dissolved in tetrahydrofuran (5 mL), a 2 mol/L solution (0.22 mL) of methylamine in tetrahydrofuran was added, and the mixture was stirred at room temperature for 4 hr. A solution (2 mL) of sodium borohydride (28 mg) in methanol was added to the reaction mixture, and the mixture was stirred at room temperature for 20 min. A aqueous sodium hydrogencarbonate solution was added, and the mixture was extracted with ethyl acetate. The extract was washed with saturated brine, dried over anhydrous sodium sulfate, and concentrated under reduced pressure. The residue was purified by silica gel column chromatography (eluent: ethyl acetate→ethyl acetate-methanol=1:4) to give a free salt of the title compound. To a solution (2 mL) of the obtained free salt in ethanol was added a 4 mol/L hydrogen chloride-ethyl acetate solution (1 mL). After allowing to stand at room temperature for 30 min, the mixture was concentrated under reduced pressure, and the residue was recrystallized from ethanol to give the title compound as a colorless solid (yield 30.7 mg, 20%).

$^1$H-NMR (DMSO-$d_6$) δ: 2.56-2.59 (3H, m), 4.03-4.05 (2H, m), 7.14-7.16 (2H, m), 7.41-7.48 (3H, m), 7.53-7.62 (1H, m), 7.80-7.85 (2H, m), 8.50 (1H, d, J=2.4 Hz), 8.88-8.89 (1H, m), 9.07 (2H, br), 1H not detected.

melting point 201-203° C.

Example 42

1-[4-fluoro-5-phenyl-1-(pyridin-3-ylsulfonyl)-1H-pyrrol-3-yl]-N-methylmethanamine 4-Fluoro-5-phenyl-1-(pyridin-3-ylsulfonyl)-1H-pyrrole-3-carbaldehyde (0.27 g) was dissolved in tetrahydrofuran (10 mL), a 2 mol/L solution (0.8 mL) of methylamine in tetrahydrofuran was added, and the mixture was stirred at room temperature for 2 hr. Sodium borohydride (91 mg) and methanol (7 mL) were added, and the mixture was stirred at the same temperature for further 30 min. The reaction mixture was concentrated under reduced pressure. A saturated aqueous sodium hydrogencarbonate solution was added to the residue, and the mixture was extracted with ethyl acetate. The extract was dried over magnesium sulfate and concentrated under reduced pressure. The residue was purified by basic silica gel column chromatography (hexane-ethyl acetate=19:1→0:1). The above-mentioned operation was repeated to give the title compound (0.22 g, yield 39%) as a colorless solid.

$^1$H-NMR (CDCl$_3$) δ: 2.48 (3H, s), 3.63 (2H, s), 7.22-7.42 (7H, m), 7.56-7.60 (1H, m), 8.55 (1H, d, J=2.1 Hz), 8.73 (1H, dd, J=4.8, 1.8 Hz), 1H not detected.

melting point 98-99° C.

Example 43

1-[4-fluoro-5-phenyl-1-(pyridin-3-ylsulfonyl)-1H-pyrrol-3-yl]-N-methylmethanamine 0.5 fumarate 1-[4-Fluoro-5-phenyl-1-(pyridin-3-ylsulfonyl)-1H-pyrrol-3-yl]-N-methylmethanamine (32 mg) was dissolved in ethanol (2 mL), fumaric acid (10 mg) was added, and the mixture was stood at room temperature for 1 hr. The precipitate was collected by filtration to give the title compound as a colorless solid (yield 16 mg, 42%).

$^1$H-NMR (DMSO-$d_6$) δ: 2.30 (3H, s), 3.60 (2H, s), 6.50 (1H, s), 7.18-7.21 (2H, m), 7.39-7.50 (4H, m), 7.57-7.61 (1H, m), 7.79-7.83 (1H, m), 8.50 (1H, d, J=2.1 Hz), 8.87 (1H, dd, J=5.1, 1.8 Hz), 2H not detected.

melting point 163-166° C.

Example 44

1-{5-(2-fluorophenyl)-1-[(6-methylpyridin-3-yl)sulfonyl]-1H-pyrrol-3-yl}-N-methylmethanamine dihydrochloride By a similar reaction as in Example 12 and using 5-(2-fluorophenyl)-1-[(6-methylpyridin-3-yl)sulfonyl]-1H-pyrrole-3-carbaldehyde (134 mg), the title compound was obtained as a colorless solid (yield 96.1 mg, 57%). More specifically, 5-(2-fluorophenyl)-1-[(6-methylpyridin-3-yl)sulfonyl]-1H-pyrrole-3-carbaldehyde (134 mg) was dissolved in tetrahydrofuran (10 mL), a 2 mol/L solution (0.6 mL) of methylamine in tetrahydrofuran was added, and the mixture was stirred at room temperature for 4 hr. A solution (5 mL) of sodium borohydride (76 mg) in methanol was added to the reaction mixture, and the mixture was stirred at room temperature for 20 min. An aqueous sodium hydrogencarbonate solution was added, and the mixture was extracted with ethyl acetate. The extract was washed with saturated brine, dried over anhydrous sodium sulfate, and concentrated under reduced pressure. The residue was purified by silica gel column chromatography (eluent: ethyl acetate→ethyl acetate-methanol=1:4) to give a free salt of the title compound. To a solution (2 mL) of the obtained free salt in ethanol was added a 4 mol/L hydrogen chloride-ethyl acetate solution (1 mL). After allowing to stand at room temperature for 30 min, the mixture was concentrated under reduced pressure, and the residue was recrystallized from ethanol to give the title compound as a colorless solid (yield 96.1 mg, 57%).

$^1$H-NMR (DMSO-$d_6$) δ: 2.50-2.56 (6H, m), 3.97-4.02 (2H, m), 6.55 (1H, d, J=1.8 Hz), 7.08-7.11 (1H, m), 7.22-7.26 (2H, m), 7.47-7.60 (2H, m), 7.76-7.82 (2H, m), 8.44 (1H, d, J=2.4 Hz), 9.04 (2H, br), 1H not detected.

melting point 212-213° C.

Example 45

1-[5-(2-fluorophenyl)-1-(pyridin-2-ylsulfonyl)-1H-pyrrol-3-yl]-N-methylmethanamine hydrochloride By a similar reaction as in Example 12 and using 5-(2-fluorophenyl)-1-(pyridin-2-ylsulfonyl)-1H-pyrrole-3-carbaldehyde (183 mg), the title compound was obtained as a colorless solid (yield 78.3 mg, 37%).

$^1$H-NMR (DMSO-$d_6$) δ: 2.54 (3H, s), 4.02 (2H, s), 6.52 (1H, d, J=2.1 Hz), 7.00-7.04 (1H, m), 7.11-7.19 (2H, m), 7.46-7.51 (1H, m), 7.57-7.60 (1H, m), 7.74-7.78 (2H, m), 8.03-8.08 (1H, m), 8.70-8.85 (3H, m).

Example 46

1-{5-(2-fluorophenyl)-1-[(1-methyl-1H-pyrazol-4-yl)sulfonyl]-1H-pyrrol-3-yl}-N-methylmethanamine fumarate To a solution (3 mL) of 5-(2-fluorophenyl)-1-[(1-methyl-1H-pyrazol-4-yl)sulfonyl]-1H-pyrrole-3-carbaldehyde (217 mg) in tetrahydrofuran were added a 40% methylamine methanol solution (152 mg) and methanol (1 mL) at room temperature. After stirring at room temperature for 1 hr, sodium borohydride (82 mg) was added at 0° C. After stirring at room temperature for 30 min, water was added and the mixture was extracted with ethyl acetate. The extract was washed with saturated brine, dried over anhydrous sodium sulfate, and concentrated under reduced pressure. The residue was purified by basic silica gel column chromatography (eluent: hexane-ethyl acetate=1:1→1:9) to give a free salt of the title compound as a pale-yellow oil (yield 152 mg). A solution of the obtained free salt in ethyl acetate (5 mL) was added to a solution of fumaric acid (50.6 mg) in methanol (1 mL), and the mixture was concentrated under reduced pressure. The residue was recrystallized from ethanol/water=95/5 to give the title compound as colorless crystals (yield 143 mg, 48%).

$^1$H-NMR (DMSO-$d_6$) δ: 2.46 (3H, s), 3.82 (3H, s), 3.85 (2H, s), 6.41 (1H, d, J=1.8 Hz), 6.46 (2H, s), 7.15-7.26 (3H, m), 7.46-7.56 (3H, m), 8.11 (1H, s), 3H not detected.

Example 47

N-methyl-1-[5-(2-methylphenyl)-1-(pyridin-3-ylsulfonyl)-1H-pyrrol-3-yl]methanamine fumarate To a solution of 5-(2-methylphenyl)-1-(pyridin-3-ylsulfonyl)-1H-pyrrole-3-carbaldehyde (521 mg) in tetrahydrofuran (5 mL) and methanol (5 mL) was added a 40% methylamine methanol solution (373 mg). After stirring at room temperature for 1 hr, sodium borohydride (202 mg) was added. After stirring at the same temperature for 30 min, water was added, and the mixture was extracted with ethyl acetate. The extract was washed with saturated brine, dried over anhydrous sodium sulfate, and concentrated under reduced pressure. The residue was purified by basic silica gel column chromatography (eluent:hexane-ethyl acetate=1:1→1:9) to give a free salt of the title compound as a yellow oil (yield 422 mg). A solution of the obtained free salt in ethanol (5 mL) was added to a solution (15 mL) of fumaric acid (144 mg) in ethanol, and the mixture was concentrated under reduced pressure. The residue was recrystallized from ethanol to give the title compound as colorless crystals (yield 414 mg, 56%).

$^1$H-NMR (DMSO-$d_6$) δ: 1.81 (3H, s), 2.45 (3H, s), 3.88 (2H, s), 6.33 (1H, d, J=1.8 Hz), 6.46 (2H, s), 6.83-6.85 (1H, m), 7.12-7.22 (2H, m), 7.32-7.37 (1H, m), 7.57-7.61 (1H, m), 7.69 (1H, d, J=1.8 Hz), 7.78-7.82 (1H, m), 8.44-8.45 (1H, m), 8.87-8.89 (1H, m), 3H not detected.

melting point 207-210° C.

Example 48

1-[4-chloro-5-(2-fluorophenyl)-1-(pyridin-3-ylsulfonyl)-1H-pyrrol-3-yl]-N-methylmethanamine fumarate To a solution of 4-chloro-5-(2-fluorophenyl)-1-(pyridin-3-ylsulfonyl)-1H-pyrrole-3-carbaldehyde (429 mg) in tetrahydrofuran (5 mL) and methanol (3 mL) was added a 40% methylamine methanol solution (275 mg) at room temperature. After stirring for 30 min, sodium borohydride (99 mg) was added. After stirring at the same temperature for 1 hr, water was added, and the mixture was extracted with ethyl acetate. The extract was washed with saturated brine, dried over anhydrous sodium sulfate, and concentrated under reduced pressure. The residue was purified by basic silica gel column chromatography (eluent:hexane-ethyl acetate=1:1→1:9) to give a free salt of the title compound as a yellow oil (yield 257 mg). A solution of the obtained free salt in ethyl acetate (5 mL) was added to a solution (10 mL) of fumaric acid (79 mg) in methanol, and the mixture was concentrated under reduced pressure. The residue was recrystallized from ethanol to give the title compound as colorless crystals (yield 216 mg, 36%).

$^1$H-NMR (DMSO-$d_6$) δ: 2.43 (3H, s), 3.75 (2H, s), 6.54 (2H, s), 7.13-7.19 (1H, m), 7.24-7.32 (2H, m), 7.55-7.66 (2H, m), 7.81 (1H, s), 7.88-7.92 (1H, m), 8.56-8.57 (1H, m), 8.90-8.92 (1H, m), 3H not detected.

Example 49

1-[4-fluoro-5-(2-fluorophenyl)-1-(pyridin-3-ylsulfonyl)-1H-pyrrol-3-yl]-N-methylmethanamine fumarate To a solution of 4-fluoro-5-(2-fluorophenyl)-1-(pyridin-3-ylsulfonyl)pyrrole-3-carbaldehyde (0.60 g) in tetrahydrofuran (6 mL) and methanol (6 mL) was added a 40% methylamine methanol solution (1.8 mL) and the mixture was stirred at room temperature for 30 min. Sodium borohydride (84 mg) was added at room temperature and the mixture was stirred for 5 min and concentrated under reduced pressure. A saturated aqueous sodium hydrogencarbonate solution was added to the residue, and the mixture was extracted with ethyl acetate. The extract was washed with a saturated aqueous sodium hydrogencarbonate solution, water and saturated brine, dried over anhydrous sodium sulfate, and concentrated under reduced pressure. The residue was purified by basic silica gel column chromatography (eluent:ethyl acetate) to give a free salt of the title compound as a pale-yellow oil (yield 0.36 g). The obtained free salt (0.36 g) was dissolved in ethanol (10 mL), and a solution of fumaric acid (0.12 g) in ethanol (10 mL) was added at room temperature. The reaction mixture was stirred for 14 hr, and concentrated under reduced pressure. The residue was recrystallized from ethanol to give the title compound as colorless crystals (yield 0.73 g, 43%).

$^1$H-NMR (DMSO-$d_6$) δ: 2.36 (3H, s), 3.69 (2H, s), 6.54 (2H, s), 7.21-7.32 (3H, m), 7.54-7.65 (3H, m), 7.86-7.90 (1H, m), 8.57 (1H, d, J=2.4 Hz), 8.89-8.91 (1H, m), 3H not detected.

Example 50

1-[4-fluoro-5-(2-methylphenyl)-1-(pyridin-3-ylsulfonyl)-1H-pyrrol-3-yl]-N-methylmethanamine fumarate To a solution (5 mL) of 4-fluoro-5-(2-methylphenyl)-1-(pyridin-3-ylsulfonyl)pyrrole-3-carbaldehyde (0.45 g) in tetrahydrofuran were added a 40% methylamine methanol solution (1.5 mL) and methanol (5 mL) and the mixture was stirred at room temperature for 30 min. Sodium borohydride (76 mg) was added at room temperature and the mixture was stirred for 30 min and concentrated under reduced pressure. A saturated aqueous sodium hydrogencarbonate solution was added to the residue, and the mixture was extracted with ethyl acetate. The extract was washed with a saturated aqueous sodium hydrogencarbonate solution, water and saturated brine, dried over anhydrous sodium sulfate, and concentrated under reduced pressure. The residue was purified by basic silica gel column chromatography (eluent:ethyl acetate) to give a free salt of the title compound as a pale-yellow oil (yield 0.33 g). The obtained free salt (0.33 g) was dissolved in ethanol (4 mL), and a solution of fumaric acid (0.10 g) in ethanol (10 mL) was added at room temperature. After stirring for 30 min, the reaction mixture was concentrated under reduced pressure. The residue was recrystallized from ethanol to give the title compound as colorless crystals (yield 0.32 g, 54%).

$^1$H-NMR (DMSO-$d_6$) δ: 1.76 (3H, s), 2.43 (3H, s), 3.80 (2H, s), 6.52 (2H, s), 6.97-6.99 (1H, m), 7.19-7.26 (2H, m), 7.37-7.42 (1H, m), 7.58-7.65 (2H, m), 7.80-7.84 (1H, m), 7.46 (1H, d, J=2.4 Hz), 8.89-8.91 (1H, m), 3H not detected.

Example 51

1-[2-chloro-5-(2,6-difluorophenyl)-1-(pyridin-3-ylsulfonyl)-1H-pyrrol-3-yl]-N-methylmethanamine fumarate 2-chloro-5-(2,6-difluorophenyl)-1-(pyridin-3-ylsulfonyl)-1H-pyrrole-3-carbaldehyde (160 mg) was added to a mixture of 40% methylamine methanol solution (325 mg) and methanol (20 mL) at room temperature. After stirring for 30 min, sodium borohydride (48 mg) was added and the mixture was stirred for 1 hr. The reaction mixture was concentrated under reduced pressure at 30° C. The residue was extracted with a saturated aqueous sodium hydrogencarbonate solution and ethyl acetate. The extract was washed with saturated brine, dried over anhydrous magnesium sulfate, and concentrated under reduced pressure. The residue was purified by silica gel column chromatography (eluent:ethyl acetate-methanol=1:0→7:3) and dissolved in ethanol (2 mL), and a solution of fumaric acid (48 mg) in ethanol (2 mL) was added. Crystallization from the mixture gave the title compound as colorless crystals (yield 29 mg, 14%).

$^1$H-NMR (DMSO-$d_6$) δ: 2.28 (3H, s), 3.65 (2H, s), 6.51 (2H, s), 6.73 (1H, s), 7.21-7.28 (2H, m), 7.55-7.65 (1H, m), 7.73-7.77 (1H, m), 8.08-8.12 (1H, m), 8.82 (1H, d, J=2.4 Hz), 8.96 (1H, dd, J=4.9, 1.5 Hz), 3H not detected.

Example 52

1-[2-chloro-5-(2-fluorophenyl)-1-(pyridin-3-ylsulfonyl)-1H-pyrrol-3-yl]-N-methylmethanamine fumarate To a solution of methylamine hydrochloride (232 mg) in methanol (10 mL) was added 2-chloro-5-(2-fluorophenyl)-1-(pyridin-3-ylsulfonyl)-1H-pyrrole-3-carbaldehyde (250 mg) and the mixture was stirred for 30 min. Sodium triacetoxyborohydride (218 mg) was added and the mixture was stirred for 2 hr. The reaction mixture was concentrated under reduced pressure at 30° C. and extracted with a saturated aqueous sodium hydrogencarbonate solution and ethyl acetate. The extract was washed with saturated brine, dried over anhydrous magnesium sulfate, and concentrated under reduced pressure. The residue was purified by silica gel column chromatography (eluent:ethyl acetate-methanol=1:0→17:3) and dissolved in ethyl acetate (10 mL), and a solution of fumaric acid (80 mg) in methanol (2 mL) was added. Crystallization from the mixture gave the title compound as colorless crystals (yield 97 mg, 29%).

$^1$H-NMR (DMSO-$d_6$) δ: 2.23 (3H, s), 3.61 (2H, s), 6.51 (2H, s), 6.61 (1H, s), 7.27-7.33 (2H, m), 7.43-7.56 (2H, m), 7.69-7.74 (1H, m), 8.02-8.06 (1H, m), 8.80 (1H, brs), 8.94 (1H, dd, J=4.8, 1.4 Hz), 3H not detected.

Example 53

1-{1-[(5-bromopyridin-3-yl)sulfonyl]-5-phenyl-1H-pyrrol-3-yl}-N-methylmethanamine hydrochloride tert-Butyl({1-[(5-bromopyridin-3-yl)sulfonyl]-5-phenyl-3-yl-1H-pyrrol-3-yl}methyl)methylcarbamate (120 mg) was dissolved in ethanol (3 mL), and a 4 mol/L hydrogen chloride-ethyl acetate solution (1 mL) was added. After stirring at room temperature for 4 hr, the mixture was concentrated under reduced pressure, and the residue was recrystallized from ethanol to give the title compound as a solid (yield 51.3 mg, 49%).

$^1$H-NMR (DMSO-$d_6$) δ: 2.50 (3H, s), 3.96 (2H, m), 6.51 (1H, s), 7.15-7.17 (2H, m), 7.39-7.50 (3H, m), 7.77 (1H, s), 7.84 (1H, s), 8.48 (1H, s), 8.89 (2H, br), 9.03 (1H, s).

Example 54

5-({4-[(methylamino)methyl]-2-phenyl-1H-pyrrol-1-yl}sulfonyl)nicotinonitrile hydrochloride A mixture of tert-butyl({1-[(5-bromopyridin-3-yl)sulfonyl]-5-phenyl-3-yl-1H-pyrrol-3-yl}methyl)methylcarbamate (112 mg), zinc cyanide (50 mg) and N,N-dimethylformamide (4 mL) was degassed with argon gas. Tetrakis(triphenylphosphine)palladium (46 mg) was added, and the mixture was stirred at 100° C. for 1.5 hr. After cooling the reaction mixture to room temperature, a saturated aqueous sodium hydrogencarbonate solution was added, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=19:1→3:2) to give a colorless oil. The obtained oil was dissolved in ethanol (2 mL), and a 4 mol/L hydrogen chloride-ethyl acetate solution (2 mL) was added. After stirring at room temperature for 1 hr, the mixture was concentrated under reduced pressure, and recrystallized from ethanol to give the title compound as a solid (yield 32.7 mg, 42%).

$^1$H-NMR (DMSO-$d_6$) δ: 2.50-2.52 (3H, m), 3.98 (2H, s), 6.50 (1H, s), 7.13-7.16 (2H, m), 7.37-7.50 (3H, m), 7.76 (1H, d, J=1.8 Hz), 8.28 (1H, d, J=2.1 Hz), 8.66 (1H, d, J=2.4 Hz), 8.82 (2H, br), 9.31 (1H, d, J=2.1 Hz).

Example 55 methyl 5-({4-[(methylamino)methyl]-2-phenyl-1H-pyrrol-1-yl}sulfonyl)nicotinate hydrochloride A mixture of tert-butyl({1-[(5-bromopyridin-3-yl)sulfonyl]-5-phenyl-3-yl-1H-pyrrol-3-yl}methyl)methylcarbamate (112 mg), dichloro[bis(triphenylphosphine)]palladium (28 mg), triethylamine (0.25 mL) and methanol (15 mL) was stirred under a carbon monoxide atmosphere (3 atm) at 100° C. for 12 hr. After cooling to room temperature, the reaction mixture was concentrated under reduced pressure. A saturated aqueous sodium hydrogencarbonate solution was added to the residue, and the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=19:1→3:2) to give a colorless oil. The obtained oil was dissolved in ethanol (2 mL), and a 4 mol/L hydrogen chloride-ethyl acetate solution (2 mL) was added. After stirring at room temperature for 1 hr, the mixture was concentrated under reduced pressure, and recrystallized from ethanol to give the title compound as a solid (yield 47.0 mg, 56%).
$^1$H-NMR (DMSO-$d_6$) δ: 2.49-2.51 (3H, m), 3.91 (3H, s), 3.98 (2H, s), 6.50 (1H, d, J=1.8 Hz), 7.15-7.17 (2H, m), 7.37-7.50 (3H, m), 7.80 (1H, s), 7.93-7.94 (1H, m), 8.81 (1H, d, J=2.1 Hz), 8.91 (2H, br), 9.29 (1H, d, J=2.1 Hz).

Example 56

N-methyl-1-{1-[(5-methylpyridin-3-yl)sulfonyl]-5-phenyl-1H-pyrrol-3-yl}methanamine dihydrochloride Under an argon atmosphere, a mixture of tert-butyl({1-[(5-bromopyridin-3-yl)sulfonyl]-5-phenyl-3-yl-1H-pyrrol-3-yl}methyl)methylcarbamate (112 mg), methylboronic acid (18 mg), tetrakis(triphenylphosphine)palladium (23 mg), potassium carbonate (138 mg) and 1,4-dioxane (5 mL) was stirred at 80° C. for one day. The reaction mixture was poured into a saturated aqueous sodium hydrogencarbonate solution, and the mixture was extracted with ethyl acetate. The extract was washed with saturated brine, dried over magnesium sulfate, and concentrated under reduced pressure. The residue was purified by silica gel column chromatography (eluent: hexane-ethyl acetate=19:1→1:1) to give an oil. The oil was dissolved in ethanol (1 mL), and a 4 mol/L hydrogen chloride-ethyl acetate solution (1 mL) was added. After stirring at room temperature for 1 hr, the mixture was concentrated under reduced pressure. The residue was recrystallized from ethanol-ethyl acetate to give the title compound as a colorless solid (yield 32.6 mg, 39%).
$^1$H-NMR (DMSO-$d_6$) δ: 2.28 (3H, s), 2.50-2.53 (3H, m), 3.94-4.00 (2H, m), 6.48 (1H, d, J=1.8 Hz), 7.12-7.15 (2H, m), 7.37-7.52 (4H, m), 7.75 (1H, s), 8.29 (1H, d, J=2.1 Hz), 8.70 (1H, d, J=1.5 Hz), 9.08 (2H, br), 1H not detected.

Example 57

1-[5-(2,4-dimethylphenyl)-1-(pyridin-3-ylsulfonyl)-1H-pyrrol-3-yl]-N-methylmethanamine hydrochloride By a similar operation as in Example 33 and using tert-butyl{[5-(2,4-dimethylphenyl)-1-(pyridin-3-ylsulfonyl)-1H-pyrrol-3-yl]methyl}methylcarbamate (177 mg), the title compound was obtained as colorless crystals (yield 68 mg, 45%).
$^1$H-NMR (DMSO-$d_6$) δ: 1.76 (3H, s), 2.32 (3H, s), 2.49 (3H, s), 3.99 (2H, s), 6.38 (1H, d, J=1.8 Hz), 6.71 (1H, d, J=8.1 Hz), 6.95-7.03 (2H, m), 7.59-7.63 (1H, m), 7.77-7.85 (2H, m), 8.48 (1H, d, J=2.7 Hz), 8.88-8.90 (1H, m), 9.07 (2H, br).

Example 58

N-methyl-1-{5-[4-(methylsulfonyl)phenyl]-1-(pyridin-3-ylsulfonyl)-1H-pyrrol-3-yl}methanamine dihydrochloride To a solution of tert-butyl methyl{[5-[4-(methylsulfonyl)phenyl]-1-(pyridin-3-ylsulfonyl)-1H-pyrrol-3-yl]methyl}carbamate (275 mg) in ethyl acetate (2 mL) was added a 4 mol/L hydrogen chloride-ethyl acetate solution (2 mL), and the mixture was stirred at room temperature for 4 hr. The precipitated crystals were collected by filtration, washed with ethyl acetate and recrystallized from ethanol to give the title compound as white crystals (yield 157 mg, 33%).
$^1$H-NMR (DMSO-$d_6$) δ: 2.50 (3H, s), 3.29 (3H, s), 3.98 (2H, t, J=5.6 Hz), 6.67 (1H, d, J=1.9 Hz), 7.48 (2H, d, J=8.7 Hz), 7.60 (1H, dd, J=8.6, 4.4 Hz), 7.86-7.97 (4H, m), 8.59 (1H, d, J=1.9 Hz), 8.88 (1H, dd, J=4.8, 1.4 Hz), 9.20 (2H, s), 1H not detected.

Example 59

(2-{4-[(methylamino)methyl]-1-(pyridin-3-ylsulfonyl)-1H-pyrrole-2-yl}phenyl)methanol fumarate tert-Butyl({5-[2-(hydroxymethyl)phenyl]-1-(pyridin-3-ylsulfonyl)-1H-pyrrol-3-yl}methyl)methylcarbamate (132 mg) was dissolved in trifluoroacetic acid (1 mL), and the mixture was stirred at room temperature for 1 hr. The reaction mixture was basified with a saturated aqueous sodium hydrogencarbonate solution and extracted with ethyl acetate. The extract was washed with saturated brine, dried over anhydrous sodium sulfate, and the solvent was evaporated under reduced pressure. The residue was purified by basic silica gel column chromatography (eluent:ethyl acetate-methanol=1:0→9:1) to give a free salt of the title compound as a colorless oil (yield 60.3 mg). A solution of the obtained free salt in ethyl acetate (5 mL) was added to a solution of fumaric acid (19.6 mg) in methanol (2 mL), and the mixture was concentrated under reduced pressure. The residue was recrystallized from ethanol to give the title compound as colorless crystals (yield 48 mg, 35%).
$^1$H-NMR (DMSO-$d_6$) δ: 2.42 (3H, s), 3.83 (2H, s), 4.00 (2H, s), 6.35 (1H, d, J=1.5 Hz), 6.46 (2H, s), 6.81-6.83 (1H, m), 7.17-7.22 (1H, m), 7.41-7.50 (2H, m), 7.55-7.60 (1H, m), 7.65 (1H, s), 7.75-7.78 (1H, m), 8.46 (1H, d, J=2.4 Hz), 8.86 (1H, d, J=4.8 Hz), 4H not detected.

Example 60

N-methyl-1-[5-(4-methyl-3-thienyl)-1-(pyridin-3-ylsulfonyl)-1H-pyrrol-3-yl]methanamine fumarate By a similar reaction as in Example 59 and using tert-butyl{[5-(4-methyl-3-thienyl)-1-(pyridin-3-ylsulfonyl)-1H-pyrrol-3-yl]methyl}methylcarbamate (943 mg), the title compound was obtained as colorless crystals (yield 553 mg, 57%). More specifically, tert-butyl{[5-(4-methyl-3-thienyl)-

1-(pyridin-3-ylsulfonyl)-1H-pyrrol-3-yl]methyl}methylcarbamate (943 mg) was dissolved in trifluoroacetic acid (3 mL), and the mixture was stirred at room temperature for 30 min. The reaction mixture was basified with a saturated aqueous sodium hydrogencarbonate solution, and the mixture was extracted with ethyl acetate. The extract was washed with saturated brine, dried over anhydrous sodium sulfate, and the solvent was evaporated under reduced pressure. The residue was purified by basic silica gel column chromatography (eluent:hexane-ethyl acetate=1:9) to give a free salt of the title compound as a colorless oil (yield 631 mg). A solution of the obtained free salt in ethyl acetate (5 mL) was added to a solution of fumaric acid (211 mg) in methanol (2 mL), and the mixture was concentrated under reduced pressure. The residue was recrystallized from ethanol-water to give the title compound as colorless crystals (yield 553 mg, 57%).

$^1$H-NMR (DMSO-d$_6$) δ: 1.71 (3H, s), 2.42 (3H, s), 3.83 (2H, s), 6.34 (1H, d, J=1.8 Hz), 6.45 (2H, s), 7.15-7.16 (1H, m), 7.21-7.22 (1H, m), 7.56-7.60 (1H, m), 7.64-7.65 (1H, m), 7.78-7.82 (1H, m), 8.48 (1H, d, J=2.4 Hz), 8.84-8.86 (1H, m), 3H not detected.

melting point 182-183° C.

Example 61

N-methyl-1-(5-phenyl-1-(pyridin-3-ylsulfonyl)-1H-pyrrol-3-yl)methanamine fumarate 5-Phenyl-1-(pyridin-3-ylsulfonyl)-1H-pyrrole-3-carbaldehyde (650 mg) was dissolved in a mixture of a 40% methylamine methanol solution (808 mg) and methanol (30 mL) at room temperature and the mixture was stirred for 10 min. Sodium borohydride (118 mg) was added and the mixture was stirred for 10 min. The reaction mixture was concentrated under reduced pressure at 30° C. and the residue was extracted with a saturated aqueous sodium hydrogencarbonate solution (40 mL) and ethyl acetate (80 mL). The extract was washed with saturated brine (40 mL), dried over anhydrous magnesium sulfate, and concentrated under reduced pressure. The residue was purified by basic silica gel column chromatography (eluent:ethyl acetate) and a solution of fumaric acid (242 mg) in ethanol (24 mL) was added. The obtained crystals were collected by filtration and recrystallized from ethanol-water (85:15) to give the title compound as colorless crystals (yield 480 mg, 52%).

$^1$H-NMR (DMSO-d$_6$) δ: 2.42 (3H, s), 3.86 (2H, s), 6.42 (1H, d, J=1.9 Hz), 6.47 (2H, s), 7.14-7.18 (2H, m), 7.34-7.46 (3H, m), 7.54-7.58 (1H, m), 7.67 (1H, d, J=1.9 Hz), 7.76-7.80 (1H, m), 8.46 (1H, dd, J=2.5, 0.8 Hz), 8.84 (1H, dd, J=4.9, 1.5 Hz), 3H not detected.

Example 62

1-[5-mesityl-1-(pyridin-3-ylsulfonyl)-1H-pyrrol-3-yl]-N-methylmethanamine fumarate To a solution of 5-mesityl-1-(pyridin-3-ylsulfonyl)-1H-pyrrole-3-carbaldehyde (0.37 g) in tetrahydrofuran (15 mL) was added dropwise a solution of a 40% methylamine methanol solution (0.41 g) in tetrahydrofuran (1 mL) under ice-cooling, and the mixture was stirred at room temperature for 2 hr. Methanol (10 mL) was added, and the mixture was further stirred at room temperature for 2 hr. Sodium borohydride (0.06 g) was gradually added under ice-cooling, and the mixture was stirred at room temperature for 1 hr. The reaction mixture was concentrated under reduced pressure, a saturated aqueous sodium hydrogencarbonate solution was added to the residue, and the mixture was extracted with ethyl acetate. The extract was washed with saturated brine, dried over anhydrous sodium sulfate, and concentrated under reduced pressure. The residue was purified by basic silica gel column chromatography (eluent:hexane-ethyl acetate=1:1→ethyl acetate-methanol=5:1) to give a free salt of the title compound as a pale-brown oil. To a solution of the obtained free salt in ethyl acetate (5 mL) was added dropwise a solution of fumaric acid (0.14 g) in methanol (2.5 mL) under ice-cooling, and the mixture was stirred at room temperature for 15 min. The precipitate was collected by filtration and recrystallized from ethanol-water to give the title compound as white crystals (yield 0.32 g, 61%).

$^1$H-NMR (DMSO-d$_6$) δ: 1.58 (6H, s), 2.28 (3H, s), 2.44 (3H, s), 3.87 (2H, s), 6.21 (1H, s), 6.45 (2H, s), 6.83 (2H, s), 7.60 (1H, dd, J=8.1, 1.8 Hz), 7.70 (1H, s), 7.84 (1H, dd, J=8.4, 1.8 Hz), 8.46 (1H, s), 8.88 (1H, d, J=3.9 Hz), 3H not detected.

Example 63

N-methyl-1-{5-[2-(methylthio)phenyl]-1-(pyridin-3-ylsulfonyl)-1H-pyrrol-3-yl}methanamine fumarate To a solution (3 mL) of 5-[2-(methylthio)phenyl]-1-(pyridin-3-ylsulfonyl)-1H-pyrrole-3-carbaldehyde (170 mg) in tetrahydrofuran were added a 40% methylamine methanol solution (110 mg) and methanol (1 mL) at room temperature, and the mixture was stirred for 1 hr. Sodium borohydride (59.8 mg) was added under ice-cooling. After stirring at room temperature for 2 hr, water was added and the mixture was extracted with ethyl acetate. The extract was washed with saturated brine, dried over anhydrous sodium sulfate, and concentrated under reduced pressure. The residue was purified by basic silica gel column chromatography (eluent:hexane-ethyl acetate=1:1→1:9) to give a free salt of the title compound as a colorless oil. The obtained free salt was dissolved in ethyl acetate, and added to a solution (1 mL) of fumaric acid (33.2 mg) in methanol. The solvent was evaporated under reduced pressure, and the residue was recrystallized from ethanol to give the title compound as colorless crystals (yield 89.3 mg, 38%).

$^1$H-NMR (DMSO-d$_6$) δ: 2.11 (3H, s), 2.43 (3H, s), 3.86 (2H, s), 6.38 (1H, d, J=1.8 Hz), 6.46 (2H, s), 7.07-7.20 (3H, m), 7.41-7.46 (1H, m), 7.53-7.58 (1H, m), 7.68 (1H, d, J=1.8 Hz), 7.79-7.83 (1H, m), 8.43 (1H, d, J=2.4 Hz), 8.82-8.84 (1H, m), 3H not detected.

Example 64

N-methyl-1-{5-[2-(methylsulfonyl)phenyl]-1-(pyridin-3-ylsulfonyl)-1H-pyrrol-3-yl}methanamine 0.5 fumarate By a similar operation as in Example 63 and using 5-[2-(methylsulfonyl)phenyl]-1-(pyridin-3-ylsulfonyl)-1H-pyrrole-3-carbaldehyde (72.0 mg), the title compound was obtained as colorless crystals (yield 56.4 mg, 66%).

$^1$H-NMR (DMSO-d$_6$) δ: 2.37 (3H, s), 3.00 (3H, s), 3.71 (2H, s), 6.41 (1H, s), 6.48 (1H, d, J=1.5 Hz), 7.14-7.17 (1H, m), 7.61-7.65 (2H, m), 7.70-7.80 (2H, m), 7.93-7.97 (1H, m), 8.02-8.05 (1H, m), 8.66 (1H, d, J=2.1 Hz), 8.87-8.89 (1H, m), 2H not detected.

Example 65

2-{4-[(methylamino)methyl]-1-(pyridin-3-ylsulfonyl)-1H-pyrrole-2-yl}benzonitrile fumarate By a similar operation as in Example 63 and using 2-[4-formyl-1-(pyridin-3-ylsulfonyl)-1H-pyrrole-2-yl]benzonitrile (129 mg), the title compound was obtained as colorless crystals (yield 69 mg, 38%).

$^1$H-NMR (DMSO-$d_6$) δ: 2.39 (3H, s), 3.82 (2H, s), 6.47 (2H, s), 6.58 (1H, d, J=1.8 Hz), 7.34-7.36 (1H, m), 7.59-7.76 (4H, m), 7.84-7.89 (2H, m), 8.53 (1H, d, J=2.4 Hz), 8.87-8.89 (1H, m), 3H not detected.

Example 66

1-[5-(2,6-dimethylphenyl)-1-(pyridin-3-ylsulfonyl)-1H-pyrrol-3-yl]-N-methylmethanamine fumarate To a solution of 5-(2,6-dimethylphenyl)-1-(pyridin-3-ylsulfonyl)-1H-pyrrole-3-carbaldehyde (0.42 g) in tetrahydrofuran (15 mL) was added dropwise a solution of a 40% methylamine methanol solution (0.48 g) in tetrahydrofuran (1 mL) under ice-cooling, and the mixture was stirred at room temperature for 2 hr. Methanol (10 mL) was added, and the mixture was further stirred at room temperature for 2 hr. Sodium borohydride (0.07 g) was gradually added under ice-cooling, and the mixture was stirred at room temperature for 1 hr. The reaction mixture was concentrated under reduced pressure, a saturated aqueous sodium hydrogencarbonate solution was added to the residue, and the mixture was extracted with ethyl acetate. The extract was washed with saturated brine, dried over anhydrous sodium sulfate, and concentrated under reduced pressure. The residue was purified by basic silica gel column chromatography (eluent: hexane-ethyl acetate=1:1→ethyl acetate-methanol=5:1) to give a free salt of the title compound as a pale-brown oil. To a solution of the obtained free salt in ethyl acetate (5 mL) was added dropwise a solution of fumaric acid (0.12 g) in methanol (2 mL) under ice-cooling and the mixture was stirred at room temperature for 15 min. The precipitate was collected by filtration, and recrystallized from ethanol-water to give the title compound as white crystals (yield 0.18 g, 50%).

$^1$H-NMR (DMSO-$d_6$) δ: 1.62 (6H, s), 2.45 (3H, s), 3.88 (2H, s), 6.25 (1H, d, J=1.5 Hz), 6.45 (2H, s), 7.02 (2H, d, J=7.5 Hz), 7.24 (1H, d, J=7.5 Hz), 7.58-7.62 (1H, m), 7.71 (1H, s), 7.81-7.85 (1H, m), 8.44 (1H, d, J=2.7 Hz), 8.89 (1H, dd, J=4.8, 1.5 Hz), 3H not detected.

Example 67

N-methyl-1-{5-[2-(methylsulfinyl)phenyl]-1-(pyridin-3-ylsulfonyl)-1H-pyrrol-3-yl}methanamine fumarate To a suspension (5 mL) of sodium hydride (60% in oil, 39.5 mg) in tetrahydrofuran were added a solution (3 mL) of 5-[2-(methylsulfinyl)phenyl]-1H-pyrrole-3-carbaldehyde (160 mg) in N,N-dimethylformamide, 15-crown-5 (181 mg), and pyridin-3-ylsulfonyl chloride (134 mg) under ice-cooling. After stirring at room temperature for 1 hr, water was added and the mixture was extracted with ethyl acetate. The extract was washed with saturated brine, dried over anhydrous sodium sulfate, and concentrated under reduced pressure. The residue was suspended in tetrahydrofuran (5 mL), a 40% methylamine methanol solution (160 mg) was added at room temperature and the mixture was stirred for 1 hr. Sodium borohydride (86.5 mg) was added under ice-cooling. After stirring at room temperature for 2 hr, water was added and the mixture was extracted twice with ethyl acetate. The extract was washed with saturated brine, dried over anhydrous sodium sulfate, and concentrated under reduced pressure. The residue was purified by basic silica gel column chromatography (eluent:hexane-ethyl acetate=1:1→ethyl acetate) to give a free salt of the title compound as a pale-yellow oil. The obtained free salt was dissolved in ethyl acetate, and added to a solution (1 mL) of fumaric acid (28.1 mg) in methanol. The solvent was evaporated under reduced pressure, and the residue was recrystallized from ethanol to give the title compound as colorless crystals (yield 83.9 mg, 24%).

$^1$H-NMR (DMSO-$d_6$) δ: 2.41 (3H, s), 2.49-2.51 (3H, m), 3.81 (2H, s), 6.46 (2H, s), 6.50 (1H, d, J=1.5 Hz), 7.00 (1H, br), 7.50-8.00 (6H, m), 8.57 (1H, br), 8.87-8.89 (1H, m), 3H not detected.

Example 68

2-(2-fluorophenyl)-4-[(methylamino)methyl]-1-(pyridin-3-ylsulfonyl)-1H-pyrrole-3-carbonitrile fumarate 2-(2-Fluorophenyl)-4-formyl-1-(pyridin-3-ylsulfonyl)-1H-pyrrole-3-carbonitrile (295 mg) was dissolved in a solution of methylamine hydrochloride (1.12 g) in methanol (20 mL) and the mixture was stirred for 30 min. Sodium triacetoxyborohydride (1.06 g) was added and the mixture was stirred for 2 hr. The reaction mixture was concentrated under reduced pressure at 30° C., a saturated aqueous sodium hydrogencarbonate solution (40 mL) was added to the residue and the mixture was extracted with ethyl acetate (80 mL). The extract was washed with saturated brine (40 mL), dried over anhydrous magnesium sulfate, and concentrated under reduced pressure. The residue was purified by silica gel column chromatography (eluent:ethyl acetate-methanol=85:15→75:25), and then by basic silica gel column chromatography (eluent:ethyl acetate), and a solution of fumaric acid (96 mg) in ethanol (5 mL) was added. Crystallization from the mixture gave the title compound as colorless crystals (yield 120 mg, 30%).

$^1$H-NMR (DMSO-$d_6$) δ: 2.40 (3H, s), 3.76 (2H, s), 6.57 (2H, s), 7.28-7.37 (3H, m), 7.63-7.71 (2H, m), 7.87 (1H, s), 7.95-7.99 (1H, m), 8.64 (1H, dd, J=2.5, 0.6 Hz), 8.94 (1H, dd, J=4.9, 1.5 Hz), 3H not detected.

Example 69

5-(2-fluorophenyl)-3-[(methylamino)methyl]-1-(pyridin-3-ylsulfonyl)-1H-pyrrole-2-carbonitrile fumarate 5-Phenyl-1-(pyridin-3-ylsulfonyl)-1H-pyrrole-3-carbaldehyde (650 mg) was dissolved in a mixture of a 40% methylamine methanol solution (808 mg) and methanol (30 mL) at room temperature and the mixture was stirred for 10 min. Sodium borohydride (118 mg) was added and the mixture was stirred for 10 min. The reaction mixture was concentrated under reduced pressure at 30° C., a saturated aqueous sodium hydrogencarbonate solution (40 mL) was added to the residue and the mixture was extracted with ethyl acetate (80 mL). The extract was washed with saturated brine (40 mL), dried over anhydrous magnesium sulfate, and concentrated under reduced pressure. The residue was purified by basic silica gel column chromatography (eluent:ethyl acetate) and a solution of fumaric acid (242 mg) in ethanol (24 mL) was added. The obtained crystals were collected by filtration, and recrystallized from ethanol-water (85:15) to give the title compound as colorless crystals (yield 480 mg, 52%).

$^1$H-NMR (DMSO-d$_6$) δ: 2.27 (3H, s), 3.74 (2H, s), 6.57 (2H, s), 6.71 (1H, s), 7.29-7.38 (3H, m), 7.58-7.64 (1H, m), 7.71-7.75 (1H, m), 7.96-8.00 (1H, m), 8.66 (1H, d, J=2.3 Hz), 8.97 (1H, dd, J=4.9, 1.5 Hz), 3H not detected.

Example 70

4-{4-[(methylamino)methyl]-1-(pyridin-3-ylsulfonyl)-1H-pyrrol-2-yl}benzonitrile fumarate To a solution (2 mL) of tert-butyl{[5-(4-cyanophenyl)-1-(pyridin-3-ylsulfonyl)-1H-pyrrol-3-yl]methyl}methylcarbamate (382 mg) in ethyl acetate was added a 4 mol/L hydrogen chloride-ethyl acetate solution (3 mL) at room temperature. The mixture was stirred for 3 hr, and basified with a saturated aqueous sodium hydrogencarbonate solution. The mixture was extracted with ethyl acetate. The extract was washed with saturated brine, dried over anhydrous sodium sulfate, and concentrated under reduced pressure. The residue was purified by basic silica gel column chromatography (eluent:hexane-ethyl acetate=1:1→1:9) to give a free salt of the title compound as a pale-yellow oil. The obtained free salt was dissolved in ethyl acetate, and added to a solution (2 mL) of fumaric acid (77.1 mg) in methanol. The solvent was evaporated under reduced pressure, and the residue was recrystallized from a mixed solvent of ethanol and water to give the title compound as colorless crystals (yield 218 mg, 55%).

$^1$H-NMR (DMSO-d$_6$) δ: 2.37 (3H, s), 3.79 (2H, s), 6.47 (2H, s), 6.55 (1H, d, J=1.8 Hz), 7.40-7.44 (2H, m), 7.55-7.60 (1H, m), 7.70-7.71 (1H, m), 7.81-7.87 (3H, m), 8.55-8.56 (1H, m), 8.84-8.86 (1H, m), 3H not detected.

Example 71

4-fluoro-3-{4-[(methylamino)methyl]-1-(pyridin-3-ylsulfonyl)-1H-pyrrol-2-yl}benzonitrile 0.5 fumarate By a similar operation as in Example 70 and using tert-butyl{[5-(5-cyano-2-fluorophenyl)-1-(pyridin-3-ylsulfonyl)-1H-pyrrol-3-yl]methyl}methylcarbamate (100 mg), the title compound was obtained as colorless crystals (yield 37.1 mg, 40%).

$^1$H-NMR (DMSO-d$_6$) δ: 2.34 (3H, s), 3.71 (2H, s), 6.44 (1H, s), 6.55 (1H, brs), 7.52 (1H, t, J=9.0 Hz), 7.60-7.68 (2H, m), 7.73-7.75 (1H, m), 7.91-7.93 (1H, m), 8.03-8.08 (1H, m), 8.64 (1H, d, J=2.4 Hz), 8.88-8.90 (1H, m), 2H not detected.

Example 72

1-[5-(2-fluoro-5-methoxyphenyl)-1-(pyridin-3-ylsulfonyl)-1H-pyrrol-3-yl]-N-methylmethanamine fumarate tert-Butyl{[5-(2-fluoro-5-methoxyphenyl)-1-(pyridin-3-ylsulfonyl)-1H-pyrrol-3-yl]methyl}methylcarbamate (475 mg) was dissolved in ethanol (10 mL), a 4 mol/L hydrogen chloride-ethyl acetate solution (2 mL) was added and the mixture was stirred at 70° C. for 30 min. The reaction mixture was concentrated under reduced pressure, a saturated aqueous sodium hydrogencarbonate solution was added, and the mixture was extracted with ethyl acetate. The extract was washed with saturated brine, dried over anhydrous magnesium sulfate, and concentrated under reduced pressure. The residue was dissolved in ethyl acetate, added to a solution (13 mL) of fumaric acid (116 mg) in methanol, and the obtained crystals were collected by filtration to give the title compound as colorless crystals (yield 385 mg, 78%).

$^1$H-NMR (DMSO-d$_6$) δ: 2.41 (3H, s), 3.71 (3H, s), 3.82 (2H, s), 6.47 (1H, d, J=1.9 Hz), 6.48 (2H, s), 6.57-6.60 (1H, m), 7.02-7.07 (1H, m), 7.12-7.18 (1H, m), 7.60-7.64 (1H, m), 7.70 (1H, d, J=1.5 Hz), 7.89-7.93 (1H, m), 8.60 (1H, d, J=2.3 Hz), 8.88 (1H, dd, J=4.9, 1.5 Hz), 3H not detected.

Example 73

1-(2-fluoro-3-{4-[(methylamino)methyl]-1-(pyridin-3-ylsulfonyl)-1H-pyrrol-2-yl}phenyl)ethanone fumarate By a similar operation as in Example 70 and using tert-butyl{[5-(3-acetyl-2-fluorophenyl)-1-(pyridin-3-ylsulfonyl)-1H-pyrrol-3-yl]methyl}methylcarbamate (118 mg), the title compound was obtained as colorless crystals (yield 44.7 mg, 37%).

$^1$H-NMR (DMSO-d$_6$) δ: 2.40 (3H, s), 2.49-2.53 (3H, m), 3.80 (2H, m), 6.47 (2H, s), 6.52 (1H, d, J=1.8 Hz), 7.32-7.40 (2H, m), 7.59-7.64 (1H, m), 7.73 (1H, d, J=1.8 Hz), 7.86-7.93 (2H, m), 8.60 (1H, d, J=2.7 Hz), 8.87-8.89 (1H, m), 3H not detected.

Example 74

1-[5-(2-fluoropyridin-3-yl)-1-(pyridin-3-ylsulfonyl)-1H-pyrrol-3-yl]-N-methylmethanamine fumarate To a solution of tert-butyl{[5-(2-fluoropyridin-3-yl)-1-(pyridin-3-ylsulfonyl)-1H-pyrrol-3-yl]methyl}methylcarbamate (2.48 g) in ethyl acetate (10 mL) and methanol (10 mL) was added a 4 mol/L hydrogen chloride-ethyl acetate solution (20 mL) at room temperature. After stirring for 5 hr, the mixture was concentrated under reduced pressure. The residue was basified with a saturated aqueous sodium hydrogencarbonate solution and extracted with ethyl acetate. The extract was washed with saturated brine, dried over anhydrous sodium sulfate, and concentrated under reduced pressure. The residue was purified by basic silica gel column chromatography (eluent:hexane-ethyl acetate=1:1→1:9) to give a free salt of the title compound as a pale-yellow oil. The obtained free salt was dissolved in ethyl acetate (10 mL) and added to a solution of (10 mL) fumaric acid (350 mg) in methanol. The solvent was evaporated under reduced pressure and the residue was recrystallized from a mixed solvent of ethanol and water to give the title compound as colorless crystals (yield 793 mg, 29%).

$^1$H-NMR (DMSO-d$_6$) δ: 2.39 (3H, s), 3.78 (2H, s), 6.48 (2H, s), 6.56 (1H, d, J=1.8 Hz), 7.40-7.44 (1H, m), 7.61-7.65 (1H, m), 7.72-7.79 (2H, m), 7.89-7.93 (1H, m), 8.32-8.34 (1H, m), 8.62 (1H, d, J=1.8 Hz), 8.88-8.90 (1H, m), 3H not detected.

melting point 183-184° C.

Example 75

1-[5-(3-fluoropyridin-4-yl)-1-(pyridin-3-ylsulfonyl)-1H-pyrrol-3-yl]-N-methylmethanamine fumarate tert-Butyl{[5-(3-fluoropyridin-4-yl)-1-(pyridin-3-ylsulfonyl)-1H-pyrrol-3-yl]methyl}methylcarbamate (60 mg) was dissolved in methanol (5 mL), a 4 mol/L hydrogen chloride-ethyl acetate solution (1.5 mL) was added and the mixture was stirred at 70° C. for 30 min. The reaction mixture was concentrated under reduced pressure and a saturated aqueous sodium hydrogencarbonate solution was added. The mixture was extracted with ethyl acetate. The extract was washed with saturated brine, dried over anhydrous magnesium sulfate, and concentrated under reduced pressure. The residue was dissolved in ethyl acetate (8 mL), a solution of fumaric acid (58 mg) in methanol (2 mL) was added, and the obtained crystals were collected by filtration to give the title compound as colorless crystals (yield 45 mg, 72%).

$^1$H-NMR (DMSO-$d_6$) δ: 2.37 (3H, s), 3.78 (2H, s), 6.49 (2H, s), 6.64 (1H, d, J=1.5 Hz), 7.30-7.33 (1H, m), 7.62-7.66 (1H, m), 7.77 (1H, d, J=1.5 Hz), 7.94-7.98 (1H, m), 8.49-8.51 (1H, m), 8.64 (1H, d, J=1.5 Hz), 8.69 (1H, d, J=2.3 Hz), 8.90 (1H, dd, J=4.9, 1.5 Hz), 3H not detected.

Example 76

1-[5-(2-chloropyridin-3-yl)-1-(pyridin-3-ylsulfonyl)-1H-pyrrol-3-yl]-N-methylmethanamine fumarate tert-Butyl{[5-(2-chloropyridin-3-yl)-1-(pyridin-3-ylsulfonyl)-1H-pyrrol-3-yl]methyl}methylcarbamate (280 mg) was dissolved in ethanol (10 mL), a 4 mol/L hydrogen chloride-ethyl acetate solution (2 mL) was added and the mixture was stirred at 70° C. for 30 min. The reaction mixture was concentrated under reduced pressure, a saturated aqueous sodium hydrogencarbonate solution was added, and the mixture was extracted with ethyl acetate. The extract was washed with saturated brine, and concentrated under reduced pressure. The residue was dissolved in ethyl acetate (10 mL), a solution of fumaric acid (116 mg) in methanol (3 mL) was added, and the obtained crystals were collected by filtration to give the title compound as colorless crystals (yield 197 mg, 68%).

$^1$H-NMR (DMSO-$d_6$) δ: 2.40 (3H, s), 3.81 (2H, s), 6.49 (2H, s), 6.52 (1H, d, J=1.9 Hz), 7.47-7.52 (1H, m), 7.61-7.73 (3H, m), 7.90-7.94 (1H, m), 8.50 (1H, dd, J=4.9, 1.9 Hz), 8.63-8.64 (1H, m), 8.90 (1H, dd, J=4.5, 1.5 Hz), 3H not detected.

Example 77

1-[5-(6-chloropyridin-3-yl)-1-(pyridin-3-ylsulfonyl)-1H-pyrrol-3-yl]-N-methylmethanamine 1.5 fumarate tert-butyl{[5-(6-chloropyridin-3-yl)-1-(pyridin-3-ylsulfonyl)-1H-pyrrol-3-yl]methyl}methylcarbamate (100 mg) was dissolved in methanol (8 mL), a 4 mol/L hydrogen chloride-ethyl acetate solution (2 mL) was added and the mixture was stirred at 70° C. for 30 min. The reaction mixture was concentrated under reduced pressure, a saturated aqueous sodium hydrogencarbonate solution was added, and the mixture was extracted with ethyl acetate. The extract was washed with saturated brine, and concentrated under reduced pressure. The residue was purified by basic silica gel column chromatography (eluent:ethyl acetate-methanol=99:1→19:1) to give a free salt of the title compound. The obtained free salt was dissolved in ethyl acetate (8 mL), a solution of fumaric acid (116 mg) in methanol (2 mL) was added, and the obtained crystals were collected by filtration to give the title compound as colorless crystals (yield 60 mg, 52%).

$^1$H-NMR (DMSO-$d_6$) δ: 2.41 (3H, s), 3.83 (2H, s), 6.52 (3H, s), 6.58 (1H, d, J=1.5 Hz), 7.57-7.63 (2H, m), 7.75-7.78 (2H, m), 7.85-7.89 (1H, m), 8.20 (1H, d, J=2.3 Hz), 8.61 (1H, d, J=2.6 Hz), 8.88 (1H, dd, J=4.9, 1.5 Hz), 4H not detected.

Example 78

1-[5-(6'-chloro-2,3'-bipyridin-5-yl)-1-(pyridin-3-ylsulfonyl)-1H-pyrrol-3-yl]-N-methylmethanamine 0.5 fumarate tert-Butyl{[5-(6'-chloro-2,3'-bipyridin-5-yl)-1-(pyridin-3-ylsulfonyl)-1H-pyrrol-3-yl]methyl}methylcarbamate (100 mg) was dissolved in ethanol (8 mL), a 4 mol/L hydrogen chloride-ethyl acetate solution (2 mL) was added and the mixture was stirred at 70° C. for 30 min. The reaction mixture was concentrated under reduced pressure, a saturated aqueous sodium hydrogencarbonate solution was added, and the mixture was extracted with ethyl acetate. The extract was washed with saturated brine, and concentrated under reduced pressure. The residue was purified by basic silica gel column chromatography (eluent:ethyl acetate-methanol=99:1→19:1) to give a free salt of the title compound. The obtained free salt was dissolved in ethyl acetate (8 mL), a solution of fumaric acid (116 mg) in methanol (2 mL) was added, and the obtained crystals were collected by filtration to give the title compound as colorless crystals (yield 61 mg, 66%).

$^1$H-NMR (DMSO-$d_6$) δ: 2.33 (3H, s), 3.69 (2H, s), 6.46 (1H, s), 6.58-6.59 (1H, m), 7.57-7.62 (1H, m), 7.66-7.70 (2H, m), 7.83-7.88 (2H, m), 8.15 (1H, d, J=8.3 Hz), 8.52 (1H, d, J=1.9 Hz), 8.57 (1H, d, J=2.3 Hz), 8.60-8.61 (1H, m), 8.86 (1H, d, J=4.9 Hz), 9.18 (1H, d, J=2.3 Hz), 2H not detected.

Example 79

1-{5-(2-fluoropyridin-3-yl)-1-[(6-methoxypyridin-3-yl)sulfonyl]-1H-pyrrol-3-yl}-N-methylmethanamine hydrochloride By a similar operation as in Example 24 and using tert-butyl({5-(2-fluoropyridin-3-yl)-1-[(6-methoxypyridin-3-yl)sulfonyl]-1H-pyrrol-3-yl}methyl)methylcarbamate (289 mg), the title compound was obtained as colorless crystals (yield 74.2 mg, 29%).

$^1$H-NMR (DMSO-$d_6$) δ: 2.52 (3H, s), 3.94 (3H, s), 3.99 (2H, s), 6.65 (1H, d, J=1.8 Hz), 6.99-7.02 (1H, m), 7.42-7.47 (1H, m), 7.73-7.80 (2H, m), 7.84 (1H, d, J=1.8 Hz), 8.27-8.28 (1H, m), 8.34-8.36 (1H, m), 9.10 (2H, brs).

Example 80

(2-fluoro-3-{4-[(methylamino)methyl]-1-(pyridin-3-ylsulfonyl)-1H-pyrrol-2-yl}phenyl)methanol fumarate By a similar operation as in Example 70 and using tert-butyl({5-[2-fluoro-3-(hydroxymethyl)phenyl]-1-(pyridin-3-ylsulfonyl)-1H-pyrrol-3-yl}methyl)methylcarbamate (238 mg), the title compound was obtained as colorless crystals (yield 55.3 mg, 22%).

$^1$H-NMR (DMSO-$d_6$) δ: 2.40 (3H, s), 3.80 (2H, s), 4.49 (2H, s), 6.43 (1H, d, J=1.8 Hz), 6.47 (2H, s), 6.97-7.02 (1H, m), 7.17-7.22 (1H, m), 7.54-7.62 (2H, m), 7.68 (1H, d, J=1.2 Hz), 7.84-7.88 (1H, m), 8.56 (1H, d, J=2.1 Hz), 8.86-8.88 (1H, m), 4H not detected.

Example 81

1-(2-fluoro-3-{4-[(methylamino)methyl]-1-(pyridin-3-ylsulfonyl)-1H-pyrrol-2-yl}phenyl)ethanol fumarate By a similar operation as in Example 70 and using tert-butyl({5-[2-fluoro-3-(1-hydroxyethyl)phenyl]-1-(pyridin-3-ylsulfonyl)-1H-pyrrol-3-yl}methyl)methylcarbamate (318 mg), the title compound was obtained as colorless crystals (yield 69.7 mg, 21%).

$^1$H-NMR (DMSO-d$_6$) δ: 1.31 (3H, d, J=6.3 Hz), 2.40 (3H, s), 3.81 (2H, s), 4.90 (1H, q, J=6.3 Hz), 6.43 (1H, d, J=1.8 Hz), 6.47 (2H, s), 6.94-7.00 (1H, m), 7.16-7.22 (1H, m), 7.58-7.68 (3H, m), 7.84-7.87 (1H, m), 8.55 (1H, d, J=2.7 Hz), 8.86-8.88 (1H, m), 4H not detected.

Example 82

1-[5-(2-fluoro-3-methoxyphenyl)-1-(pyridin-3-ylsulfonyl)-1H-pyrrol-3-yl]-N-methylmethanamine fumarate tert-Butyl{[5-(2-fluoro-3-methoxyphenyl)-1-(pyridin-3-ylsulfonyl)-1H-pyrrol-3-yl]methyl}methylcarbamate (475 mg) was dissolved in methanol (20 mL), a 4 mol/L hydrogen chloride-ethyl acetate solution (2 mL) was added and the mixture was stirred at 70° C. for 20 min. The reaction mixture was concentrated under reduced pressure, a saturated aqueous sodium hydrogencarbonate solution was added, and the mixture was extracted with ethyl acetate. The extract was washed with saturated brine, dried over anhydrous magnesium sulfate, and concentrated under reduced pressure. The residue was dissolved in ethanol (13 mL), fumaric acid (116 mg) was added, and the obtained crystals were collected by filtration to give the title compound as colorless crystals (yield 310 mg, 63%).

$^1$H-NMR (DMSO-d$_6$) δ: 2.41 (3H, s), 3.82 (2H, s), 3.86 (3H, s), 6.45 (1H, d, J=1.7 Hz), 6.48 (2H, s), 6.58-6.63 (1H, m), 7.10-7.16 (1H, m), 7.24-7.30 (1H, m), 7.59-7.63 (1H, m), 7.70 (1H, d, J=1.5 Hz), 7.86-7.90 (1H, m), 8.58 (1H, dd, J=2.3, 0.7 Hz), 8.87-8.89 (1H, m), 3H not detected.

Example 83

1-[5-(2-fluoro-6-methoxyphenyl)-1-(pyridin-3-ylsulfonyl)-1H-pyrrol-3-yl]-N-methylmethanamine fumarate tert-Butyl{[5-(2-fluoro-6-methoxyphenyl)-1-(pyridin-3-ylsulfonyl)-1H-pyrrol-3-yl]methyl}methylcarbamate (100 mg) was dissolved in methanol (20 mL), a 4 mol/L hydrogen chloride-ethyl acetate solution (2 mL) was added and the mixture was stirred at 70° C. for 20 min. The reaction mixture was concentrated under reduced pressure, a saturated aqueous sodium hydrogencarbonate solution was added, and the mixture was extracted with ethyl acetate. The obtained organic layer was washed with saturated brine, dried over anhydrous magnesium sulfate, and concentrated under reduced pressure. The residue was dissolved in ethanol (6 mL), fumaric acid (49 mg) was added, and the obtained crystals were collected by filtration to give the title compound as colorless crystals (yield 53 mg, 51%).

$^1$H-NMR (DMSO-d$_6$) δ: 2.45 (3H, s), 3.44 (3H, s), 3.83 (2H, s), 6.36 (1H, d, J=1.5 Hz), 6.48 (2H, s), 6.79-6.86 (2H, m), 7.44-7.52 (1H, m), 7.60-7.65 (1H, m), 7.70 (1H, d, J=1.5 Hz), 7.88-7.92 (1H, m), 8.56 (1H, d, J=1.9 Hz), 8.88 (1H, dd, J=4.7, 1.7 Hz), 3H not detected.

Example 84

1-{5-[4-(difluoromethoxy)phenyl]-1-(pyridin-3-ylsulfonyl)-1H-pyrrol-3-yl}-N-methylmethanamine fumarate By a similar operation as in Example 70 and using tert-butyl({5-[4-(difluoromethoxy)phenyl]-1-(pyridin-3-ylsulfonyl)-1H-pyrrol-3-yl}methyl)methylcarbamate (550 mg), the title compound was obtained as colorless crystals (yield 313 mg, 62% for 2 steps).

$^1$H-NMR (DMSO-d$_6$) δ: 2.38 (3H, s), 3.78 (2H, s), 6.40 (1H, s), 6.47 (2H, s), 7.15-7.24 (4H, m), 7.32 (1H, t, J=73.5 Hz), 7.54-7.58 (1H, m), 7.62 (1H, s), 7.77-7.80 (1H, m), 8.50 (1H, d, J=2.4 Hz), 8.84 (1H, d, J=4.5 Hz), 3H not detected.

Example 85

N-methyl-1-[5-(4-methylpyridin-3-yl)-1-(pyridin-3-ylsulfonyl)-1H-pyrrol-3-yl]methanamine fumarate tert-Butyl methyl{[5-(4-methylpyridin-3-yl)-1-(pyridin-3-ylsulfonyl)-1H-pyrrol-3-yl]methyl}carbamate (230 mg) was dissolved in methanol (20 mL), a 4 mol/L hydrogen chloride-ethyl acetate solution (2 mL) was added and the mixture was stirred at 70° C. for 20 min. The reaction mixture was concentrated under reduced pressure, a saturated aqueous sodium hydrogencarbonate solution was added, and the mixture was extracted with ethyl acetate. The obtained organic layer was washed with saturated brine, dried over anhydrous magnesium sulfate, and concentrated under reduced pressure. The residue was purified by basic silica gel column chromatography (eluent:ethyl acetate-methanol (99:1→95:5) to give a free salt of the title compound. This was dissolved in ethyl acetate (8 mL), a solution of fumaric acid (90 mg) in methanol (2 mL) was added, and the obtained crystals were collected by filtration to give the title compound as colorless crystals (yield 115 mg, 48%).

$^1$H-NMR (DMSO-d$_6$) δ: 1.89 (3H, s), 2.43 (3H, s), 3.84 (2H, s), 6.45 (1H, d, J=1.9 Hz), 6.48 (2H, s), 7.29 (1H, d, J=4.9 Hz), 7.60-7.65 (1H, m), 7.73 (1H, d, J=1.9 Hz), 7.81-7.85 (1H, m), 7.98 (1H, s), 8.47 (1H, d, J=4.9 Hz), 8.51 (1H, d, J=1.9 Hz), 8.90 (1H, dd, J=4.9, 1.5 Hz), 3H not detected.

Example 86

N-methyl-1-[5-(2-methylpyridin-3-yl)-1-(pyridin-3-ylsulfonyl)-1H-pyrrol-3-yl]methanamine fumarate By a similar operation as in Example 70 and using tert-butyl methyl{[5-(2-methylpyridin-3-yl)-1-(pyridin-3-ylsulfonyl)-1H-pyrrol-3-yl]methyl}carbamate (278 mg), the title compound was obtained as colorless crystals (yield 93 mg, 32%).

$^1$H-NMR (DMSO-d$_6$) δ: 2.00 (3H, s), 2.43 (3H, s), 3.83 (2H, s), 6.42 (1H, s), 6.47 (2H, s), 7.20-7.24 (1H, m), 7.28-

7.31 (1H, m), 7.59-7.63 (1H, m), 7.70 (1H, s), 7.80-7.84 (1H, m), 8.49-8.51 (2H, m), 8.88-8.90 (1H, m), 3H not detected.

Example 87

1-{5-(2-fluoropyridin-3-yl)-1-[(6-methylpyridin-3-yl)sulfonyl]-1H-pyrrol-3-yl}-N-methylmethanamine 0.5 fumarate To a solution of tert-butyl({5-(2-fluoropyridin-3-yl)-1-[(6-methylpyridin-3-yl)sulfonyl]-1H-pyrrol-3-yl}methyl)methylcarbamate (86 mg) in ethanol (2 mL) was added a 4 mol/L hydrogen chloride-ethyl acetate solution (2 mL) at room temperature. The mixture was stirred for 2 hr, and concentrated under reduced pressure. The residue was basified with a saturated aqueous sodium hydrogencarbonate solution, and the mixture was extracted with ethyl acetate. The extract was washed successively with a saturated aqueous sodium hydrogencarbonate solution, water and saturated brine, dried over anhydrous sodium sulfate, and concentrated under reduced pressure to give a free salt of the title compound as a pale-yellow oil. The obtained free salt was dissolved in ethyl acetate (2 mL) and added to a solution (2 mL) of fumaric acid (11.3 mg) in ethanol, and the solvent was evaporated under reduced pressure. The residue was recrystallized from ethanol to give the title compound as colorless crystals (yield 14 mg, 18%).

$^1$H-NMR (DMSO-$d_6$) δ: 2.33 (3H, s), 2.56 (3H, s), 3.68 (2H, s), 6.44 (1H, s), 6.53 (1H, s), 7.41-7.50 (2H, m), 7.64 (1H, s), 7.74-7.81 (2H, m), 8.34 (1H, s), 8.48 (1H, s), 2H not detected.

Example 88

1-[4-chloro-5-(2-fluoropyridin-3-yl)-1-(pyridin-3-ylsulfonyl)-1H-pyrrol-3-yl]-N-methylmethanamine fumarate 4-Chloro-5-(2-fluoropyridin-3-yl)-1-(pyridin-3-ylsulfonyl)-1H-pyrrole-3-carbaldehyde (320 mg) was dissolved in a solution of methylamine hydrochloride (591 mg) in methanol (32 mL) and the mixture was stirred for 30 min. Sodium triacetoxyborohydride (557 mg) was added and the mixture was stirred for 3 hrs. The reaction mixture was concentrated under reduced pressure at 30° C., a saturated aqueous sodium hydrogencarbonate solution was added to the residue and the mixture was extracted with ethyl acetate. The extract was washed with saturated brine, dried over anhydrous magnesium sulfate, and concentrated under reduced pressure. The residue was purified by basic silica gel column chromatography (eluent:ethyl acetate-methanol=99:1→95:5) to give a free salt of the title compound. This was dissolved in ethyl acetate (8 mL), a solution of fumaric acid (102 mg) in methanol (2 mL) was added, and the obtained crystals were collected by filtration to give the title compound as colorless crystals (yield 52 mg, 12%).

$^1$H-NMR (DMSO-$d_6$) δ: 2.39 (3H, s), 3.70 (2H, s), 6.65 (2H, s), 7.48-7.53 (1H, m), 7.63-7.68 (1H, m), 7.81 (1H, s), 7.84-7.96 (2H, m), 8.40-8.42 (1H, m), 8.65 (1H, d, J=1.9 Hz), 8.93 (1H, dd, J=4.9, 1.5 Hz), 3H not detected.

Example 89

N-methyl-1-[1-(pyridin-3-ylsulfonyl)-5-(2-thienyl)-1H-pyrrol-3-yl]methanamine fumarate By a similar operation as in Example 70 and using tert-butyl methyl{[1-(pyridin-3-ylsulfonyl)-5-(2-thienyl)-1H-pyrrol-3-yl]methyl}carbamate (315 mg), the title compound was obtained as colorless crystals (yield 165 mg, 51%).

$^1$H-NMR (DMSO-$d_6$) δ: 2.43 (3H, s), 3.83 (2H, s), 6.47 (2H, s), 6.52 (1H, d, J=1.8 Hz), 7.07-7.12 (2H, m), 7.55-7.62 (2H, m), 7.70 (1H, d, J=1.8 Hz), 7.84-7.88 (1H, m), 8.53-8.54 (1H, m), 8.83-8.85 (1H, m), 3H not detected.

Example 90

N-methyl-1-[5-(3-methylpyridin-2-yl)-1-(pyridin-3-ylsulfonyl)-1H-pyrrol-3-yl]methanamine fumarate By a similar operation as in Example 70 and using tert-butyl methyl{[5-(3-methylpyridin-2-yl)-1-(pyridin-3-ylsulfonyl)-1H-pyrrol-3-yl]methyl}carbamate (229 mg), the title compound was obtained as colorless crystals (yield 124 mg, 53%).

$^1$H-NMR (DMSO-$d_6$) δ: 2.18 (3H, s), 2.44 (3H, s), 3.86 (2H, s), 6.46 (2H, s), 6.52 (1H, d, J=1.8 Hz), 7.32-7.36 (1H, m), 7.66-7.74 (3H, m), 8.17-8.21 (1H, m), 8.28-8.30 (1H, m), 8.87-8.90 (2H, m), 3H not detected.

Example 91

2-fluoro-3-{4-[(methylamino)methyl]-1-(pyridin-3-ylsulfonyl)-1H-pyrrol-2-yl}benzonitrile fumarate By a similar operation as in Example 70 and using tert-butyl{[5-(3-cyano-2-fluorophenyl)-1-(pyridin-3-ylsulfonyl)-1H-pyrrol-3-yl]methyl}methylcarbamate (170 mg), the title compound was obtained as colorless crystals (yield 96 mg, 74%).

$^1$H-NMR (DMSO-$d_6$) δ: 2.39 (3H, s), 3.80 (2H, s), 6.47 (2H, s), 6.59 (1H, d, J=1.5 Hz), 7.43-7.48 (1H, m), 7.52-7.57 (1H, m), 7.60-7.65 (1H, m), 7.76 (1H, d, J=1.8 Hz), 7.89-7.93 (1H, m), 8.02-8.07 (1H, m), 8.59-8.60 (1H, m), 8.89-8.91 (1H, m), 3H not detected.

Example 92

4-{4-[(methylamino)methyl]-1-(pyridin-3-ylsulfonyl)-1H-pyrrol-2-yl}thiophene-3-carbonitrile fumarate By a similar operation as in Example 70 and using tert-butyl{[5-(4-cyano-3-thienyl)-1-(pyridin-3-ylsulfonyl)-1H-pyrrol-3-yl]methyl}methylcarbamate (297 mg), the title compound was obtained as colorless crystals (yield 155 mg, 50%).

$^1$H-NMR (DMSO-$d_6$) δ: 2.41 (3H, s), 3.84 (2H, s), 6.47 (2H, s), 6.56 (1H, d, J=2.1 Hz), 7.59-7.74 (1H, m), 7.67 (1H, d, J=3.0 Hz), 7.73-7.74 (1H, m), 7.86-7.90 (1H, m), 8.57-8.59 (2H, m), 8.87-8.89 (1H, m), 3H not detected.

The structures of the compounds described in Reference Examples are shown in Tables 1-14.

TABLE 1

Structure: Pyrrole with substituents R1a (on N), R2a (position 2), R3a (position 3), R4a (position 4), R5a (position 5).

| Ref. Ex. No. | R1a | R2a | R3a | R4a | R5a |
|---|---|---|---|---|---|
| 6 | H | phenyl | H | CO2Et | Cl |
| 7 | H | 2-fluorophenyl | H | CO2Et | Cl |
| 8 | H | 2-fluorophenyl | Me | CO2Me | Cl |
| 9 | H | phenyl | H | CO2Et | H |
| 10 | H | 2-fluorophenyl | H | CO2Et | H |
| 11 | H | 2-fluorophenyl | Me | CO2Me | H |
| 12 | H | 2-(trifluoromethyl)phenyl | H | CO2Et | H |
| 13 | H | phenyl | H | CH2OH | H |
| 14 | H | 2-fluorophenyl | Me | CH2OH | H |
| 15 | H | phenyl | H | CHO | H |
| 16 | H | 2-fluorophenyl | Me | CHO | H |

TABLE 1-continued

| Ref. Ex. No. | R1a | R2a | R3a | R4a | R5a |
|---|---|---|---|---|---|
| 17 | H | 2-fluorophenyl | H | CHO | H |
| 18 | H | 2-(trifluoromethyl)phenyl | H | CHO | H |
| 19 | H | H | H | CO2Me | H |
| 20 | H | H | Me | CO2Me | H |
| 21 | H | H | H | CO2Et | Me |
| 22 | H | Br | H | CO2Me | H |

TABLE 2

Structure: Pyrrole with substituents R1a, R2a, R3a, R4a, R5a.

| Ref. Ex. No. | R1a | R2a | R3a | R4a | R5a |
|---|---|---|---|---|---|
| 23 | H | Br | Me | CO2Me | H |
| 24 | H | Br | H | CO2Et | Me |
| 36 | 2-chloropyrimidin-5-yl-sulfonylmethyl (2-chloropyrimidine-5-SO2-Me) | 4-methylphenyl | H | CO2Et | H |
| 37 | 2-methylpyrimidin-5-yl-sulfonylmethyl | 4-methylphenyl | H | CO2Et | H |
| 38 | 2-aminopyrimidin-5-yl-sulfonylmethyl | 4-methylphenyl | H | CO2Et | H |
| 39 | imidazo[1,2-a]pyrimidin-6-yl-sulfonylmethyl | 4-methylphenyl | H | CO2Et | H |

TABLE 2-continued

Structure: Pyrrole with R$^{2a}$, R$^{3a}$, R$^{4a}$, R$^{5a}$ on ring carbons and R$^{1a}$ on N.

| Ref. Ex. No. | R$^{1a}$ | R$^{2a}$ | R$^{3a}$ | R$^{4a}$ | R$^{5a}$ |
|---|---|---|---|---|---|
| 40 | pyridazin-3-yl-SO$_2$- | phenyl | H | CO$_2$Et | H |
| 41 | phenyl-SO$_2$- | Br | H | CO$_2$Me | H |
| 42 | phenyl-SO$_2$- | Br | Me | CO$_2$Me | H |
| 43 | phenyl-SO$_2$- | H | H | CO$_2$Et | Me |
| 44 | pyridin-3-yl-SO$_2$- | Br | H | CO$_2$Et | Me |
| 45 | pyridin-3-yl-SO$_2$- | phenyl | H | CO$_2$Et | Me |
| 46 | phenyl-SO$_2$- | Br | H | CH$_2$OH | H |
| 47 | phenyl-SO$_2$- | H | H | CH$_2$OH | Me |
| 48 | phenyl-SO$_2$- | Br | H | CHO | H |
| 49 | phenyl-SO$_2$- | Br | Me | CHO | H |
| 50 | H | phenyl | | Me | CHO | H |

TABLE 3

Structure: Pyrrole with R$^{2a}$, R$^{3a}$, R$^{4a}$, R$^{5a}$ on ring carbons and R$^{1a}$ on N.

| Ref. Ex. No. | R$^{1a}$ | R$^{2a}$ | R$^{3a}$ | R$^{4a}$ | R$^{5a}$ |
|---|---|---|---|---|---|
| 51 | phenyl-SO$_2$- | H | H | CHO | Me |
| 52 | H | H | H | CHO | Me |
| 53 | pyridin-3-yl-SO$_2$- | H | H | CHO | Me |
| 54 | pyridin-3-yl-SO$_2$- | Br | H | CHO | Me |
| 55 | pyridin-3-yl-SO$_2$- | phenyl | H | CHO | H |
| 56 | 6-MeO-pyridin-3-yl-SO$_2$- | phenyl | H | CHO | H |
| 57 | 6-Cl-pyridin-3-yl-SO$_2$- | phenyl | H | CHO | H |
| 58 | 2-Cl-pyridin-3-yl-SO$_2$- | phenyl | H | CHO | H |
| 59 | 2-Cl-pyrimidin-5-yl-SO$_2$- | phenyl | H | CHO | H |
| 60 | 6-Cl-5-Me-pyridin-3-yl-SO$_2$- | phenyl | H | CHO | H |
| 61 | pyridin-3-yl-SO$_2$- | phenyl | H | CHO | Me |
| 62 | 2-Me-pyrimidin-5-yl-SO$_2$- | phenyl | H | CHO | H |

TABLE 3-continued
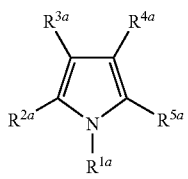
| Ref. Ex. No. | R$^{1a}$ | R$^{2a}$ | R$^{3a}$ | R$^{4a}$ | R$^{5a}$ |
|---|---|---|---|---|---|
| 63 | 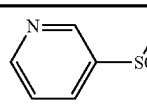 | 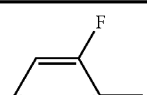 | H | CHO | H |
| 64 | 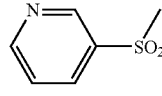 | 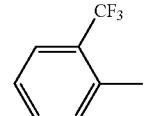 | H | CHO | H |
| 65 | 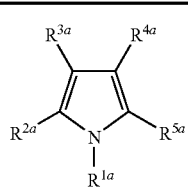 | 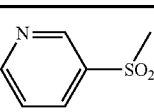 | Me | CHO | H |
| 66 | 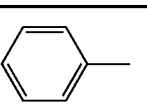 | 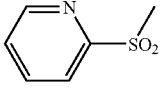 | Me | CHO | H |
TABLE 4
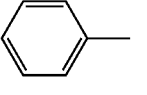
| Ref. Ex. No. | R$^{1a}$ | R$^{2a}$ | R$^{3a}$ | R$^{4a}$ | R$^{5a}$ |
|---|---|---|---|---|---|
| 67 | 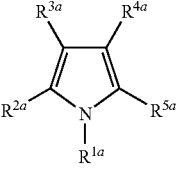 | 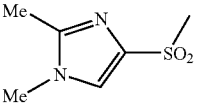 | Me | CHO | H |
| 68 | 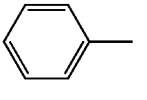 | 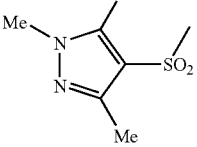 | Me | CHO | H |
| 69 | 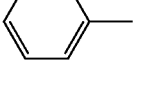 | 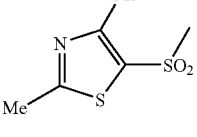 | Me | CHO | H |
| 70 | 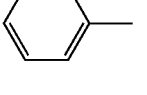 | 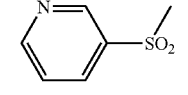 | Me | CHO | H |
| 71 | 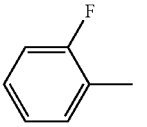 | Br | H | CH$_2$NHMe | H |
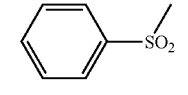

TABLE 4-continued
| Ref. Ex. No. | R$^{1a}$ | R$^{2a}$ | R$^{3a}$ | R$^{4a}$ | R$^{5a}$ |
|---|---|---|---|---|---|
| 72 | 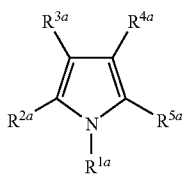 | Br | H | 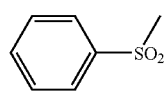 | H |
| 73 | H | Br | H | 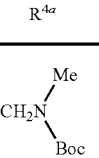 | H |
| 74 | 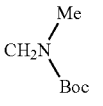 | Br | H | 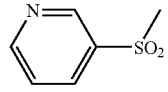 | H |
| 75 | 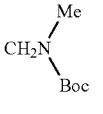 | 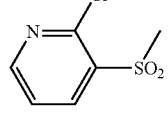 | H | 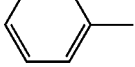 | H |
| 76 | 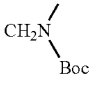 | 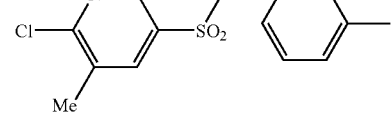 | H | 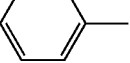 | H |
| 77 | 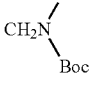 | 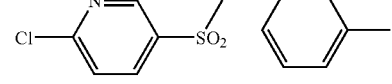 | H | 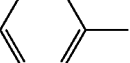 | H |
| 78 | 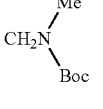 | 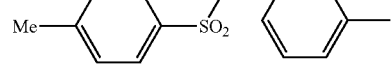 | H | 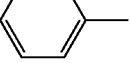 | H |
| 79 | 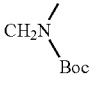 | 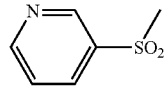 | H | 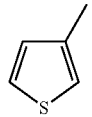 | H |
| 80 | 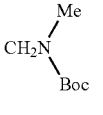 | 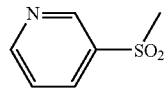 | H | 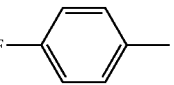 | H |

TABLE 5
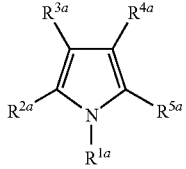
| Ref. Ex. No. | R$^{1a}$ | R$^{2a}$ | R$^{3a}$ | R$^{4a}$ | R$^{5a}$ |
|---|---|---|---|---|---|
| 81 | 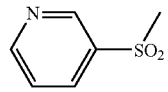 | 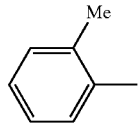 | H |  | H |
| 82 | 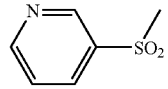 | 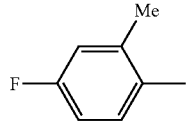 | H |  | H |
| 83 | 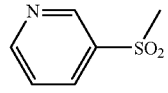 | 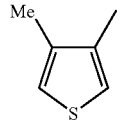 | H |  | H |
| 84 | 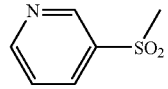 | 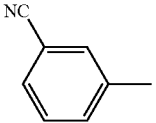 | H |  | H |
| 85 | 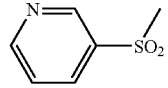 | 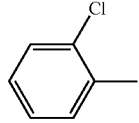 | H |  | H |
| 86 | H | 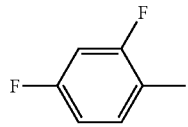 | H |  | H |
| 87 | H | 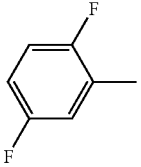 | H |  | H |
| 88 | H | 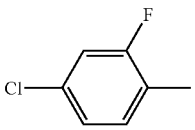 | H |  | H |
| 89 | 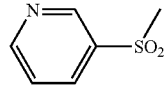 | 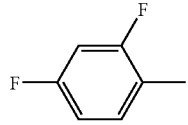 | H |  | H |

TABLE 5-continued

Structure: pyrrole with R1a on N, R2a, R3a, R4a, R5a on ring positions

| Ref. Ex. No. | R1a | R2a | R3a | R4a | R5a |
|---|---|---|---|---|---|
| 90 | 3-pyridyl-SO2- | 2,5-difluorophenyl | H | CH2N(Me)Boc | H |
| 91 | 3-pyridyl-SO2- | 4-chloro-2-fluorophenyl | H | CH2N(Me)Boc | H |
| 92 | 3-pyridyl-SO2- | 3-fluorophenyl | H | CH2N(Me)Boc | H |
| 93 | 3-pyridyl-SO2- | Br | H | CH2N(Me)Boc | Me |

TABLE 6

Structure: pyrrole with R1a on N, R2a, R3a, R4a, R5a on ring positions

| Ref. Ex. No. | R1a | R2a | R3a | R4a | R5a |
|---|---|---|---|---|---|
| 97 | H | 2,6-difluorophenyl | H | CO2Et | Cl |
| 98 | H | 4-cyclohexylphenyl | H | CO2Me | Cl |
| 99 | H | phenyl | F | CO2Me | Cl |
| 100 | H | 2,6-difluorophenyl | H | CO2Et | H |
| 101 | H | 4-cyclohexylphenyl | H | CO2Me | H |
| 102 | H | phenyl | F | CO2Me | H |

TABLE 6-continued

Pyrrole structure with R1a (N-substituent), R2a, R3a, R4a, R5a

| Ref. Ex. No. | R1a | R2a | R3a | R4a | R5a |
|---|---|---|---|---|---|
| 103 | H | 2,6-difluorophenyl | H | CH2OH | H |
| 104 | H | 4-cyclohexylphenyl | H | CH2OH | H |
| 105 | H | 2,6-difluorophenyl | H | CHO | H |
| 106 | H | 4-cyclohexylphenyl | H | CHO | H |
| 107 | H | H | H | CHO | H |
| 111 | H | 2-methylphenyl | F | H | H |
| 112 | H | Br | H | CHO | H |

TABLE 7

| Ref. Ex. No. | R1a | R2a | R3a | R4a | R5a |
|---|---|---|---|---|---|
| 113 | H | 2-methylphenyl | H | CHO | H |
| 114 | H | 2-fluorophenyl | Cl | CHO | H |
| 115 | H | 2-fluorophenyl | F | CHO | H |
| 116 | H | 2-methylphenyl | F | CHO | H |
| 122 | 5-bromopyridin-3-yl | 4-(methylsulfonyl)phenyl | H | CO2Et | H |
| 123 | 5-(trifluoromethyl)pyridin-3-yl | 4-(methylsulfonyl)phenyl | H | CO2Et | H |
| 124 | 2-methylpyridin-3-yl | 4-(methylsulfonyl)phenyl | H | CO2Et | H |
| 125 | pyridin-3-yl | 4-(methylsulfonyl)phenyl | F | CO2Me | H |
| 126 | 5-bromopyridin-3-yl | 4-(methylsulfonyl)phenyl | H | CHO | H |
| 127 | 5-(trifluoromethyl)pyridin-3-yl | 4-(methylsulfonyl)phenyl | H | CHO | H |

TABLE 7-continued
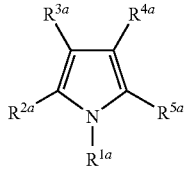
| Ref. Ex. No. | R¹ᵃ | R²ᵃ | R³ᵃ | R⁴ᵃ | R⁵ᵃ |
|---|---|---|---|---|---|
| 128 | 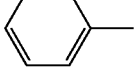 | 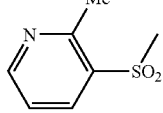 | H | CHO | H |
TABLE 8
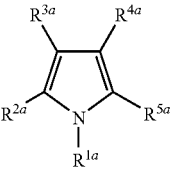
| Ref. Ex. No. | R¹ᵃ | R²ᵃ | R³ᵃ | R⁴ᵃ | R⁵ᵃ |
|---|---|---|---|---|---|
| 129 | 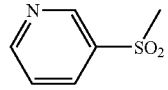 | 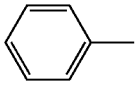 | F | CHO | H |
| 130 | 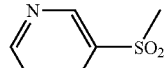 | 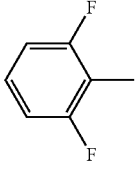 | H | CHO | H |
| 131 | 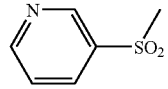 | 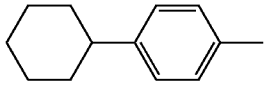 | H | CHO | H |
| 132 | 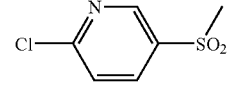 | 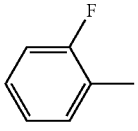 | H | CHO | H |
| 133 | 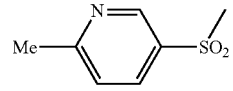 | 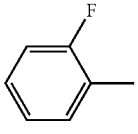 | H | CHO | H |
| 134 | 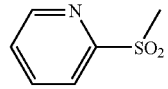 | 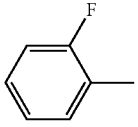 | H | CHO | H |

TABLE 8-continued

[Pyrrole structure with R¹ᵃ, R²ᵃ, R³ᵃ, R⁴ᵃ, R⁵ᵃ substituents]

| Ref. Ex. No. | R¹ᵃ | R²ᵃ | R³ᵃ | R⁴ᵃ | R⁵ᵃ |
|---|---|---|---|---|---|
| 135 | 1-methyl-1H-pyrazol-4-yl-SO₂- | 2-fluorophenyl | H | CHO | H |
| 136 | pyridin-3-yl-SO₂- | 2-methylphenyl | H | CHO | H |
| 137 | pyridin-3-yl-SO₂- | 2-fluorophenyl | Cl | CHO | H |
| 138 | pyridin-3-yl-SO₂- | 2-fluorophenyl | F | CHO | H |

TABLE 9

[Pyrrole structure with R¹ᵃ, R²ᵃ, R³ᵃ, R⁴ᵃ, R⁵ᵃ substituents]

| Ref. Ex. No. | R¹ᵃ | R²ᵃ | R³ᵃ | R⁴ᵃ | R⁵ᵃ |
|---|---|---|---|---|---|
| 139 | pyridin-3-yl-SO₂- | 2-methylphenyl | F | CHO | H |
| 140 | pyridin-3-yl-SO₂- | 2,6-difluorophenyl | H | CHO | Cl |

TABLE 9-continued
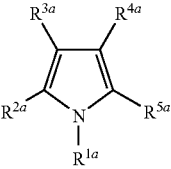
| Ref. Ex. No. | R$^{1a}$ | R$^{2a}$ | R$^{3a}$ | R$^{4a}$ | R$^{5a}$ |
|---|---|---|---|---|---|
| 141 | 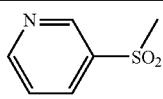 | 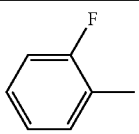 | H | CHO | Cl |
| 142 | 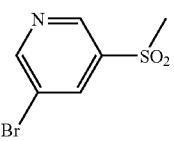 | 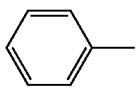 | H | 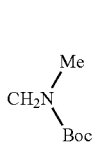 | H |
| 143 | 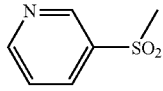 | 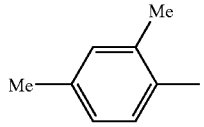 | H |  | H |
| 144 | 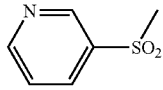 | 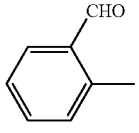 | H | 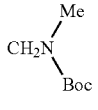 | H |
| 145 | 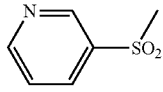 | 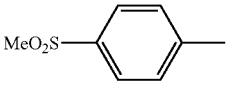 | H | 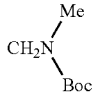 | H |
| 146 | 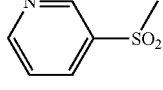 | 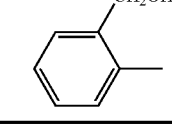 | H | 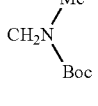 | H |
TABLE 10
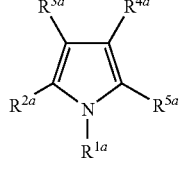
| Ref. Ex. No. | R$^{1a}$ | R$^{2a}$ | R$^{3a}$ | R$^{4a}$ | R$^{5a}$ |
|---|---|---|---|---|---|
| 147 | H | 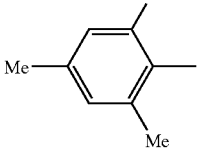 | H | CHO | H |
| 148 | H | 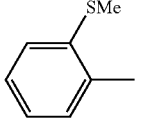 | H | CHO | H |

TABLE 10-continued

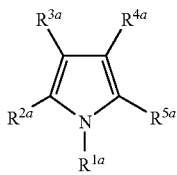

| Ref. Ex. No. | R¹ᵃ | R²ᵃ | R³ᵃ | R⁴ᵃ | R⁵ᵃ |
|---|---|---|---|---|---|
| 149 | H | 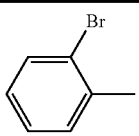 2-bromophenyl | H | CHO | H |
| 150 | H | 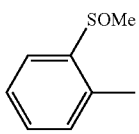 2-(SOMe)phenyl | H | CHO | H |
| 151 | H | 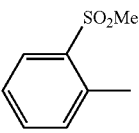 2-(SO₂Me)phenyl | H | CHO | H |
| 152 | H | 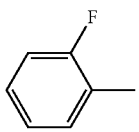 2-fluorophenyl | I | CHO | H |
| 153 | 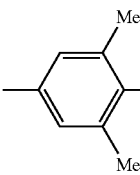 3-pyridyl-SO₂-Me | 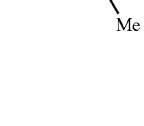 2,4,6-trimethylphenyl | H | CHO | H |

TABLE 10-continued

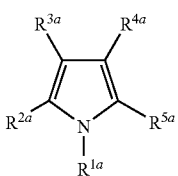

| Ref. Ex. No. | R¹ᵃ | R²ᵃ | R³ᵃ | R⁴ᵃ | R⁵ᵃ |
|---|---|---|---|---|---|
| 154 | 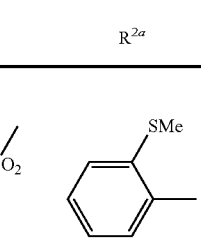 | 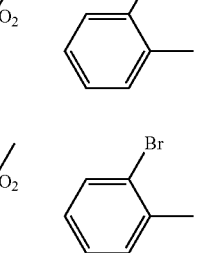 2-(SMe)phenyl | H | CHO | H |
| 155 | 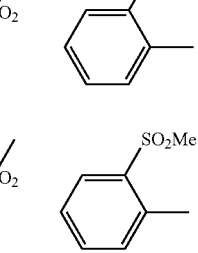 | 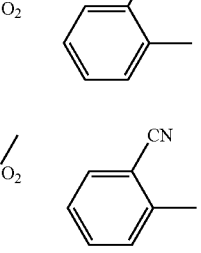 2-bromophenyl | H | CHO | H |
| 156 | 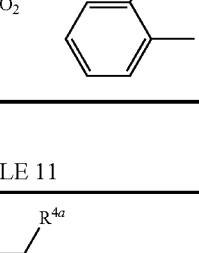 | 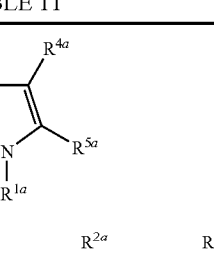 2-(SO₂Me)phenyl | H | CHO | H |
| 157 | 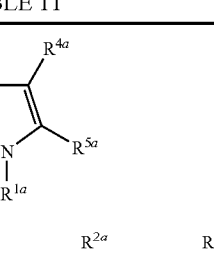 | 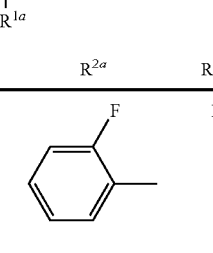 2-cyanophenyl | H | CHO | H |

TABLE 11

| Ref. Ex. No. | R¹ᵃ | R²ᵃ | R³ᵃ | R⁴ᵃ | R⁵ᵃ |
|---|---|---|---|---|---|
| 158 | 3-pyridyl-SO₂-Me | 2-fluorophenyl | F | I | CHO | H |
| 159 | 3-pyridyl-SO₂-Me | 2,6-dimethylphenyl | Me | H | CHO | H |

TABLE 11-continued

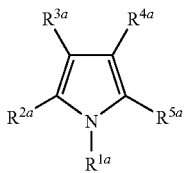

| Ref. Ex. No. | R¹ᵃ | R²ᵃ | R³ᵃ | R⁴ᵃ | R⁵ᵃ |
|---|---|---|---|---|---|
| 160 | 3-pyridyl-SO₂- | 2-fluorophenyl | H | CHO | Br |
| 161 | 3-pyridyl-SO₂- | 2-fluorophenyl | CN | CHO | H |
| 162 | 3-pyridyl-SO₂- | 2-fluorophenyl | H | CHO | CN |
| 163 | 6-methoxy-3-pyridyl-SO₂- | Br | H | CH₂N(Me)Boc | H |
| 164 | 3-pyridyl-SO₂- | 4-cyanophenyl | H | CH₂N(Me)Boc | H |
| 165 | 3-pyridyl-SO₂- | 4-fluoro-3-methyl-5-cyanophenyl | H | CH₂N(Me)Boc | H |
| 166 | 3-pyridyl-SO₂- | 4-fluoro-3-methyl-5-methoxyphenyl | H | CH₂N(Me)Boc | H |
| 167 | 3-pyridyl-SO₂- | 2-fluoro-3-methyl-6-formylphenyl | H | CH₂N(Me)Boc | H |

TABLE 12
| Ref. Ex. No. | R^{1a} | R^{2a} | R^{3a} | R^{4a} | R^{5a} |
|---|---|---|---|---|---|
| 168 | 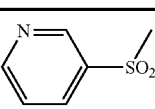 | 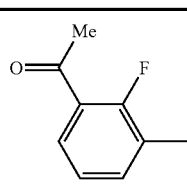 | H | CH$_2$N(Me)Boc | H |
| 169 |  | 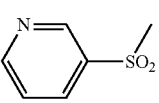 | H | CH$_2$N(Me)Boc | H |
| 170 | 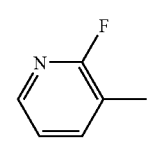 |  | H | CH$_2$N(Me)Boc | H |
| 171 | 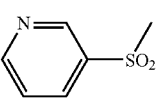 | 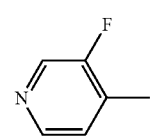 | H | CH$_2$N(Me)Boc | H |
| 172 |  | 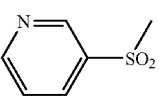 | H | CH$_2$N(Me)Boc | H |
| 173 | 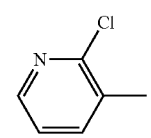 |  | H | CH$_2$N(Me)Boc | H |
| 174 | 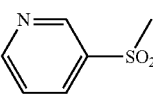 | 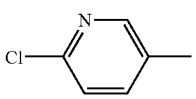 | H | CH$_2$N(Me)Boc | H |
| 175 |  | 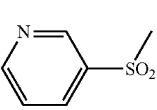 | H | CH$_2$N(Me)Boc | H |
| 176 | 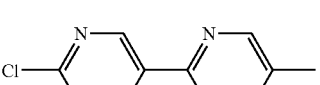 |  | H | CH$_2$N(Me)Boc | H |
| 177 | 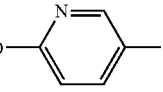 | 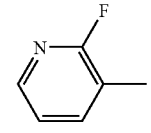 | H | CH$_2$N(Me)Boc | H |

TABLE 12-continued

Structure: Pyrrole with R$^{2a}$, R$^{3a}$, R$^{4a}$, R$^{5a}$ substituents on carbons and R$^{1a}$ on N.

| Ref. Ex. No. | R$^{1a}$ | R$^{2a}$ | R$^{3a}$ | R$^{4a}$ | R$^{5a}$ |
|---|---|---|---|---|---|
| 178 | pyridin-3-yl-SO$_2$-CH$_2$- (3-pyridyl-SO$_2$-methylene) | 3-fluoro-2-methyl-6-methoxyphenyl (F, Me, OMe substituted phenyl) | H | CH$_2$N(Me)(Boc) | H |

TABLE 13

Structure: Pyrrole with R$^{2a}$, R$^{3a}$, R$^{4a}$, R$^{5a}$ substituents on carbons and R$^{1a}$ on N.

| Ref. Ex. No. | R$^{1a}$ | R$^{2a}$ | R$^{3a}$ | R$^{4a}$ | R$^{5a}$ |
|---|---|---|---|---|---|
| 180 | pyridin-3-yl-SO$_2$-CH$_2$- | 4-(OCHF$_2$)-phenyl | H | CH$_2$N(Me)(Boc) | H |
| 181 | pyridin-3-yl-SO$_2$-CH$_2$- | 4-methylpyridin-3-yl | H | CH$_2$N(Me)(Boc) | H |
| 183 | pyridin-3-yl-SO$_2$-CH$_2$- | 2-methylpyridin-3-yl | H | CH$_2$N(Me)(Boc) | H |
| 187 | (6-methylpyridin-3-yl)-SO$_2$-CH$_2$- | Br | H | CH$_2$N(Me)(Boc) | H |
| 188 | (6-methylpyridin-3-yl)-SO$_2$-CH$_2$- | 2-fluoropyridin-3-yl | H | CH$_2$N(Me)(Boc) | H |
| 189 | phenyl-SO$_2$-CH$_2$- | 2-fluoropyridin-3-yl | H | CHO | H |

TABLE 13-continued

Structure: pyrrole with R¹ᵃ on N, R²ᵃ and R⁵ᵃ at 2,5-positions, R³ᵃ and R⁴ᵃ at 3,4-positions.

| Ref. Ex. No. | R¹ᵃ | R²ᵃ | R³ᵃ | R⁴ᵃ | R⁵ᵃ |
|---|---|---|---|---|---|
| 190 | H | 2-fluoro-3-methylpyridin-... | H | CHO | H |
| 191 | H | 2-fluoro-3-methylpyridin-... | Cl | CHO | H |
| 192 | pyridin-3-ylsulfonyl | 2-fluoro-3-methylpyridin-... | Cl | CHO | H |
| 194 | pyridin-3-ylsulfonyl | 2-methylthiophen-... | H | CH₂N(Me)Boc | H |
| 196 | pyridin-3-ylsulfonyl | 2,3-dimethylpyridin-... | H | CH₂N(Me)Boc | H |

TABLE 14

Structure: pyrrole with R¹ᵃ on N, R²ᵃ and R⁵ᵃ at 2,5-positions, R³ᵃ and R⁴ᵃ at 3,4-positions.

| Ref. Ex. No. | R¹ᵃ | R²ᵃ | R³ᵃ | R⁴ᵃ | R⁵ᵃ |
|---|---|---|---|---|---|
| 197 | pyridin-3-ylsulfonyl | HON=CH-(2-fluoro-3-methylphenyl) | H | CH₂N(Me)Boc | H |
| 198 | pyridin-3-ylsulfonyl | NC-(2-fluoro-3-methylphenyl) | H | CH₂N(Me)Boc | H |

TABLE 14-continued
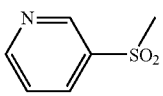
| Ref. Ex. No. | R¹ᵃ | R²ᵃ | R³ᵃ | R⁴ᵃ | R⁵ᵃ |
|---|---|---|---|---|---|
| 199 |  |  | H | 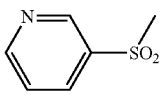 | H |
| 200 |  |  | H | 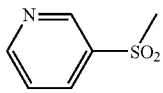 | H |
The structures of the compounds described in Examples are shown in Tables 15-23.
TABLE 15
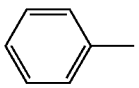
| Ex. No. | R¹ᵇ | R²ᵇ | R³ᵇ | R⁴ᵇ | addition salt |
|---|---|---|---|---|---|
| 1 | 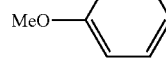 | 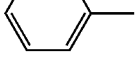 | H | H | 2HCl |
| 2 | 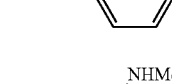 | 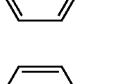 | H | H | HCl |
| 3 | 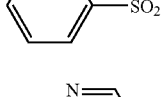 |  | H | H | 2HCl |
| 4 | 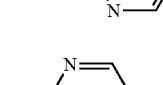 | 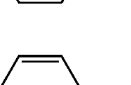 | H | H | 2HCl |
| 5 | 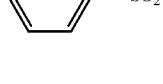 | 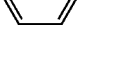 | H | H | HCl |
| 6 | 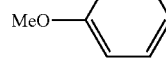 | 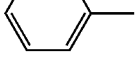 | H | Me | 2HCl |

TABLE 15-continued

| Ex. No. | R¹ᵇ | R²ᵇ | R³ᵇ | R⁴ᵇ | addition salt |
|---|---|---|---|---|---|
| 7 | 2-methyl-pyrimidin-5-yl-SO₂ | phenyl | H | H | 2HCl |
| 8 | pyridin-3-yl-SO₂ | 2-fluorophenyl | H | H | HOOC-CH=CH-COOH |
| 9 | pyridin-3-yl-SO₂ | 2-(trifluoromethyl)phenyl | H | H | 2HCl |
| 10 | pyridin-3-yl-SO₂ | phenyl | Me | H | 2HCl |
| 11 | pyridin-2-yl-SO₂ | phenyl | Me | H | HCl |
| 12 | 1,2-dimethyl-imidazol-4-yl-SO₂ | phenyl | Me | H | 2HCl |
| 13 | 5-chloro-1,3-dimethyl-pyrazol-4-yl-SO₂ | phenyl | Me | H | HCl |
| 14 | 1,3-dimethyl-pyrazol-4-yl-SO₂ | phenyl | Me | H | HCl |

TABLE 16

| Ex. No. | R¹ᵇ | R²ᵇ | R³ᵇ | R⁴ᵇ | addition salt |
|---|---|---|---|---|---|
| 15 | 2,4-dimethyl-thiazol-5-yl-SO₂- | phenyl | Me | H | CF₃COOH |
| 16 | pyridin-3-yl-SO₂- | 2-fluorophenyl | Me | H | HCl |
| 17 | 2-chloropyridin-3-yl-SO₂- | phenyl | H | H | HCl |
| 18 | 2-aminopyrimidin-5-yl-SO₂- | phenyl | H | H | |
| 19 | imidazo[1,2-a]pyrimidin-6-yl-SO₂- | phenyl | H | H | 2HCl |
| 20 | pyridazin-3-yl-SO₂- | phenyl | H | H | HOOC-CH=CH-COOH |
| 21 | 5-methylpyridin-3-yl-SO₂- | phenyl | H | H | HOOC-CH=CH-COOH |
| 22 | 6-hydroxypyridin-3-yl-SO₂- | phenyl | H | H | HCl |
| 23 | 6-cyanopyridin-3-yl-SO₂- | phenyl | H | H | HCl |
| 24 | 6-methylpyridin-3-yl-SO₂- | phenyl | H | H | 2HCl |
| 25 | pyridin-3-yl-SO₂- | 3-methylthiophen-3-yl | H | H | HCl |

TABLE 16-continued
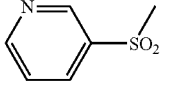
| Ex. No. | R$^{1b}$ | R$^{2b}$ | R$^{3b}$ | R$^{4b}$ | addition salt |
|---|---|---|---|---|---|
| 26 |  | 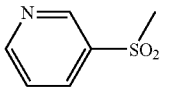 | H | H | 2HCl |
| 27 | 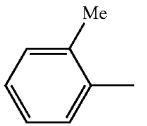 | 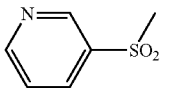 | H | H | 2HCl |
| 28 | 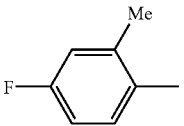 | 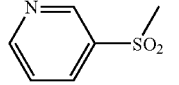 | H | H | 2HCl |
TABLE 17
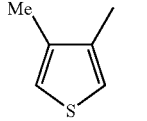
| Ex. No. | R$^{1b}$ | R$^{2b}$ | R$^{3b}$ | R$^{4b}$ | addition salt |
|---|---|---|---|---|---|
| 29 | 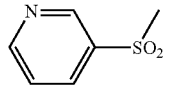 | 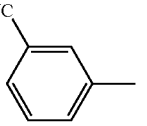 | H | H | 2HCl |
| 30 | 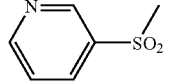 | 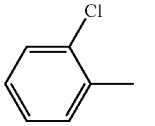 | H | H | HCl |
| 31 | 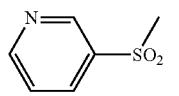 | 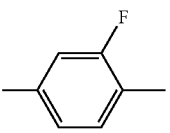 | H | H | 2HCl |
| 32 | | | H | H | 2HCl |

TABLE 17-continued

Structure: pyrrole ring with substituents R$^{2b}$, R$^{3b}$, R$^{4b}$, N-R$^{1b}$, and a CH$_2$-NH-Me group.

| Ex. No. | R$^{1b}$ | R$^{2b}$ | R$^{3b}$ | R$^{4b}$ | addition salt |
|---|---|---|---|---|---|
| 33 | pyridin-3-yl-SO$_2$- | 2,5-difluorophenyl | H | H | HCl |
| 34 | pyridin-3-yl-SO$_2$- | 4-chloro-2-fluorophenyl | H | H | 2HCl |
| 35 | pyridin-3-yl-SO$_2$- | 3-fluorophenyl | H | H | HCl |
| 36 | pyridin-3-yl-SO$_2$- | 2-fluorophenyl | H | Me | HOOC-CH=CH-COOH |

TABLE 18

Structure: pyrrole ring with substituents R$^{2b}$, R$^{3b}$, R$^{4b}$, N-R$^{1b}$, and a CH$_2$-NH-Me group.

| Ex. No. | R$^{1b}$ | R$^{2b}$ | R$^{3b}$ | R$^{4b}$ | addition salt |
|---|---|---|---|---|---|
| 37 | 5-(trifluoromethyl)pyridin-3-yl-SO$_2$- | phenyl | H | H | HCl |
| 38 | 2-methylpyridin-3-yl-SO$_2$- | phenyl | H | H | 2HCl |

TABLE 18-continued

| Ex. No. | R¹ᵇ | R²ᵇ | R³ᵇ | R⁴ᵇ | addition salt |
|---|---|---|---|---|---|
| 39 | pyridin-3-yl-SO₂-CH₂- | 2,6-difluorophenyl | H | H | fumaric acid |
| 40 | pyridin-3-yl-SO₂-CH₂- | 4-cyclohexylphenyl | H | H | 2HCl |
| 41 | pyridin-3-yl-SO₂-CH₂- | phenyl | F | H | 2HCl |
| 42 | pyridin-3-yl-SO₂-CH₂- | phenyl | F | H | |
| 43 | pyridin-3-yl-SO₂-CH₂- | phenyl | F | H | 0.5 fumaric acid |
| 44 | 6-methylpyridin-3-yl-SO₂-CH₂- | 2-fluorophenyl | H | H | 2HCl |
| 45 | pyridin-2-yl-SO₂-CH₂- | 3-fluorophenyl | H | H | HCl |
| 46 | 1-methylpyrazol-4-yl-SO₂-CH₂- | 2-fluorophenyl | H | H | fumaric acid |
| 47 | pyridin-3-yl-SO₂-CH₂- | 2-methylphenyl | H | H | fumaric acid |

TABLE 19
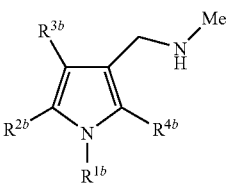
| Ex. No. | R¹ᵇ | R²ᵇ | R³ᵇ | R⁴ᵇ | addition salt |
|---|---|---|---|---|---|
| 48 | 3-pyridyl-SO₂- | 2-F-phenyl | Cl | H | fumarate |
| 49 | 3-pyridyl-SO₂- | 2-F-phenyl | F | H | fumarate |
| 50 | 3-pyridyl-SO₂- | 2-Me-phenyl | F | H | fumarate |
| 51 | 3-pyridyl-SO₂- | 2,6-diF-phenyl | H | Cl | fumarate |
| 52 | 3-pyridyl-SO₂- | 2-F-phenyl | H | Cl | fumarate |
| 53 | 5-Br-3-pyridyl-SO₂- | phenyl | H | H | HCl |
| 54 | 5-CN-3-pyridyl-SO₂- | phenyl | H | H | HCl |
| 55 | 5-MeO₂C-3-pyridyl-SO₂- | phenyl | H | H | HCl |
| 56 | 5-Me-3-pyridyl-SO₂- | phenyl | H | H | 2HCl |

TABLE 19-continued
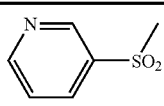
| Ex. No. | R[1b] | R[2b] | R[3b] | R[4b] | addition salt |
|---|---|---|---|---|---|
| 57 | 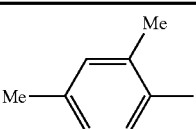 | 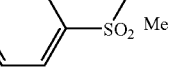 | H | H | HCl |
TABLE 20
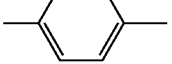
| Ex. No. | R[1b] | R[2b] | R[3b] | R[4b] | addition salt |
|---|---|---|---|---|---|
| 58 | 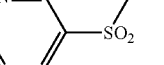 |  | H | H | 2HCl |
| 59 |  | 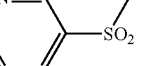 | H | H | 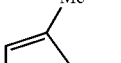 |
| 60 |  | 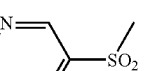 | H | H | 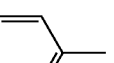 |
TABLE 21
| Ex. No. | R[1c] | R[2c] | R[3c] | R[4c] | R[5c] | addition salt |
|---|---|---|---|---|---|---|
| 61 | (pyridyl-SO2) | (phenyl) | H | CH2NHMe | H | fumaric acid |

TABLE 21-continued

| Ex. No. | R¹ᶜ | R²ᶜ | R³ᶜ | R⁴ᶜ | R⁵ᶜ | addition salt |
|---|---|---|---|---|---|---|
| 62 | pyridin-3-yl-SO₂-CH₂– | 2,3,5-trimethylphenyl | H | CH₂NHMe | H | fumaric acid (HO₂C–CH=CH–CO₂H) |
| 63 | pyridin-3-yl-SO₂-CH₂– | 2-methyl-6-SMe-phenyl | H | CH₂NHMe | H | fumaric acid |
| 64 | pyridin-3-yl-SO₂-CH₂– | 2-methyl-6-SO₂Me-phenyl | H | CH₂NHMe | H | 0.5 fumaric acid |
| 65 | pyridin-3-yl-SO₂-CH₂– | 2-methyl-6-CN-phenyl | H | CH₂NHMe | H | fumaric acid |
| 66 | pyridin-3-yl-SO₂-CH₂– | 2,3-dimethylphenyl | H | CH₂NHMe | H | fumaric acid |
| 67 | pyridin-3-yl-SO₂-CH₂– | 2-methyl-6-SOMe-phenyl | H | CH₂NHMe | H | fumaric acid |
| 68 | pyridin-3-yl-SO₂-CH₂– | 2-fluoro-6-methylphenyl | CN | CH₂NHMe | H | fumaric acid |
| 69 | pyridin-3-yl-SO₂-CH₂– | 2-fluoro-6-methylphenyl | H | CH₂NHMe | CN | fumaric acid |
| 70 | pyridin-3-yl-SO₂-CH₂– | 4-methyl-2-CN-phenyl | H | CH₂NHMe | H | fumaric acid |

TABLE 21-continued
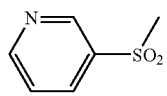
| Ex. No. | R1c | R2c | R3c | R4c | R5c | addition salt |
|---|---|---|---|---|---|---|
| 71 | 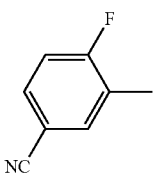 | 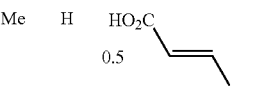 | H | CH2NHMe | H | 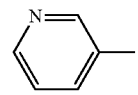 0.5 |
TABLE 22
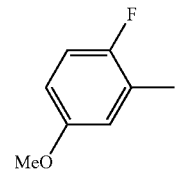
| Ex. No. | R1c | R2c | R3c | R4c | R5c | addition salt |
|---|---|---|---|---|---|---|
| 72 |  | 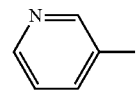 | H | CH2NHMe | H | 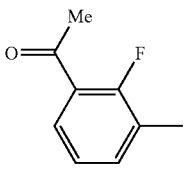 |
| 73 |  | 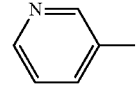 | H | CH2NHMe | H | 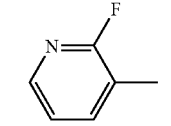 |
| 74 |  | 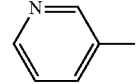 | H | CH2NHMe | H | 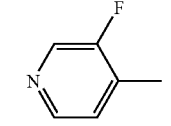 |
| 75 |  | 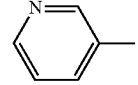 | H | CH2NHMe | H | 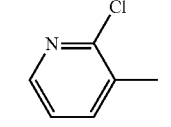 |
| 76 |  | 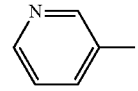 | H | CH2NHMe | H | 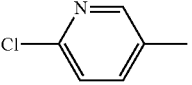 |
| 77 | 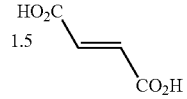 |  | H | CH2NHMe | H | 1.5 |

TABLE 22-continued
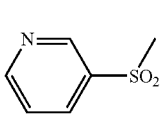
| Ex. No. | R¹ᶜ | R²ᶜ | R³ᶜ | R⁴ᶜ | R⁵ᶜ | addition salt |
|---|---|---|---|---|---|---|
| 78 | 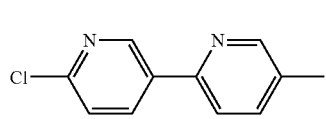 | 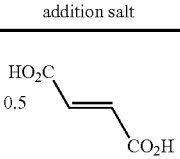 | H | CH₂NHMe | H | 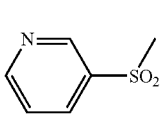 0.5 |
| 79 | 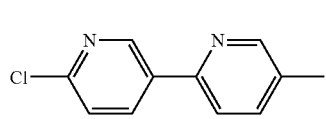 | 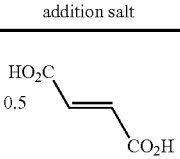 | H | CH₂NHMe | H | HCl |
| 80 | 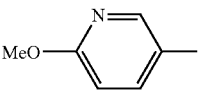 | 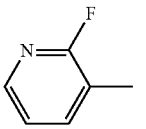 | H | CH₂NHMe | H | 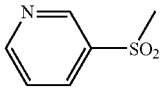 |
| 81 | 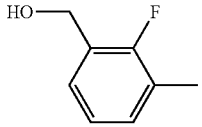 | 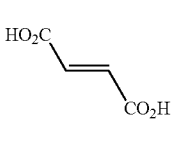 | H | CH₂NHMe | H | 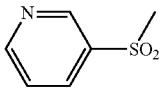 |
| 82 | 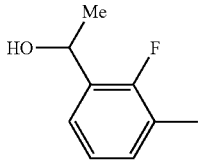 | 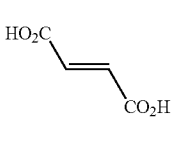 | H | CH₂NHMe | H | 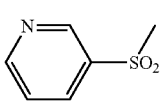 |
TABLE 23
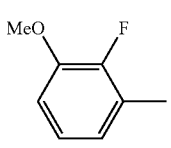
| Ex. No. | R¹ᶜ | R²ᶜ | R³ᶜ | R⁴ᶜ | R⁵ᶜ | addition salt |
|---|---|---|---|---|---|---|
| 83 | 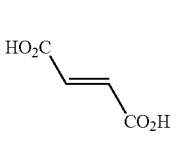 | 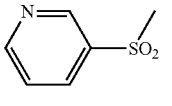 | H | CH₂NHMe | H | 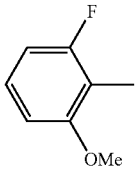 |
| 84 | 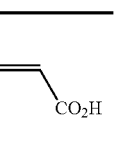 | 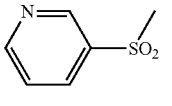 | H | CH₂NHMe | H | 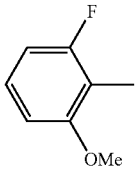 |

TABLE 23-continued

[Pyrrole core structure with substituents $R^{1c}$ (on N), $R^{2c}$, $R^{3c}$, $R^{4c}$, $R^{5c}$]

| Ex. No. | $R^{1c}$ | $R^{2c}$ | $R^{3c}$ | $R^{4c}$ | $R^{5c}$ | addition salt |
|---|---|---|---|---|---|---|
| 85 | (pyridin-3-yl)SO$_2$CH$_2$– | 4-methylpyridin-3-yl | H | CH$_2$NHMe | H | HO$_2$C–CH=CH–CO$_2$H |
| 86 | (pyridin-3-yl)SO$_2$CH$_2$– | 3-methylpyridin-2-yl | H | CH$_2$NHMe | H | HO$_2$C–CH=CH–CO$_2$H |
| 87 | (6-methylpyridin-3-yl)SO$_2$CH$_2$– | 2-fluoropyridin-3-yl | H | CH$_2$NHMe | H | 0.5 HO$_2$C–CH=CH–CO$_2$H |
| 88 | (pyridin-3-yl)SO$_2$CH$_2$– | 2-fluoropyridin-3-yl | Cl | CH$_2$NHMe | H | HO$_2$C–CH=CH–CO$_2$H |
| 89 | (pyridin-3-yl)SO$_2$CH$_2$– | thiophen-2-yl | H | CH$_2$NHMe | H | HO$_2$C–CH=CH–CO$_2$H |
| 90 | (pyridin-3-yl)SO$_2$CH$_2$– | 3-methylpyridin-2-yl | H | CH$_2$NHMe | H | HO$_2$C–CH=CH–CO$_2$H |
| 91 | (pyridin-3-yl)SO$_2$CH$_2$– | 3-cyano-2-fluorophenyl | H | CH$_2$NHMe | H | HO$_2$C–CH=CH–CO$_2$H |
| 92 | (pyridin-3-yl)SO$_2$CH$_2$– | 3-cyanothiophen-2-yl | H | CH$_2$NHMe | H | HO$_2$C–CH=CH–CO$_2$H |

Experimental Example 1

Proton Potassium-adenosine triphosphatase ($H^+,K^+$-ATPase) Inhibitory Activity Test According to the method [*Biochim. Biophys. Acta,* 728, 31 (1983)] of Wallmark et al., a gastric mucous membrane microsomal fraction was prepared from the stomach of swine. First, the stomach was removed, washed with tap water, immersed in 3 mol/L brine, and the surface of the mucous membrane was wiped with a paper towel. The gastric mucous membrane was detached, chopped, and homogenized in a 0.25 mol/L saccharose solution (pH 6.8) containing 1 mmol/L EDTA and 10 mmol/L tris-hydrochloric acid using polytron (Kinematica). The obtained homogenate was centrifuged at 20,000×g for 30 min and the supernatant was centrifuged at 100,000×g for 90 min. The precipitate was suspended in 0.25 mol/L saccharose solution, superimposed on a 0.25 mol/L saccharose solution containing 7.5% Ficoll, and centrifuged at 100,000×g for 5 hr. The fraction containing the interface between the both layers was recovered, and centrifugally washed with 0.25 mol/L saccharose solution.

The obtained microsomal fraction was used as a proton, potassium-adenosine triphosphatase standard product.

To 40 μL of a 50 mmol/L HEPES-tris buffer (5 mmol/L magnesium chloride, 10 mmol/L potassium chloride, 10 μmol/L valinomycin, pH=6.5) containing 2.5 μg/mL (based on the protein concentration) of the enzyme standard product was added a test compound (5 μL) dissolved in a 10% aqueous dimethyl sulfoxide solution, and the mixture was incubated at 37° C. for 30 min. The enzyme reaction was started by adding 5 μL of a 2 mmol/L adenosine triphosphate tris salt solution (50 mmol/L HEPES-tris buffer (5 mmol/L magnesium chloride, pH 6.5)). The enzyme reaction was carried out at 37° C. for 20 min, and 15 μL of a malachite green solution (0.12% malachite green solution in sulfuric acid (2.5 mol/L), 7.5% ammonium molybdate and 11% Tween 20 were mixed at a ratio of 100:25:2) was added to quench the reaction. After allowing to stand at room temperature for 15 min, the resulting reaction product of inorganic phosphorus with malachite green was calorimetrically determined at a wavelength of 610 nm. In addition, the amount of the inorganic phosphoric acid in the reaction solution free of potassium chloride was measured in the same manner, which was subtracted from the inorganic phosphoric acid amount in the presence of potassium chloride to determine the proton, potassium-adenosine triphosphatase activity. The inhibitory rate (%) was determined from the activity value of the control and the activity values of various concentrations of the test compound, and the 50% inhibitory concentration ($IC_{50}$) of the proton, potassium-adenosine triphosphatase was determined. The results are shown in Table 24.

Experimental Example 2

Human liver cancer-derived cell line HepG2 (ATCC No. HB-8065) was passaged using Dulbecco's Modified Eagle medium (DMEM; Invitrogen) containing 10% fetal bovine serum (FBS; TRACE SCIENTIFIC LTD.), 1 mmol/L sodium pyruvate (Invitrogen), 2 mmol/L L-glutamine (Invitrogen), 50 IU/mL penicillin (Invitrogen) and 50 μg/mL streptomycin (Invitrogen) at 5% $CO_2$, 37° C. The test reagent was prepared with DMSO to 10 mM, and further diluted with DMEM medium containing 0.5% FBS, 1 mmol/L sodium pyruvate, 2 mmol/L L-glutamine, 50 IU/mL penicillin and 50 μg/mL streptomycin to a final concentration of DMSO of 0.1%. HepG2 ($2\times10^4$ cells/well) was cultured on a 96 well white plate (Costar) with the test reagent at 5% $CO_2$, 37° C. After culture for one day, the intracellular ATP content was measured using ATPLite™ (PerkinElmer Life Sciences). The results are shown in Table 24 (n≧3, average value±SD) as a relative value (%) to control (without addition of drug) at 30 μM.

TABLE 24

| Example No. | $H^+/K^+$-ATPase inhibitory activity ($IC_{50}$, nM) | ATP content (%, 30 μM) |
|---|---|---|
| 2 | 13 | 45.2 |
| 5 | 65 | 73.9 |
| 7 | 34 | 76.5 |
| 8 | 22 | 87.9 |
| 29 | 41 | 71.5 |
| 32 | 8.9 | 53.6 |
| 41 | 43 | 86.7 |
| 44 | 48 | 78.5 |
| 47 | 58 | 81.8 |
| 74 | 210 | 95.2 |

From the results of Table 24, it is clear that compound (I) of the present invention has a superior $H^+/K^+$-ATPase inhibitory activity, and further shows low cytotoxicity.

INDUSTRIAL APPLICABILITY

Since compound (I) of the present invention shows a superior proton pump inhibitory effect (while conventional proton pump inhibitors such as omeprazole, lansoprazole etc. form a covalent bond with a cysteine residue of H+/K+-ATPase and irreversibly inhibit the enzyme activity, since compound (I) inhibits the proton pump (H+/K+-ATPase) activity reversibly and in a K+ antagonist inhibitory manner to consequently suppress acid secretion, it is sometimes referred to as a potassium-competitive acid blocker: P-CAB or an acid pump antagonist (ACPA or APA)), it can provide a clinically useful pharmaceutical composition for the prophylaxis and/or treatment of peptic ulcer, Zollinger-Ellison syndrome, gastritis, erosive esophagitis, reflux esophagitis, symptomatic gastroesophageal reflux disease (symptomatic GERD), functional dyspepsia, gastric cancer, stomach MALT lymphoma, or gastric hyperacidity; or an inhibitor of upper gastrointestinal hemorrhage due to peptic ulcer, acute stress ulcer, hemorrhagic gastritis or invasive stress. Since compound (I) shows low toxicity and is superior in water-solubility, in vivo kinetics and efficacy expression, it is useful as a pharmaceutical composition. Moreover, since compound (I) is stable even under acidic conditions, which enables oral administration of the compound as a conventional tablet and the like without formulating an enteric-coated preparation. This has a consequence that the preparation of tablet and the like can be made smaller, which is advantageous in that it is easily swallowed by patients having difficulty in swallowing, particularly the elderly and children. In addition, since a sustained release effect afforded by enteric-coated preparations is absent, expression of a gastric acid secretion-suppressive action is rapid, and alleviation of symptoms such as pain and the like is rapid.

This application is based on patent application Nos. 2005-250356 and 2006-100626 filed in Japan, the contents of which are incorporated in full herein by this reference.

The invention claimed is:
1. 1-[5-(2-Fluorophenyl)-1-(pyridin-3-ylsulfonyl)-1H-pyrrol-3-yl]-N-methylmethanamine or a salt thereof.

* * * * *

UNITED STATES PATENT AND TRADEMARK OFFICE
CERTIFICATE OF CORRECTION

PATENT NO. : 7,977,488 B2  
APPLICATION NO. : 11/991307  
DATED : July 12, 2011  
INVENTOR(S) : Masahiro Kajino et al.

It is certified that error appears in the above-identified patent and that said Letters Patent is hereby corrected as shown below:

In the Specification

In column 190, Table 24, delete data for lines of Example No. "7" and Example No. "32" so that Table 24 reads as follows:

Table 24

| Example No. | H+/K+-ATPase inhibitory activity ($IC_{50}$, nM) | ATP content (%, 30 μM) |
|---|---|---|
| 2 | 13 | 45.2 |
| 5 | 65 | 73.9 |
| 8 | 22 | 87.9 |
| 29 | 41 | 71.5 |
| 41 | 43 | 86.7 |
| 44 | 48 | 78.5 |
| 47 | 58 | 81.8 |
| 74 | 210 | 95.2 |

Signed and Sealed this  
Thirtieth Day of June, 2015

Michelle K. Lee  
*Director of the United States Patent and Trademark Office*

UNITED STATES PATENT AND TRADEMARK OFFICE

(12)  CERTIFICATE EXTENDING PATENT TERM
      UNDER 35 U.S.C. § 156

(68) PATENT NO.        : 7,977,488

(45) ISSUED            : July 12, 2011

(75) INVENTOR          : Kajino et al.

(73) PATENT OWNER      : Takeda Pharmaceutical Company Limited

(95) PRODUCT           : VOQUEZNA® Dual Pak (vonoprazan fumarate tablets, amoxicillin capsules)

This is to certify that an application under 35 U.S.C. § 156 has been filed in the United States Patent and Trademark Office, requesting extension of the term of U.S. Patent No. 7,977,488 based upon the regulatory review of the product VOQUEZNA® Dual Pak (vonoprazan fumarate tablets, amoxicillin capsules) by the Food and Drug Administration. According to United States Patent and Trademark Office records, the original expiration date of the patent as of the date of issuance of this certificate is August 11, 2028. Because it appears that the requirements of the law have been met, this certificate extends the term of the patent for the period of

(94)                   607 days subject to the payment of maintenance fees as provided by law, with all rights pertaining thereto as provided by 35 U.S.C. § 156.

I have caused the seal of the United States Patent and Trademark Office to be affixed this 17th day of November 2025.

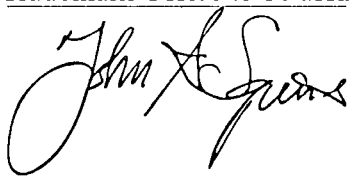

John A. Squires
Under Secretary of Commerce for Intellectual Property and Director of the United States Patent and Trademark Office